US012594410B2

(12) United States Patent
Ziebol et al.

(10) Patent No.: US 12,594,410 B2
(45) Date of Patent: Apr. 7, 2026

(54) DEVICE FOR DELIVERING AN ANTIMICROBIAL COMPOSITION INTO A MEDICAL DEVICE

(71) Applicant: ICU Medical, Inc., San Clemente, CA (US)

(72) Inventors: Robert J. Ziebol, Shoreview, MN (US); Matthew David Beilke, Plymouth, MN (US)

(73) Assignee: ICU Medical, Inc., San Clemente, CA (US)

( * ) Notice: Subject to any disclaimer, the term of this patent is extended or adjusted under 35 U.S.C. 154(b) by 237 days.

(21) Appl. No.: 18/061,385

(22) Filed: Dec. 2, 2022

(65) Prior Publication Data

US 2023/0121450 A1 Apr. 20, 2023

Related U.S. Application Data

(63) Continuation of application No. 16/558,921, filed on Sep. 3, 2019, now Pat. No. 11,517,732, which is a
(Continued)

(51) Int. Cl.
*A61M 39/10* (2006.01)
*A61M 5/178* (2006.01)

(52) U.S. Cl.
CPC ........ *A61M 39/1011* (2013.01); *A61M 5/178* (2013.01); *A61M 2039/1033* (2013.01);
(Continued)

(58) Field of Classification Search
CPC .............. A61M 39/1011; A61M 5/178; A61M 2039/1033; A61M 2039/1083; A61M 2039/1088; A61M 2205/0205
See application file for complete search history.

(56) References Cited

U.S. PATENT DOCUMENTS 382,297 A 5/1888 Fry
559,697 A 5/1896 Tiugti et al.
(Continued)

FOREIGN PATENT DOCUMENTS

AU 2013 224680 9/2016
CA 2 148 847 12/1995
(Continued)

OTHER PUBLICATIONS

Antibiotic Lock Therapy Guideline, Stanford Hospital and Clinics, Pharmacy Department Policies and Procedures, issued Jun. 2011.
(Continued)

*Primary Examiner* — Lauren P Farrar
(74) *Attorney, Agent, or Firm* — Knobbe Martens Olson & Bear, LLP

(57) ABSTRACT

The present disclosure is directed to a device for delivering an antimicrobial composition into a medical device. Some embodiments disclosed herein provide a method for preventing infection and microbial ingress in medical device connections. The device includes a male connector with a distal tip and a recess at the distal tip. The surface of the recess includes an antimicrobial composition. In certain implementations a male luer comprises a tapered sealing member further comprising a recess containing chlorhexidine acetate.

20 Claims, 89 Drawing Sheets

Related U.S. Application Data continuation-in-part of application No. 16/553,704, filed on Aug. 28, 2019, now Pat. No. 11,400,195, which is a continuation-in-part of application No. 16/449,180, filed on Jun. 21, 2019, now Pat. No. 11,541,221, which is a continuation-in-part of application No. 16/447,671, filed on Jun. 20, 2019, now Pat. No. 11,541,220, which is a continuation-in-part of application No. 16/444,486, filed on Jun. 18, 2019, now Pat. No. 11,534,595, which is a continuation-in-part of application No. 16/404,378, filed on May 6, 2019, now Pat. No. 10,525,250.

(60) Provisional application No. 62/756,967, filed on Nov. 7, 2018.

(52) U.S. Cl.
CPC .............. *A61M 2039/1083* (2013.01); *A61M 2039/1088* (2013.01); *A61M 2205/0205* (2013.01)

(56) References Cited

U.S. PATENT DOCUMENTS

| | | |
|---|---|---|
| 877,946 A | 2/1908 | Overton |
| 975,939 A | 11/1910 | Edwards et al. |
| 1,445,642 A | 2/1923 | O'Neill |
| 1,793,068 A | 2/1931 | Dickinson |
| 2,098,340 A | 11/1937 | Henahan |
| 2,436,297 A | 2/1948 | Guarnaschelli |
| 2,457,052 A | 12/1948 | Le Clair |
| 2,771,644 A | 11/1956 | Martin |
| 2,842,382 A | 7/1958 | Franck |
| 2,968,497 A | 1/1961 | Treleman |
| 3,127,892 A | 4/1964 | Bellamy, Jr. et al. |
| 3,262,448 A | 7/1966 | Ring et al. |
| 3,270,743 A | 9/1966 | Gingras |
| 3,301,392 A | 1/1967 | Eddingfield |
| 3,304,047 A | 2/1967 | Martin |
| 3,334,860 A | 8/1967 | Bolton, Jr. |
| 3,411,665 A | 11/1968 | Blum |
| 3,484,121 A | 12/1969 | Quinton |
| 3,485,416 A | 12/1969 | Fohrman |
| 3,538,950 A | 11/1970 | Porteners |
| 3,595,241 A | 7/1971 | Sheridan |
| 3,604,582 A | 9/1971 | Boudin |
| 3,707,972 A | 1/1973 | Villari et al. |
| 3,729,031 A | 4/1973 | Baldwin |
| 3,882,858 A | 5/1975 | Klemm |
| 3,977,401 A | 8/1976 | Pike |
| 3,977,517 A | 8/1976 | Kadlecik et al. |
| 3,987,930 A | 10/1976 | Fuson |
| 3,993,066 A | 11/1976 | Virag |
| 4,041,934 A | 8/1977 | Genese |
| 4,046,889 A | 9/1977 | Ondetti et al. |
| 4,052,511 A | 10/1977 | Cushman et al. |
| 4,053,052 A | 10/1977 | Jasper |
| 4,053,651 A | 10/1977 | Ondetti et al. |
| 4,066,067 A | 1/1978 | Micheli |
| 4,076,285 A | 2/1978 | Martinez |
| 4,078,686 A | 3/1978 | Karesh et al. |
| 4,079,738 A | 3/1978 | Dunn et al. |
| 4,095,810 A | 6/1978 | Kulle |
| 4,113,751 A | 9/1978 | Arnold |
| 4,121,585 A | 10/1978 | Becker, Jr. |
| 4,129,571 A | 12/1978 | Ondetti et al. |
| 4,133,441 A | 1/1979 | Mittleman et al. |
| 4,143,853 A | 3/1979 | Abramson |
| 4,150,845 A | 4/1979 | Kopacz et al. |
| 4,154,840 A | 5/1979 | Ondetti et al. |
| 4,154,960 A | 5/1979 | Ondetti et al. |
| 4,192,443 A | 3/1980 | McLaren |
| 4,194,509 A | 3/1980 | Pickering et al. |
| 4,195,632 A | 4/1980 | Parker et al. |
| 4,233,982 A | 11/1980 | Bauer et al. |
| 4,243,035 A | 1/1981 | Barrett |
| 4,245,635 A | 1/1981 | Kontos |
| 4,264,664 A | 4/1981 | Kunz |
| 4,280,632 A | 7/1981 | Yuhara |
| 4,294,370 A | 10/1981 | Toeppen |
| 4,317,446 A | 3/1982 | Ambrosio et al. |
| 4,324,239 A | 4/1982 | Gordon et al. |
| 4,325,368 A | 4/1982 | Kaemmerer |
| 4,331,783 A | 5/1982 | Stoy |
| 4,334,551 A | 6/1982 | Pfister |
| 4,335,756 A | 6/1982 | Sharp et al. |
| 4,337,327 A | 6/1982 | Stoy |
| 4,340,049 A | 7/1982 | Munsch |
| 4,340,052 A | 7/1982 | Dennehey et al. |
| 4,354,490 A | 10/1982 | Rogers |
| 4,369,294 A | 1/1983 | Stoy |
| 4,370,451 A | 1/1983 | Stoy |
| 4,379,458 A | 4/1983 | Bauer et al. |
| 4,379,874 A | 4/1983 | Stoy |
| 4,384,589 A | 5/1983 | Morris |
| 4,387,879 A | 6/1983 | Tauschinski |
| 4,390,016 A | 6/1983 | Riess |
| 4,397,442 A | 8/1983 | Larkin |
| 4,402,691 A | 9/1983 | Rosenthal et al. |
| 4,405,312 A | 9/1983 | Gross et al. |
| 4,417,890 A | 11/1983 | Dennehey et al. |
| 4,420,589 A | 12/1983 | Stoy |
| 4,427,126 A | 1/1984 | Ostrowsky |
| 4,430,073 A | 2/1984 | Bemis et al. |
| 4,432,764 A | 2/1984 | Lopez |
| 4,432,766 A | 2/1984 | Bellotti et al. |
| 4,436,125 A | 3/1984 | Blenkush |
| 4,439,179 A | 3/1984 | Lueders et al. |
| 4,439,184 A | 3/1984 | Wheeler |
| 4,440,207 A | 4/1984 | Genatempo et al. |
| 4,444,310 A | 4/1984 | Odel |
| 4,446,967 A | 5/1984 | Halkyard |
| 4,447,419 A | 5/1984 | Quadro |
| 4,457,749 A | 7/1984 | Bellotti et al. |
| 4,461,368 A | 7/1984 | Plourde |
| 4,461,896 A | 7/1984 | Portlock |
| 4,480,940 A | 11/1984 | Woodruff |
| 4,507,111 A | 3/1985 | Gordon et al. |
| 4,511,359 A | 4/1985 | Vaillancourt |
| 4,534,764 A | 8/1985 | Mittleman et al. |
| 4,538,836 A | 9/1985 | Kruetten |
| 4,559,043 A | 12/1985 | Whitehouse |
| 4,568,675 A | 2/1986 | Bush et al. |
| 4,585,758 A | 4/1986 | Huang et al. |
| 4,602,042 A | 7/1986 | Chantler et al. |
| 4,610,469 A | 9/1986 | Wolff-Mooij |
| 4,619,640 A | 10/1986 | Potolsky et al. |
| 4,623,332 A | 11/1986 | Lindmayer et al. |
| 4,624,664 A | 11/1986 | Peluso et al. |
| 4,626,545 A | 12/1986 | Taub |
| 4,629,159 A | 12/1986 | Wellenstam |
| 4,631,188 A | 12/1986 | Stoy |
| 4,642,091 A | 2/1987 | Richmond |
| 4,660,803 A | 4/1987 | Johnston et al. |
| 4,662,878 A | 5/1987 | Lindmayer |
| 4,666,057 A | 5/1987 | Come et al. |
| 4,666,427 A | 5/1987 | Larsson et al. |
| 4,671,306 A | 6/1987 | Spector |
| 4,671,412 A | 6/1987 | Gatten |
| 4,681,886 A | 7/1987 | Haugwitz et al. |
| 4,692,458 A | 9/1987 | Ryan et al. |
| 4,692,459 A | 9/1987 | Ryan et al. |
| 4,700,744 A | 10/1987 | Rutter et al. |
| 4,703,762 A | 11/1987 | Rathbone et al. |
| 4,705,790 A | 11/1987 | Hubele et al. |
| 4,723,603 A | 2/1988 | Plummer |
| 4,728,075 A | 3/1988 | Paradis |
| 4,728,321 A | 3/1988 | Chen |
| 4,738,668 A | 4/1988 | Bellotti et al. |
| 4,745,950 A | 5/1988 | Mathieu |
| 4,747,502 A | 5/1988 | Luenser |
| 4,748,160 A | 5/1988 | Bennion et al. |

(56) References Cited

U.S. PATENT DOCUMENTS

| | | | |
|---|---|---|---|
| 4,752,983 A | 6/1988 | Grieshaber |
| 4,769,013 A | 9/1988 | Lorenz et al. |
| 4,774,964 A | 10/1988 | Bonaldo |
| 4,774,965 A | 10/1988 | Rodriguez et al. |
| 4,778,447 A | 10/1988 | Velde et al. |
| 4,781,702 A | 11/1988 | Herrli |
| 4,799,926 A | 1/1989 | Haber |
| 4,804,015 A | 2/1989 | Albinsson |
| 4,808,158 A | 2/1989 | Kreuzer et al. |
| 4,810,241 A | 3/1989 | Rogers |
| 4,811,847 A | 3/1989 | Reif et al. |
| 4,813,933 A | 3/1989 | Turner |
| 4,816,024 A | 3/1989 | Sitar et al. |
| 4,834,271 A | 5/1989 | Litwin |
| 4,862,913 A | 9/1989 | Wildfang |
| 4,874,366 A | 10/1989 | Zdeb et al. |
| 4,883,483 A | 11/1989 | Lindmayer |
| 4,889,255 A | 12/1989 | Schiemann et al. |
| 4,894,056 A | 1/1990 | Bommarito |
| 4,898,580 A | 2/1990 | Crowley |
| 4,915,687 A | 4/1990 | Sivert |
| 4,917,669 A | 4/1990 | Bonaldo |
| 4,919,658 A | 4/1990 | Badia |
| 4,927,019 A | 5/1990 | Haber et al. |
| 4,935,010 A | 6/1990 | Cox et al. |
| 4,941,873 A | 7/1990 | Fischer |
| 4,950,260 A | 8/1990 | Bonaldo |
| 4,957,637 A | 9/1990 | Cornell |
| 4,963,132 A | 10/1990 | Gibson |
| D313,277 S | 12/1990 | Haining |
| D314,050 S | 1/1991 | Sone |
| 4,983,161 A | 1/1991 | Dadson et al. |
| 4,985,017 A | 1/1991 | Theeuwes |
| 4,989,733 A | 2/1991 | Patry |
| 4,991,629 A | 2/1991 | Ernesto et al. |
| 4,997,371 A | 3/1991 | Fischer |
| 4,999,210 A | 3/1991 | Solomon et al. |
| 5,002,964 A | 3/1991 | Loscalzo |
| 5,006,114 A | 4/1991 | Rogers et al. |
| 5,015,238 A | 5/1991 | Solomon et al. |
| 5,019,096 A | 5/1991 | Fox, Jr. et al. |
| 5,021,059 A | 6/1991 | Kensey et al. |
| 5,024,657 A | 6/1991 | Needham et al. |
| 5,025,001 A | 6/1991 | Loscalzo et al. |
| 5,026,359 A | 6/1991 | Burroughs |
| 5,031,622 A | 7/1991 | LaHaye |
| 5,033,961 A | 7/1991 | Kandler et al. |
| 5,047,021 A | 9/1991 | Utterberg |
| 5,049,139 A | 9/1991 | Gilchrist |
| 5,059,186 A | 10/1991 | Yamamoto et al. |
| 5,065,783 A | 11/1991 | Ogle, II |
| 5,070,885 A | 12/1991 | Bonaldo |
| 5,071,411 A | 12/1991 | Hillstead |
| 5,071,413 A | 12/1991 | Utterberg |
| 5,098,385 A | 3/1992 | Walsh |
| 5,108,376 A | 4/1992 | Bonaldo |
| 5,122,123 A | 6/1992 | Vaillancourt |
| 5,127,626 A | 7/1992 | Hilal et al. |
| 5,129,824 A | 7/1992 | Keller |
| 5,139,483 A | 8/1992 | Ryan |
| 5,143,104 A | 9/1992 | Iba et al. |
| 5,147,333 A | 9/1992 | Raines |
| 5,154,703 A | 10/1992 | Bonaldo |
| 5,154,920 A | 10/1992 | Flesher et al. |
| 5,184,742 A | 2/1993 | DeCaprio et al. |
| 5,190,534 A | 3/1993 | Kendell |
| 5,195,957 A | 3/1993 | Tollini |
| RE34,223 E | 4/1993 | Bonaldo |
| 5,199,948 A | 4/1993 | McPhee |
| 5,201,725 A | 4/1993 | Kling |
| 5,203,775 A | 4/1993 | Frank et al. |
| 5,205,820 A | 4/1993 | Kriesel |
| 5,205,821 A | 4/1993 | Kruger et al. |
| 5,207,706 A | 5/1993 | Menaker |
| 5,211,634 A | 5/1993 | Vaillancourt |
| 5,212,204 A | 5/1993 | Keefer et al. |
| 5,215,537 A | 6/1993 | Lynn et al. |
| 5,240,675 A | 8/1993 | Wilk et al. |
| 5,242,421 A | 9/1993 | Chan |
| 5,242,425 A | 9/1993 | White et al. |
| 5,246,011 A | 9/1993 | Caillouette |
| 5,250,550 A | 10/1993 | Keefer et al. |
| 5,251,873 A | 10/1993 | Atkinson et al. |
| D342,134 S | 12/1993 | Mongeon |
| 5,269,771 A | 12/1993 | Thomas et al. |
| 5,278,192 A | 1/1994 | Fung et al. |
| 5,281,206 A | 1/1994 | Lopez |
| 5,284,475 A | 2/1994 | Mackal |
| 5,295,657 A | 3/1994 | Atkinson |
| 5,297,310 A | 3/1994 | Cox et al. |
| 5,301,686 A | 4/1994 | Newman |
| 5,304,130 A | 4/1994 | Button |
| 5,306,243 A | 4/1994 | Bonaldo |
| 5,312,377 A | 5/1994 | Dalton |
| 5,324,270 A | 6/1994 | Kayan et al. |
| 5,324,647 A | 6/1994 | Rubens et al. |
| 5,330,235 A | 7/1994 | Wagner et al. |
| 5,330,426 A | 7/1994 | Kriesel et al. |
| 5,330,450 A | 7/1994 | Lopez |
| 5,330,899 A | 7/1994 | Devaughn et al. |
| 5,337,730 A | 8/1994 | Maguire |
| 5,344,414 A | 9/1994 | Lopez et al. |
| 5,352,410 A | 10/1994 | Hansen et al. |
| 5,354,267 A | 10/1994 | Niermann et al. |
| 5,356,396 A | 10/1994 | Wyatt et al. |
| 5,360,413 A | 11/1994 | Leason et al. |
| 5,366,505 A | 11/1994 | Farber |
| 5,366,997 A | 11/1994 | Keefer et al. |
| 5,370,614 A | 12/1994 | Amundson et al. |
| 5,370,636 A | 12/1994 | Von Witzleben |
| 5,370,640 A | 12/1994 | Kolff |
| 5,375,589 A | 12/1994 | Bhatta |
| 5,380,306 A | 1/1995 | Brinon |
| 5,380,758 A | 1/1995 | Stamler et al. |
| 5,391,150 A | 2/1995 | Richmond |
| 5,402,826 A | 4/1995 | Molnar et al. |
| 5,405,331 A | 4/1995 | Behnke et al. |
| 5,405,333 A | 4/1995 | Richmond |
| 5,405,919 A | 4/1995 | Keefer et al. |
| 5,407,807 A | 4/1995 | Markus |
| 5,409,012 A | 4/1995 | Sahatjian |
| 5,411,499 A | 5/1995 | Dudar et al. |
| 5,417,673 A | 5/1995 | Gordon |
| 5,425,465 A | 6/1995 | Healy |
| 5,428,070 A | 6/1995 | Cooke et al. |
| 5,433,330 A | 7/1995 | Yatsko et al. |
| 5,433,705 A | 7/1995 | Giebel et al. |
| 5,439,451 A | 8/1995 | Collinson et al. |
| 5,441,487 A | 8/1995 | Vedder |
| 5,445,623 A | 8/1995 | Richmond |
| 5,456,668 A | 10/1995 | Ogle, II |
| 5,456,675 A | 10/1995 | Wolbring et al. |
| 5,464,399 A | 11/1995 | Boettger |
| 5,470,307 A | 11/1995 | Lindall |
| 5,470,327 A | 11/1995 | Helgren et al. |
| 5,471,706 A | 12/1995 | Wallock et al. |
| 5,474,536 A | 12/1995 | Bonaldo |
| 5,480,393 A | 1/1996 | Bommarito |
| 5,485,827 A | 1/1996 | Zapol et al. |
| 5,492,147 A | 2/1996 | Challender et al. |
| 5,496,288 A | 3/1996 | Sweeney |
| 5,501,426 A | 3/1996 | Atkinson et al. |
| 5,507,733 A | 4/1996 | Larkin et al. |
| 5,507,744 A | 4/1996 | Tay et al. |
| 5,514,177 A | 5/1996 | Kurz et al. |
| 5,518,026 A | 5/1996 | Benjey |
| 5,520,665 A | 5/1996 | Fleetwood |
| 5,520,666 A | 5/1996 | Choudhury et al. |
| 5,525,357 A | 6/1996 | Keefer et al. |
| 5,531,695 A | 7/1996 | Swisher |
| 5,533,708 A | 7/1996 | Atkinson et al. |
| 5,533,983 A | 7/1996 | Haining |
| 5,535,785 A | 7/1996 | Werge et al. |
| 5,536,241 A | 7/1996 | Zapol |

(56)             References Cited

U.S. PATENT DOCUMENTS

| | | | |
|---|---|---|---|
| 5,536,258 A | 7/1996 | Folden |
| 5,540,661 A | 7/1996 | Tomisaka et al. |
| 5,545,614 A | 8/1996 | Stamler et al. |
| 5,549,566 A | 8/1996 | Elias et al. |
| 5,549,651 A | 8/1996 | Lynn |
| 5,552,115 A | 9/1996 | Malchesky |
| 5,552,118 A | 9/1996 | Mayer |
| 5,554,127 A | 9/1996 | Crouther et al. |
| 5,554,135 A | 9/1996 | Menyhay |
| 5,555,908 A | 9/1996 | Edwards et al. |
| 5,569,235 A | 10/1996 | Ross et al. |
| 5,573,516 A | 11/1996 | Tyner |
| 5,575,769 A | 11/1996 | Vaillancourt |
| 5,578,059 A | 11/1996 | Patzer |
| 5,580,530 A | 12/1996 | Kowatsch et al. |
| 5,584,819 A | 12/1996 | Kopfer |
| 5,591,137 A | 1/1997 | Stevens |
| 5,591,143 A | 1/1997 | Trombley, III et al. |
| 5,597,536 A | 1/1997 | Mayer |
| 5,599,352 A | 2/1997 | Dinh et al. |
| 5,605,696 A | 2/1997 | Eury et al. |
| 5,607,072 A | 3/1997 | Rigney et al. |
| 5,613,615 A | 3/1997 | Zeyfang et al. |
| 5,616,130 A | 4/1997 | Mayer |
| 5,620,088 A | 4/1997 | Martin et al. |
| 5,620,427 A | 4/1997 | Werschmidt et al. |
| 5,624,402 A | 4/1997 | Imbert |
| 5,628,733 A | 5/1997 | Zinreich et al. |
| RE35,539 E | 6/1997 | Bonaldo |
| 5,645,538 A | 7/1997 | Richmond |
| 5,665,077 A | 9/1997 | Resen et al. |
| 5,674,206 A | 10/1997 | Allton et al. |
| 5,676,346 A | 10/1997 | Leinsing |
| 5,685,835 A | 11/1997 | Brugger |
| 5,685,866 A | 11/1997 | Lopez |
| 5,685,868 A | 11/1997 | Lundquist |
| 5,688,253 A | 11/1997 | Lundquist |
| 5,694,978 A | 12/1997 | Heilmann et al. |
| 5,699,821 A | 12/1997 | Paradis |
| 5,700,248 A | 12/1997 | Lopez |
| 5,702,017 A | 12/1997 | Goncalves |
| 5,716,339 A | 2/1998 | Tanaka et al. |
| 5,722,537 A | 3/1998 | Sigler |
| 5,735,826 A | 4/1998 | Richmond |
| 5,738,144 A | 4/1998 | Rogers |
| 5,743,892 A | 4/1998 | Loh et al. |
| 5,749,861 A | 5/1998 | Guala et al. |
| 5,763,409 A | 6/1998 | Bayol et al. |
| 5,770,645 A | 6/1998 | Stamler et al. |
| 5,776,116 A | 7/1998 | Lopez |
| 5,782,808 A | 7/1998 | Folden |
| 5,782,816 A | 7/1998 | Werschmidt et al. |
| 5,785,693 A | 7/1998 | Haining |
| 5,792,120 A | 8/1998 | Menyhay |
| 5,797,887 A | 8/1998 | Rosen et al. |
| 5,806,831 A | 9/1998 | Paradis |
| 5,810,792 A | 9/1998 | Fangrow, Jr. et al. |
| 5,814,024 A | 9/1998 | Thompson et al. |
| 5,814,666 A | 9/1998 | Green et al. |
| 5,820,601 A | 10/1998 | Mayer |
| 5,820,604 A | 10/1998 | Fox et al. |
| 5,827,244 A | 10/1998 | Boettger |
| 5,839,715 A | 11/1998 | Leinsing |
| 5,848,994 A | 12/1998 | Richmond |
| 5,902,631 A | 5/1999 | Wang et al. |
| 5,941,857 A | 8/1999 | Nguyen et al. |
| 5,947,296 A | 9/1999 | Castora |
| 5,947,954 A | 9/1999 | Bonaldo |
| 5,951,519 A | 9/1999 | Utterberg |
| 5,954,957 A | 9/1999 | Chin-Loy et al. |
| 5,971,972 A | 10/1999 | Rosenbaum |
| D416,086 S | 11/1999 | Parris et al. |
| 5,989,229 A | 11/1999 | Chiappetta |
| 5,994,444 A | 11/1999 | Trescony |
| 5,996,779 A | 12/1999 | Klardie et al. |
| 6,029,946 A | 2/2000 | Doyle |
| 6,036,171 A | 3/2000 | Weinheimer et al. |
| 6,041,805 A | 3/2000 | Gydesen et al. |
| 6,045,539 A | 4/2000 | Menyhay |
| 6,045,623 A | 4/2000 | Cannon |
| 6,050,978 A | 4/2000 | Orr et al. |
| 6,059,107 A | 5/2000 | Nosted et al. |
| 6,063,062 A | 5/2000 | Paradis |
| 6,068,011 A | 5/2000 | Paradis |
| 6,068,475 A | 5/2000 | Stoyka, Jr. et al. |
| 6,068,617 A | 5/2000 | Richmond |
| 6,071,413 A | 6/2000 | Dyke |
| 6,079,432 A | 6/2000 | Paradis |
| 6,087,479 A | 7/2000 | Stamler et al. |
| 6,093,743 A | 7/2000 | Lai et al. |
| 6,095,356 A | 8/2000 | Rits |
| 6,099,519 A | 8/2000 | Olsen et al. |
| 6,105,812 A | 8/2000 | Riordan |
| 6,106,502 A | 8/2000 | Richmond |
| 6,113,068 A | 9/2000 | Ryan |
| 6,113,572 A | 9/2000 | Gailey et al. |
| 6,116,468 A | 9/2000 | Nilson |
| 6,117,114 A | 9/2000 | Paradis |
| 6,126,640 A | 10/2000 | Tucker |
| 6,142,446 A | 11/2000 | Leinsing |
| 6,143,318 A | 11/2000 | Gilchrist et al. |
| 6,146,363 A | 11/2000 | Giebel et al. |
| 6,152,913 A | 11/2000 | Feith et al. |
| 6,158,614 A | 12/2000 | Haines et al. |
| 6,162,487 A | 12/2000 | Darouiche |
| 6,170,522 B1 | 1/2001 | Tanida |
| 6,171,287 B1 | 1/2001 | Lynn et al. |
| 6,174,539 B1 | 1/2001 | Stamler et al. |
| 6,179,141 B1 | 1/2001 | Nakamura |
| 6,183,450 B1 | 2/2001 | Lois |
| 6,202,870 B1 | 3/2001 | Pearce |
| 6,202,901 B1 | 3/2001 | Gerber et al. |
| 6,206,134 B1 | 3/2001 | Stark et al. |
| 6,206,860 B1 | 3/2001 | Richmond |
| 6,207,855 B1 | 3/2001 | Toone et al. |
| 6,217,564 B1 | 4/2001 | Peters et al. |
| 6,227,391 B1 | 5/2001 | King |
| 6,232,406 B1 | 5/2001 | Stoy |
| 6,232,434 B1 | 5/2001 | Stamler et al. |
| 6,237,800 B1 | 5/2001 | Barrett et al. |
| 6,242,393 B1 | 6/2001 | Ishida et al. |
| 6,245,048 B1 | 6/2001 | Fangrow et al. |
| 6,245,056 B1 | 6/2001 | Walker et al. |
| 6,248,380 B1 | 6/2001 | Kocher et al. |
| 6,250,315 B1 | 6/2001 | Ernster |
| 6,255,277 B1 | 7/2001 | Stamler et al. |
| 6,267,754 B1 | 7/2001 | Peters |
| 6,299,132 B1 | 10/2001 | Weinheimer et al. |
| 6,315,113 B1 | 11/2001 | Britton et al. |
| 6,315,761 B1 | 11/2001 | Shcherbina et al. |
| 6,359,167 B2 | 3/2002 | Toone et al. |
| 6,359,182 B1 | 3/2002 | Stamler et al. |
| 6,375,231 B1 | 4/2002 | Picha et al. |
| 6,379,660 B1 | 4/2002 | Saavedra et al. |
| 6,379,691 B1 | 4/2002 | Tedeschi et al. |
| 6,394,983 B1 | 5/2002 | Mayoral et al. |
| 6,402,207 B1 | 6/2002 | Segal et al. |
| 6,403,759 B2 | 6/2002 | Stamler et al. |
| 6,409,716 B1 | 6/2002 | Sahatjian et al. |
| 6,428,520 B1 | 8/2002 | Lopez |
| 6,431,219 B1 | 8/2002 | Redler et al. |
| 6,444,318 B1 | 9/2002 | Guire et al. |
| 6,468,259 B1 | 10/2002 | Djokic et al. |
| 6,471,978 B1 | 10/2002 | Stamler et al. |
| 6,488,951 B2 | 12/2002 | Toone et al. |
| 6,491,965 B1 | 12/2002 | Berry et al. |
| 6,499,719 B1 | 12/2002 | Clancy et al. |
| 6,508,792 B2 | 1/2003 | Szames et al. |
| 6,508,807 B1 | 1/2003 | Peters |
| 6,538,116 B2 | 3/2003 | Stamler et al. |
| 6,541,802 B2 | 4/2003 | Doyle |
| 6,543,745 B1 | 4/2003 | Enerson |
| 6,550,493 B2 | 4/2003 | Williamson et al. |
| 6,555,504 B1 | 4/2003 | Ayai et al. |

(56) References Cited

U.S. PATENT DOCUMENTS

| | | | |
|---|---|---|---|
| 6,562,781 B1 | 5/2003 | Berry et al. |
| 6,581,906 B2 | 6/2003 | Pott et al. |
| 6,583,311 B2 | 6/2003 | Toone et al. |
| 6,585,691 B1 | 7/2003 | Vitello |
| 6,595,964 B2 | 7/2003 | Finley et al. |
| 6,595,981 B2 | 7/2003 | Huet |
| 6,605,294 B2 | 8/2003 | Sawhney |
| 6,605,751 B1 | 8/2003 | Gibbins et al. |
| 6,609,696 B2 | 8/2003 | Enerson |
| 6,632,199 B1 | 10/2003 | Tucker et al. |
| 6,634,498 B2 | 10/2003 | Kayerod et al. |
| 6,656,217 B1 | 12/2003 | Herzog, Jr. et al. |
| 6,666,852 B2 | 12/2003 | Niedospial, Jr. |
| 6,673,891 B2 | 1/2004 | Stamler et al. |
| 6,679,395 B1 | 1/2004 | Pfefferkorn et al. |
| 6,679,870 B1 | 1/2004 | Finch et al. |
| 6,681,803 B2 | 1/2004 | Taneya et al. |
| 6,685,694 B2 | 2/2004 | Finch et al. |
| 6,692,468 B1 | 2/2004 | Waldenburg |
| 6,695,817 B1 | 2/2004 | Fangrow |
| 6,716,396 B1 | 4/2004 | Anderson |
| 6,722,705 B2 | 4/2004 | Korkor |
| 6,725,492 B2 | 4/2004 | Moore et al. |
| 6,745,998 B2 | 6/2004 | Doyle |
| 6,786,884 B1 | 9/2004 | DeCant, Jr. et al. |
| 6,808,510 B1 | 10/2004 | DiFiore |
| 6,827,766 B2 | 12/2004 | Carnes et al. |
| 6,840,501 B2 | 1/2005 | Doyle |
| 6,871,087 B1 | 3/2005 | Hughes et al. |
| 6,875,205 B2 | 4/2005 | Leinsing |
| 6,875,840 B2 | 4/2005 | Stamler et al. |
| 6,880,706 B2 | 4/2005 | Braconnot et al. |
| 6,887,994 B2 | 5/2005 | Stamler et al. |
| 6,899,315 B2 | 5/2005 | Mailville et al. |
| 6,911,025 B2 | 6/2005 | Miyahar |
| 6,916,051 B2 | 7/2005 | Fisher |
| 6,929,005 B2 | 8/2005 | Sullivan et al. |
| 6,943,035 B1 | 9/2005 | Davies et al. |
| 6,955,669 B2 | 10/2005 | Curutcharry |
| 6,964,406 B2 | 11/2005 | Doyle |
| 7,004,934 B2 | 2/2006 | Vaillancourt |
| 7,015,347 B2 | 3/2006 | Toone et al. |
| 7,030,238 B2 | 4/2006 | Stamler et al. |
| 7,037,302 B2 | 5/2006 | Vaillancourt |
| 7,040,598 B2 | 5/2006 | Raybuck |
| 7,044,441 B2 | 5/2006 | Doyle |
| 7,045,585 B2 | 5/2006 | Berry et al. |
| 7,049,308 B2 | 5/2006 | Stamler et al. |
| 7,052,711 B2 | 5/2006 | West et al. |
| 7,056,308 B2 | 6/2006 | Utterberg |
| 7,067,659 B2 | 6/2006 | Stamler et al. |
| 7,081,109 B2 | 7/2006 | Tighe et al. |
| 7,083,605 B2 | 8/2006 | Miyahara |
| 7,087,709 B2 | 8/2006 | Stamler et al. |
| 7,097,850 B2 | 8/2006 | Chappa et al. |
| 7,100,891 B2 | 9/2006 | Doyle |
| 7,125,396 B2 | 10/2006 | Leinsing et al. |
| 7,140,592 B2 | 11/2006 | Phillips |
| 7,147,625 B2 | 12/2006 | Sarangapani et al. |
| 7,160,272 B1 | 1/2007 | Eyal et al. |
| 7,182,313 B2 | 2/2007 | Doyle |
| 7,195,615 B2 | 3/2007 | Tan |
| 7,198,611 B2 | 4/2007 | Connell et al. |
| 7,244,249 B2 | 7/2007 | Leinsing et al. |
| 7,259,250 B2 | 8/2007 | Stamler et al. |
| 7,279,176 B1 | 10/2007 | West et al. |
| 7,282,186 B2 | 10/2007 | Lake, Jr. et al. |
| 7,306,197 B2 | 12/2007 | Parrino et al. |
| 7,306,198 B2 | 12/2007 | Doyle |
| 7,306,566 B2 | 12/2007 | Raybuck |
| 7,309,326 B2 | 12/2007 | Fangrow, Jr. |
| 7,316,669 B2 | 1/2008 | Ranalletta |
| 7,347,458 B2 | 3/2008 | Rome et al. |
| 7,347,853 B2 | 3/2008 | DiFiore et al. |
| 7,350,764 B2 | 4/2008 | Raybuck |
| 7,361,164 B2 | 4/2008 | Simpson et al. |
| 7,417,109 B2 | 8/2008 | Stamler et al. |
| 7,431,712 B2 | 10/2008 | Kim |
| 7,442,402 B2 | 10/2008 | Chudzik et al. |
| 7,452,349 B2 | 11/2008 | Miyahar |
| 7,485,107 B2 | 2/2009 | DiFiore et al. |
| 7,491,192 B2 | 2/2009 | DiFiore |
| 7,497,484 B2 | 3/2009 | Ziman |
| 7,516,846 B2 | 4/2009 | Hansen |
| 7,588,563 B2 | 9/2009 | Guala |
| 7,611,505 B2 | 11/2009 | Ranalletta et al. |
| 7,614,426 B2 | 11/2009 | Kitani et al. |
| 7,615,034 B2 | 11/2009 | DiFiore |
| 7,625,907 B2 | 12/2009 | Stamler et al. |
| 7,635,344 B2 | 12/2009 | Tennican et al. |
| D607,325 S | 1/2010 | Rogers et al. |
| 7,645,274 B2 | 1/2010 | Whitley |
| 7,651,481 B2 | 1/2010 | Raybuck |
| 7,666,170 B2 | 2/2010 | Guala |
| 7,708,714 B2 | 5/2010 | Connell et al. |
| 7,731,678 B2 | 6/2010 | Tennican et al. |
| 7,731,679 B2 | 6/2010 | Tennican et al. |
| 7,749,189 B2 | 7/2010 | Tennican et al. |
| 7,753,891 B2 | 7/2010 | Tennican et al. |
| 7,758,530 B2 | 7/2010 | DiFiore et al. |
| 7,758,566 B2 | 7/2010 | Simpson et al. |
| 7,762,524 B2 | 7/2010 | Cawthon et al. |
| 7,763,006 B2 | 7/2010 | Tennican |
| 7,766,182 B2 | 8/2010 | Trent et al. |
| 7,766,897 B2 | 8/2010 | Ramsey et al. |
| 7,776,011 B2 | 8/2010 | Tennican et al. |
| 7,780,794 B2 | 8/2010 | Rogers et al. |
| 7,785,616 B2 | 8/2010 | Stamler et al. |
| 7,794,675 B2 | 9/2010 | Lynn |
| 7,799,010 B2 | 9/2010 | Tennican |
| 7,803,139 B2 | 9/2010 | Fangrow, Jr. |
| 7,803,140 B2 | 9/2010 | Fangrow, Jr. |
| 7,815,614 B2 | 10/2010 | Fangrow, Jr. |
| 7,857,793 B2 | 12/2010 | Raulerson et al. |
| 7,922,701 B2 | 4/2011 | Buchman |
| 7,922,711 B2 | 4/2011 | Ranalletta et al. |
| 7,928,079 B2 | 4/2011 | Hrabie et al. |
| 7,938,795 B2 | 5/2011 | DiFiore et al. |
| 7,956,062 B2 | 6/2011 | Stamler et al. |
| 7,959,026 B2 | 6/2011 | Bertani |
| 7,963,565 B2 | 6/2011 | Suter |
| 7,972,137 B2 | 7/2011 | Rosen |
| 7,972,322 B2 | 7/2011 | Tennican |
| 7,981,090 B2 | 7/2011 | Plishka et al. |
| 7,985,302 B2 | 7/2011 | Rogers et al. |
| 7,993,309 B2 | 8/2011 | Schweikert |
| 7,998,134 B2 | 8/2011 | Fangrow et al. |
| 8,034,454 B2 | 10/2011 | Terry |
| 8,065,773 B2 | 11/2011 | Vaillancourt et al. |
| 8,066,670 B2 | 11/2011 | Cluff et al. |
| 8,069,523 B2 | 12/2011 | Vaillancourt et al. |
| 8,113,837 B2 | 2/2012 | Zegarelli |
| 8,146,757 B2 | 4/2012 | Abreu et al. |
| 8,162,899 B2 | 4/2012 | Tennican |
| 8,167,847 B2 | 5/2012 | Anderson et al. |
| 8,172,825 B2 | 5/2012 | Solomon et al. |
| 8,177,761 B2 | 5/2012 | Howlett et al. |
| 8,177,772 B2 | 5/2012 | Christensen et al. |
| 8,197,749 B2 | 6/2012 | Howlett et al. |
| 8,206,514 B2 | 6/2012 | Rogers et al. |
| 8,231,587 B2 | 7/2012 | Solomon et al. |
| 8,231,602 B2 | 7/2012 | Anderson et al. |
| 8,252,247 B2 | 8/2012 | Ferlic |
| 8,262,628 B2 | 9/2012 | Fangrow, Jr. |
| 8,262,643 B2 | 9/2012 | Tennican |
| 8,273,303 B2 | 9/2012 | Ferlic et al. |
| 8,281,824 B2 | 10/2012 | Molema et al. |
| 8,328,767 B2 | 12/2012 | Solomon et al. |
| 8,336,152 B2 | 12/2012 | Kerr et al. |
| 8,343,112 B2 | 1/2013 | Solomon et al. |
| 8,361,408 B2 | 1/2013 | Lynn |
| 8,372,045 B2 | 2/2013 | Needle et al. |
| 8,377,040 B2 | 2/2013 | Burkholz et al. |
| 8,414,547 B2 | 4/2013 | DiFiore et al. |

(56) References Cited

U.S. PATENT DOCUMENTS

| | | |
|---|---|---|
| 8,454,579 B2 | 6/2013 | Fangrow, Jr. |
| 8,480,968 B2 | 7/2013 | Lynn |
| 8,491,546 B2 | 7/2013 | Hoang et al. |
| 8,500,717 B2 | 8/2013 | Becker |
| 8,506,527 B2 | 8/2013 | Carlyon |
| 8,506,538 B2 | 8/2013 | Chelak |
| 8,523,798 B2 | 9/2013 | DiFiore |
| 8,523,831 B2 | 9/2013 | Solomon et al. |
| 8,533,887 B2 | 9/2013 | Hirst |
| 8,545,479 B2 | 10/2013 | Kitani et al. |
| 8,568,371 B2 | 10/2013 | Siopes et al. |
| 8,622,995 B2 | 1/2014 | Ziebol et al. |
| 8,622,996 B2 | 1/2014 | Ziebol et al. |
| 8,641,684 B2 | 2/2014 | Utterberg et al. |
| 8,647,308 B2 | 2/2014 | Solomon et al. |
| 8,647,326 B2 | 2/2014 | Solomon et al. |
| 8,651,271 B1 | 2/2014 | Shen |
| 8,740,864 B2 | 6/2014 | Hoang et al. |
| 8,758,307 B2 | 6/2014 | Grimm et al. |
| 8,777,504 B2 | 7/2014 | Shaw et al. |
| 8,791,073 B2 | 7/2014 | West et al. |
| 8,845,593 B2 | 9/2014 | Anderson et al. |
| 8,877,231 B2 | 11/2014 | Rosen |
| 8,910,919 B2 | 12/2014 | Bonnal et al. |
| 8,920,404 B2 | 12/2014 | DiFiore et al. |
| 8,968,268 B2 | 3/2015 | Anderson et al. |
| 8,981,139 B2 | 3/2015 | Schoenfisch et al. |
| 8,999,073 B2 | 4/2015 | Rogers et al. |
| 9,022,984 B2 | 5/2015 | Ziebol et al. |
| 9,072,296 B2 | 7/2015 | Mills et al. |
| 9,072,868 B2 | 7/2015 | Ziebol et al. |
| 9,078,992 B2 | 7/2015 | Ziebol et al. |
| 9,089,680 B2 | 7/2015 | Ueda et al. |
| 9,101,685 B2 | 8/2015 | Li et al. |
| 9,149,624 B2 | 10/2015 | Lewis |
| 9,192,449 B2 | 11/2015 | Kerr et al. |
| 9,205,248 B2 | 12/2015 | Wu et al. |
| 9,248,093 B2 | 2/2016 | Kelley, III et al. |
| 9,248,229 B2 | 2/2016 | Devouassoux et al. |
| 9,259,284 B2 | 2/2016 | Rogers et al. |
| 9,259,535 B2 | 2/2016 | Anderson et al. |
| 9,283,367 B2 | 3/2016 | Hoang et al. |
| 9,283,368 B2 | 3/2016 | Hoang et al. |
| 9,296,525 B2 | 3/2016 | Murphy et al. |
| 9,302,049 B2 | 4/2016 | Tekeste |
| 9,320,858 B2 | 4/2016 | Grimm et al. |
| 9,320,859 B2 | 4/2016 | Grimm et al. |
| 9,320,860 B2 | 4/2016 | Grimm et al. |
| 9,352,080 B2 | 5/2016 | Goodall et al. |
| 9,352,142 B2 | 5/2016 | Ziebol et al. |
| 9,381,339 B2 | 7/2016 | Wu et al. |
| 9,399,125 B2 | 7/2016 | Burkholz |
| 9,527,660 B2 | 12/2016 | Tennican |
| 9,592,375 B2 | 3/2017 | Tennican |
| 9,700,676 B2 | 7/2017 | Anderson et al. |
| 9,700,677 B2 | 7/2017 | Anderson et al. |
| 9,700,710 B2 | 7/2017 | Anderson et al. |
| 9,707,348 B2 | 7/2017 | Anderson et al. |
| 9,707,349 B2 | 7/2017 | Anderson et al. |
| 9,707,350 B2 | 7/2017 | Anderson et al. |
| 9,809,355 B2 | 11/2017 | Solomon et al. |
| 9,849,276 B2 | 12/2017 | Ziebol et al. |
| 9,867,975 B2 | 1/2018 | Gardner et al. |
| 9,907,617 B2 | 3/2018 | Rogers |
| 9,933,094 B2 | 4/2018 | Fangrow |
| 9,999,471 B2 | 6/2018 | Rogers et al. |
| 10,016,587 B2 | 7/2018 | Gardner et al. |
| 10,046,156 B2 | 8/2018 | Gardner et al. |
| 10,159,829 B2 | 12/2018 | Ziebol et al. |
| 10,166,381 B2 | 1/2019 | Gardner et al. |
| 10,195,000 B2 | 2/2019 | Rogers et al. |
| 10,201,692 B2 | 2/2019 | Chang |
| 10,328,207 B2 | 6/2019 | Anderson et al. |
| 10,524,982 B2 | 1/2020 | Fangrow |
| 10,525,250 B1 | 1/2020 | Ziebol et al. |
| 10,695,550 B2 | 6/2020 | Gardner et al. |
| 10,744,316 B2 | 8/2020 | Fangrow |
| 10,806,919 B2 | 10/2020 | Gardner et al. |
| 10,821,278 B2 | 11/2020 | Gardner et al. |
| 11,160,932 B2 | 11/2021 | Anderson et al. |
| 11,229,746 B2 | 1/2022 | Anderson et al. |
| 11,351,353 B2 | 6/2022 | Ziebol et al. |
| 11,389,634 B2 | 7/2022 | Ziebol et al. |
| 11,400,195 B2 | 8/2022 | Ziebol et al. |
| 11,433,215 B2 | 9/2022 | Ziebol et al. |
| 11,497,904 B2 | 11/2022 | Fangrow et al. |
| 11,517,732 B2 | 12/2022 | Ziebol et al. |
| 11,517,733 B2 | 12/2022 | Fangrow |
| 11,534,595 B2 | 12/2022 | Ziebol et al. |
| 11,541,220 B2 | 1/2023 | Ziebol et al. |
| 11,541,221 B2 | 1/2023 | Ziebol et al. |
| 11,559,467 B2 | 1/2023 | Fangrow |
| 11,684,720 B2 | 6/2023 | Anderson et al. |
| 11,826,539 B2 | 11/2023 | Ziebol et al. |
| 11,944,776 B2 | 4/2024 | Ziebol et al. |
| 11,998,715 B2 | 6/2024 | Gardner |
| 12,042,640 B2 | 7/2024 | Anderson et al. |
| 12,076,521 B2 | 9/2024 | Gardner et al. |
| 12,109,365 B2 | 10/2024 | Ziebol |
| 12,186,520 B2 | 1/2025 | Ziebol et al. |
| 12,201,760 B2 | 1/2025 | Ziebol et al. |
| 2002/0077693 A1 | 6/2002 | Barclay et al. |
| 2002/0082682 A1 | 6/2002 | Barclay et al. |
| 2002/0098278 A1 | 7/2002 | Bates et al. |
| 2003/0039697 A1 | 2/2003 | Zhao et al. |
| 2003/0062376 A1 | 4/2003 | Sears et al. |
| 2003/0072783 A1 | 4/2003 | Stamler et al. |
| 2003/0078242 A1 | 4/2003 | Raad et al. |
| 2003/0153865 A1 | 8/2003 | Connell et al. |
| 2003/0199835 A1 | 10/2003 | Leinsing et al. |
| 2003/0208165 A1 | 11/2003 | Christensen et al. |
| 2004/0034042 A1 | 2/2004 | Tsuji et al. |
| 2004/0034329 A1 | 2/2004 | Mankus et al. |
| 2004/0037836 A1 | 2/2004 | Stamler et al. |
| 2004/0048542 A1 | 3/2004 | Thomaschefsky et al. |
| 2004/0052689 A1 | 3/2004 | Yao |
| 2004/0052831 A1 | 3/2004 | Modak et al. |
| 2004/0073176 A1 | 4/2004 | Utterberg |
| 2004/0156908 A1 | 8/2004 | Polaschegg et al. |
| 2004/0210201 A1 | 10/2004 | Farnan |
| 2004/0215148 A1 | 10/2004 | Hwang et al. |
| 2004/0247640 A1 | 12/2004 | Zhao et al. |
| 2004/0249337 A1 | 12/2004 | DiFiore |
| 2004/0249338 A1 | 12/2004 | DeCant, Jr. et al. |
| 2004/0258560 A1 | 12/2004 | Lake, Jr. et al. |
| 2005/0008763 A1 | 1/2005 | Schachter |
| 2005/0013836 A1 | 1/2005 | Raad |
| 2005/0015075 A1 | 1/2005 | Wright et al. |
| 2005/0065479 A1 | 3/2005 | Schiller et al. |
| 2005/0098527 A1 | 5/2005 | Yates et al. |
| 2005/0124942 A1 | 6/2005 | Richmond |
| 2005/0124970 A1 | 6/2005 | Kunin et al. |
| 2005/0147524 A1 | 7/2005 | Bousquet |
| 2005/0147525 A1 | 7/2005 | Bousquet |
| 2005/0148930 A1 | 7/2005 | Hseih et al. |
| 2005/0152891 A1 | 7/2005 | Toone et al. |
| 2005/0171493 A1 | 8/2005 | Nicholls |
| 2005/0197634 A1 | 9/2005 | Raad et al. |
| 2005/0214185 A1 | 9/2005 | Castaneda |
| 2005/0220882 A1 | 10/2005 | Pritchard et al. |
| 2005/0228362 A1 | 10/2005 | Vaillancourt |
| 2005/0228482 A1 | 10/2005 | Herzog et al. |
| 2005/0256461 A1 | 11/2005 | DiFiore et al. |
| 2005/0265958 A1 | 12/2005 | West et al. |
| 2005/0267421 A1 | 12/2005 | Wing |
| 2005/0271711 A1 | 12/2005 | Lynch et al. |
| 2005/0288551 A1 | 12/2005 | Callister et al. |
| 2006/0004316 A1 | 1/2006 | DiFiore et al. |
| 2006/0024372 A1 | 2/2006 | Utterberg et al. |
| 2006/0030827 A1 | 2/2006 | Raulerson et al. |
| 2006/0058734 A1 | 3/2006 | Phillips |
| 2006/0096348 A1 | 5/2006 | DiFiore |
| 2006/0118122 A1 | 6/2006 | Martens et al. |
| 2006/0129109 A1 | 6/2006 | Shaw et al. |

(56) References Cited

U.S. PATENT DOCUMENTS

| | | |
|---|---|---|
| 2006/0142730 A1 | 6/2006 | Proulx et al. |
| 2006/0149191 A1 | 7/2006 | DiFiore |
| 2006/0161115 A1 | 7/2006 | Fangrow |
| 2006/0195117 A1 | 8/2006 | Rucker et al. |
| 2006/0202146 A1 | 9/2006 | Doyle |
| 2006/0206178 A1 | 9/2006 | Kim |
| 2006/0253084 A1 | 11/2006 | Nordgren |
| 2006/0261076 A1 | 11/2006 | Anderson |
| 2007/0003603 A1 | 1/2007 | Karandikar et al. |
| 2007/0088292 A1 | 4/2007 | Fangrow |
| 2007/0088293 A1 | 4/2007 | Fangrow |
| 2007/0088294 A1 | 4/2007 | Fangrow |
| 2007/0106205 A1 | 5/2007 | Connell et al. |
| 2007/0112333 A1 | 5/2007 | Hoang et al. |
| 2007/0154621 A1 | 7/2007 | Raad |
| 2007/0156118 A1 | 7/2007 | Ramsey et al. |
| 2007/0167910 A1 | 7/2007 | Tennican et al. |
| 2007/0176117 A1 | 8/2007 | Redmond et al. |
| 2007/0179453 A1 | 8/2007 | Lim et al. |
| 2007/0187353 A1 | 8/2007 | Fox et al. |
| 2007/0202177 A1 | 8/2007 | Hoang |
| 2007/0212381 A1 | 9/2007 | DiFiore et al. |
| 2007/0231315 A1 | 10/2007 | Lichte et al. |
| 2007/0248676 A1 | 10/2007 | Stamler et al. |
| 2007/0249996 A1 | 10/2007 | Tennican et al. |
| 2007/0265578 A1 | 11/2007 | Tennican et al. |
| 2007/0282280 A1 | 12/2007 | Tennican |
| 2007/0287989 A1 | 12/2007 | Crawford et al. |
| 2008/0014005 A1 | 1/2008 | Kitabatake |
| 2008/0027399 A1 | 1/2008 | Harding et al. |
| 2008/0027401 A1 | 1/2008 | Ou-Yang |
| 2008/0033371 A1 | 2/2008 | Updegraff et al. |
| 2008/0039803 A1 | 2/2008 | Lynn |
| 2008/0058733 A1 | 3/2008 | Vogt et al. |
| 2008/0093245 A1 | 4/2008 | Periasamy et al. |
| 2008/0095680 A1 | 4/2008 | Steffens et al. |
| 2008/0097315 A1 | 4/2008 | Miner et al. |
| 2008/0097407 A1 | 4/2008 | Plishka |
| 2008/0103485 A1 | 5/2008 | Kruger |
| 2008/0128646 A1 | 6/2008 | Clawson |
| 2008/0132880 A1 | 6/2008 | Buchman |
| 2008/0147047 A1 | 6/2008 | Davis et al. |
| 2008/0161763 A1 | 7/2008 | Harding et al. |
| 2008/0172007 A1 | 7/2008 | Bousquet |
| 2008/0173651 A1 | 7/2008 | Ping |
| 2008/0177250 A1 | 7/2008 | Howlett et al. |
| 2008/0187460 A1 | 8/2008 | Utterberg et al. |
| 2008/0188791 A1 | 8/2008 | DiFiore et al. |
| 2008/0190485 A1 | 8/2008 | Guala |
| 2008/0193211 A1* | 8/2008 | Burton .............. A61M 39/1011 |
| | | 604/533 |
| 2008/0235888 A1 | 10/2008 | Vaillancourt et al. |
| 2008/0262465 A1 | 10/2008 | Zinger et al. |
| 2008/0287920 A1 | 11/2008 | Fangrow et al. |
| 2008/0318333 A1 | 12/2008 | Nielsen et al. |
| 2008/0319423 A1 | 12/2008 | Tanghoj et al. |
| 2009/0008393 A1 | 1/2009 | Howlett et al. |
| 2009/0012426 A1 | 1/2009 | Tennican |
| 2009/0024096 A1 | 1/2009 | Hai et al. |
| 2009/0028750 A1 | 1/2009 | Ryan |
| 2009/0062766 A1 | 3/2009 | Howlett et al. |
| 2009/0093757 A1 | 4/2009 | Tennican |
| 2009/0099529 A1 | 4/2009 | Anderson et al. |
| 2009/0126867 A1 | 5/2009 | Decant, Jr. et al. |
| 2009/0137969 A1 | 5/2009 | Colantonio et al. |
| 2009/0149820 A1 | 6/2009 | DiFiore |
| 2009/0163876 A1 | 6/2009 | Chebator et al. |
| 2009/0205151 A1 | 8/2009 | Fisher et al. |
| 2009/0205656 A1 | 8/2009 | Nishibayashi et al. |
| 2009/0247485 A1 | 10/2009 | Ahmed et al. |
| 2009/0259194 A1 | 10/2009 | Pinedjian et al. |
| 2009/0270832 A1 | 10/2009 | Vancaillie et al. |
| 2009/0293882 A1 | 12/2009 | Terry |
| 2010/0004510 A1 | 1/2010 | Kuroshima |
| 2010/0047123 A1 | 2/2010 | Solomon et al. |
| 2010/0049170 A1 | 2/2010 | Solomon et al. |
| 2010/0050351 A1 | 3/2010 | Colantonio et al. |
| 2010/0064456 A1 | 3/2010 | Ferlic |
| 2010/0074932 A1 | 3/2010 | Talsma |
| 2010/0106102 A1 | 4/2010 | Ziebol et al. |
| 2010/0106103 A1 | 4/2010 | Ziebol et al. |
| 2010/0137472 A1 | 6/2010 | Ou-Yang |
| 2010/0143427 A1 | 6/2010 | King et al. |
| 2010/0152670 A1 | 6/2010 | Low |
| 2010/0160894 A1 | 6/2010 | Julian et al. |
| 2010/0172794 A1 | 7/2010 | Ferlic et al. |
| 2010/0242993 A1 | 9/2010 | Hoang et al. |
| 2010/0253070 A1 | 10/2010 | Cheon et al. |
| 2010/0280805 A1 | 11/2010 | DiFiore |
| 2010/0292673 A1 | 11/2010 | Korogi et al. |
| 2010/0292674 A1 | 11/2010 | Jepson et al. |
| 2010/0306938 A1 | 12/2010 | Rogers et al. |
| 2010/0318040 A1 | 12/2010 | Kelley, III et al. |
| 2011/0030726 A1 | 2/2011 | Vaillancourt et al. |
| 2011/0044850 A1 | 2/2011 | Solomon et al. |
| 2011/0046564 A1 | 2/2011 | Zhong |
| 2011/0046603 A1 | 2/2011 | Felsovalyi et al. |
| 2011/0054440 A1 | 3/2011 | Lewis |
| 2011/0062703 A1 | 3/2011 | Lopez |
| 2011/0064512 A1 | 3/2011 | Shaw et al. |
| 2011/0071475 A1 | 3/2011 | Horvath et al. |
| 2011/0082431 A1 | 4/2011 | Burgess et al. |
| 2011/0150958 A1 | 6/2011 | Davis et al. |
| 2011/0175347 A1 | 7/2011 | Okiyama |
| 2011/0184338 A1 | 7/2011 | McKay |
| 2011/0184382 A1 | 7/2011 | Cady |
| 2011/0208128 A1 | 8/2011 | Wu et al. |
| 2011/0232020 A1 | 9/2011 | Rogers et al. |
| 2011/0265825 A1 | 11/2011 | Rogers et al. |
| 2011/0276031 A1 | 11/2011 | Hoang et al. |
| 2011/0277788 A1 | 11/2011 | Rogers et al. |
| 2011/0282302 A1 | 11/2011 | Lopez et al. |
| 2011/0290799 A1 | 12/2011 | Anderson et al. |
| 2011/0314619 A1 | 12/2011 | Schweikert |
| 2012/0022469 A1 | 1/2012 | Albert et al. |
| 2012/0029483 A1 | 2/2012 | Griffith et al. |
| 2012/0031904 A1 | 2/2012 | Kuhn et al. |
| 2012/0039764 A1 | 2/2012 | Solomon et al. |
| 2012/0083730 A1 | 4/2012 | Rush et al. |
| 2012/0083750 A1 | 4/2012 | Sansoucy |
| 2012/0157965 A1 | 6/2012 | Wotton et al. |
| 2012/0191029 A1 | 7/2012 | Hopf et al. |
| 2012/0195807 A1 | 8/2012 | Ferlic |
| 2012/0216359 A1 | 8/2012 | Rogers et al. |
| 2012/0216360 A1 | 8/2012 | Rogers et al. |
| 2012/0220955 A1 | 8/2012 | Maseda et al. |
| 2012/0283693 A1 | 11/2012 | Anderson et al. |
| 2012/0283696 A1 | 11/2012 | Cronenberg et al. |
| 2012/0296284 A1 | 11/2012 | Anderson et al. |
| 2012/0302968 A1 | 11/2012 | Tennican |
| 2012/0302970 A1 | 11/2012 | Tennican |
| 2012/0302997 A1 | 11/2012 | Gardner et al. |
| 2012/0315201 A1 | 12/2012 | Ferlic et al. |
| 2013/0006194 A1 | 1/2013 | Anderson et al. |
| 2013/0023828 A1 | 1/2013 | Anderson et al. |
| 2013/0030414 A1 | 1/2013 | Gardner et al. |
| 2013/0035667 A1 | 2/2013 | Anderson et al. |
| 2013/0039953 A1 | 2/2013 | Dudnyk et al. |
| 2013/0053751 A1 | 2/2013 | Holtham |
| 2013/0072908 A1 | 3/2013 | Solomon et al. |
| 2013/0072909 A1 | 3/2013 | Solomon et al. |
| 2013/0085313 A1 | 4/2013 | Fowler et al. |
| 2013/0085474 A1 | 4/2013 | Charles et al. |
| 2013/0098938 A1 | 4/2013 | Efthimiadis |
| 2013/0102950 A1 | 4/2013 | DiFiore |
| 2013/0123754 A1 | 5/2013 | Solomon et al. |
| 2013/0134161 A1 | 5/2013 | Fogel et al. |
| 2013/0138085 A1 | 5/2013 | Tennican |
| 2013/0144258 A1 | 6/2013 | Ziebol et al. |
| 2013/0150795 A1 | 6/2013 | Snow |
| 2013/0164189 A1 | 6/2013 | Hadden |
| 2013/0171030 A1 | 7/2013 | Ferlic et al. |
| 2013/0183635 A1 | 7/2013 | Wilhoit |
| 2013/0184679 A1 | 7/2013 | Ziebol et al. |

(56) References Cited

U.S. PATENT DOCUMENTS

| | | | |
|---|---|---|---|
| 2013/0197485 A1 | 8/2013 | Gardner et al. | |
| 2013/0204231 A1* | 8/2013 | Ziebol | A61L 29/14 |
| | | | 604/508 |
| 2013/0255061 A1 | 10/2013 | Burkholz | |
| 2013/0274686 A1 | 10/2013 | Ziebol et al. | |
| 2014/0042116 A1 | 2/2014 | Shen et al. | |
| 2014/0048079 A1 | 2/2014 | Gardner et al. | |
| 2014/0052074 A1 | 2/2014 | Tekeste | |
| 2014/0101876 A1 | 4/2014 | Rogers et al. | |
| 2014/0155868 A1 | 6/2014 | Nelson et al. | |
| 2014/0227144 A1 | 8/2014 | Liu et al. | |
| 2014/0228775 A1 | 8/2014 | Burkholz et al. | |
| 2014/0243797 A1 | 8/2014 | Jensen et al. | |
| 2014/0261758 A1* | 9/2014 | Wlodarczyk | A61M 5/14566 |
| | | | 285/305 |
| 2014/0336610 A1 | 11/2014 | Michel et al. | |
| 2015/0086441 A1 | 3/2015 | She et al. | |
| 2015/0141934 A1 | 5/2015 | Gardner et al. | |
| 2015/0148287 A1 | 5/2015 | Woo et al. | |
| 2015/0157799 A1 | 6/2015 | Chen et al. | |
| 2015/0157800 A1 | 6/2015 | Chen | |
| 2015/0217106 A1 | 8/2015 | Banik et al. | |
| 2015/0258324 A1 | 9/2015 | Chida et al. | |
| 2015/0298893 A1 | 10/2015 | Welp | |
| 2015/0306367 A1 | 10/2015 | DiFiore | |
| 2015/0314119 A1 | 11/2015 | Anderson et al. | |
| 2015/0320992 A1 | 11/2015 | Bonnet et al. | |
| 2015/0343174 A1 | 12/2015 | Ziebol et al. | |
| 2016/0001056 A1 | 1/2016 | Nelson et al. | |
| 2016/0001058 A1 | 1/2016 | Ziebol et al. | |
| 2016/0015863 A1 | 1/2016 | Gupta et al. | |
| 2016/0045629 A1 | 2/2016 | Gardner et al. | |
| 2016/0088995 A1 | 3/2016 | Ueda et al. | |
| 2016/0089530 A1 | 3/2016 | Sathe | |
| 2016/0101223 A1 | 4/2016 | Kelley, III et al. | |
| 2016/0101276 A1 | 4/2016 | Tekeste | |
| 2016/0106969 A1 | 4/2016 | Neftel | |
| 2016/0158521 A1 | 6/2016 | Hoang et al. | |
| 2016/0158522 A1 | 6/2016 | Hoang et al. | |
| 2016/0213912 A1 | 7/2016 | Daneluzzi | |
| 2016/0220790 A1 | 8/2016 | Borowicz | |
| 2016/0250420 A1 | 9/2016 | Maritan et al. | |
| 2016/0354596 A1 | 12/2016 | DiFiore | |
| 2017/0020911 A1 | 1/2017 | Berry et al. | |
| 2017/0042636 A1 | 2/2017 | Young | |
| 2017/0143447 A1 | 5/2017 | Rogers et al. | |
| 2017/0182241 A1 | 6/2017 | DiFiore | |
| 2017/0203092 A1 | 7/2017 | Ryan et al. | |
| 2017/0239443 A1 | 8/2017 | Abitabilo et al. | |
| 2018/0028403 A1 | 2/2018 | Fangrow | |
| 2018/0085568 A1 | 3/2018 | Drmanovic | |
| 2018/0200500 A1 | 7/2018 | Ziebol et al. | |
| 2018/0200501 A1* | 7/2018 | Her | F16L 55/10 |
| 2018/0214684 A1 | 8/2018 | Avula et al. | |
| 2019/0201681 A1 | 7/2019 | Ziebol et al. | |
| 2019/0351211 A1 | 11/2019 | Dombrowski et al. | |
| 2020/0069931 A1 | 3/2020 | Fangrow | |
| 2020/0085690 A1 | 3/2020 | Fangrow | |
| 2020/0121858 A1 | 4/2020 | Anderson et al. | |
| 2020/0139037 A1 | 5/2020 | Ziebol et al. | |
| 2020/0139101 A1 | 5/2020 | Ziebol et al. | |
| 2020/0139102 A1 | 5/2020 | Ziebol et al. | |
| 2020/0139103 A1 | 5/2020 | Ziebol et al. | |
| 2020/0139104 A1 | 5/2020 | Ziebol et al. | |
| 2020/0155794 A1 | 5/2020 | Ziebol et al. | |
| 2020/0324102 A1 | 10/2020 | Fangrow | |
| 2020/0330741 A1 | 10/2020 | Fangrow et al. | |
| 2020/0406020 A1 | 12/2020 | Fangrow | |
| 2021/0106805 A1 | 4/2021 | Fangrow | |
| 2021/0162194 A1 | 6/2021 | Gardner | |
| 2021/0205596 A1 | 7/2021 | Ziebol et al. | |
| 2021/0308442 A1 | 10/2021 | Gardner | |
| 2022/0226629 A1 | 7/2022 | Ziebel | |
| 2022/0288258 A1 | 9/2022 | Gardner | |
| 2022/0288376 A1 | 9/2022 | Ziebol | |

| | | | |
|---|---|---|---|
| 2022/0313977 A1 | 10/2022 | Gugel et al. | |
| 2022/0379035 A1 | 12/2022 | Anderson | |
| 2022/0387685 A1 | 12/2022 | Ziebol | |
| 2023/0030414 A1 | 2/2023 | Charrier et al. | |
| 2023/0069367 A1 | 3/2023 | Ziebol | |
| 2023/0105566 A1 | 4/2023 | Fangrow | |
| 2023/0288258 A1 | 9/2023 | Gardner | |
| 2024/0050729 A1 | 2/2024 | Ziebol | |
| 2024/0050730 A1 | 2/2024 | Fangrow | |
| 2024/0139489 A1 | 5/2024 | Ziebol | |
| 2024/0216667 A1 | 7/2024 | Ziebol | |
| 2025/0025663 A1 | 1/2025 | Ziebol | |
| 2025/0099686 A1 | 3/2025 | Anderson | |
| 2025/0099732 A1 | 3/2025 | Gardner | |
| 2025/0099733 A1 | 3/2025 | Gardner | |
| 2025/0121174 A1 | 4/2025 | Ziebol | |

FOREIGN PATENT DOCUMENTS

| | | |
|---|---|---|
| CA | 2825217 | 3/2007 |
| CA | 2 769 157 | 2/2011 |
| CA | 2 841 832 | 6/2019 |
| CN | 2402327 Y | 10/2000 |
| CN | 2815392 Y | 9/2006 |
| CN | 201150420 Y | 11/2008 |
| CN | 101405042 | 4/2009 |
| CN | 201519335 U | 7/2010 |
| CN | 102202716 | 9/2011 |
| CN | 102 844 073 A | 12/2012 |
| CN | 103260696 A | 8/2013 |
| CN | 103796704 | 12/2016 |
| CN | 106902402 | 6/2017 |
| CN | 106902405 | 6/2017 |
| CN | 107837428 | 3/2018 |
| DE | 3515665 | 5/1986 |
| DE | 89 06 628 U1 | 9/1989 |
| DE | 43 34 272 | 4/1995 |
| DE | 29617133 | 1/1997 |
| DE | 102007025900 | 12/2008 |
| EP | 0 063 640 | 11/1982 |
| EP | 0 088 341 | 9/1983 |
| EP | 0 108 785 | 5/1984 |
| EP | 0 174 162 | 3/1986 |
| EP | 0 227 219 | 7/1987 |
| EP | 0 237 239 | 9/1987 |
| EP | 0 245 872 | 11/1987 |
| EP | 0 257 485 | 3/1988 |
| EP | 0 639 385 | 2/1995 |
| EP | 0 734 721 | 10/1996 |
| EP | 0 769 265 | 4/1997 |
| EP | 1 061 000 | 10/2000 |
| EP | 1 331 020 | 7/2003 |
| EP | 1 471 011 | 10/2004 |
| EP | 1 442 753 | 2/2007 |
| EP | 1 813 293 | 8/2007 |
| EP | 1 977 714 | 10/2008 |
| EP | 1 312 008 | 4/2009 |
| EP | 2 444 117 | 4/2012 |
| EP | 2 606 930 | 6/2013 |
| EP | 2 671 604 | 12/2013 |
| EP | 2 731 658 | 5/2014 |
| FR | 2 493 149 A | 5/1982 |
| FR | 2 506 162 | 11/1982 |
| FR | 2 782 910 | 3/2000 |
| GB | 123221 | 2/1919 |
| GB | 2 296 182 | 6/1996 |
| GB | 2 333 097 | 7/1999 |
| GB | 2 387 772 | 10/2003 |
| JP | 57-131462 U | 8/1982 |
| JP | 04-99950 | 2/1992 |
| JP | 05-31180 A | 2/1993 |
| JP | 8-81695 A | 3/1996 |
| JP | 09-216661 A | 8/1997 |
| JP | 2000-157630 A | 6/2000 |
| JP | 2002-210011 A | 7/2002 |
| JP | 2002-234567 A | 8/2002 |
| JP | 2002-291906 | 10/2002 |
| JP | 2005-218649 | 8/2005 |
| JP | 2006-182663 A | 7/2006 |

(56) References Cited

FOREIGN PATENT DOCUMENTS

| | | |
|---|---|---|
| JP | 2006-223583 A | 8/2006 |
| JP | 2009-006148 | 1/2009 |
| JP | 2009-544450 A | 12/2009 |
| JP | 2011-036691 | 2/2011 |
| JP | 2011-528647 | 11/2011 |
| JP | 2012-020125 | 2/2012 |
| JP | 2013-509274 | 3/2013 |
| JP | 2013-520287 | 6/2013 |
| JP | 2014-117461 | 6/2014 |
| JP | 2014-533593 A | 12/2014 |
| JP | 2015-526195 A | 9/2015 |
| JP | 2016-506856 A | 3/2016 |
| JP | 2017-515553 A | 6/2017 |
| JP | 2020-146096 | 9/2020 |
| JP | 2020-146097 | 9/2020 |
| JP | 2013-99665 | 5/2023 |
| RU | 2 246 321 C1 | 2/2005 |
| WO | WO 83/03975 | 11/1983 |
| WO | WO 85/05040 | 11/1985 |
| WO | WO-9212746 A1 * | 8/1992 .......... A61M 5/3134 |
| WO | WO 93/20806 | 10/1993 |
| WO | WO 95/07691 | 3/1995 |
| WO | WO 96/35416 | 11/1996 |
| WO | WO 96/38136 | 12/1996 |
| WO | WO 1997/19701 | 6/1997 |
| WO | WO 98/12125 | 3/1998 |
| WO | WO 98/48872 | 11/1998 |
| WO | WO 1999/44665 | 9/1999 |
| WO | WO 2001/70199 A1 | 9/2001 |
| WO | WO 2002/05188 | 1/2002 |
| WO | WO 2002/47581 | 6/2002 |
| WO | WO 2002/49544 | 6/2002 |
| WO | WO 2003/015677 | 2/2003 |
| WO | WO 2003/070296 | 8/2003 |
| WO | WO 2004/035129 | 4/2004 |
| WO | WO 2004/112846 | 12/2004 |
| WO | WO 2005/112954 A1 | 12/2005 |
| WO | WO 2005/112974 A2 | 12/2005 |
| WO | WO 2006/007690 | 1/2006 |
| WO | WO 2006/044236 | 4/2006 |
| WO | WO 2006/102756 | 10/2006 |
| WO | WO 2007/008511 | 1/2007 |
| WO | WO 2007/056773 | 5/2007 |
| WO | WO 2007/137056 | 11/2007 |
| WO | WO 2008/014437 | 1/2008 |
| WO | WO 2008/042285 | 4/2008 |
| WO | WO 2008/086631 | 7/2008 |
| WO | WO 2008/089196 | 7/2008 |
| WO | WO 2008/100950 | 8/2008 |
| WO | WO 2008/140807 | 11/2008 |
| WO | WO 2009/002474 | 12/2008 |
| WO | WO 2009/060322 | 5/2009 |
| WO | WO 2009/117135 | 9/2009 |
| WO | WO 2009/123709 | 10/2009 |
| WO | WO 2009/136957 | 11/2009 |
| WO | WO 2009/153224 | 12/2009 |
| WO | WO 2010/002757 | 1/2010 |
| WO | WO 2010/002808 | 1/2010 |
| WO | WO 2010/011616 | 1/2010 |
| WO | WO 2010/034470 | 4/2010 |
| WO | WO 2010/039171 | 4/2010 |
| WO | WO 2010/062589 | 6/2010 |
| WO | WO 2011/012379 | 2/2011 |
| WO | WO 2011/028722 | 3/2011 |
| WO | WO 2011/053924 | 5/2011 |
| WO | WO 2011/106374 | 9/2011 |
| WO | WO 2011/119021 | 9/2011 |
| WO | WO 2012/009456 | 1/2012 |
| WO | WO 2012/118829 | 9/2012 |
| WO | WO 2012/162006 | 11/2012 |
| WO | WO 2013/009998 | 1/2013 |
| WO | WO 2013/023146 | 2/2013 |
| WO | WO 2013/082180 | 6/2013 |
| WO | WO 2013/184716 | 12/2013 |
| WO | WO 2013/192574 | 12/2013 |
| WO | WO 2014/031628 | 2/2014 |
| WO | WO 2014/074419 | 5/2014 |
| WO | WO 2014/074929 | 5/2014 |
| WO | WO 2014/126867 | 8/2014 |
| WO | WO 2014/140949 | 9/2014 |
| WO | WO 14/159346 | 10/2014 |
| WO | WO 2015/074087 | 5/2015 |
| WO | WO 2015/119940 | 8/2015 |
| WO | WO 2015/120336 | 8/2015 |
| WO | WO 2015/164129 | 10/2015 |
| WO | WO 2015/164134 | 10/2015 |
| WO | WO 2015/168677 | 11/2015 |
| WO | WO 2015/174953 | 11/2015 |
| WO | WO 2016/025775 | 2/2016 |
| WO | WO 2016/182822 | 11/2016 |
| WO | WO 2017/015047 | 1/2017 |
| WO | WO 2017/127364 | 7/2017 |
| WO | WO 2017/127365 | 7/2017 |
| WO | WO 2018/009653 | 1/2018 |
| WO | WO 2018/071717 | 4/2018 |
| WO | WO 2018/204206 | 11/2018 |
| WO | WO 2018/237090 | 12/2018 |
| WO | WO 2018/237122 | 12/2018 |
| WO | WO 2019/178560 | 9/2019 |
| WO | WO 2019/246472 | 12/2019 |
| WO | WO 2020/097366 | 5/2020 |
| WO | WO 2020/251947 | 12/2020 |
| WO | WO 2022/125474 | 6/2022 |

OTHER PUBLICATIONS

Otto, Mosby's Pocket Guide to Infusion Therapy. Elsevier Health Sciences, 2004. pp. 65-66. Accessed at: http://books.google.com/books?id=j8T14HwWdS4C&lpg=PP1&pg=PP1#v=onepage&f=false (Year: 2004).

"Small-bore connectors for liquids and gases in healthcare applications—Part : Connectors for intravascular or hypodermic applications," ISO 80369-7, Corrected version dated Dec. 1, 2016 (50 pages).

Hospira, "You Work in Neverland," Lifeshield Product Brochure in 2 pages, Published 2009.

Baxter Minicap: Photographs of the Baxter Minicap (Sep. 1, 1998) (4 pages).

Baxter, "Peritoneal Dialysis Patient Connectology," Product Descriptions in 1 page, downloaded Jul. 1, 2011.

Beta Cap II Advertisement from Quinton Instrument Co. (Aug. 1981).

Catheter Connections, "Introducing DualCap," Product Brochure in 1 page, Copyright 2011.

Charney, "Baxter Healthcare InterlinkTM IV Access System" in 1 page, from Handbook of Modern Hospital Safety. Published Mar. 1999.

Clave® Needlefree Connector, icumedial, human connections, 2 page brochure. 2012, M1-1065 Rev. 04.

Conical Fittings: International Standard, "Conical fittings with 6% (Luer) Taper for Syringes, Needles and certain Other Medical Equipment—Part 2: Lock Fittings", Ref. No. ISO 594-2:1998. International Organization for Standardization (Sep. 1, 1998) 2nd ed. (16 pages).

Devine, redacted version of letter from David A. Divine, Esq. of Lee & Hayes, dated May 16, 2011 (3 pages).

Devine, redacted version of letter from David A. Divine, Esq. of Lee & Hayes, dated May 27, 2011 (3 pages).

Du. Y, et al. Protein adsorption on polyurethane catheters modified with a novel antithrombin-heparin covalent complex, Journal of Biomedical Materials Research Part A, 2006, 216-225.

Holmer, E. et al. The molecular-weight dependence of the rate-enhancing effect of heparin on the inhibition of thrombin, Factor Xa, Factor IXa, Factor XIa, Factor XIIa and kallikrein by antithrombin, Biochem. J. (1981) 193, 395-400.

Hyprotek, "Port Protek," Product Brochure in 1 page, downloaded Sep. 19, 2011 from http://www.hyprotek.com/products.html.

ICU Medical Antimicrobial Microclave, first sold Jan. 21, 2010, p. 1-2.

(56) References Cited

OTHER PUBLICATIONS

Klement, P. et al. Chronic performance of polyurethane catheters covalently coated with ATH complex: a rabbit jugular vein model, Biomaterials, (2006), 27, 5107-5117.

Menyhay et al., "Disinfection of Needleless Catheter Connectors and Access Ports with Alcohol May Not Prevent Microbial Entry: the Promise of a Novel Antiseptic-Barrier Cap" Infection Control Hospital and Epidemiology, vol. 27, No. 1 (Jan. 2006) (5 pages).

Photographs of the Baxter Minicap (Sep. 1, 1998) (4 pages).

V-Link Luer Activated Device, with VitalShield Protective Coating, 2 page brochure, Baxter 12/09.

U.S. Appl. No. 17/108,887, filed Mar. 31, 2022.

U.S. Appl. No. 16/882,210, filed May 22, 2020.

U.S. Appl. No. 17/832,277, filed Jun. 3, 2022.

International Search Report and Written Opinion for PCT Application No. PCT/US2019/060319 mailed Mar. 25, 2020 (13 pages).

Value Plastics, Inc., "Finger Snap Luer Lock Ring (FSLLR)," drawn by Frank Lombardi, May 29, 2011.

ICU Medical SwabPack, top-access bag of disinfecting caps for needlefree connectors, on sale at least as early as Jan. 2012.

Thread Check Inc., ISO 80369-7 replaces ISO 594-2: 1998€, retrieved 2023; ISO 80369-7 published Oct. 2016, https://www.threadcheck.com/isl-80369/technicalinfo#gref (Year: 2016).

Melaiye, et al., "Silver and its application as an antimicrobial agent," Expert Opinion on Therapeutic Patents, 15:2, pp. 125-130, (Year: 2005).

* cited by examiner

← DISTAL DIRECTION                    PROXIMAL DIRECTION →

DISTAL DIRECTION          PROXIMAL DIRECTION

FIG. 9″

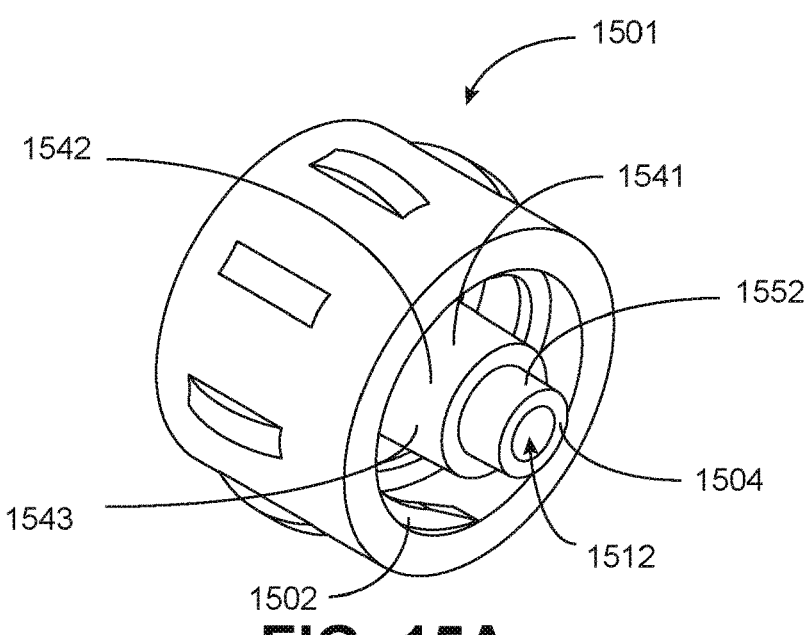
FIG. 15A
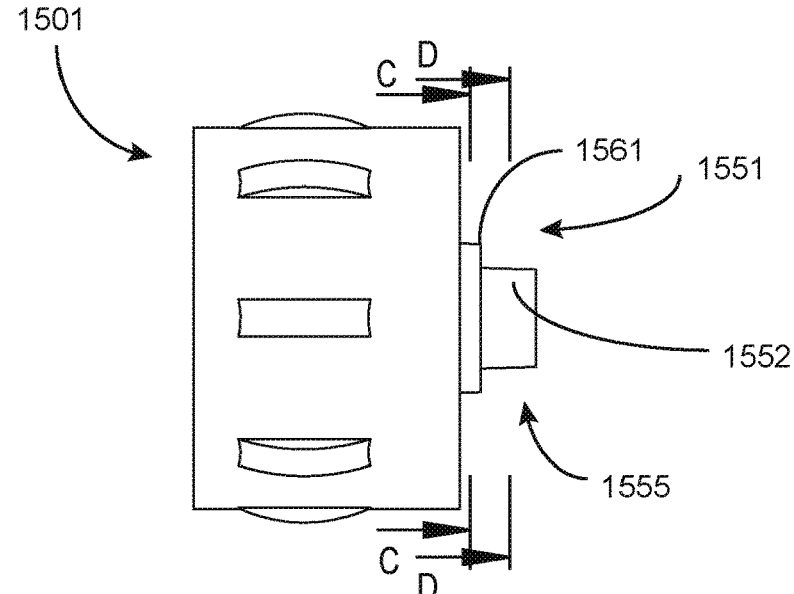
FIG. 15B
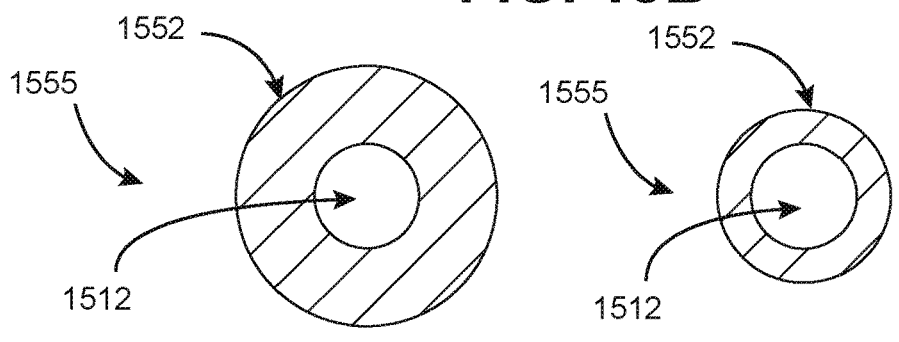
FIG. 15C          FIG. 15D

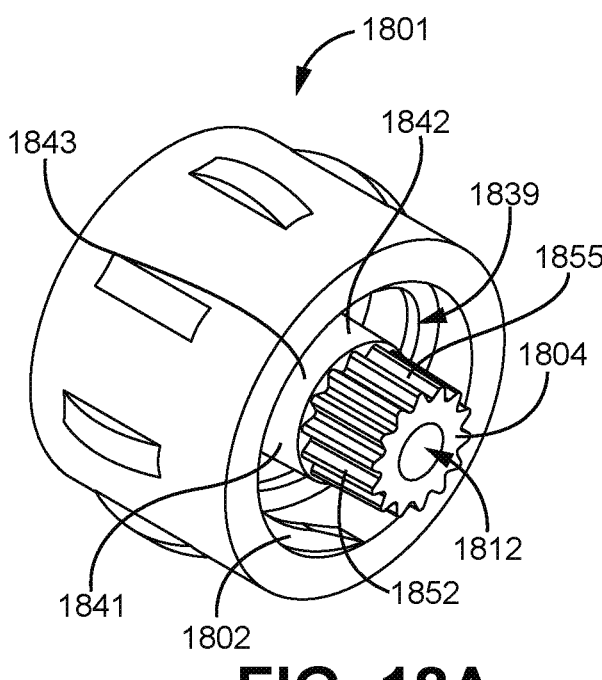
FIG. 18A
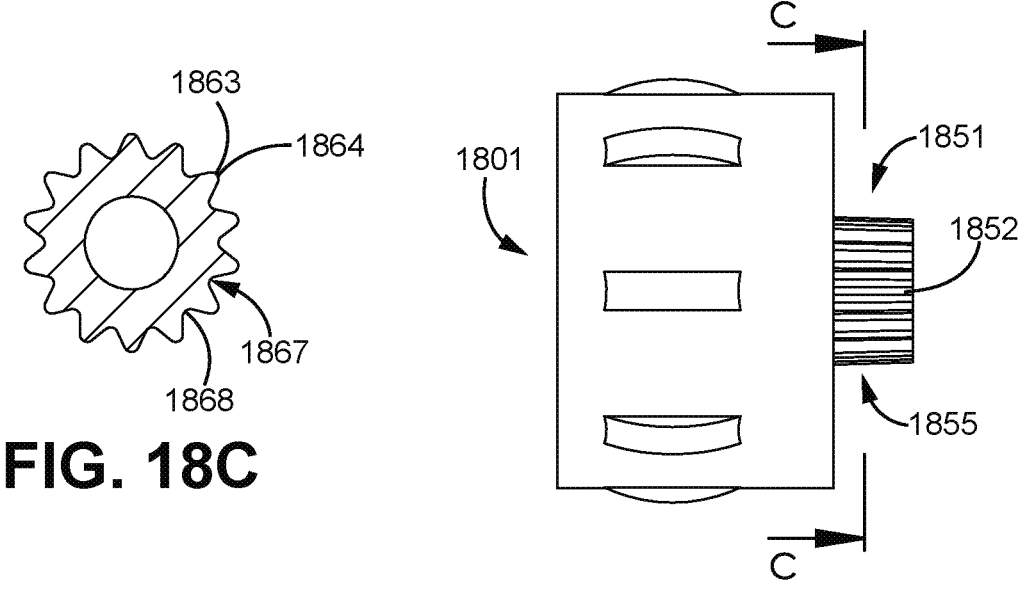
FIG. 18C
FIG 18B

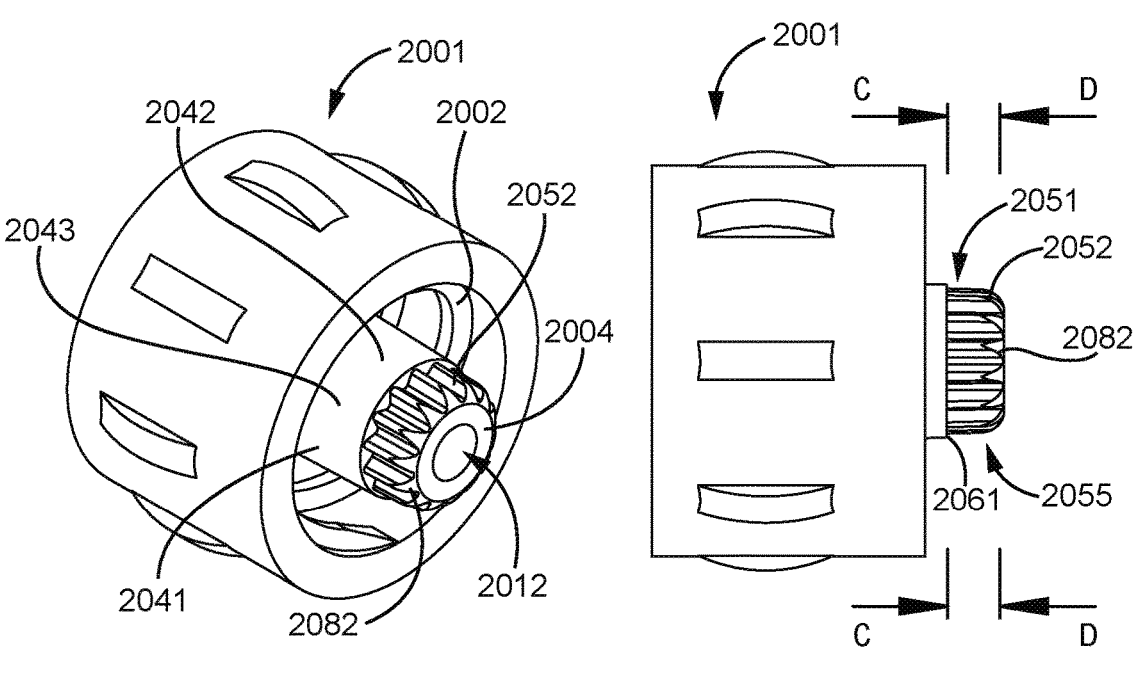
FIG. 20A              FIG. 20B
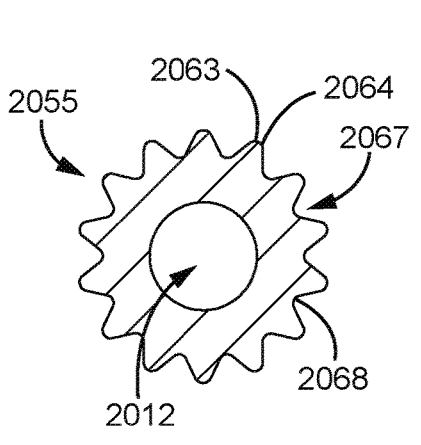
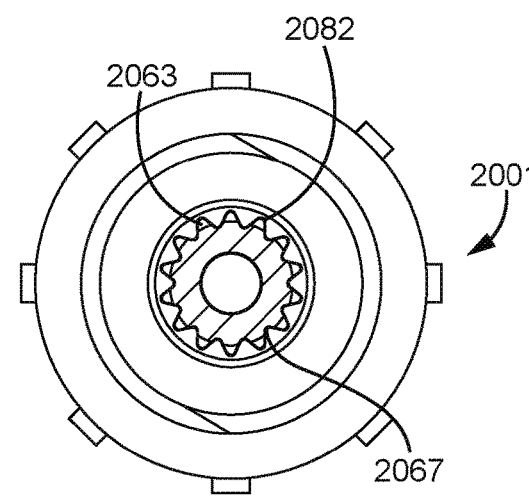
FIG. 20C              FIG. 20D

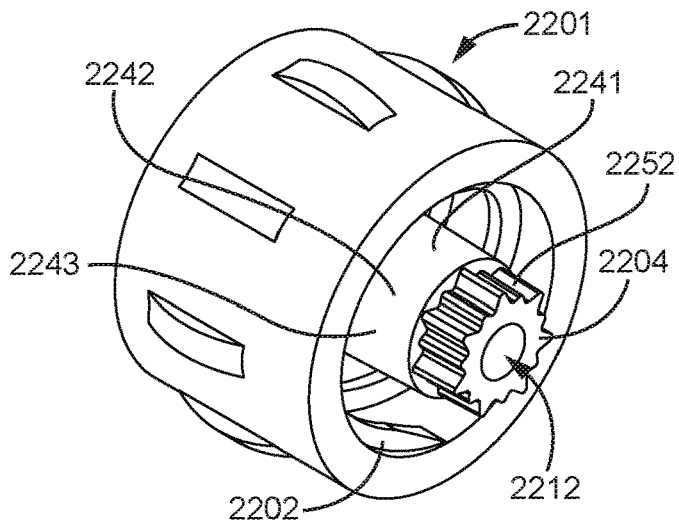
FIG. 22A
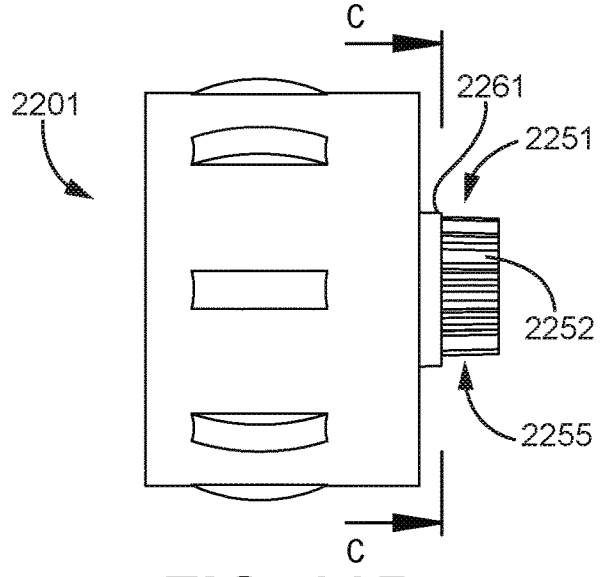
FIG. 22B
FIG. 22C

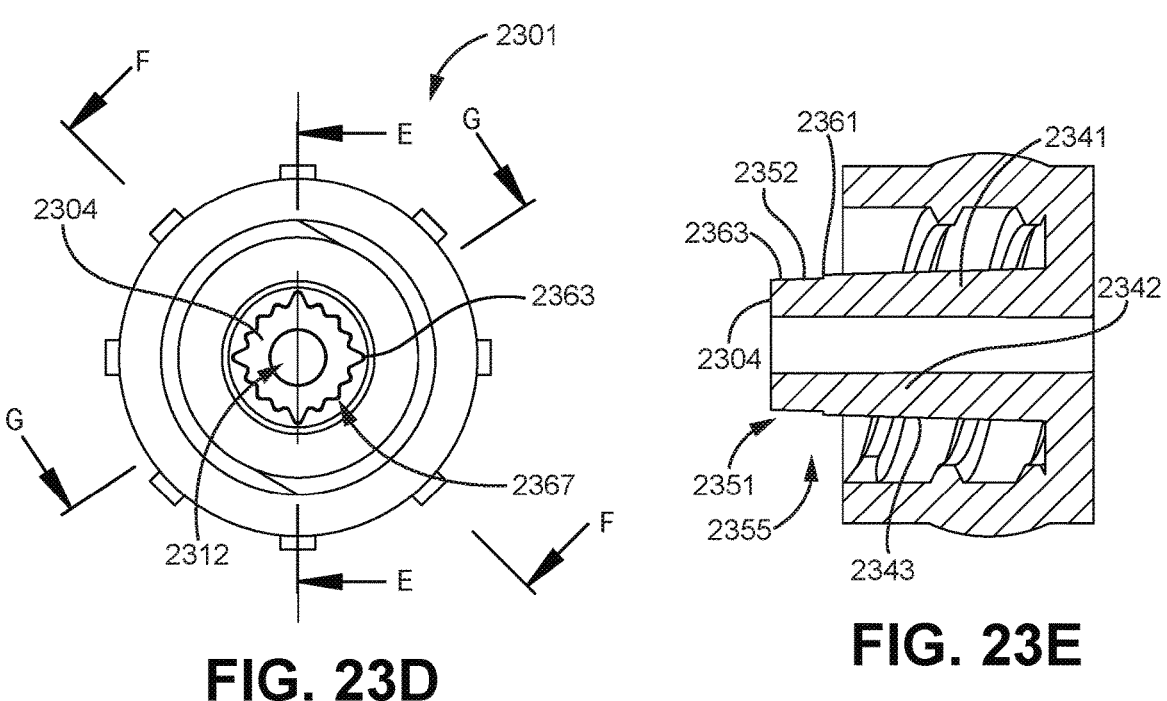
FIG. 23D
FIG. 23E
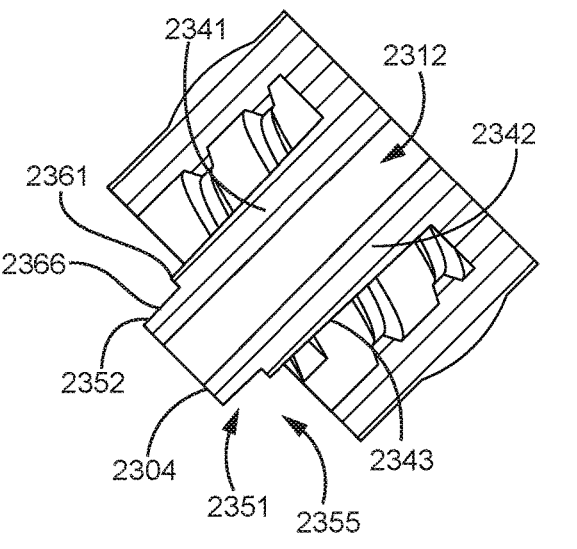
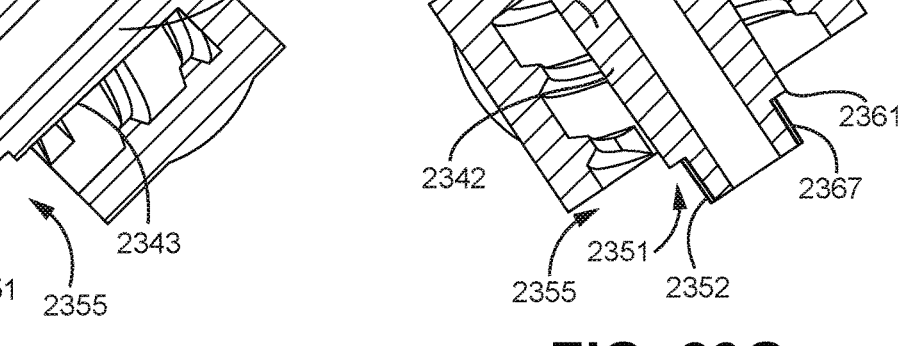
FIG. 23F
FIG. 23G

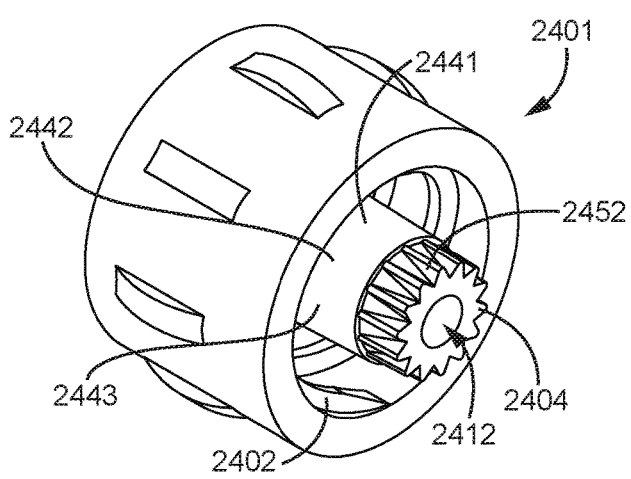
FIG. 24A
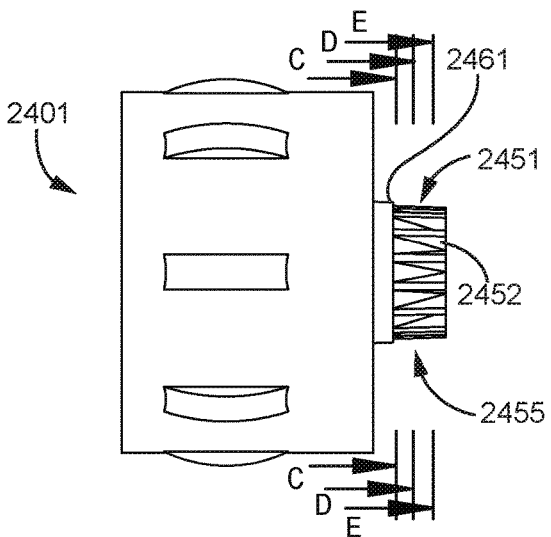
FIG. 24B
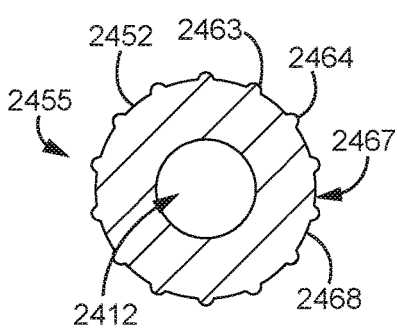
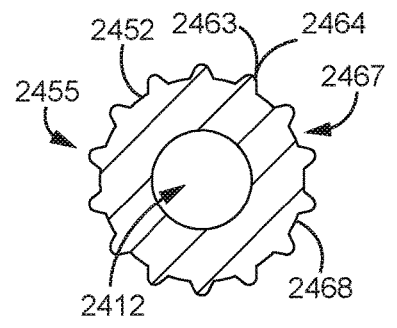
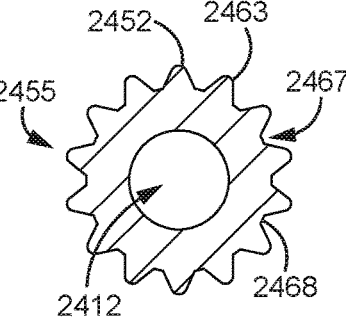
FIG. 24C          FIG. 24D          FIG. 24E

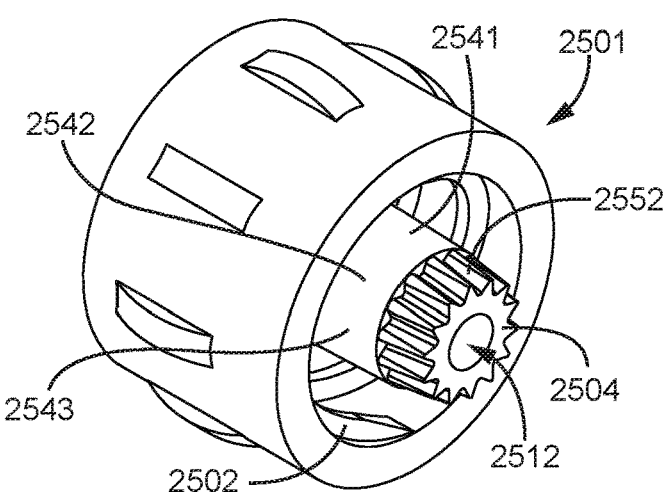
FIG. 25A
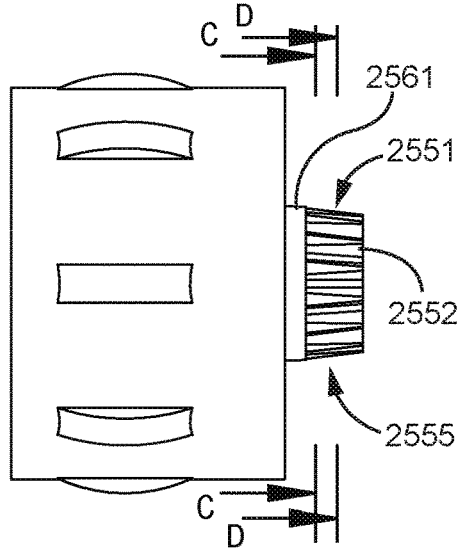
FIG. 25B
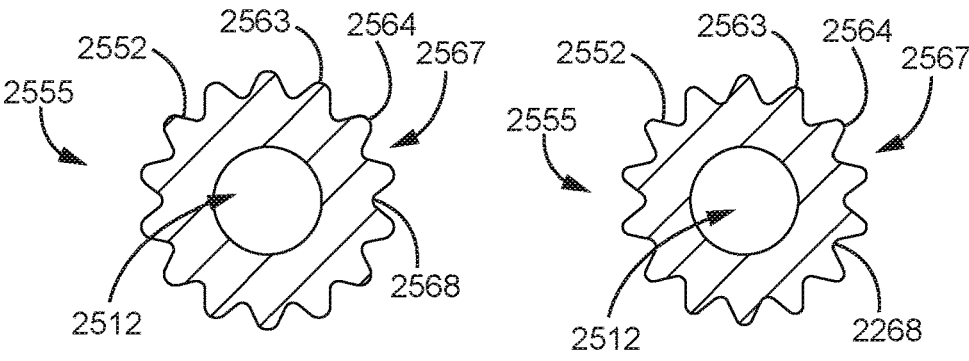
FIG. 25C            FIG. 25D

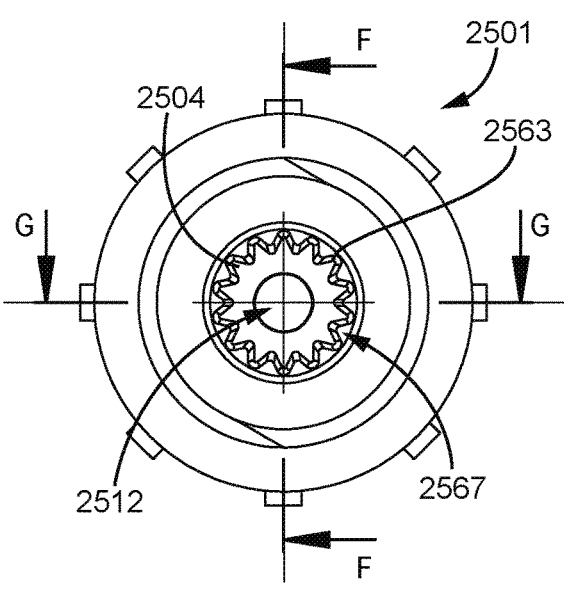
FIG. 25E
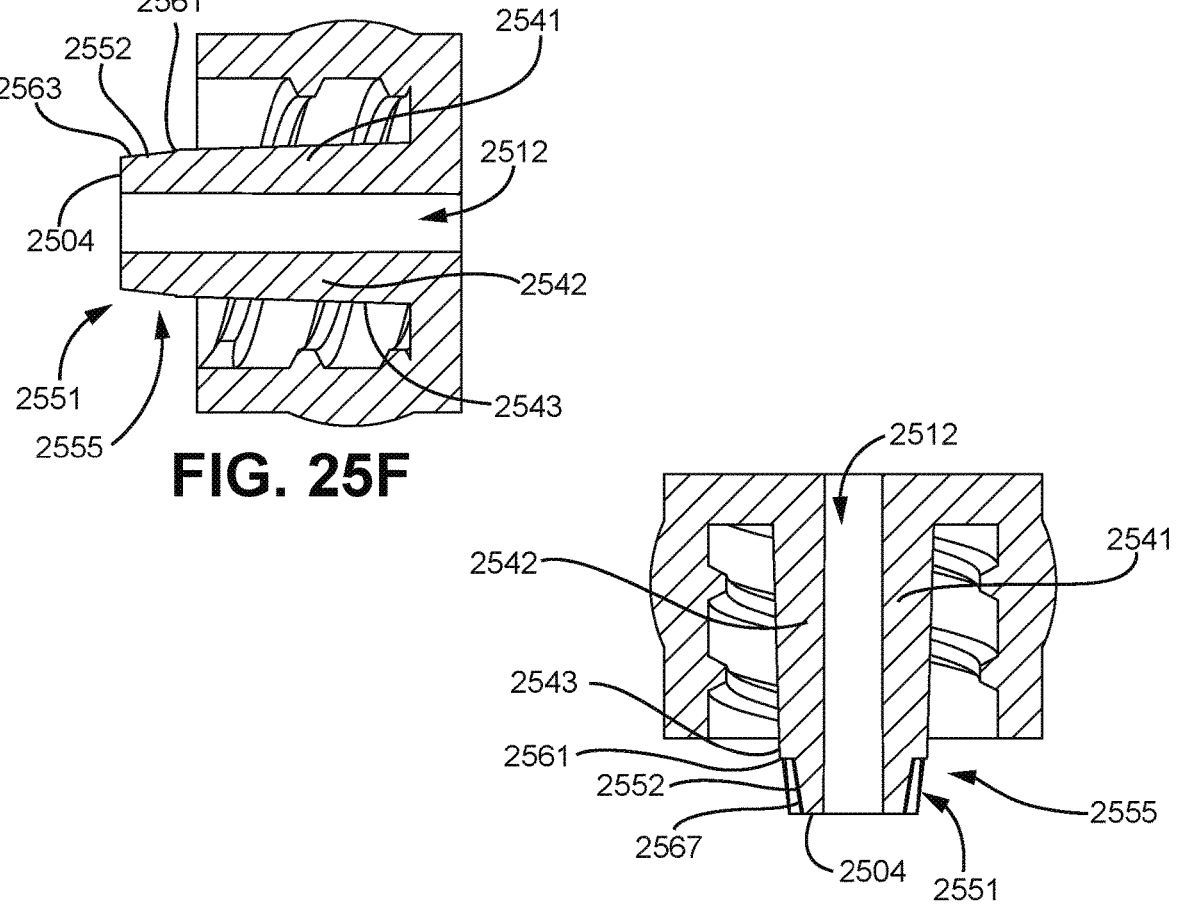
FIG. 25F
FIG. 25G

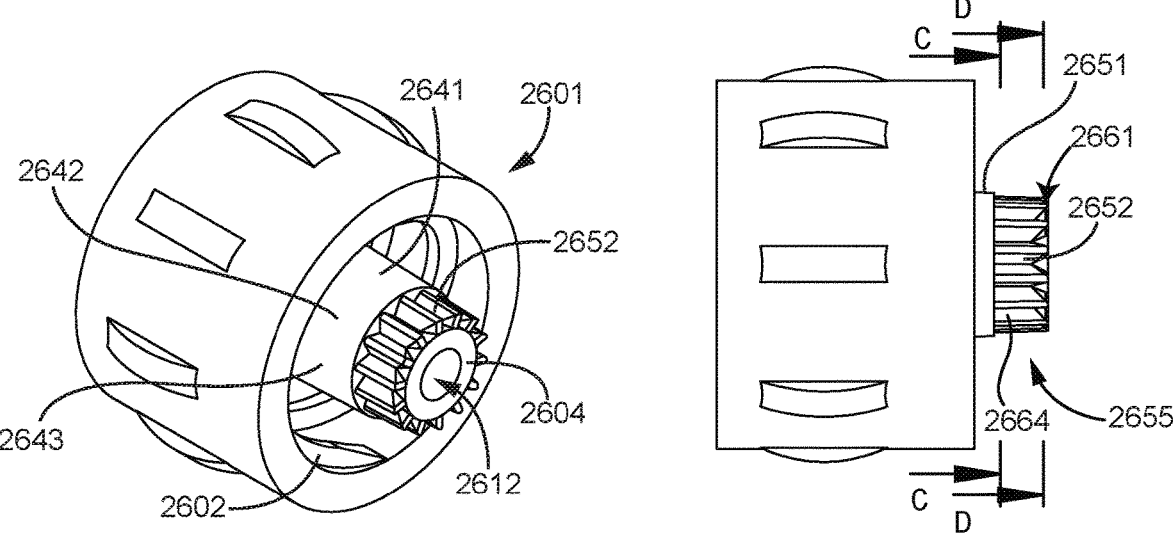
FIG. 26A                    FIG. 26B
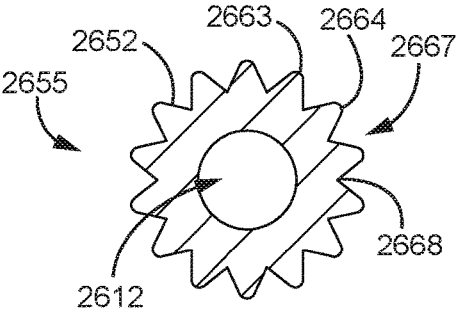
FIG. 26C
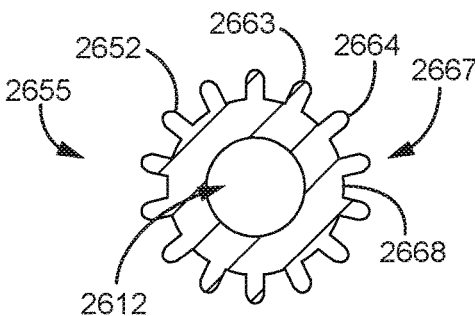
FIG. 26D

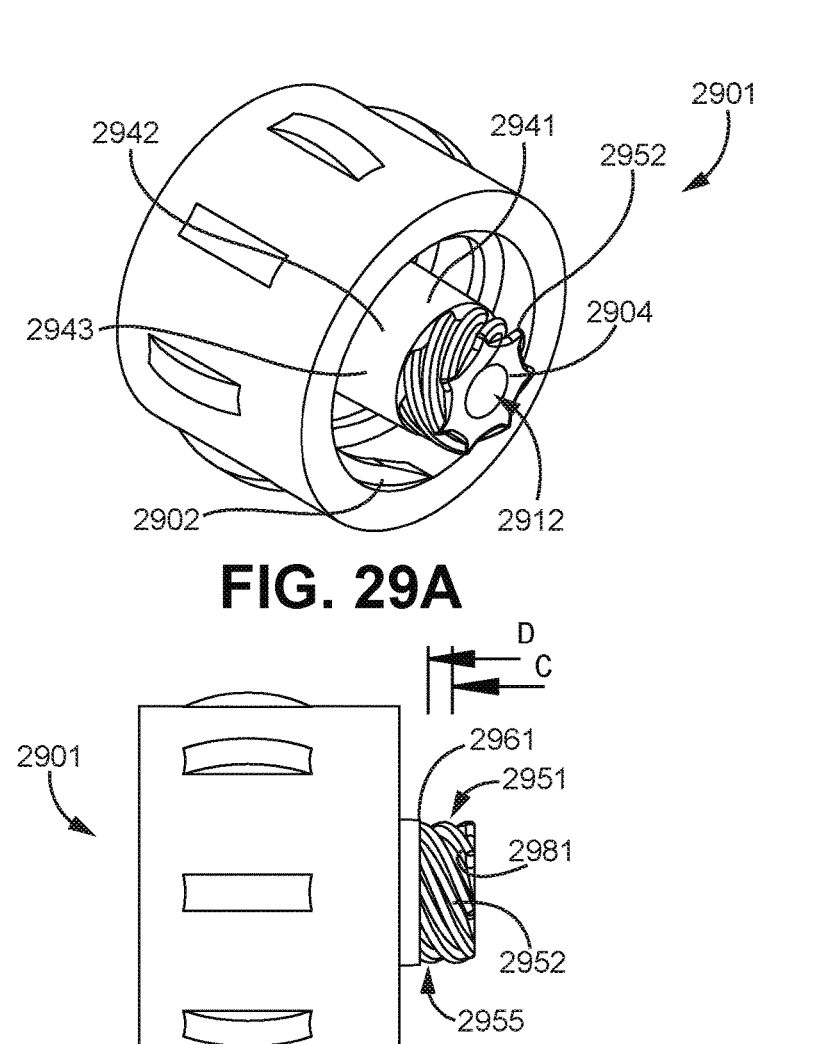
FIG. 29A
FIG. 29B
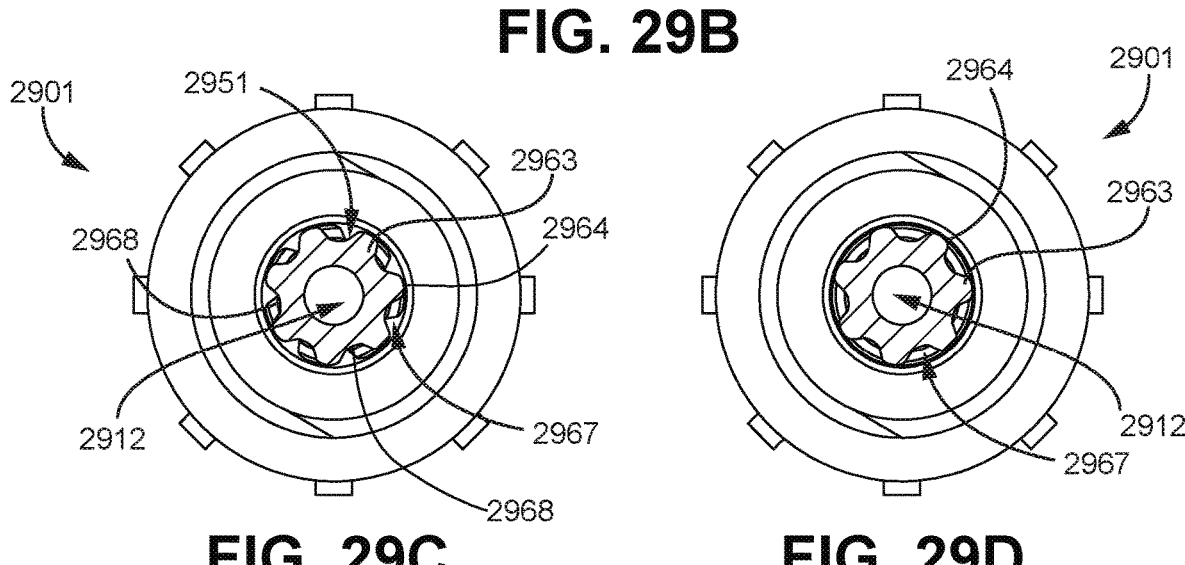
FIG. 29C          FIG. 29D

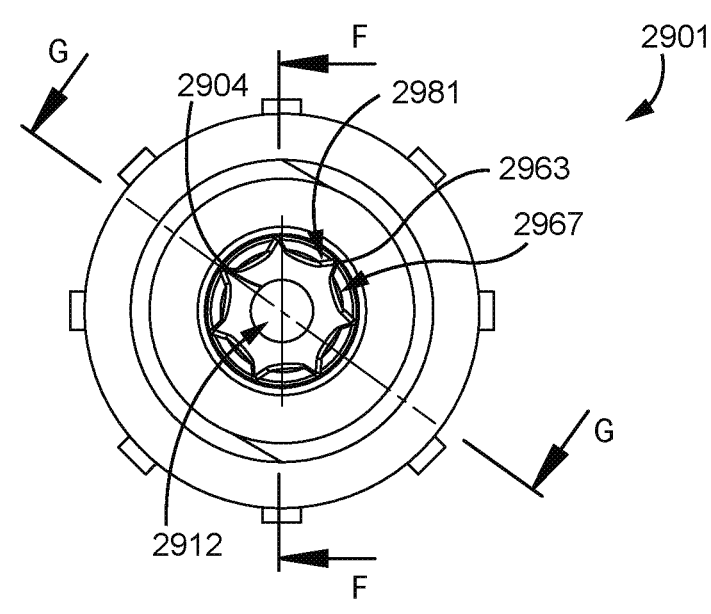
FIG. 29E
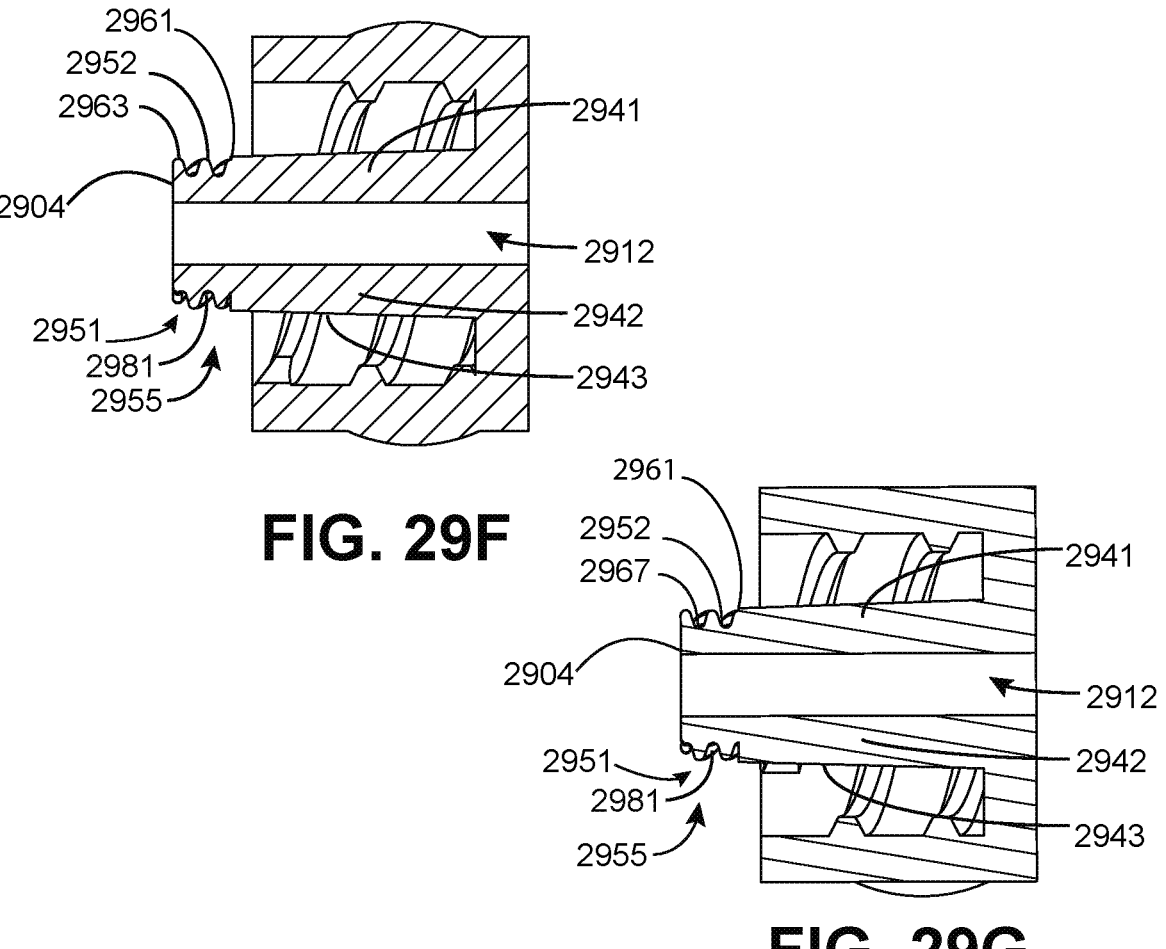
FIG. 29F
FIG. 29G

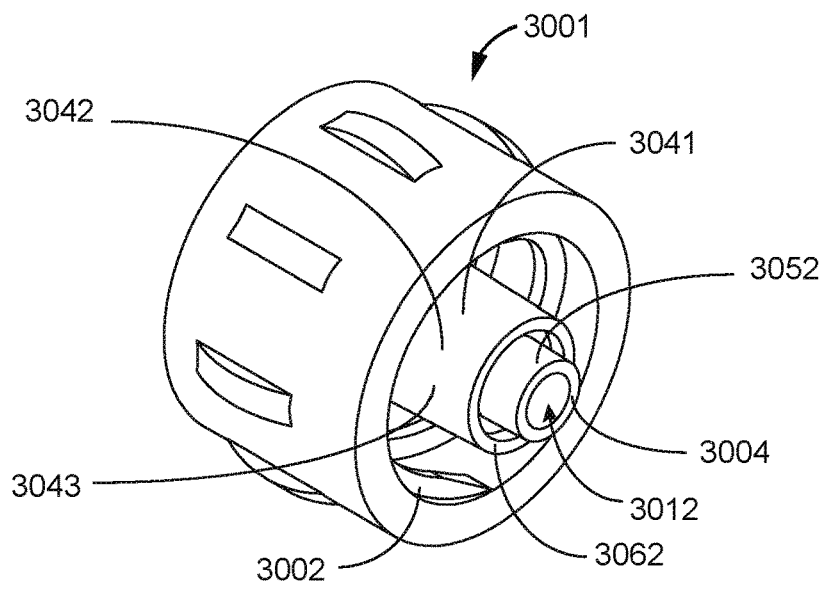
FIG. 30A
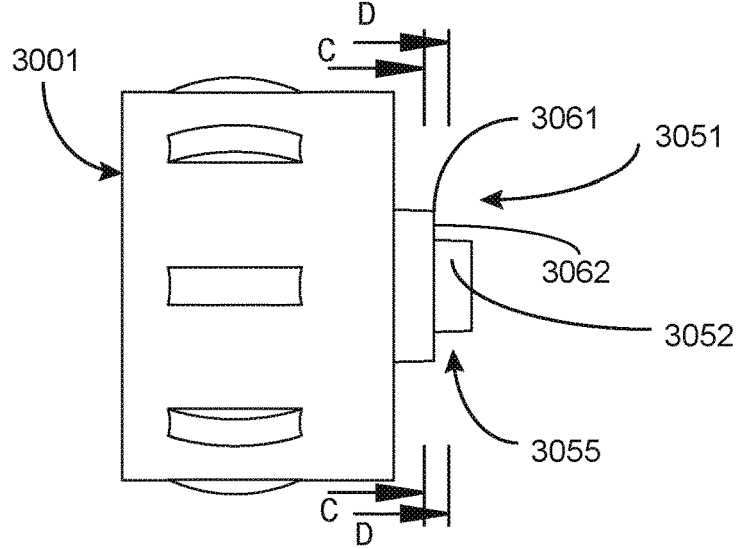
FIG. 30B
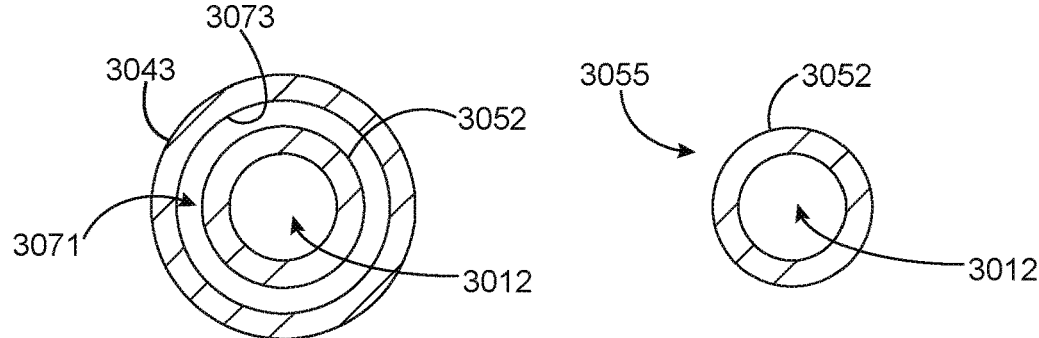
FIG. 30C          FIG. 30D

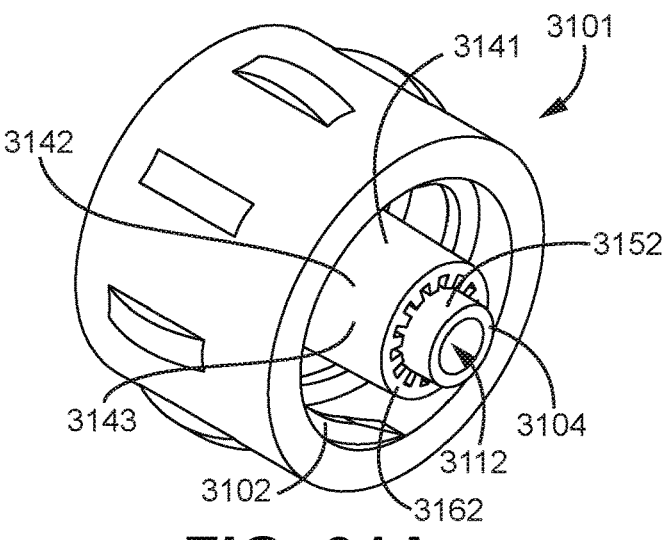
FIG. 31A
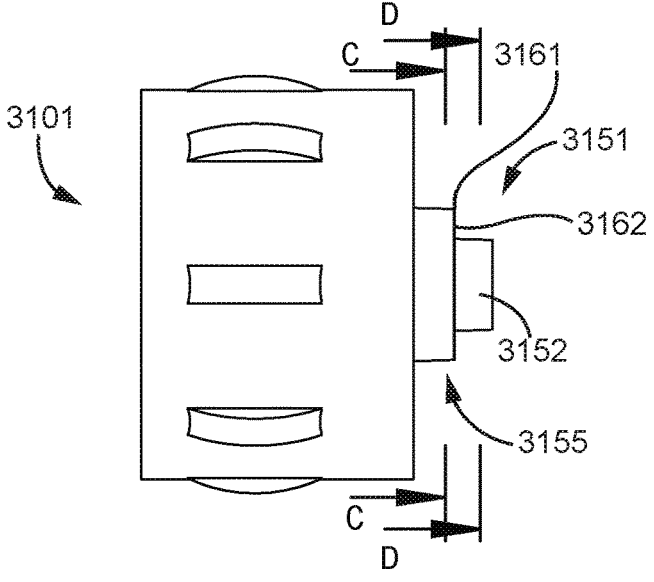
FIG. 31B
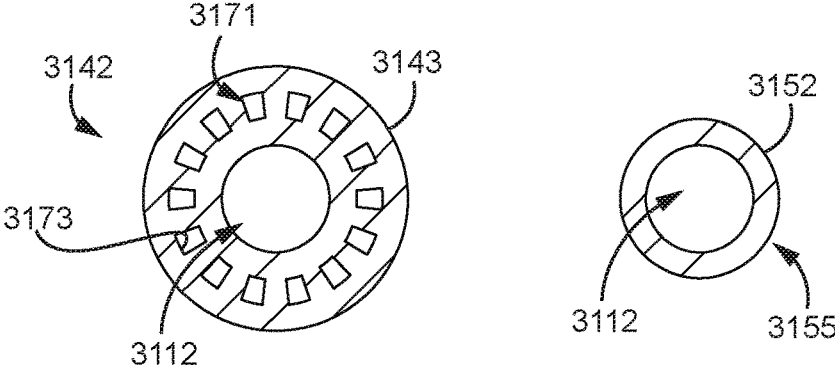
FIG. 31C          FIG. 31D

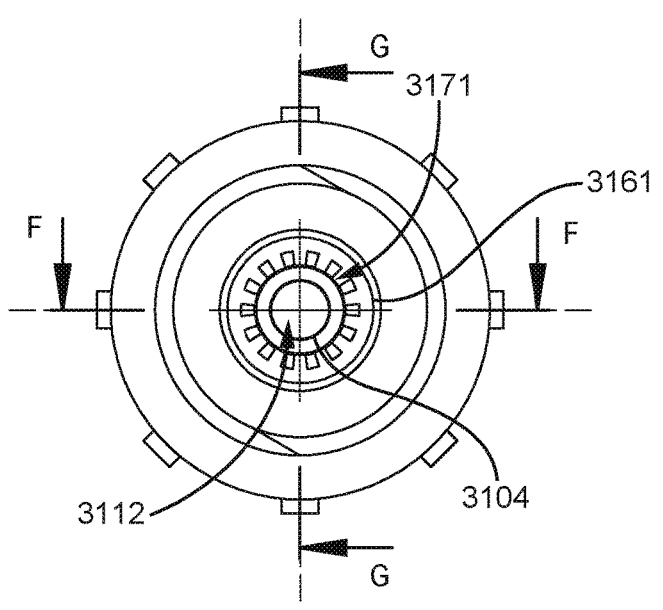
FIG. 31E
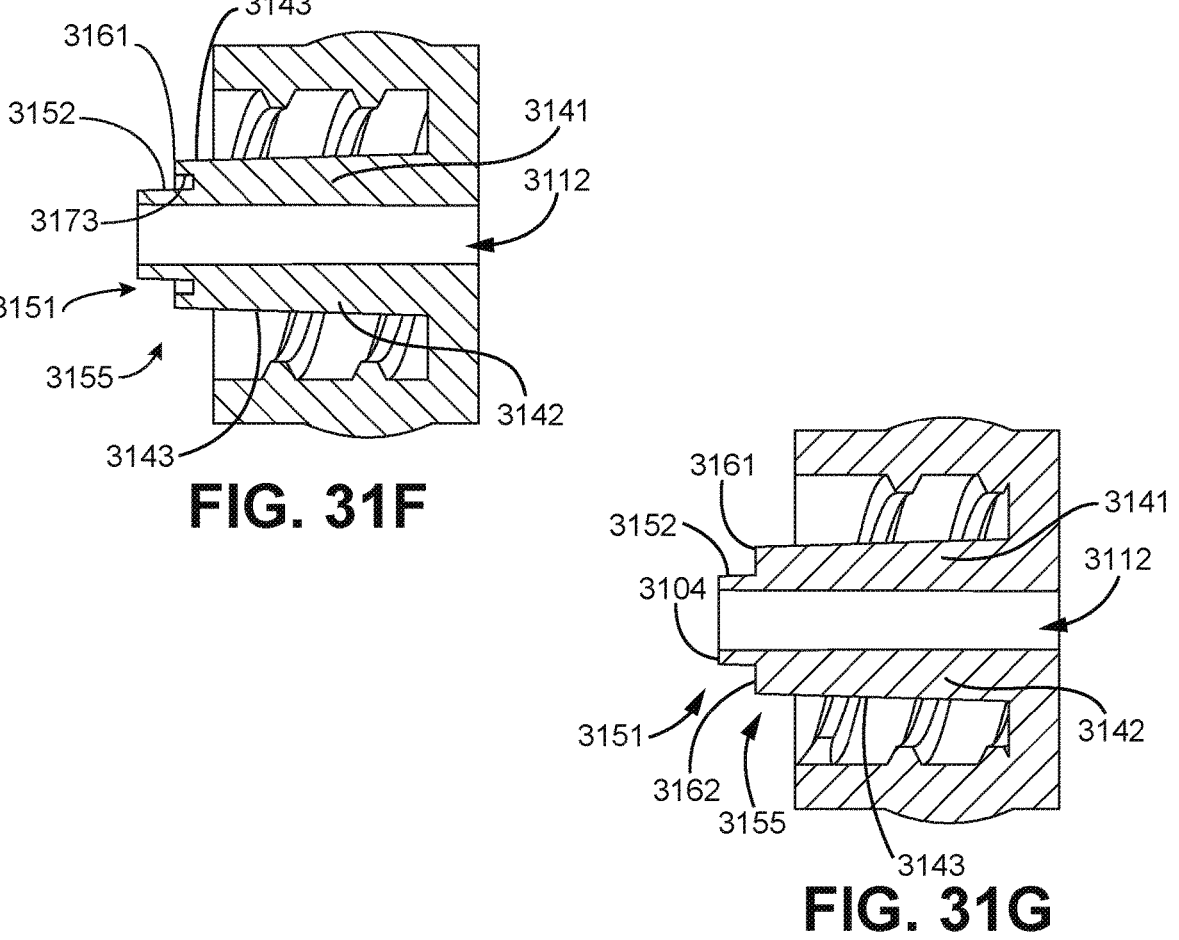
FIG. 31F
FIG. 31G

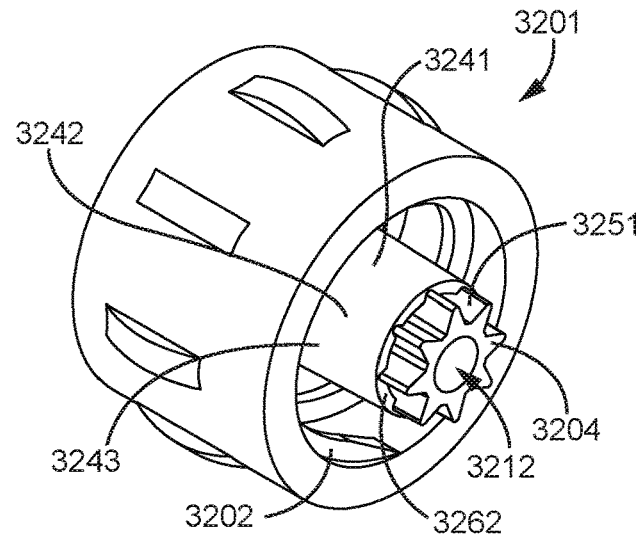
FIG. 32A
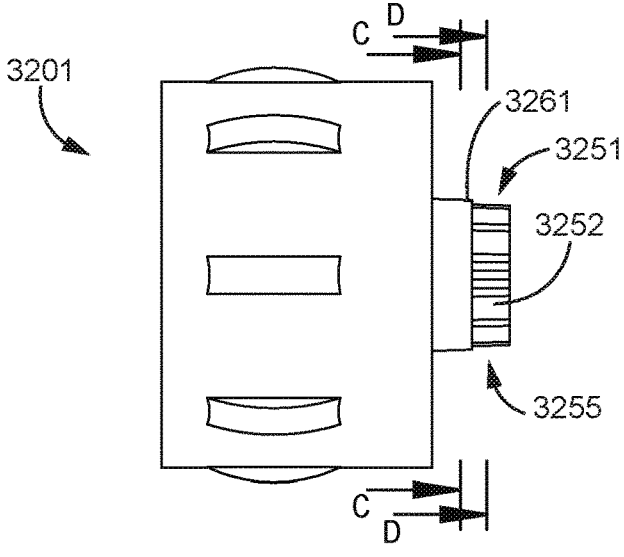
FIG. 32B
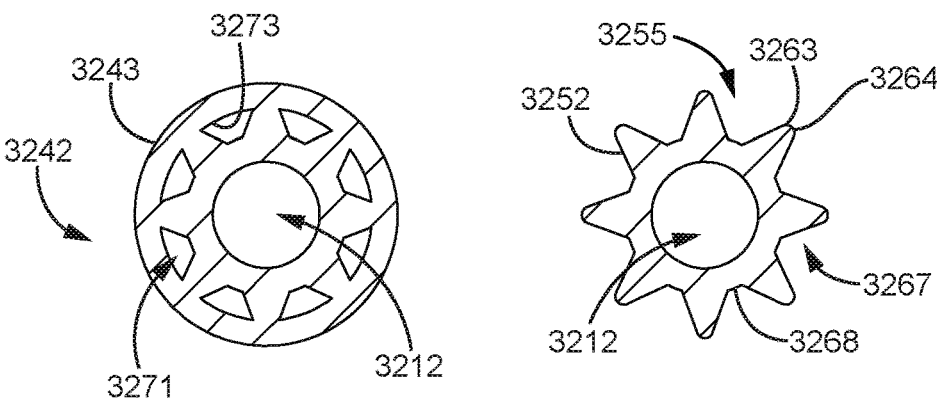
FIG. 32C        FIG. 32D

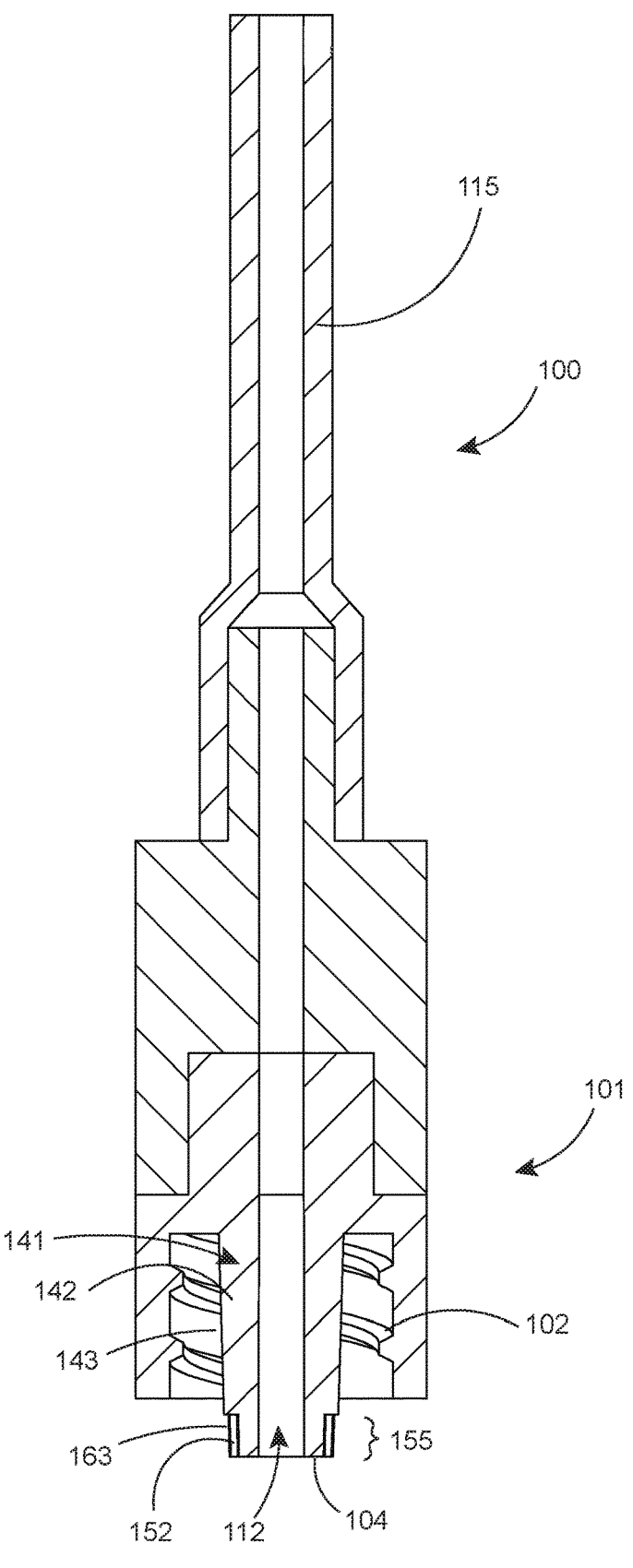
FIG. 40B

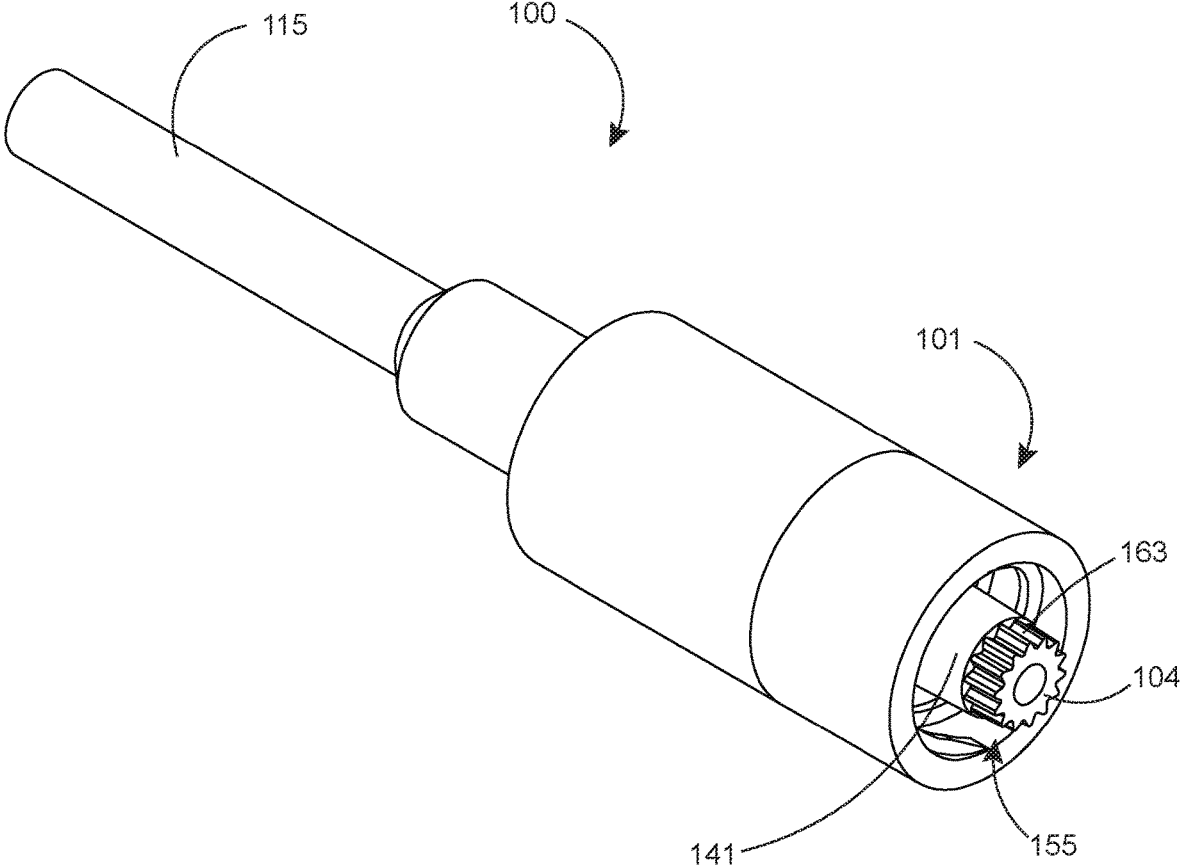
FIG. 40C

PROXIMAL DIRECTION                    DISTAL DIRECTION

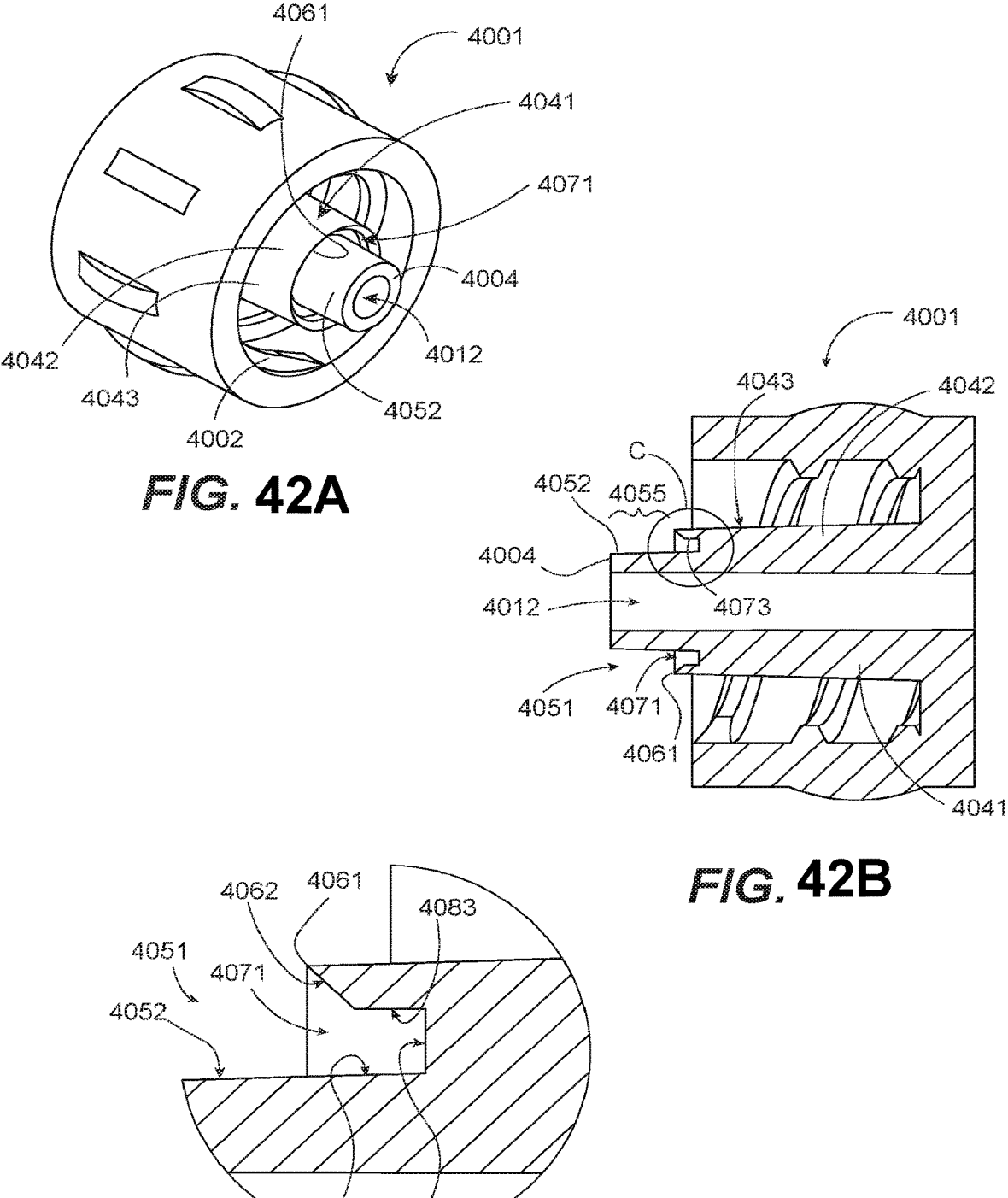
*FIG.* 42A
*FIG.* 42B
*FIG.* 42C

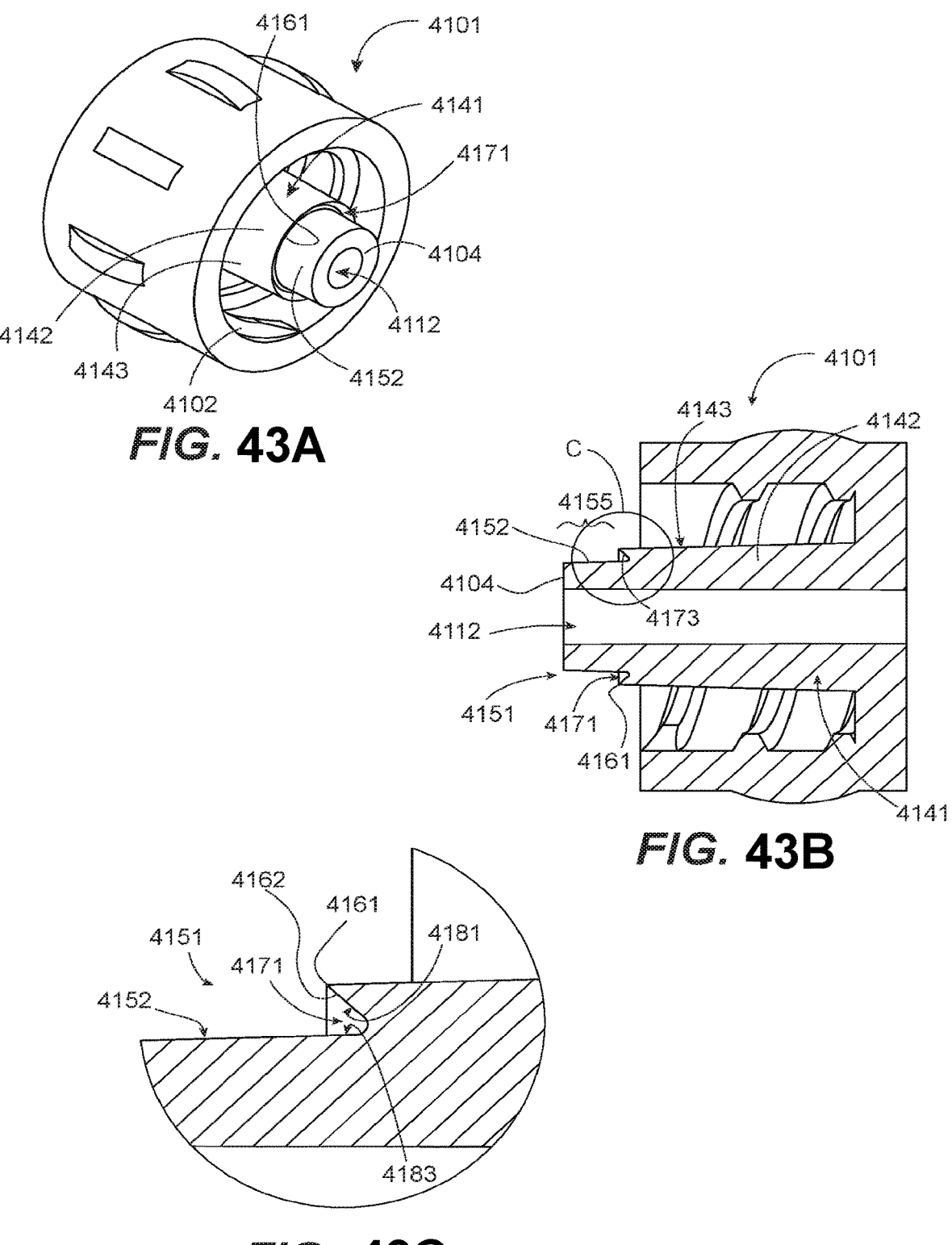
*FIG.* 43A
*FIG.* 43B
*FIG.* 43C

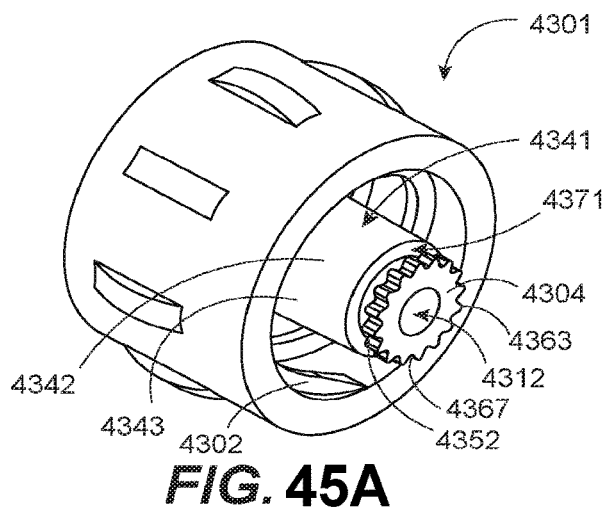
*FIG.* 45A
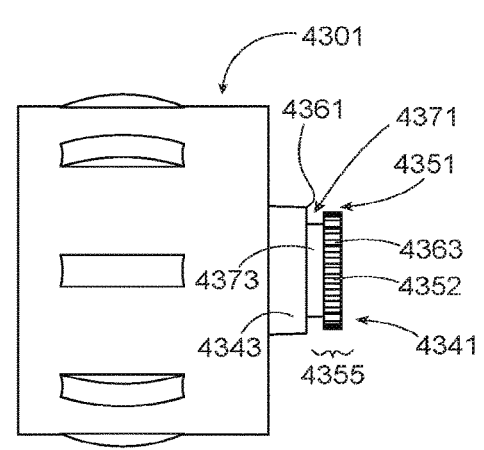
*FIG.* 45B
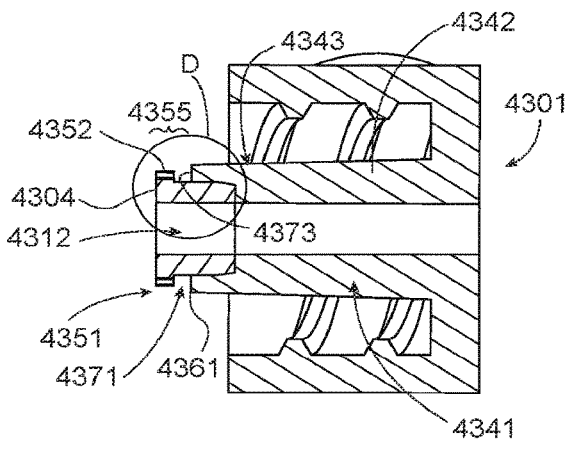
*FIG.* 45C
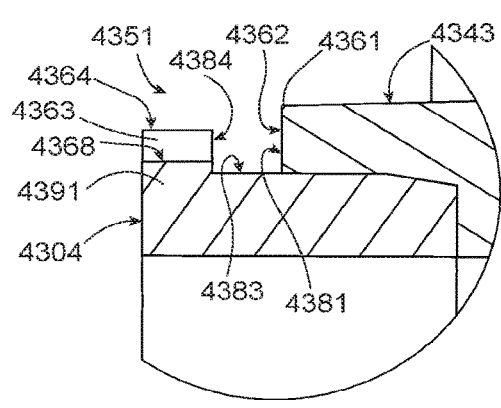
*FIG.* 45D

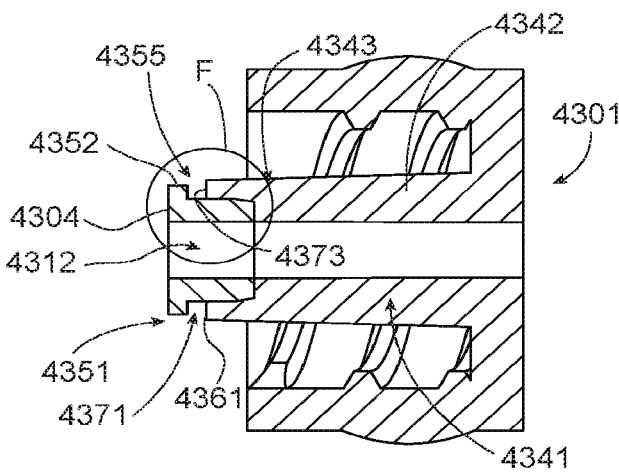
*FIG.* 45E
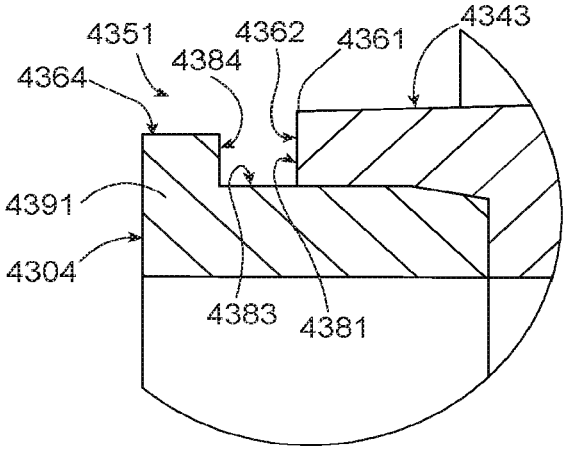
*FIG.* 45F

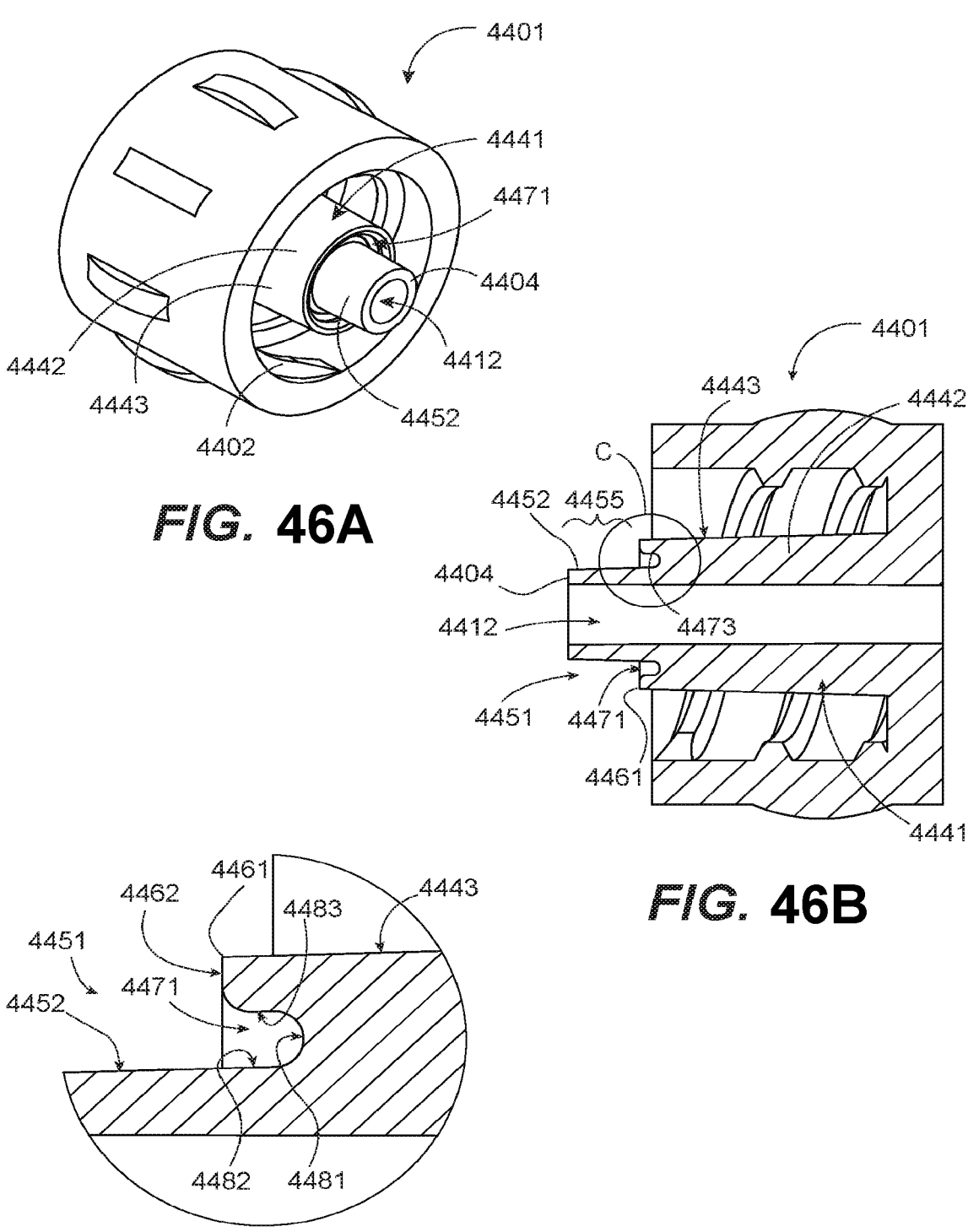
*FIG.* 46A
*FIG.* 46B
*FIG.* 46C

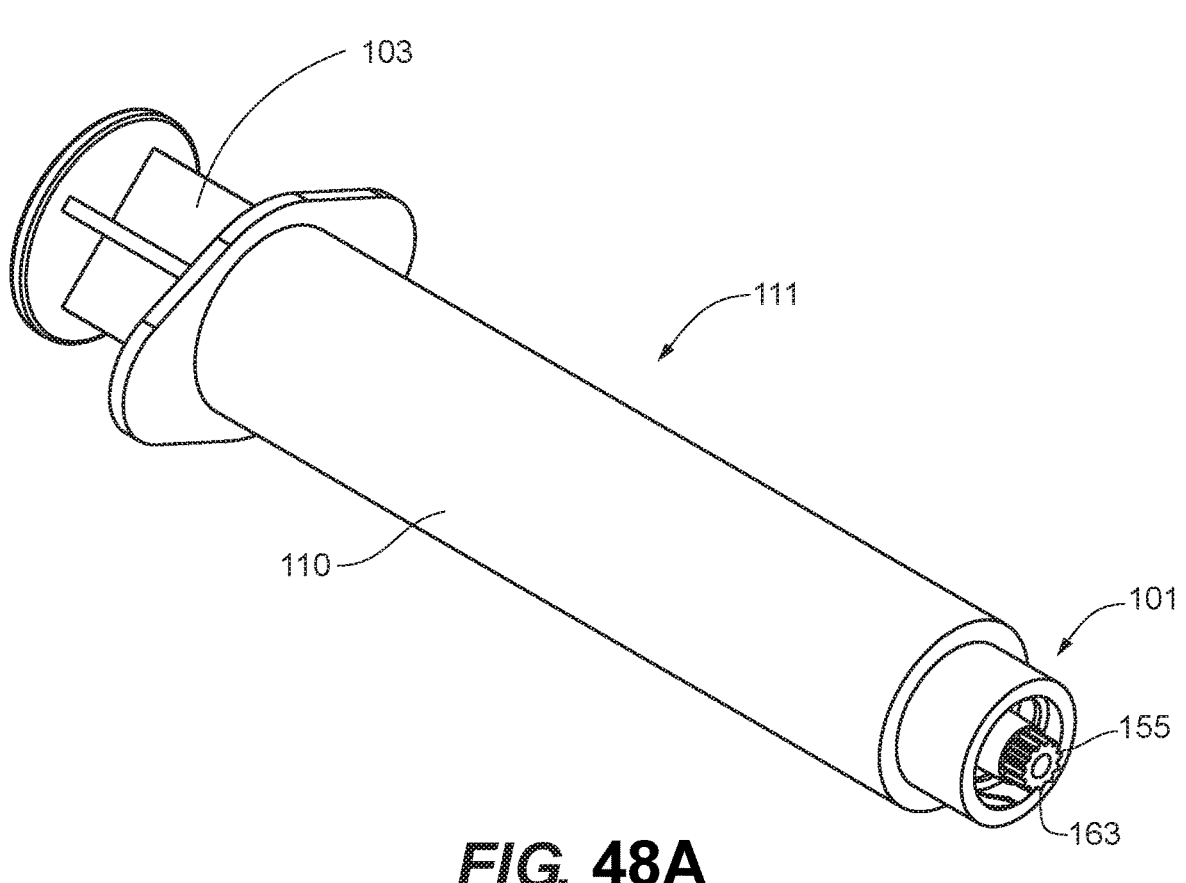
*FIG.* 48A
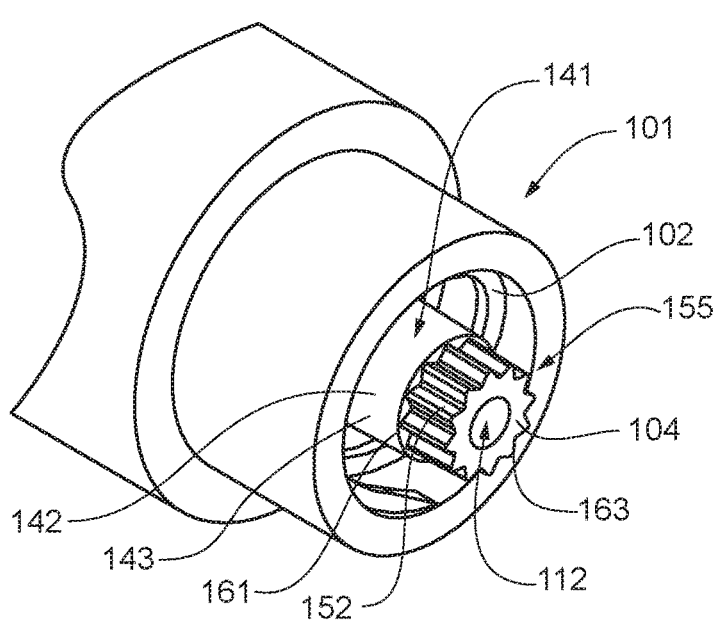
*FIG.* 48B

PROXIMAL DIRECTION          DISTAL DIRECTION

DEVICE FOR DELIVERING AN ANTIMICROBIAL COMPOSITION INTO A MEDICAL DEVICE

This application is a continuation of U.S. patent application Ser. No. 16/558,921, filed Sep. 3, 2019, which is a continuation in part of U.S. patent application Ser. No. 16/553,704, filed Aug. 28, 2019, now U.S. Pat. No. 11,400, 195, issued Aug. 2, 2022, which is a continuation in part of Ser. No. 16/449,180, filed Jun. 21, 2019, which is a continuation in part of Ser. No. 16/447,671, filed Jun. 20, 2019, which is a continuation in part of Ser. No. 16/444,486, filed Jun. 18, 2019, which is a continuation in part of U.S. patent application Ser. No. 16/404,378, filed May 6, 2019, now U.S. Pat. No. 10,525,250, issued Jan. 7, 2020, which claims the benefit of U.S. Provisional Application No. 62/756,967, filed Nov. 7, 2018, the contents of each of which are herein incorporated by reference in their entirety as if fully set forth herein.

FIELD

The present disclosure relates to medical devices, systems, and methods for killing infection-causing organisms and providing in-situ antimicrobial properties to medical devices.

BACKGROUND

Infusion devices, such as catheters and on-catheter devices, are commonly used in providing modern medical care to patients. For example, catheters such as hemodialysis catheters, peritoneal dialysis catheters, peripherally inserted central catheters, midline catheters and drainage catheters are all commonly used in providing modern medical care to patients.

Other infusion devices used in providing medical care include needleless connectors, intravenous (IV) administration sets, peritoneal dialysis lines, transfer sets, syringes, valves and filters. These infusion devices are useful for treating various medical conditions. For example, peritoneal catheters allow patients with renal disease to have waste and fluid removed from their bodies. Thus, catheters and other infusion devices make critical medical care possible and are often essential to providing improved health care outcomes.

However, long-term use of catheters has a serious drawback in that a significant percentage of catheters fail due to infection, resulting in elevated mortality rates and significantly increased healthcare costs associated with treatment. Furthermore, infections are a leading cause of death in the United States, and many of those infections are attributable to infusion devices.

The mortality rate associated with such infections is considerable. Therefore, a need exists for a manner to reduce infections relating from the use of infusion devices.

SUMMARY

Infection-causing organisms are ever present in the environment; they live on patients' skin and can survive and be transmitted in air and water. Conventional medical device connectors and caps, such as male and female connectors with tapered luers, contain a threaded region along with a tapered sealing region, such as an overlapping sealing region of the tapered portions of male and female connectors. The overlapping sealing regions seal fluid inside the medical device and keep air and organisms out. However, our testing shows that organisms can still migrate through the threaded region and penetrate a portion of the way into the sealing region. This results in organisms being present along the walls of the tapered portions of the male and female luers within a thin interstitial space of the sealing region. When the male and female connectors are separated from one another, some organisms can remain on the walls of the male and female connectors, including on tapered portions of male luer and female luer of the male and female connectors that previously formed a seal. The next time a connection is made, some of the organisms on the wall of the female luer can be pushed past the sealing surface and into the fluid path (during insertion of the male luer into the female luer). Once organisms are in the fluid path they can multiply, spread, and cause an infection.

The walls of the male luer and female luer are typically tapered, or at least partially tapered, and may also become contaminated by airborne organisms landing on the surface or through touch contamination. Upon inserting the male luer into the female luer the organisms can be pushed into the fluid path where they can also multiply, spread, and cause an infection.

A catheter and other infusion devices are generally a tubular construction, thus catheters can be characterized as a "medical tube". Similarly, other infusion devices can also be characterized as "medical tubes."

In certain aspects of the subject matter described herein, the distal end of the male luer, as well as intermediate portions (portions between the distal and proximal ends) of the male luer, contain an antimicrobial composition. As used herein, the terms "proximal end" and "distal end" are used to refer to the relative positions on an article. With regard to a catheter, for example, the proximal end is the end closest to a person servicing the catheter female connector, while the distal end is closest to a patient. For example, the distal end of a hemodialysis catheter and/or a peritoneal dialysis catheter will be inside a patient, while the proximal end will be outside the patient and have a female luer on a female connector. Similarly, the proximal end of a male cap or connector containing a male luer will be outside of the female connector when coupled to the female connector, while the distal end of the male cap or connector will be inside the female connector when coupled to the female connector. As will be discussed later, FIGS. 2 and 3A show directional arrows depicting the distal direction and the proximal direction (an intermediate location would be between the distal and proximal directions). FIG. 3A further shows a male cap 30 with the proximal and distal ends of the cap labeled. Thus "proximal" and "distal" are relative terms, showing the position relative to the patient and ends of a device.

The present disclosure is directed, in part, to infusion devices comprising a coupling, the coupling typically comprising both a male connector or cap and a female connector. In certain embodiments, the male connector will form a fluid tight seal with a female connector that complies with International Standard ISO 80369-7 Connectors for intravascular or hypodermic applications.

As used herein, the term "female connector" is used to refer to portions of a medical device containing a female connector, and the female connector generally includes a truncated conical taper referred to herein as the "female luer". For example and without limitation, the medical device can be an infusion device, a catheter including an infusion catheter, a peritoneal catheter, a female luer, and the like. The truncated conical taper forming the female luer typically has a tapered surface. Alternatively, the female connector can be comprised of a different sealing means, such as the silicone septum of the needleless connector. The female connector also includes immediately surrounding elements, such as a threaded outer portion. The term "female connector" as used herein is also sometimes referred to interchangeably in the medical field as a "female connector", "adapter", "hub", and "fitting" when describing an element containing a female luer. As used herein, the terms "male connector" and "male cap" are used to refer to connectors having a sealing extension called a male luer, and this male luer generally has a tapered surface (although in some implementations only parts of that male luer will be tapered). A male connector has a fluid flow path through it (along its axis), while a male cap is sealed and does not have a fluid flow path through a fluid flow path running through the male connector. Thus, a male connector is meant to allow fluid flow through it while a male cap is meant to while a male cap is meant to form a fluid-tight seal and prevent fluid flow out of a medical device having a female connector. In many implementations the male connector and cap will have similar or identical internal geometries, other than a central conduit for fluid flow, and in this disclosure the term "connector" is therefore sometimes used to refer to both a connector with a fluid path through it and a cap that does not have a fluid flow path through it. When describing a specific embodiment, the term "connector" or "cap" may be used to describe a specific embodiment, but this is generally not meant to be limiting.

When describing a mated pair of devices, such as a female connector combined with a male connector, the term "coupling" is used herein. Alternatively, the female connector can be combined with a male cap, which is also a "coupling" as used herein. In summary, as used herein a coupling is a female connector combined with either a male connector or a male cap. A female connector in turn is a portion of a medical device, and the female connector contains a cavity or volume known as the female luer. This cavity or volume known as the female luer typically has a tapered interior surface, but the female connector may also use other sealing means, such as the silicone septum of a needleless connector. The male connector and male cap each include a sealing extension called a male luer that fits within a female luer. The male luer typically has a tapered outer sealing surface. A seal is formed when the tapered surface of the male luer on the male connector or cap contacts the tapered surface of the female luer of the female connector. When these tapered surfaces are in contact with one another the female connector and male connector or cap combine to form a coupling. This coupling can allow flow between medical devices (such as when a female connector and male connector combine) or prevent flow (such as when a female connector and male cap combine). In both cases it is highly desirable to have the seal between the female and male luers be constructed so as to form a fluid tight seal and prevent ingress of microbes, such as bacteria and fungi.

In certain implementations described herein, the male luer of the male connector or cap delivers an antimicrobial composition to the female luer of the female connector.

In one embodiment the male luer has a distal tip near its distal end, the distal tip surface containing an antimicrobial composition. In certain implementations the male luer comprises a recess in the intermediate portion of its tapered outer sealing surface (between the proximal and distal ends of the tapered outer surface, but still on the tapered portion of the male luer), the recessed surface containing an antimicrobial composition. In certain implementations the male luer comprises a distal recessed portion (at the distal end of the male luer) and an intermediate recessed portion, with both recessed surfaces containing an antimicrobial composition. In certain implementations the male luer comprises a flat end face at its distal end. In certain implementations the male luer comprises an antimicrobial coating at the end face region. In certain implementations the male luer comprises an antimicrobial coating at a distal tip region.

Some examples of the technology herein provide a device for delivering an antimicrobial composition into a medical device, and the device comprises a male connector having a male tapered surface, where the male connector further includes a distal tip having a distal end; the distal tip having a recess surface proximal to the distal end, wherein the recess surface is radially inward of a line of taper extending along, and distal of, the male tapered surface at a first taper angle relative to a central longitudinal axis of the male connector; and a water-soluble antimicrobial composition positioned on the recess surface. In any embodiments disclosed herein, the device for delivering an antimicrobial composition can be a cap, a connector, a needleless connector, a tubing set, a peritoneal dialysis transfer set, or a syringe.

In some examples, the male connector further includes a tapered surface distal edge proximal to the distal tip of the male connector, and the tapered surface distal edge is at a distalmost end of the male tapered surface. In some examples, the tapered surface distal edge is proximal to at least part of a recess defined by the recess surface of the male connector. In some examples, the distal tip has a proximal edge abutting the tapered surface distal edge and the tapered surface distal edge has an outer diameter, the proximal edge of the distal tip has an outer diameter, and the outer diameter of the tapered surface distal edge is greater than the outer diameter of the proximal edge of the distal tip. In some examples, the tapered surface distal edge defines a portion of the recess. In some examples, the device includes a fluid flow channel through the male connector. In some examples, the antimicrobial composition comprises chlorhexidine.

In some examples, the device further includes a plurality of blades that extend radially outward from the recess surface. In some examples, the plurality of blades have a plurality of blade surfaces. In some examples, the blade surfaces contain at least a portion of the water-soluble antimicrobial composition. In some examples, the blades are arranged substantially parallel to the central longitudinal axis.

In some examples, the first taper angle is equal to a second taper angle of the recess surface relative to the central longitudinal axis. In some examples, the distal tip defines a recess and the device further includes a proximal trap comprising a cavity at least partially opening into the recess. In some examples, at least a portion of the water-soluble antimicrobial composition is contained within the proximal trap.

Some aspects of the disclosed technology provide a device for delivering an antimicrobial composition into a medical device. The device can include a male connector having a male tapered surface configured to engage a female connector of the infusion device, the female connector having a female tapered surface, such that the male tapered surface engages the female tapered surface to form a fluid-tight seal, where the male connector further includes a conical taper defined in part by the male tapered surface; a distal tip having a recess surface proximal to a distal end of the male connector, the recess surface residing inside the conical taper; a tapered surface distal edge proximal to the distal tip, the tapered surface distal edge having an outer diameter greater than the outer diameter of the distal tip; a fluid flow channel through the male connector; and a water-soluble antimicrobial composition positioned on the recess surface; wherein upon insertion of the male connector into the female connector, an annular cavity is formed between the recess surface and the female tapered surface of the female connector.

In some examples, the device is configured such that the annular cavity defines an annular volume between the male connector and the female connector, and a portion of the antimicrobial composition is dissolvable into a fluid to form a chlorhexidine precipitate on a portion of the female tapered surface. In some examples, the device further includes a plurality of blades that extend radially outward from the recess surface into the annular cavity to at least partially divide the annular cavity.

Further examples of the disclosed technology provide a device for delivering an antimicrobial composition into a medical device. The device has a male connector with a male tapered surface configured to insert into a female connector of a medical device, the female connector having a female tapered surface, such that the male tapered surface engages the female tapered surface to form a fluid-tight seal; and the male connector has a conical taper defined in part by the male tapered surface; a distal tip having an outer diameter that is less than 95 percent of an inner diameter of the female tapered surface at a point radially outward of the distal tip; a recess surface proximal to the distal tip and inside the conical taper; a fluid flow channel through the male connector; and a water-soluble antimicrobial composition positioned on the recess surface; upon insertion of the male connector into the female connector, an annular cavity is formed between the recess surface and the female tapered surface of the female connector, the annular cavity having a proximal end and a distal end, a volume between the proximal end and the distal end, a width measured radially, and a length measured axially; the male tapered surface has a distal edge that at least partially defines the proximal end of the annular cavity, the distal end of the annular cavity is in fluid communication with a fluid lumen of the infusion device, and the width of the annular cavity is less than 50 percent of the length of the annular cavity; and a fluid inside the infusion device at least partially fills the annular cavity, and at least a portion of the antimicrobial composition is dispersed within the fluid in the annular cavity.

In some examples, the distal tip defines a recess, and the device further includes a proximal trap comprising a cavity at least partially opening into the recess. In some examples, the device further includes a plurality of blades that extend radially outward from the recess surface into the annular cavity to at least partially divide the annular cavity.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

BRIEF DESCRIPTION OF THE DRAWINGS

The device may be more completely understood in connection with the following drawings, in which:

6

Figure 1:
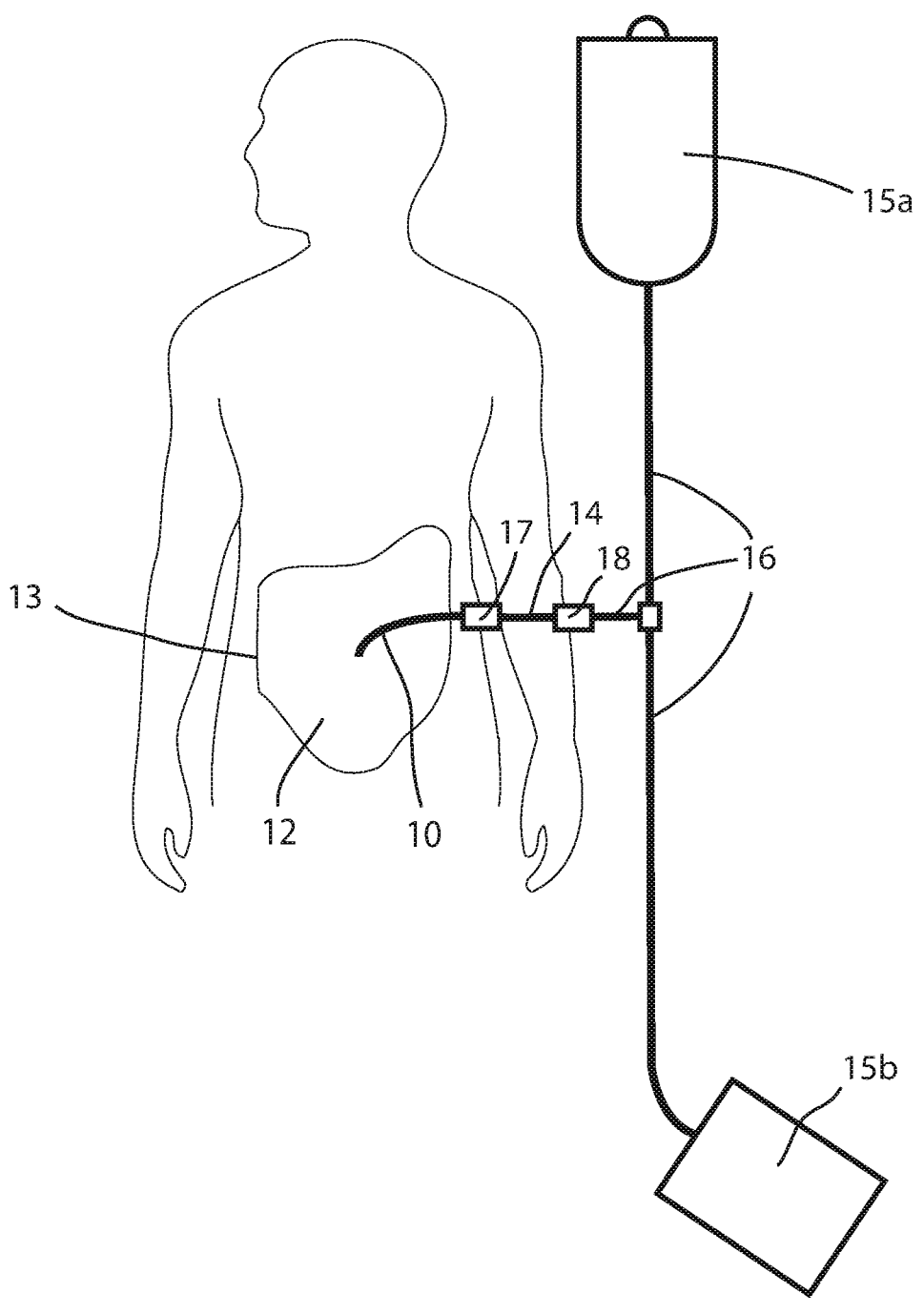

FIG. 1 is a schematic diagram of a patient undergoing peritoneal dialysis, showing a peritoneal catheter extending into a peritoneal cavity into which a dialysis solution is injected and then removed.

Figure 1A:
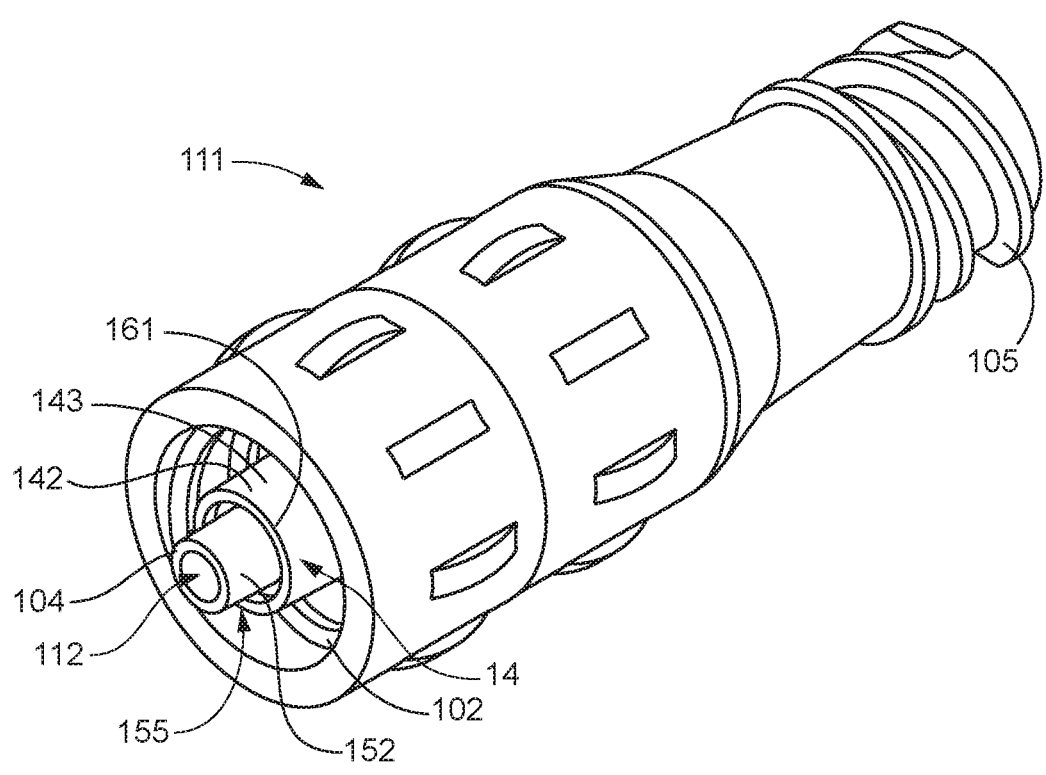

FIG. 1A is a perspective view of a needleless connector according to some examples.

Figure 1B:
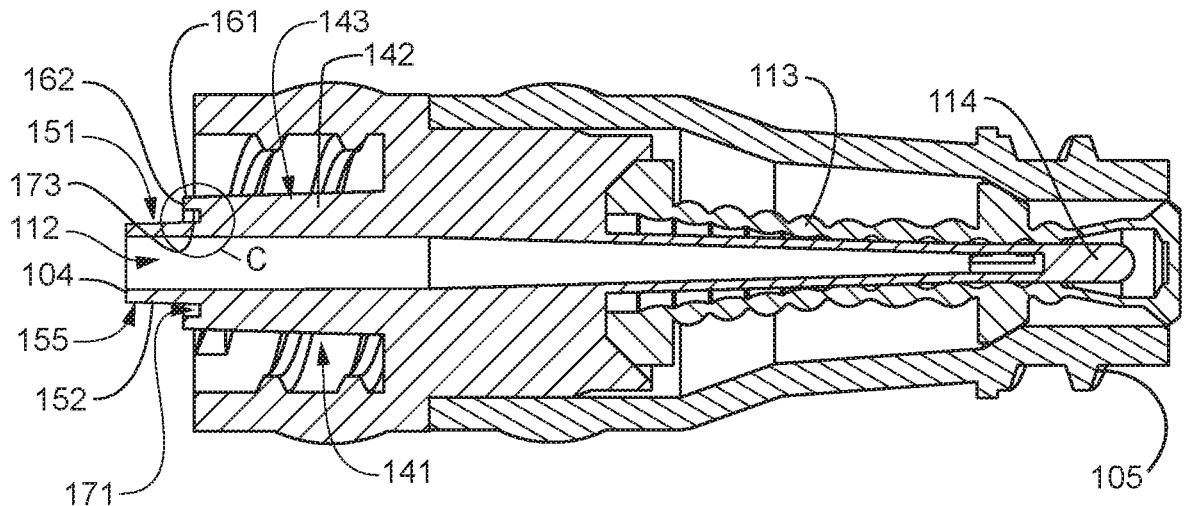

FIG. 1B is a longitudinal cross-sectional view of the needleless connector of FIG. 1A.

Figure 1C:
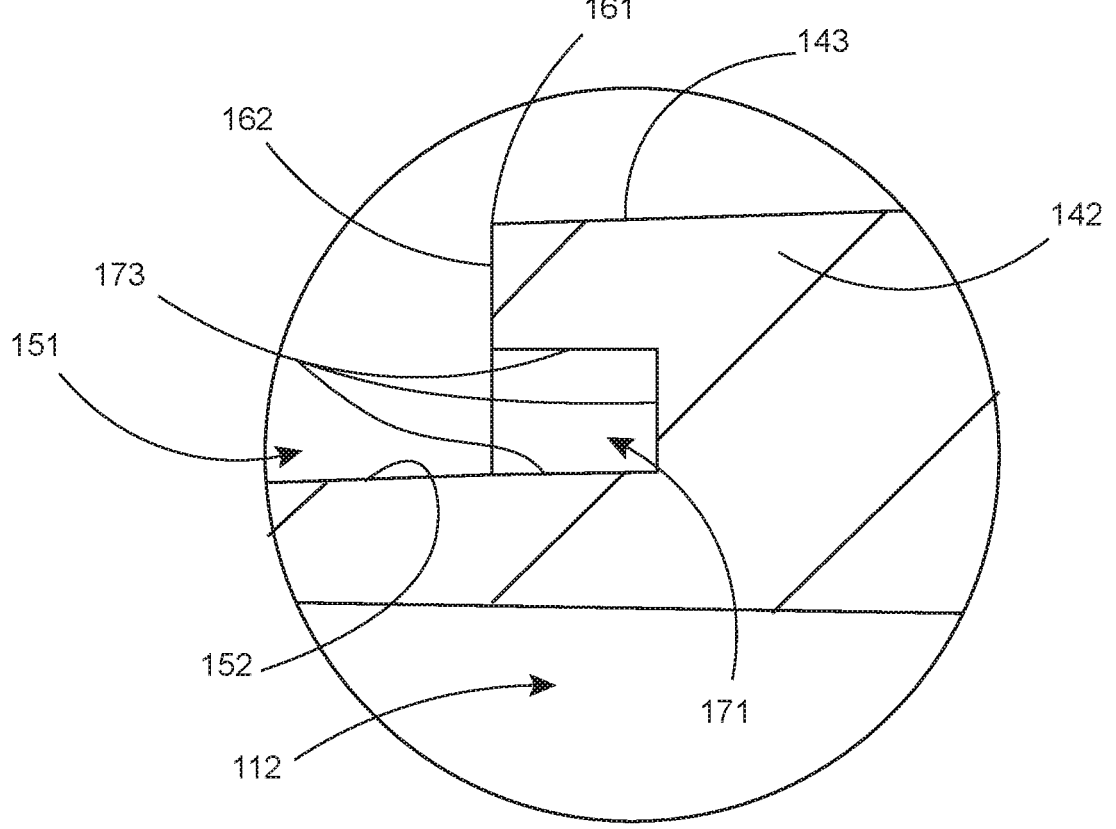

FIG. 1C is an enlarged view of FIG. 1B inside circle C.

Figure 2A:
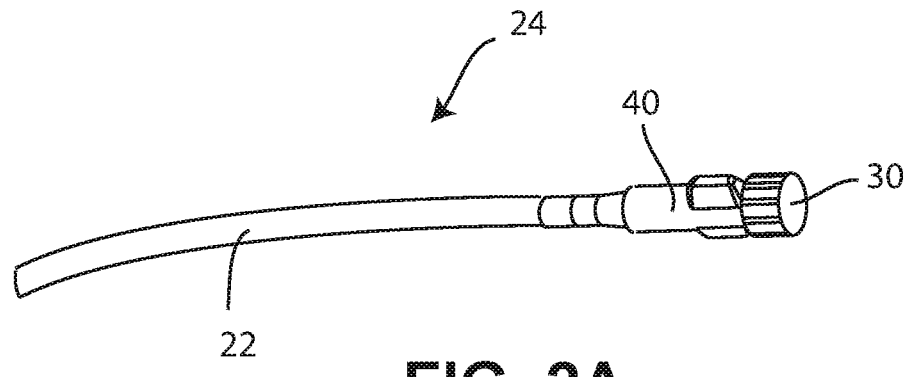

FIG. 2A is a perspective view of a proximal end of a peritoneal catheter with a male cap installed on a female connector.

Figure 2B:
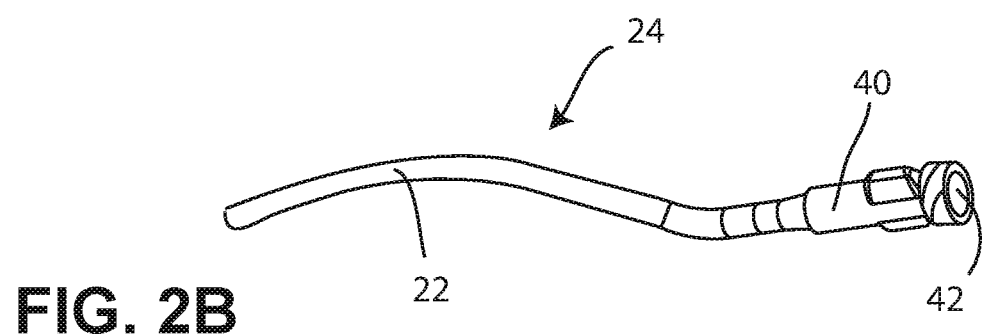

FIG. 2B is a perspective view of the proximal end of the peritoneal catheter of FIG. 2A showing the female connector after the male cap has been removed.

Figure 2C:
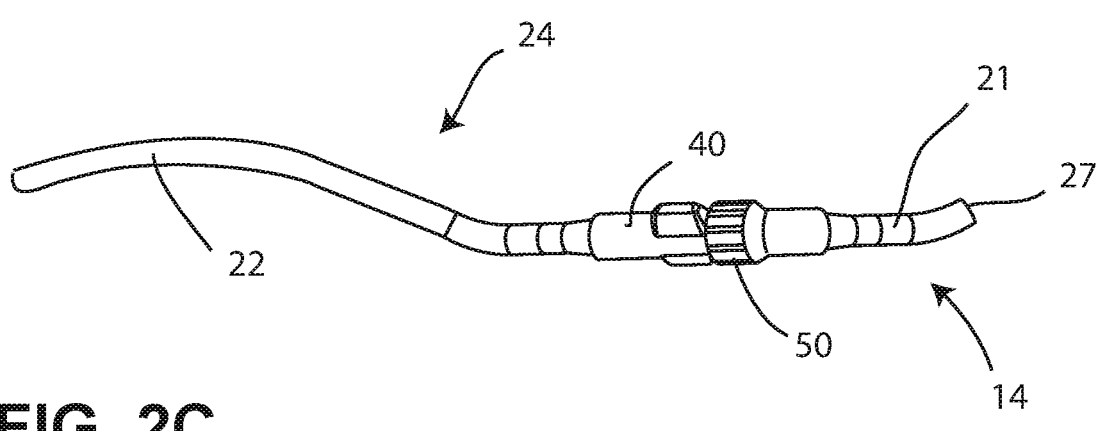

FIG. 2C is a perspective view of the proximal end of the peritoneal catheter of FIG. 2B connected to a transfer set at a coupling formed by the female connector and a male connector.

Figure 3A:
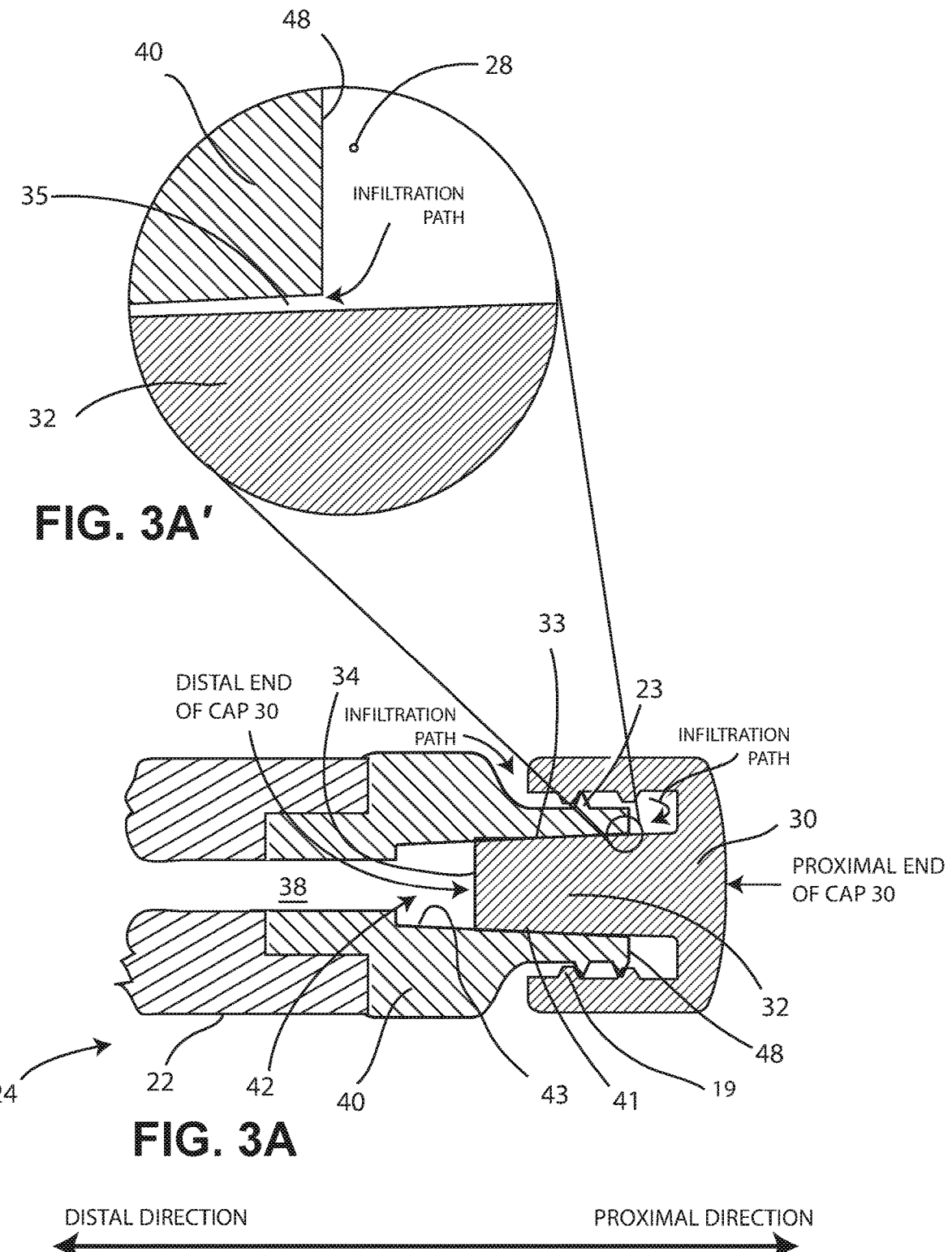

FIG. 3A is a cross-sectional view of a proximal end of a peritoneal catheter with a male cap installed on a female connector.

FIG. 3A' is a closeup cross-sectional view of a portion of the proximal end of the peritoneal catheter and the female connector and the male cap of FIG. 3A.

Figure 3B:
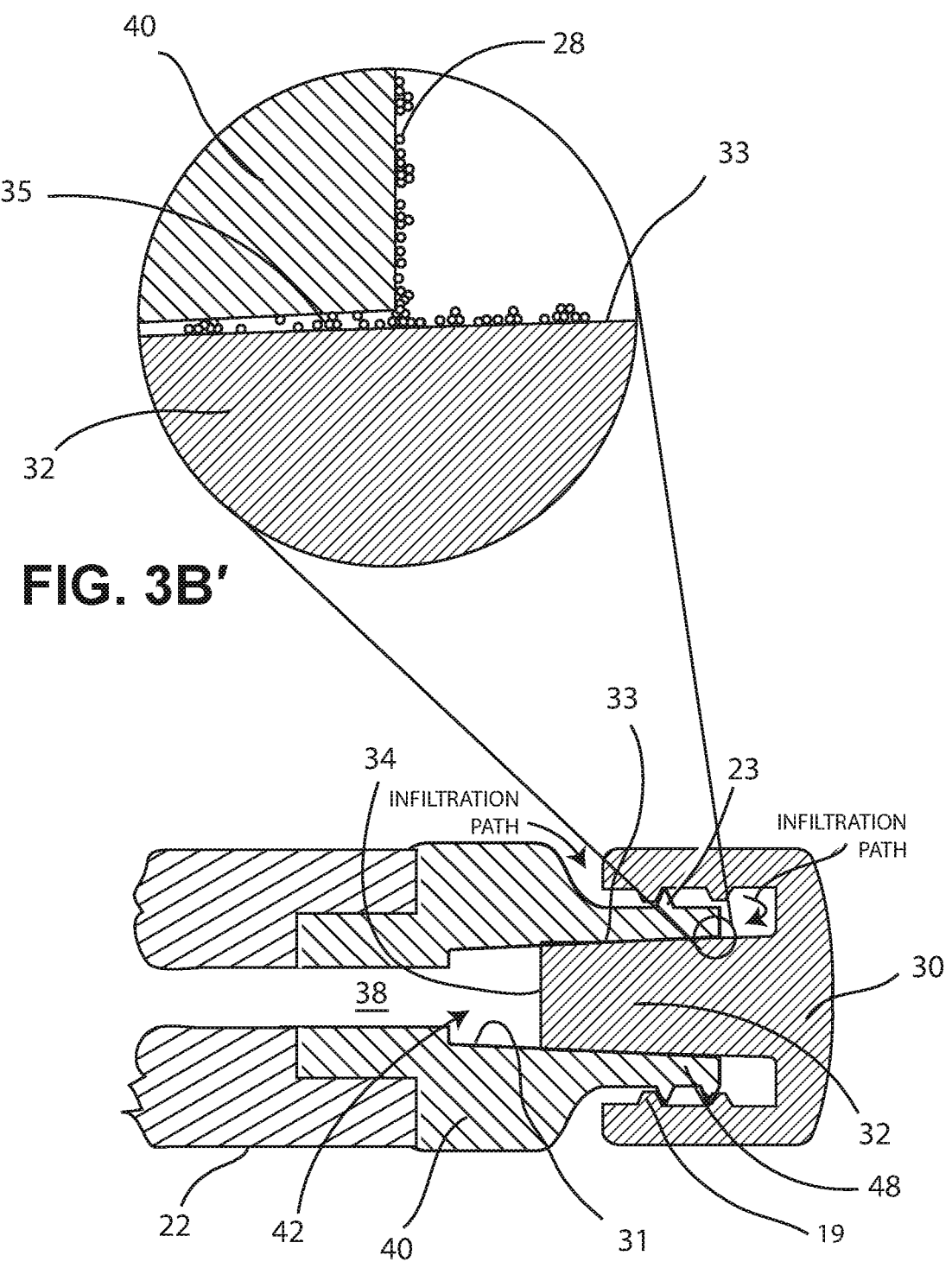

FIG. 3B is a cross-sectional view of the proximal end of the peritoneal catheter with the male cap installed on the female connector of FIG. 3A after microbes have infiltrated along a path.

FIG. 3B' is a closeup cross-sectional view of a portion of the proximal end of the peritoneal catheter, specifically of the female connector, and the male cap of FIG. 3B.

Figure 3C:
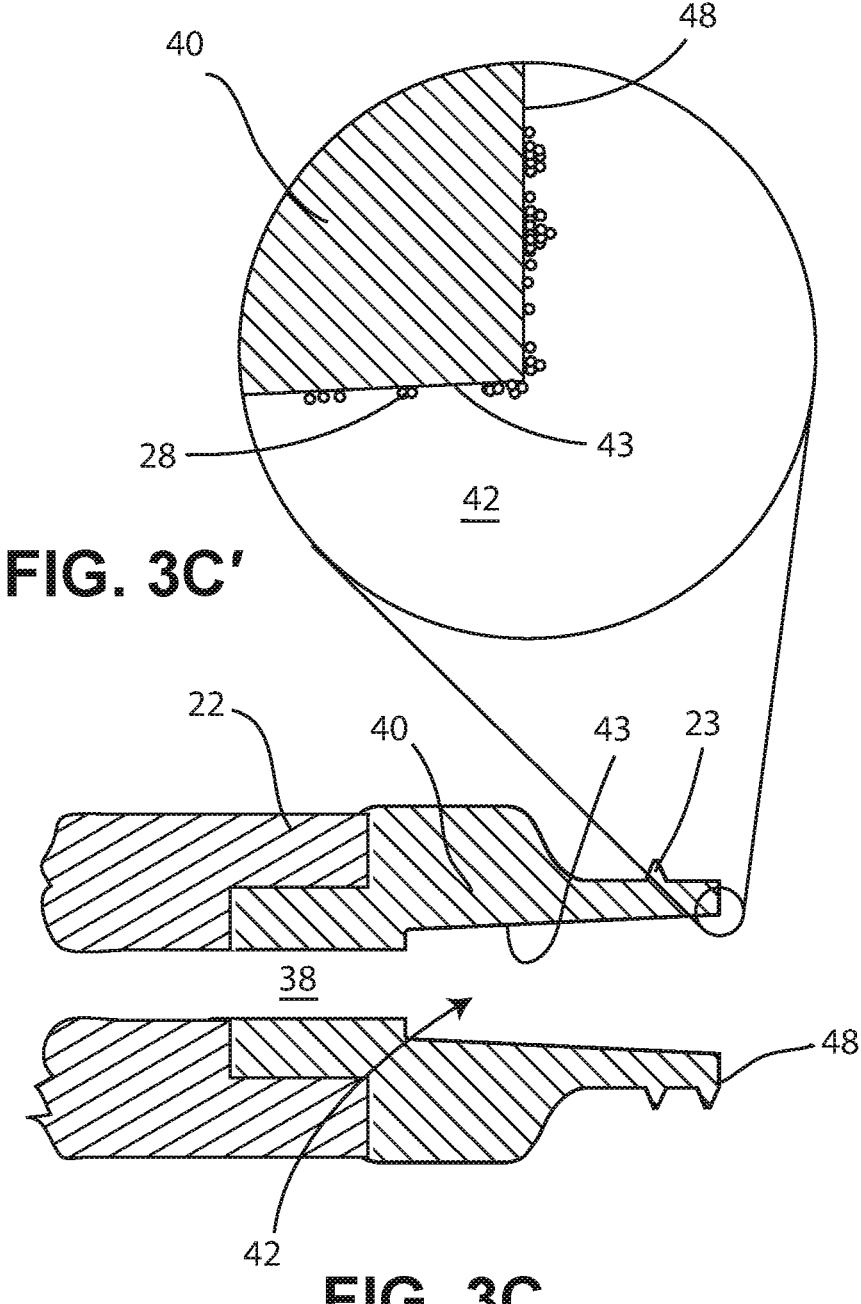

FIG. 3C is a cross-sectional view of the proximal end of the peritoneal catheter, including the female connector, of FIG. 3B with the male cap having been removed.

FIG. 3C' is a closeup cross-sectional view of a portion of the proximal end of the peritoneal catheter, including the female connector, of FIG. 3C.

Figure 3D:
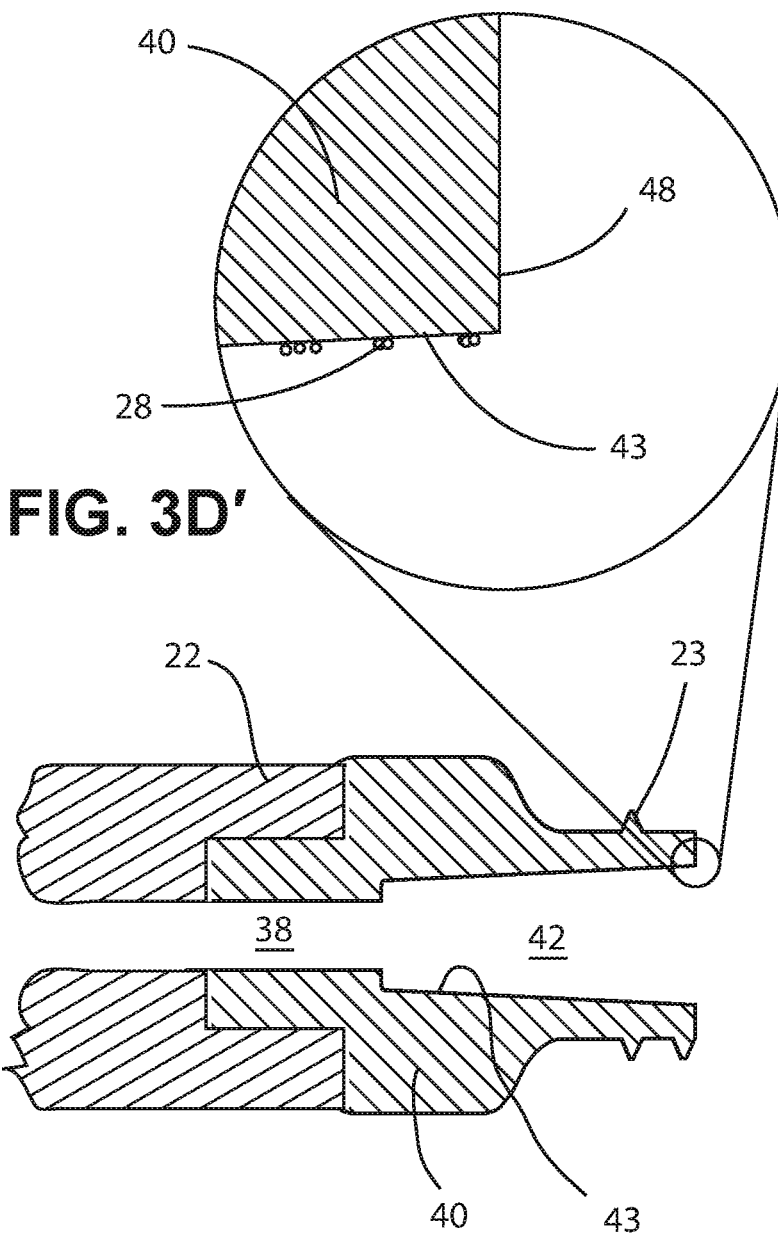

FIG. 3D is a cross-sectional view of the proximal end of the peritoneal catheter, including the female connector, of FIG. 3C after cleaning.

FIG. 3D' is a closeup cross-sectional view of a portion of the proximal end of the peritoneal catheter, including the female connector, of FIG. 3D.

Figure 3E:
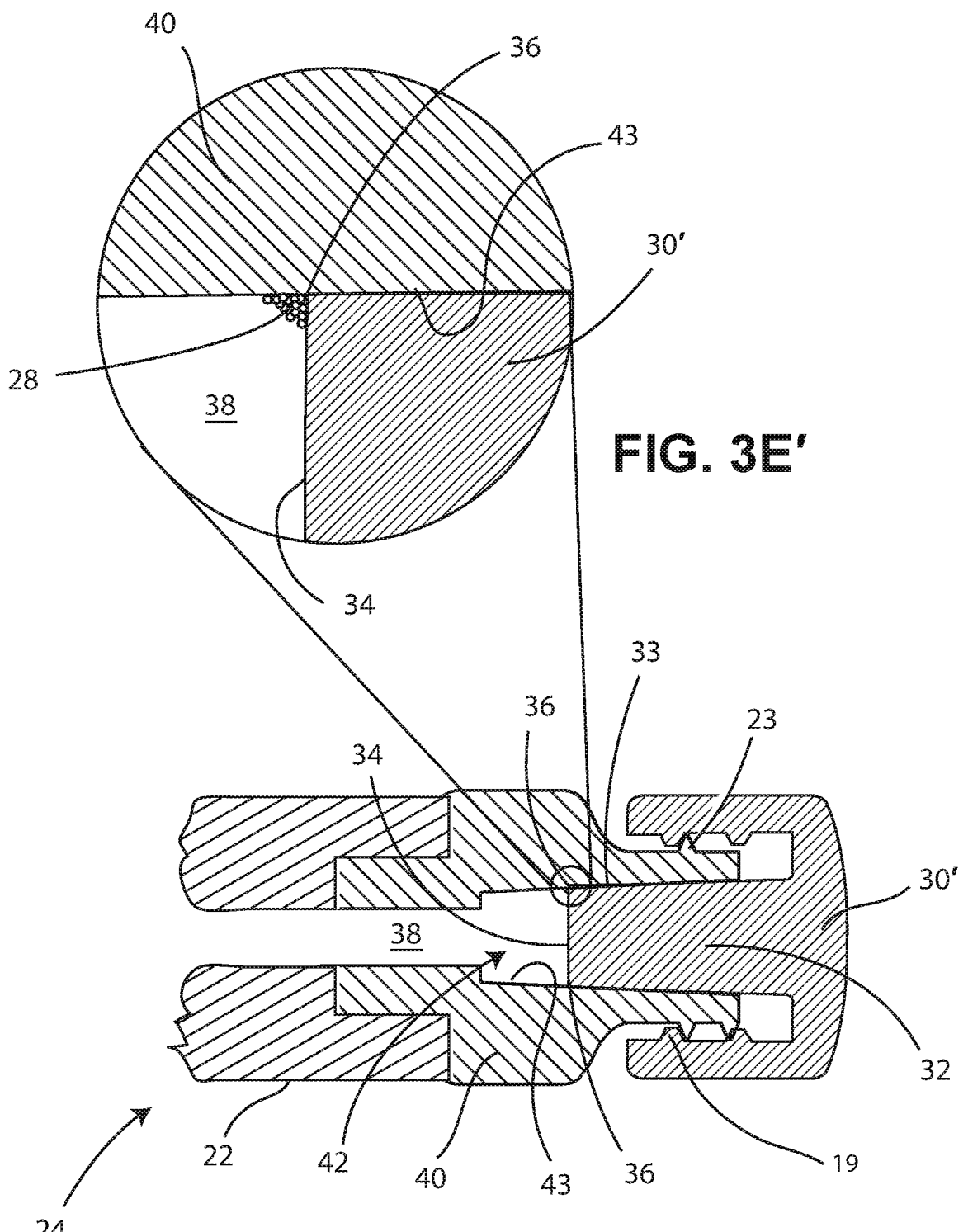

FIG. 3E is a cross-sectional view of the proximal end of the peritoneal catheter of FIG. 3D with a new male cap coupled to the female connector.

FIG. 3E' is a closeup cross-sectional view of a portion of the proximal end of the peritoneal catheter of FIG. 3E, including a male luer of the male cap.

Figure 3F:
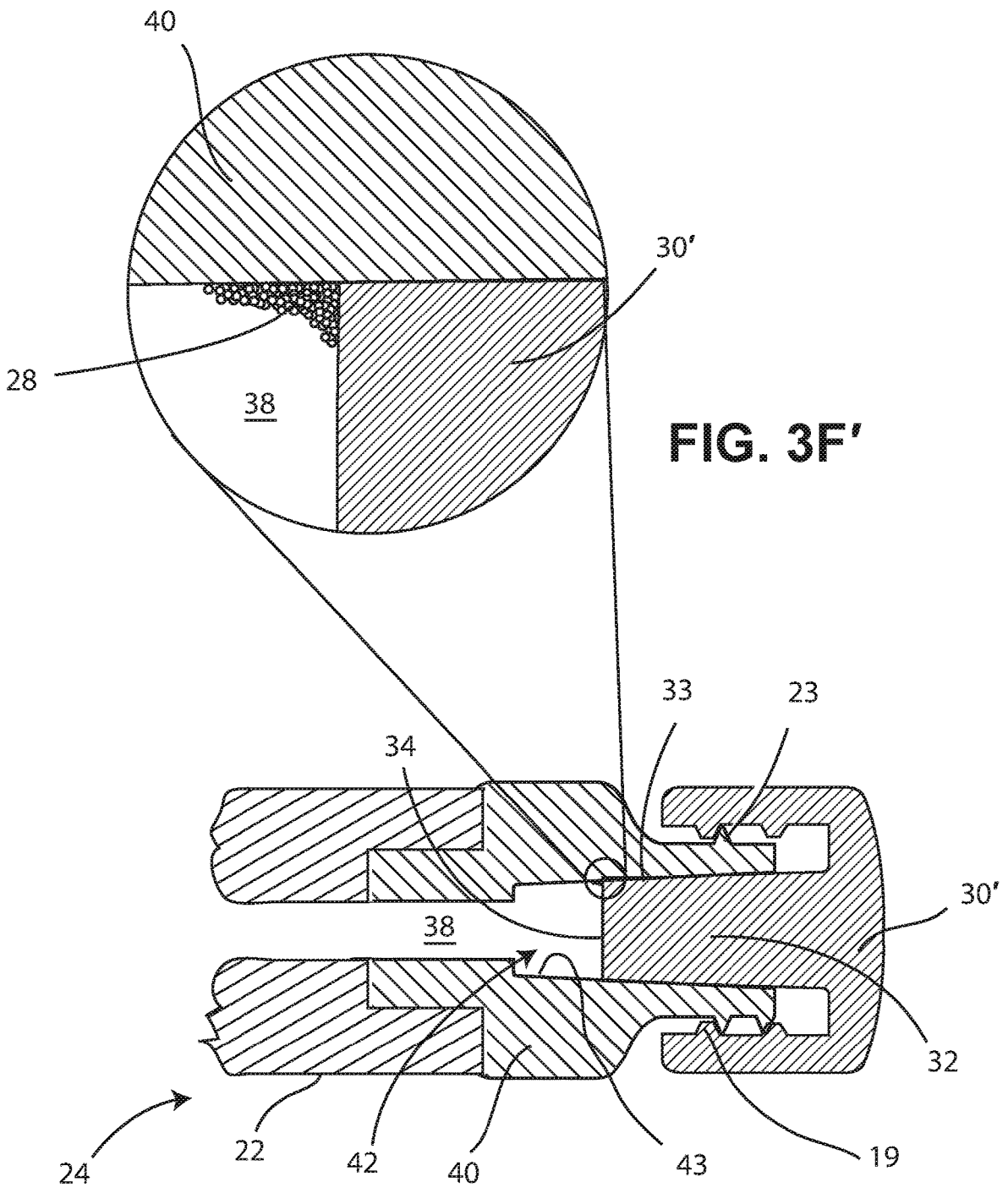

FIG. 3F is a cross-sectional view of the proximal end of the peritoneal catheter with the new male cap installed of FIG. 3E after a period of time.

FIG. 3F' is a closeup cross-sectional view of a portion of the proximal end of the peritoneal catheter with the new male cap installed of FIG. 3F, including the male luer of the male cap.

Figure 4A:
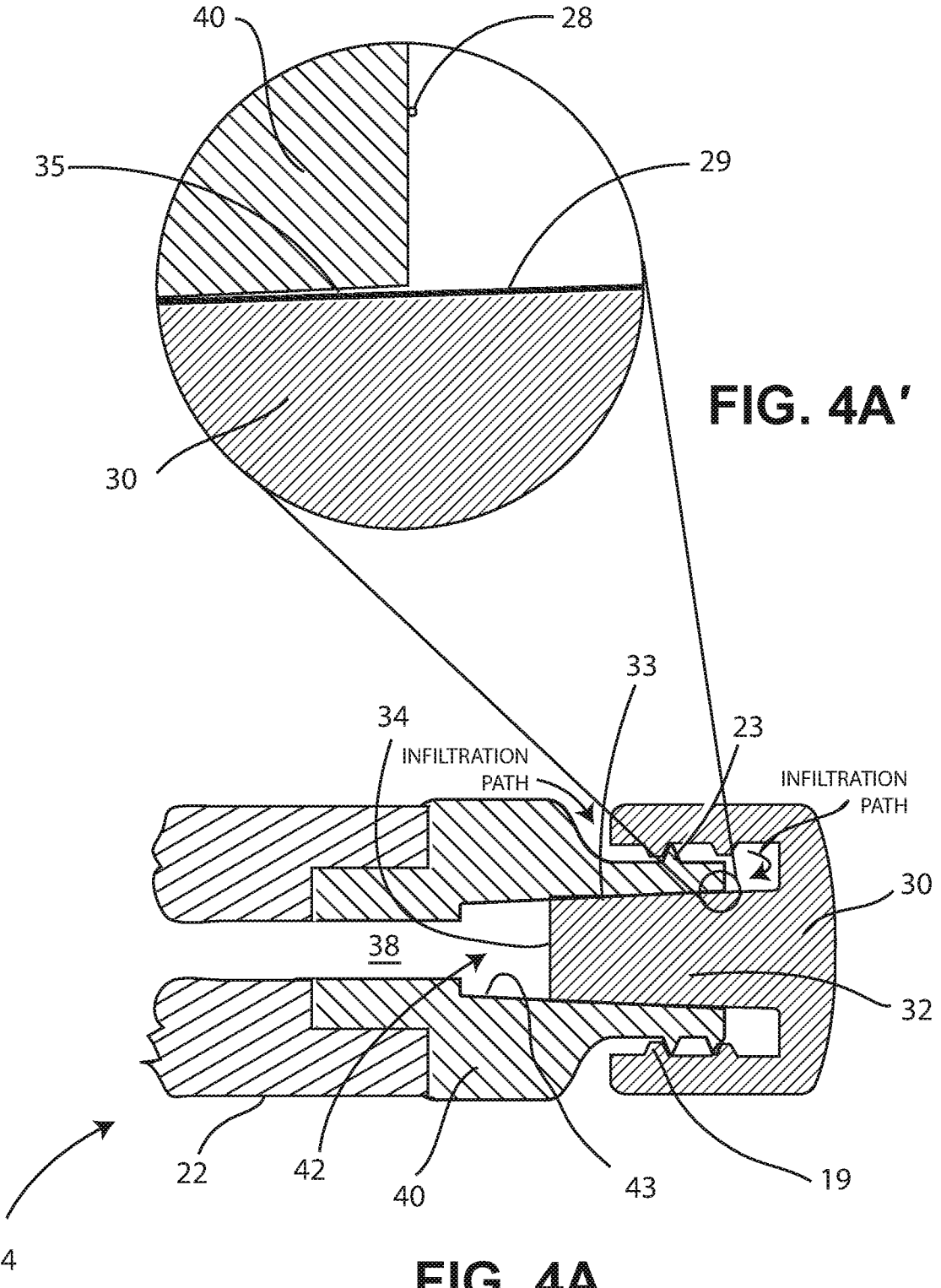

FIG. 4A is a cross-sectional view of a proximal end of a peritoneal catheter with a male cap installed on a female connector, the male cap including a male luer configured for delivery of an antimicrobial agent.

FIG. 4A' is a closeup cross-sectional view of a portion of the proximal end of the peritoneal catheter with the male cap installed on the female connector of FIG. 4A.

Figure 4B:
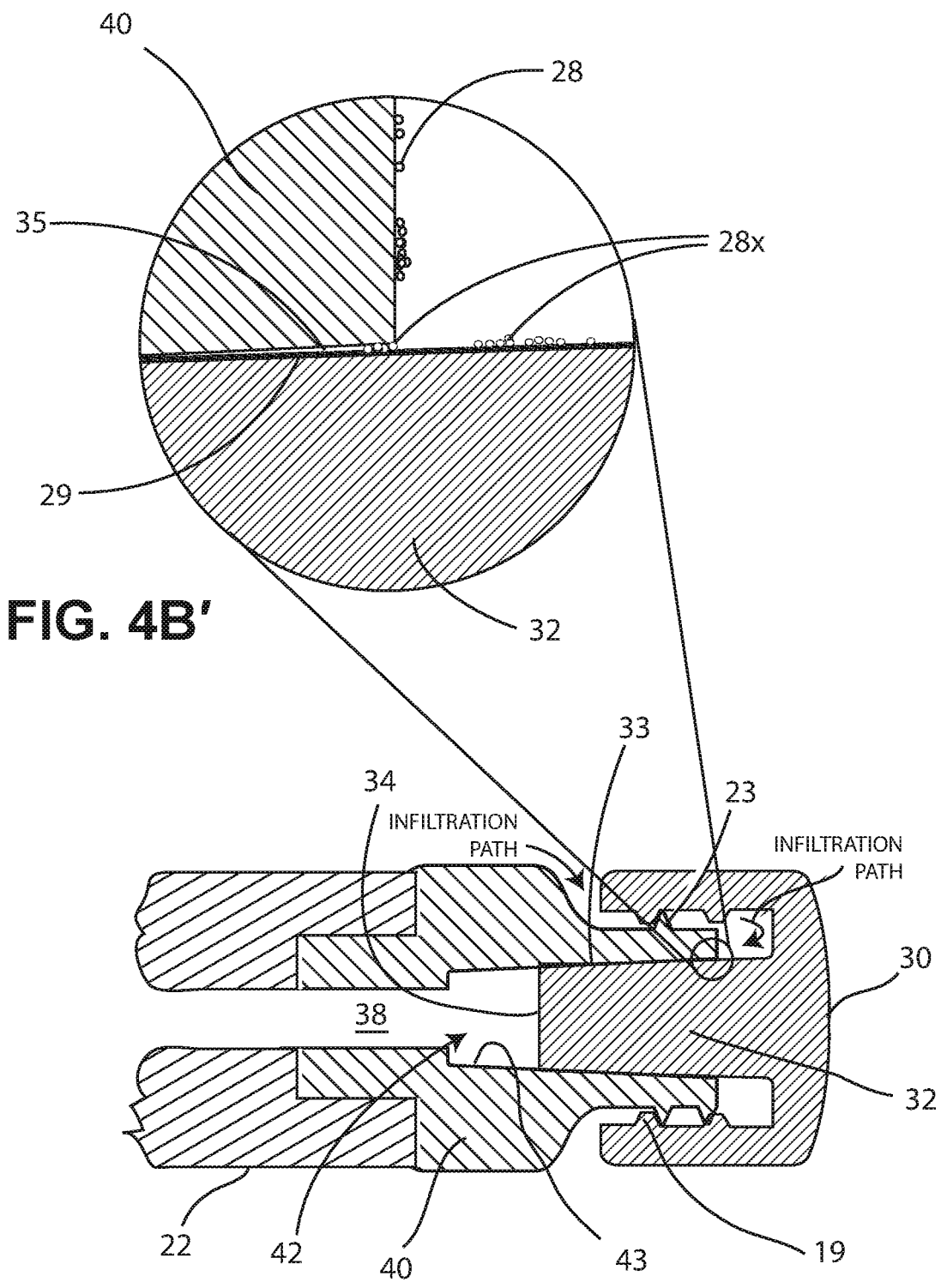

FIG. 4B is a cross-sectional view of the proximal end of the peritoneal catheter, including the female connector, with the male cap installed of FIG. 4A after microbes have infiltrated along a path.

FIG. 4B' is a closeup cross-sectional view of a portion of the proximal end of the peritoneal catheter with the male cap installed of FIG. 4B.

Figure 4C:
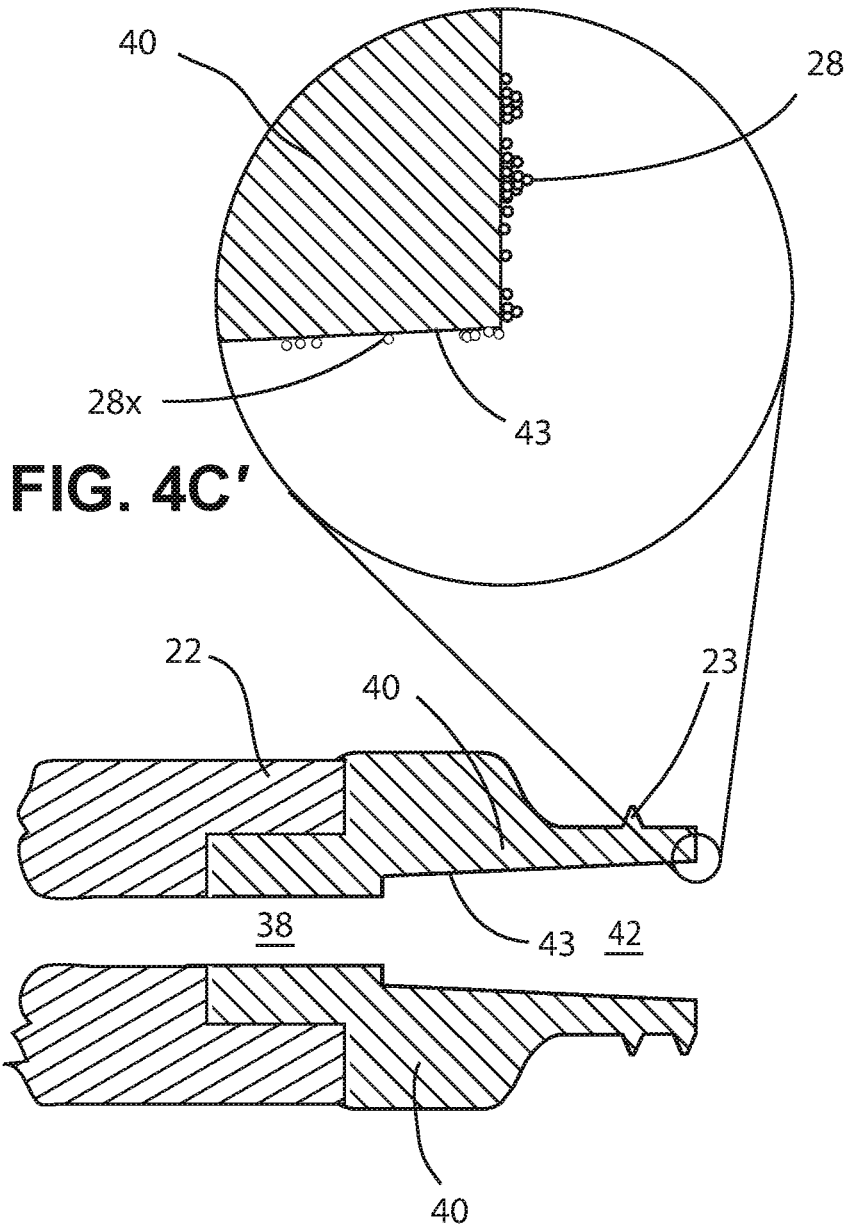

FIG. 4C is a cross-sectional view of the proximal end of the peritoneal catheter, including the female connector, of FIG. 4B with the male cap removed.

FIG. 4C' is a closeup cross-sectional view of a portion of the proximal end of the peritoneal catheter of FIG. 4C.

Figure 4D:
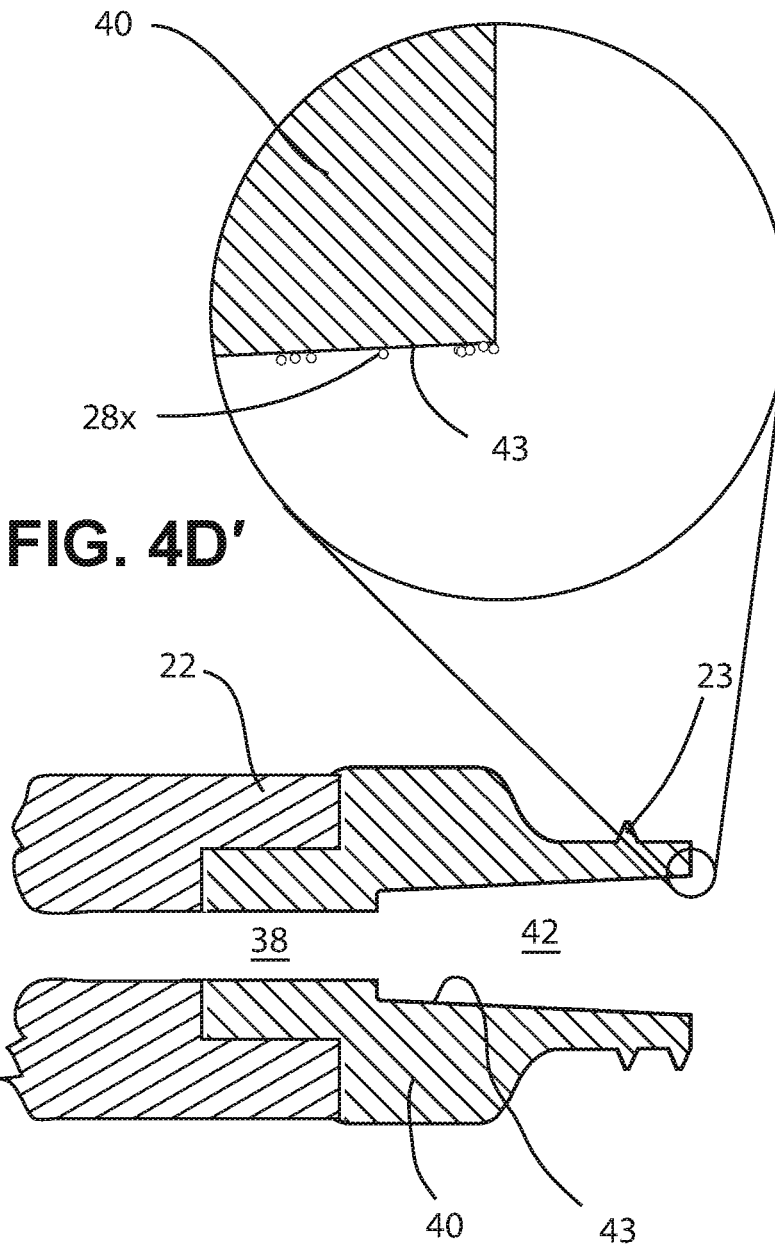

FIG. 4D is a cross-sectional view of the proximal end of the peritoneal catheter of FIG. 4C, including the female connector, after cleaning.

FIG. 4D' is a closeup cross-sectional view of a portion of the proximal end of the peritoneal catheter of FIG. 4D.

Figure 4E:
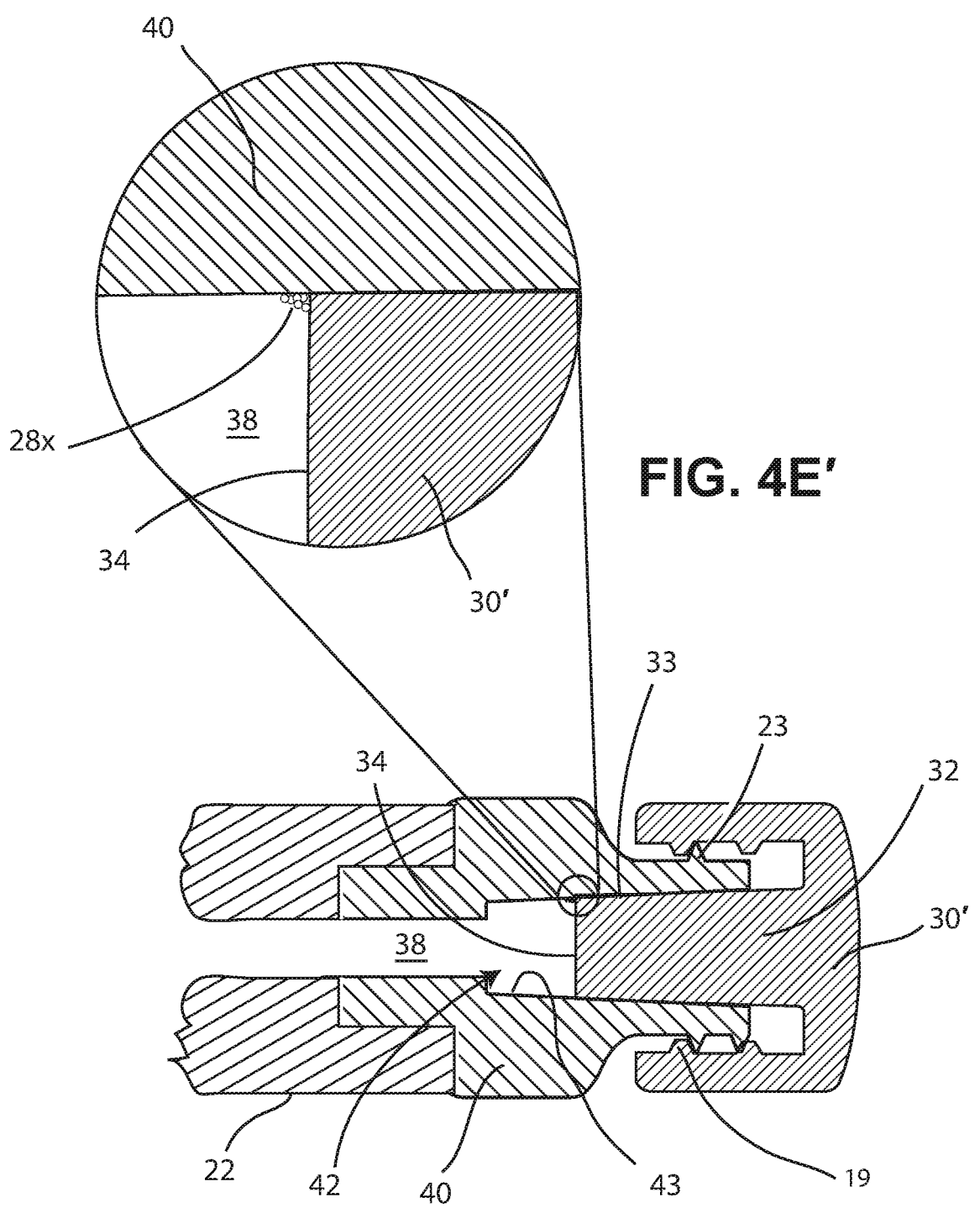

FIG. 4E is a cross-sectional view of the proximal end of the peritoneal catheter of FIG. 4D, including the female connector, with a new male cap coupled to the female connector, the male cap including a male luer configured for delivery of an antimicrobial agent.

FIG. 4E' is a closeup cross-sectional view of a portion of the proximal end of the peritoneal catheter, including the female connector, of FIG. 4E.

Figure 4F:
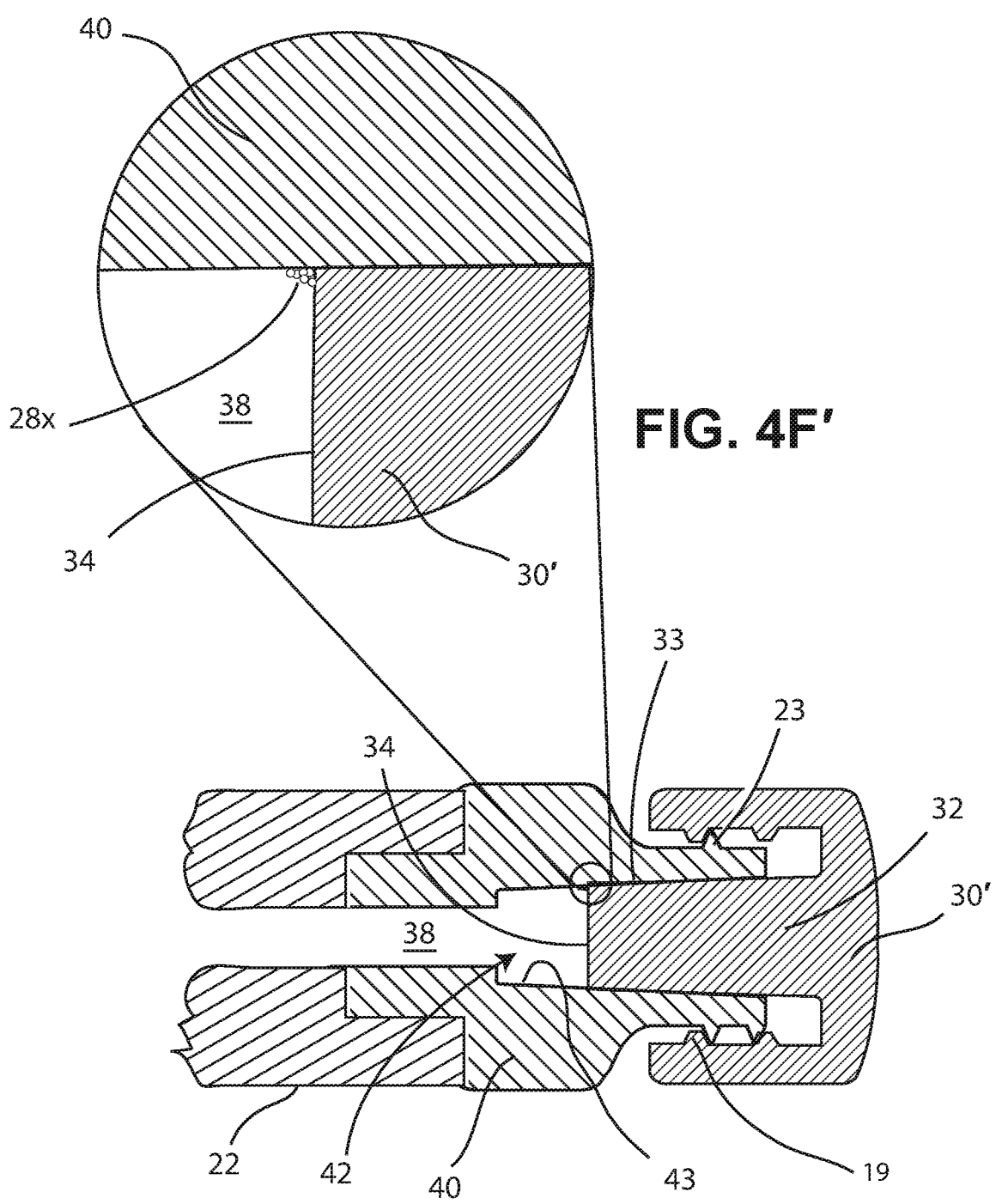

FIG. 4F is a cross-sectional view of the proximal end of the peritoneal catheter with the new male cap installed of FIG. 4E after a period of time.

FIG. 4F' is a closeup cross-sectional view of a portion of the proximal end of the peritoneal catheter with the new male cap installed of FIG. 4F.

Figure 5:
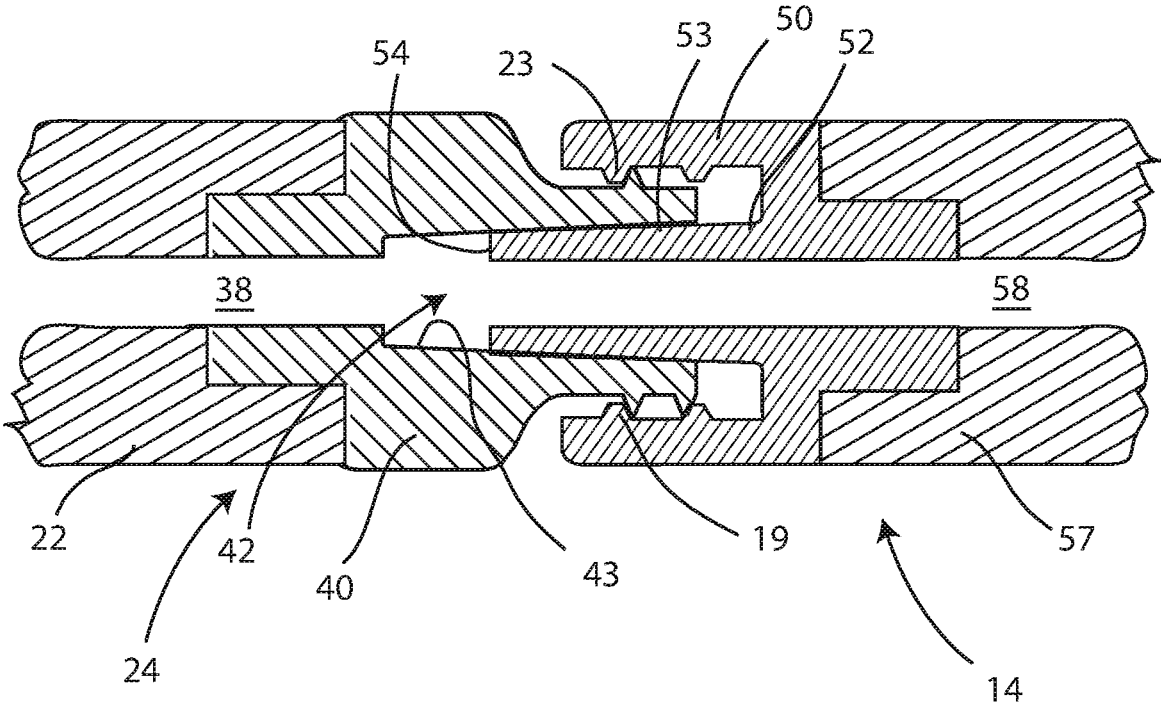

FIG. 5 is a closeup cross-sectional view of a coupling showing a female connector on a proximal end of a peritoneal catheter with a male connector on a distal end of a transfer set.

Figure 6A:
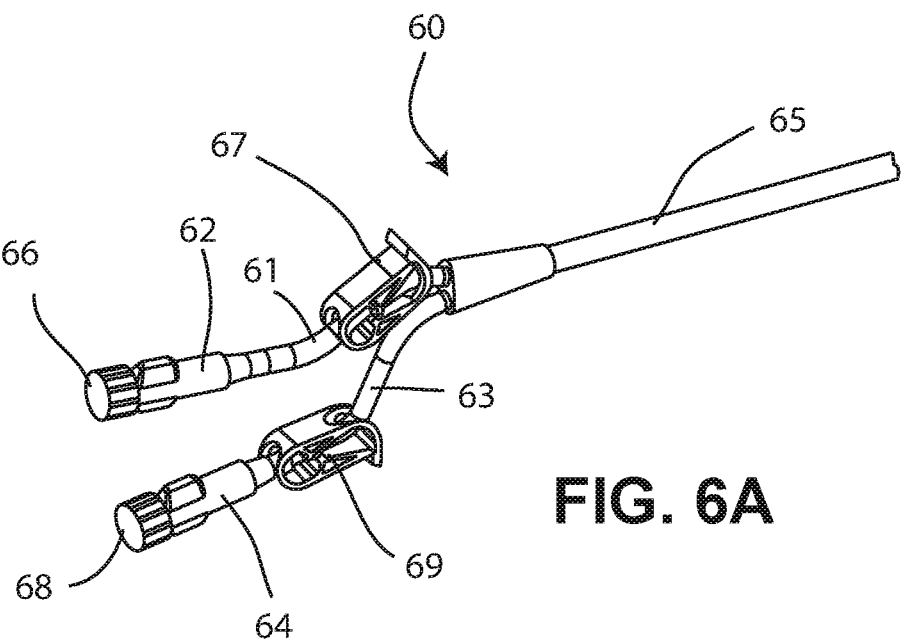

FIG. 6A is a perspective view of a hemodialysis catheter, showing the hemodialysis catheter with two female connectors to which male caps have been coupled.

Figure 6B:
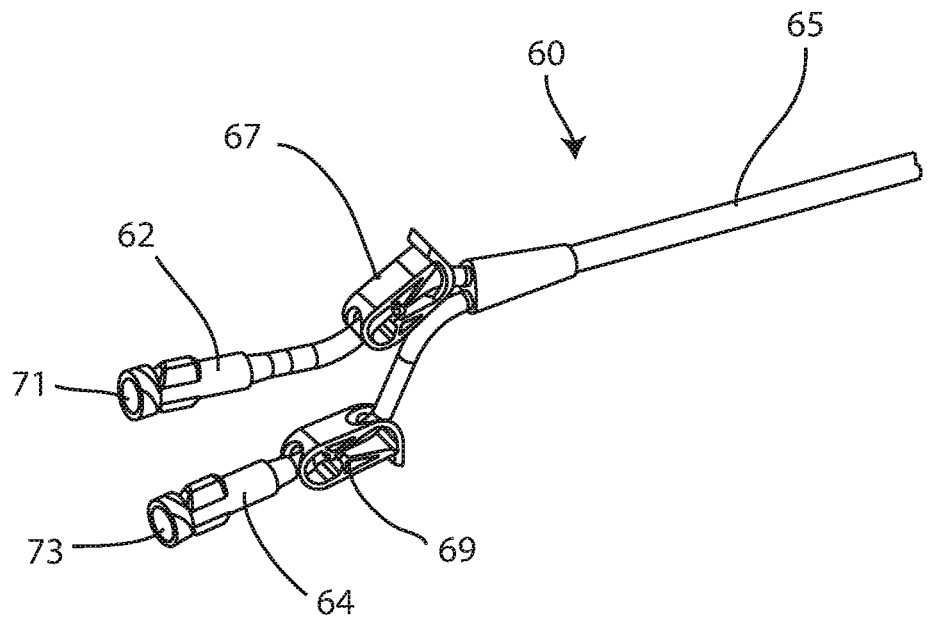

FIG. 6B is a perspective view of the hemodialysis catheter of FIG. 6A, showing the hemodialysis catheter with the two female connectors having the male caps removed.

Figure 7A:
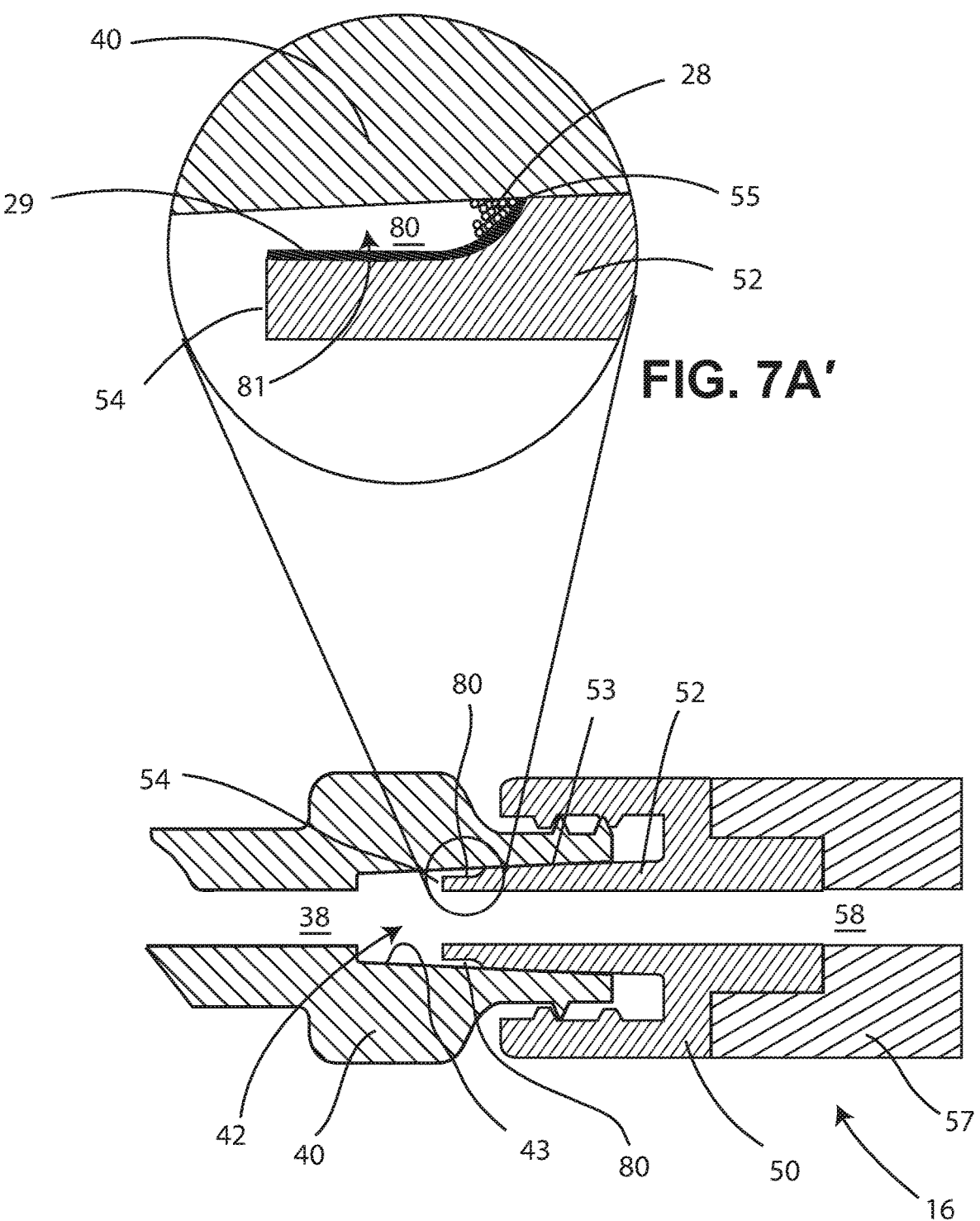

FIG. 7A is a cross-sectional view of a female connector having an infusion set connected, the infusion set comprising a male connector having a male luer including a distal recess configured for delivery of an antimicrobial agent.

Figure 7B:
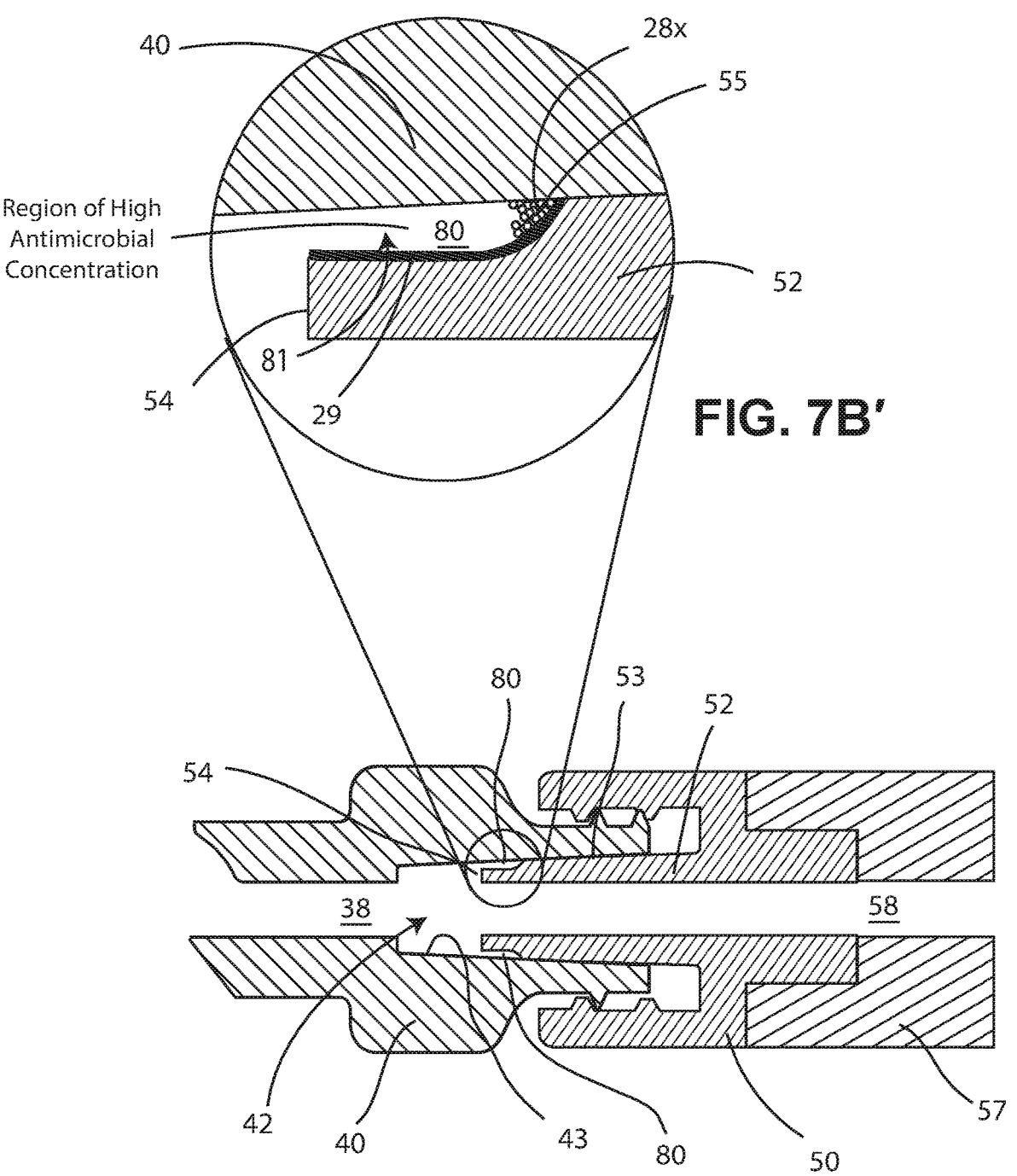

FIG. 7A' is a closeup cross-sectional view of a portion of the female connector having the infusion set coupled to it, the infusion set comprising the male connector having the male luer including the distal recess configured for delivery of the antimicrobial agent of FIG. 7A FIG. 7B is a cross-sectional view of the female connector having the infusion set connected, the infusion set comprising the male luer including the distal recess configured for delivery of the antimicrobial agent of FIG. 7A after a period of time.

FIG. 7B' is a closeup cross-sectional view of a portion of the female connector and the male luer including the distal recess configured for delivery of the antimicrobial agent of FIG. 7B.

Figure 8:
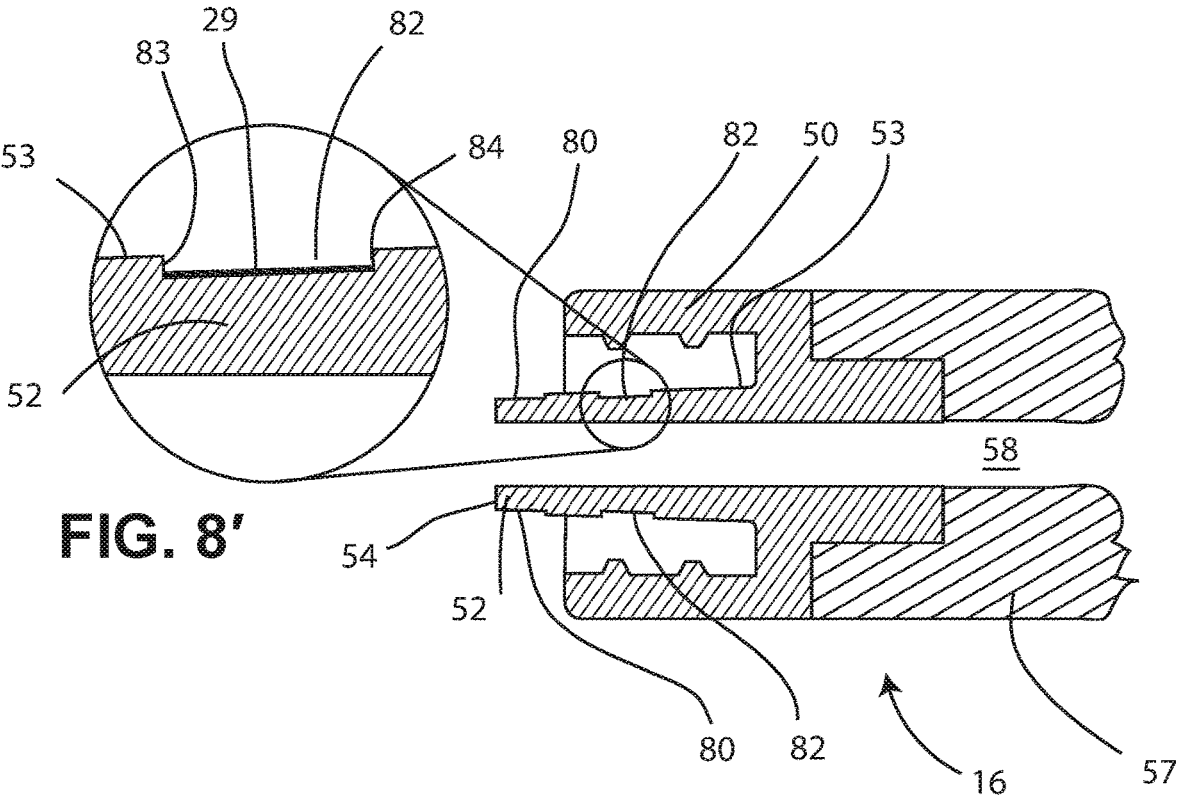

FIG. 8 is a cross-sectional view of an infusion set, the infusion set including a male connector having a tube connected, the male connector including a male luer having a distal recess and an intermediate recess configured for delivery of an antimicrobial agent.

FIG. 8' is a closeup cross-sectional view of the male luer of FIG. 8, showing the intermediate recess configured for delivery of an antimicrobial agent.

Figure 9:
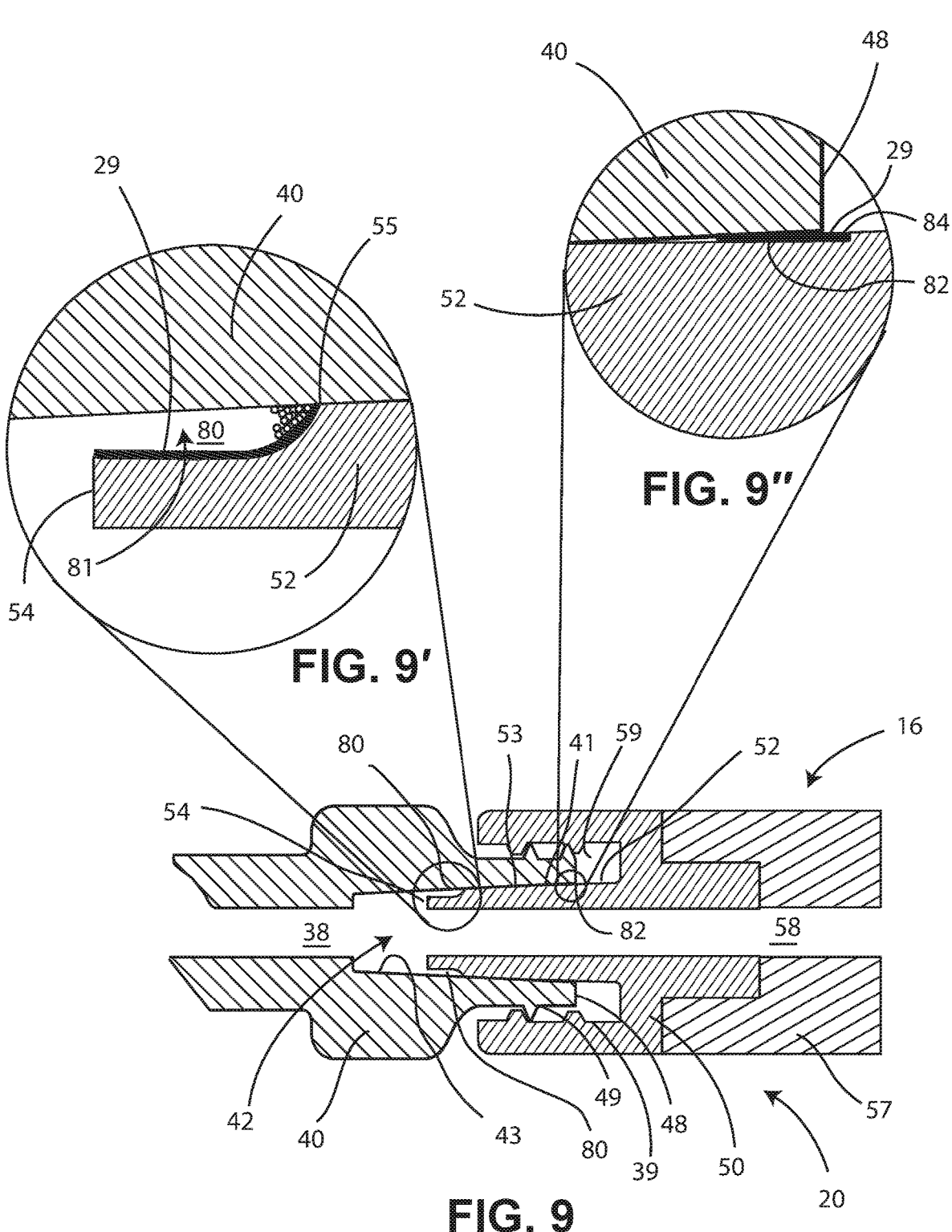

FIG. 9 is a cross-sectional view of a female connector having an infusion device connected, the infusion device comprising a male luer including a distal recess and an intermediate recess, each recess containing an antimicrobial agent and configured for delivery of the antimicrobial agent.

FIG. 9' is a closeup cross-sectional view of the female connector and the male luer of FIG. 9 showing an enlargement of the distal recess of the male luer.

FIG. 9" is a closeup cross-sectional view of the female connector and the male luer of FIG. 9 showing an enlargement of a proximal end of the female connector and the intermediate recess of the male luer.

Figure 10:
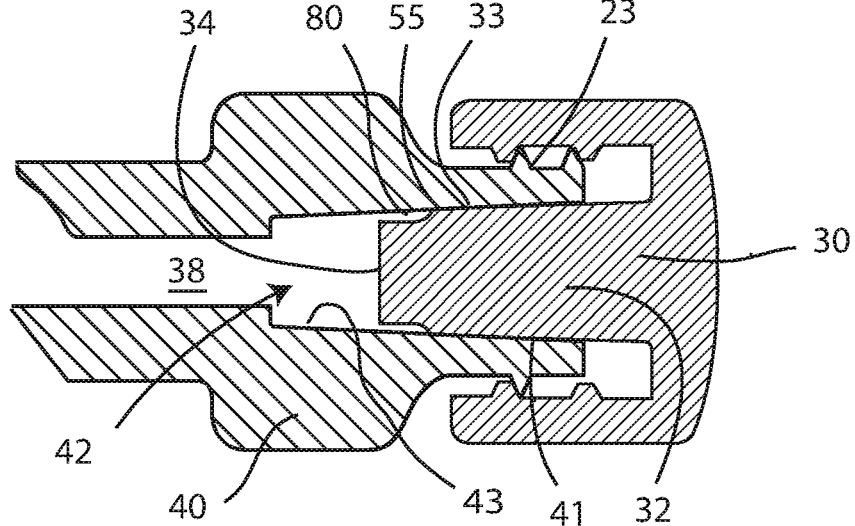

FIG. 10 is a cross-sectional view of a female connector having a male cap installed, the male cap comprising a male luer including a distal recess containing an antimicrobial agent and configured for delivery of the antimicrobial agent.

Figure 11:
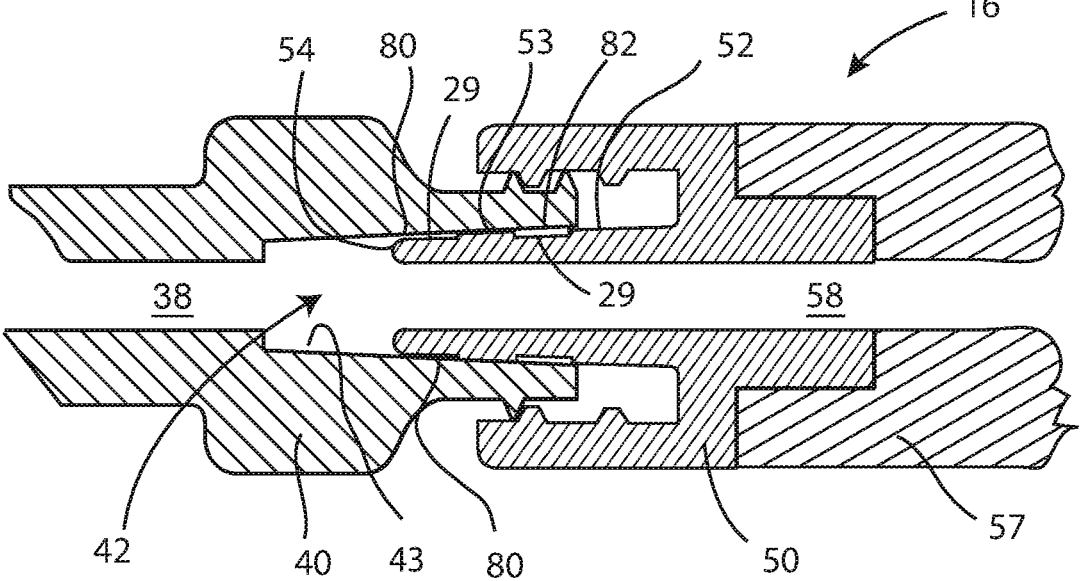

FIG. 11 is a cross-sectional view of a female connector having an infusion set connected, the infusion set comprising a male connector with a male luer including a distal recess containing an antimicrobial agent and an intermediate recess containing an antimicrobial agent.

Figure 12:
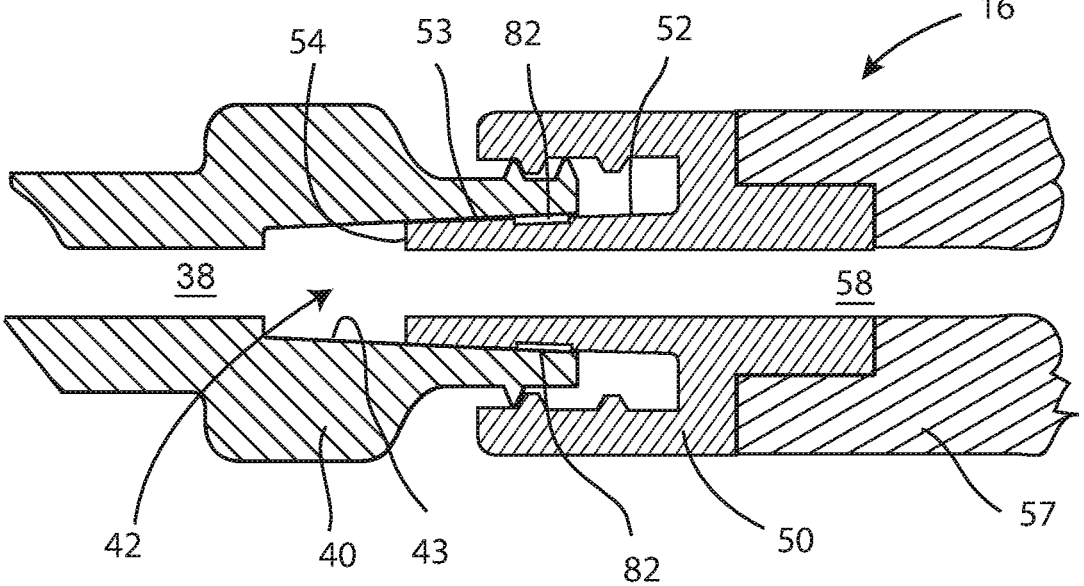

FIG. 12 is a cross-sectional view of a female connector having an infusion set connected, the infusion set having a male connector with a male luer including an intermediate recess containing an antimicrobial agent.

Figure 13:
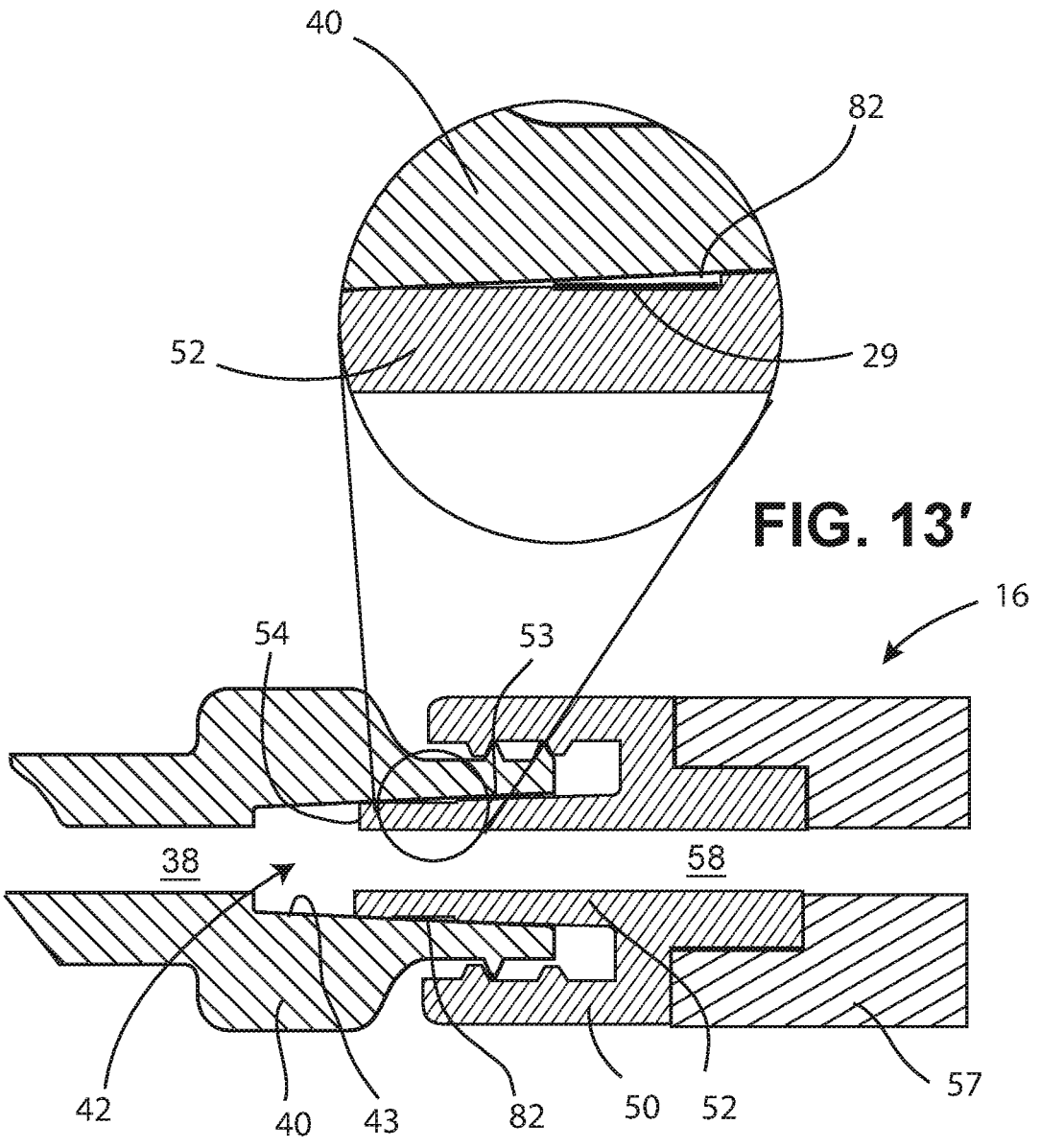

FIG. 13 is a cross-sectional view of a female connector having an infusion set connected, the infusion set having a male connector with a male luer including an intermediate recess containing an antimicrobial agent.

FIG. 13' is an enlarged cross-sectional view of the female connector and the male luer of FIG. 13.

Figures 14A, 14B, 14C:
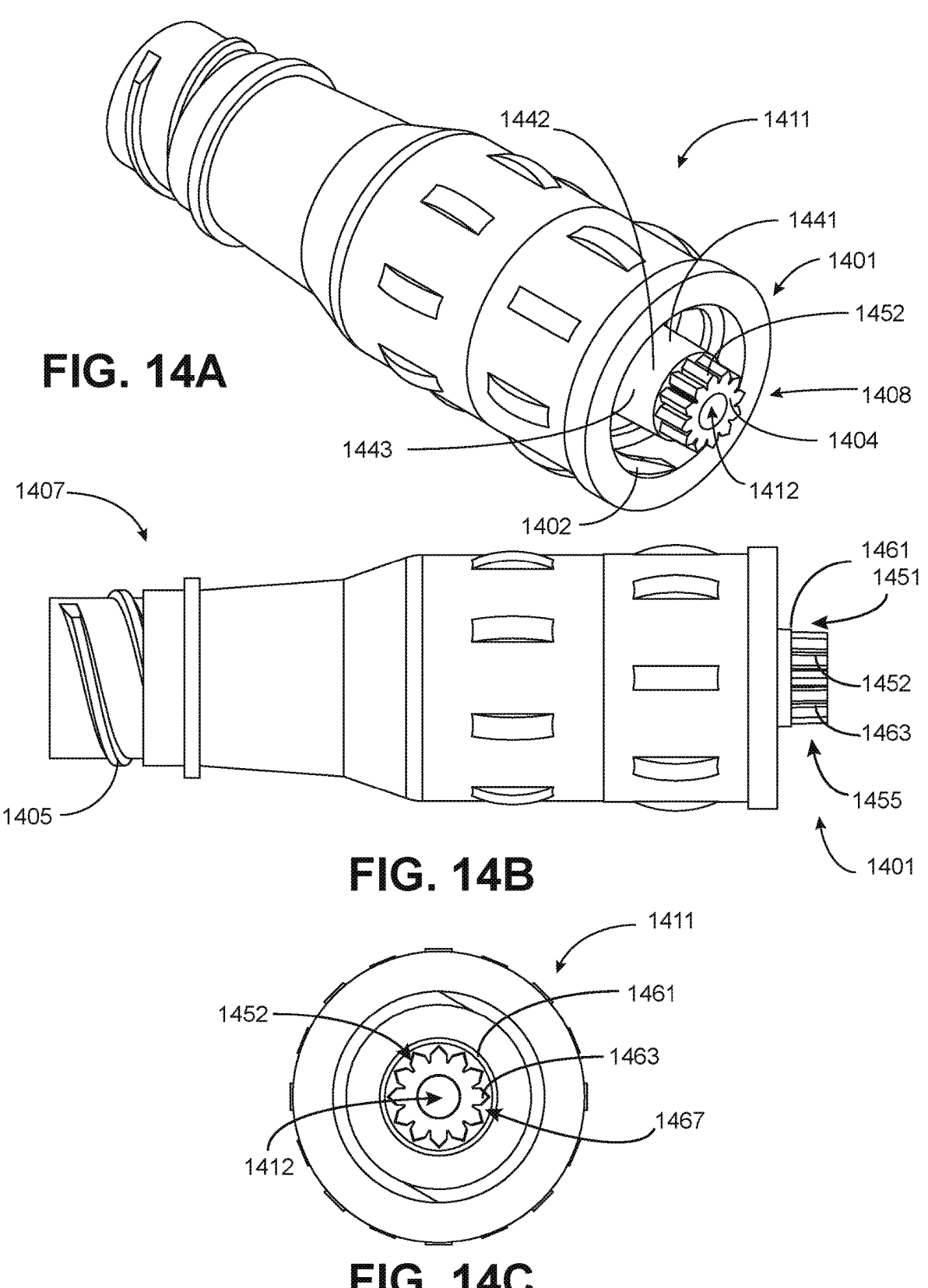

FIG. 14A is an isometric view of a needleless connector according to some examples. FIG. 14B is a side view of the needleless connector of FIG. 14A.

FIG. 14C is an end view of the needleless connector of FIG. 14A.

FIG. 15A is an isometric view of a male connector according to some examples. FIG. 15B is a side view of the male connector of FIG. 15A FIG. 15C is a cross-sectional view of the male connector of FIG. 15A along line C-C of FIG. 15B.

FIG. 15D is a cross-sectional view of the male connector of FIG. 15A along line D-D of FIG. 15B.

Figure 15E:
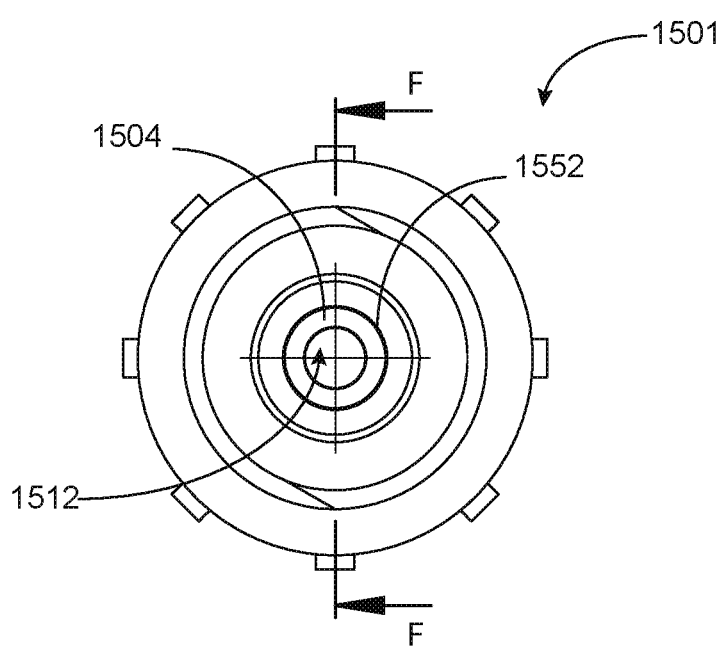

FIG. 15E is an end view of the male connector of FIG. 15A

Figure 15F:
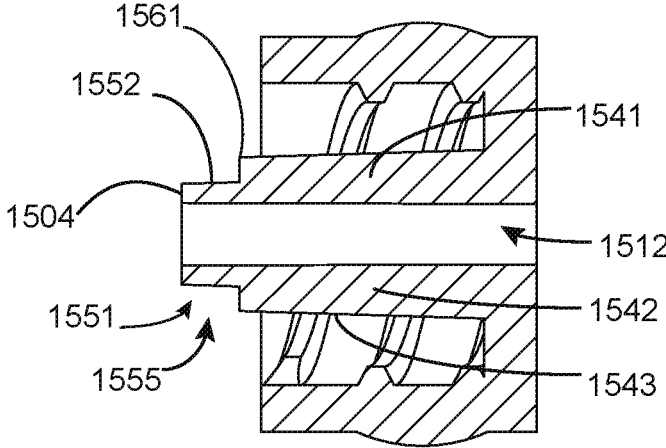

FIG. 15F is a cross-sectional view of the male connector of FIG. 15A along line F-F of FIG. 15E.

Figure 16:
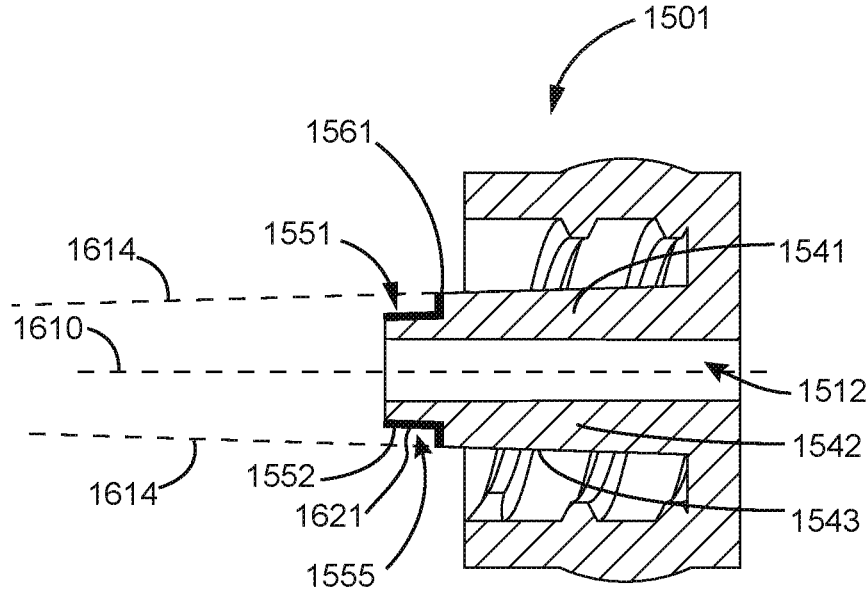
Figure 17A:
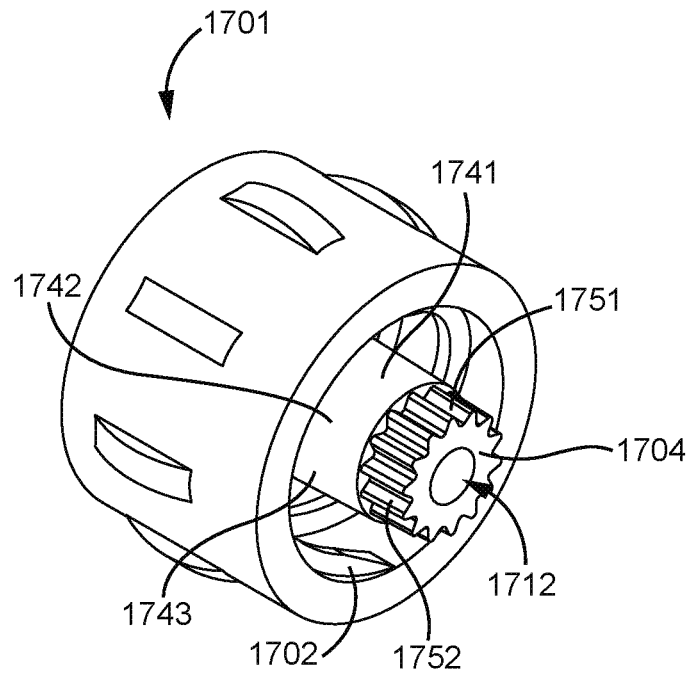

FIG. 16 is a cross-sectional view of a male connector according to some examples. FIG. 17A is an isometric view of a male connector according to some examples.

Figure 17C:
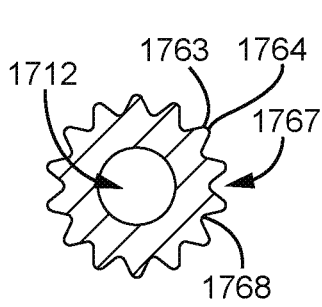
Figure 17B:
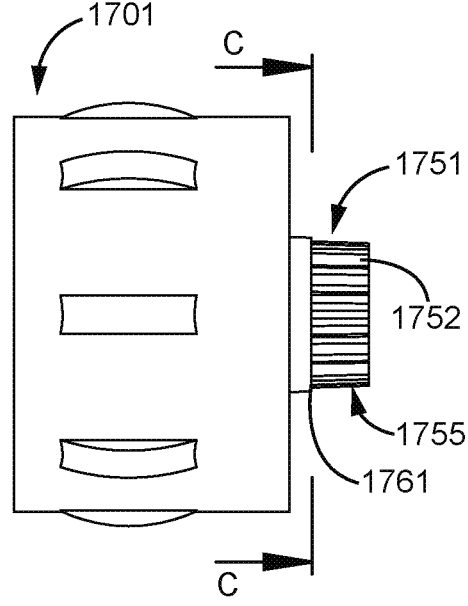

FIG. 17B is a side view of the male connector of FIG. 17A

FIG. 17C is a cross-sectional view of the male connector of FIG. 17A along line C-C of FIG. 17B.

Figures 17D, 17E, 17F:
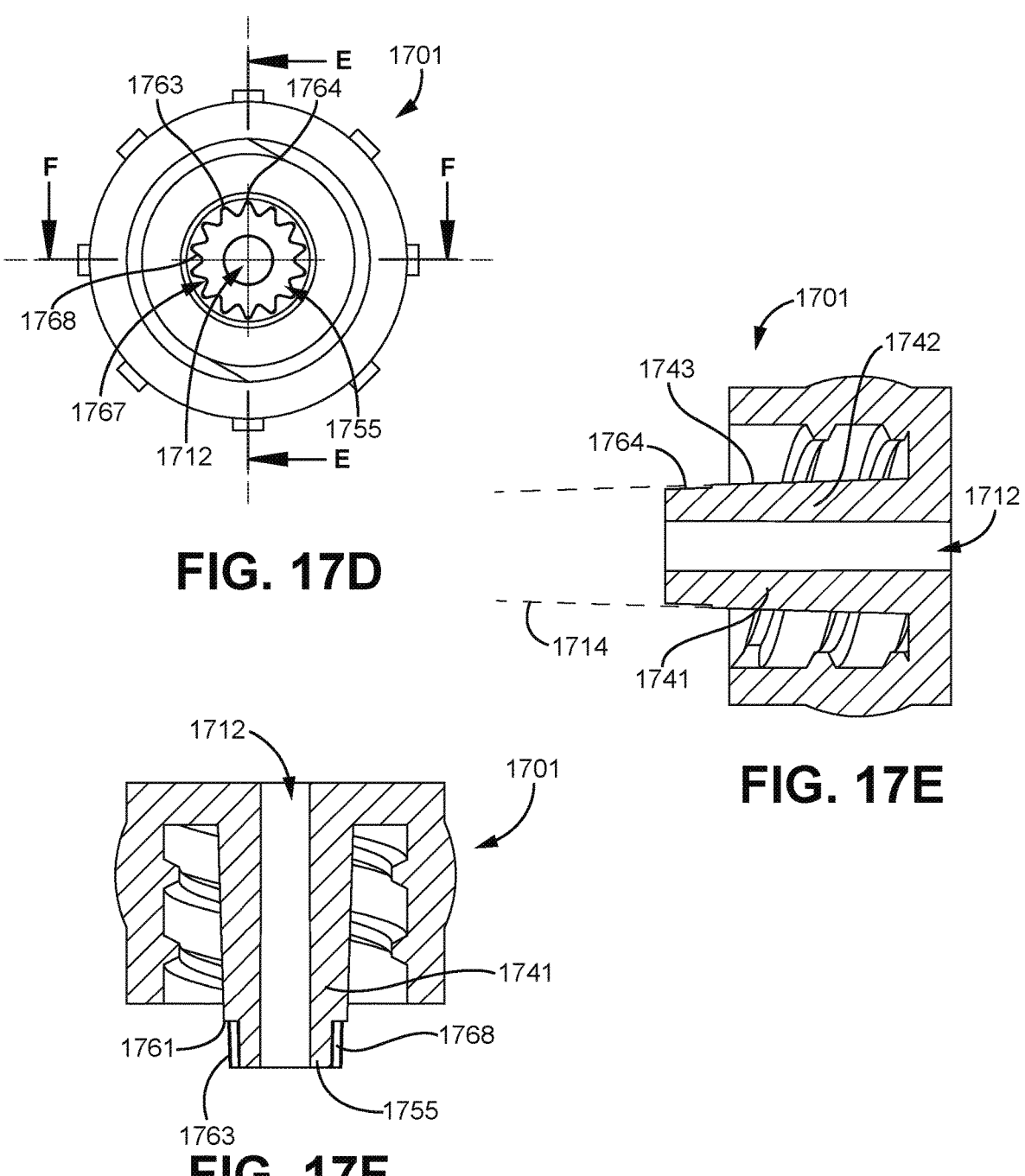

FIG. 17D is an end view of the male connector of FIG. 17A

FIG. 17E is a cross-sectional view of the male connector of FIG. 17A along line E-E of FIG. 17D.

FIG. 17F is a cross-sectional view of the male connector of FIG. 17A along line F-F of FIG. 17D.

FIG. 18A is an isometric view of a male connector according to some examples. FIG. 18B is a side view of the male connector of FIG. 18A FIG. 18C is a cross-sectional view of the male connector of FIG. 18A along line C-C of FIG. 18B.

Figure 18D:
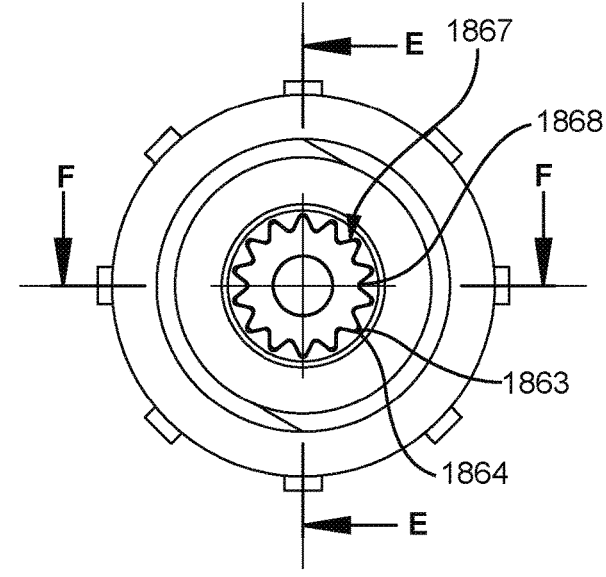

FIG. 18D is an end view of the male connector of FIG. 18A

Figure 18E:
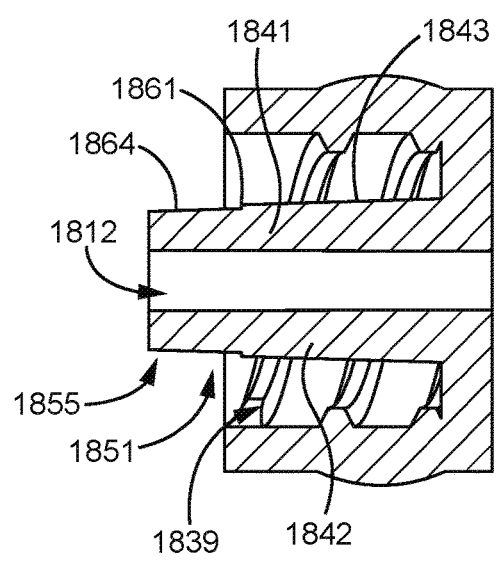

FIG. 18E is a cross-sectional view of the male connector of FIG. 18A along line E-E of FIG. 18D.

Figure 18F:
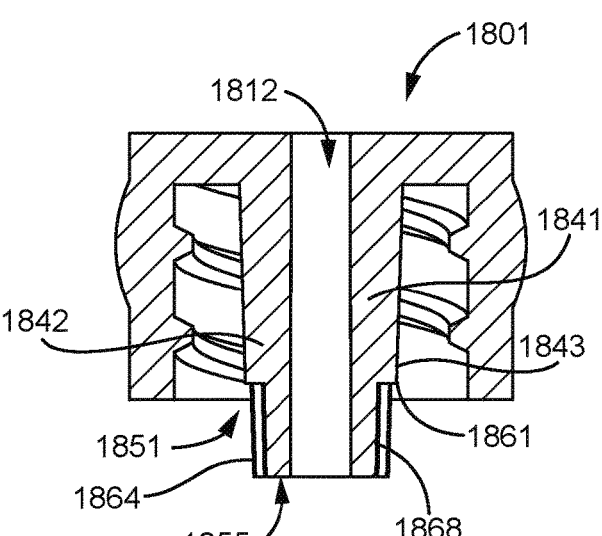

FIG. 18F is a cross-sectional view of the male connector of FIG. 18A along line F-F of FIG. 18D.

Figure 19A:
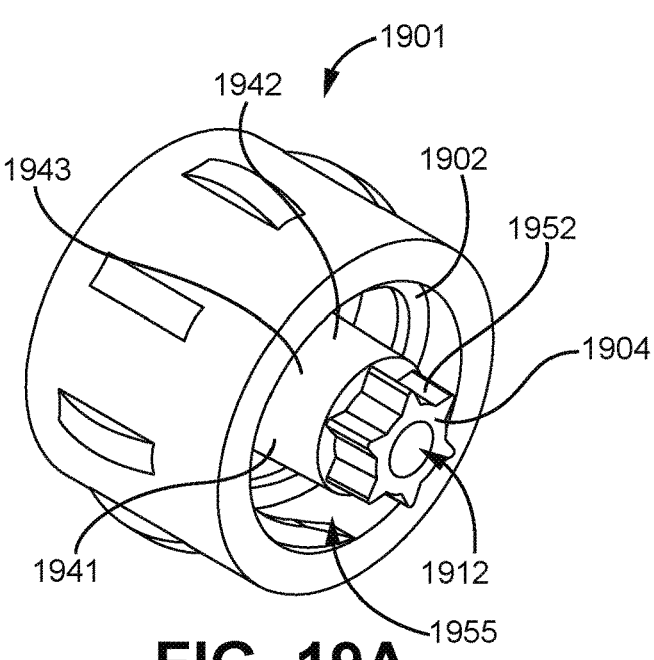
Figure 19B:
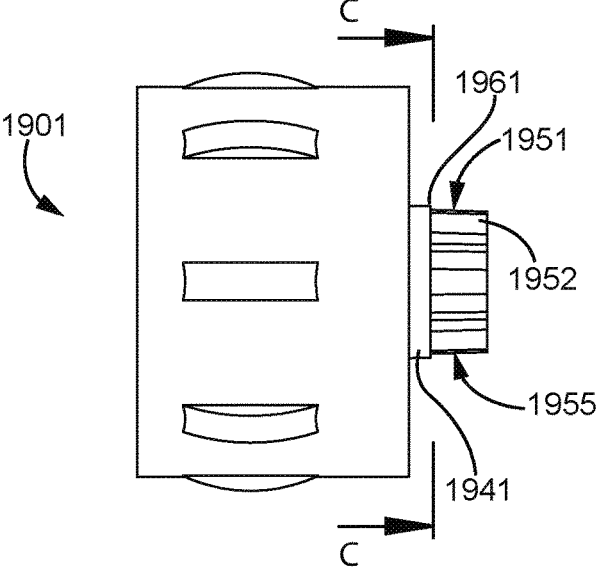
Figure 19C:
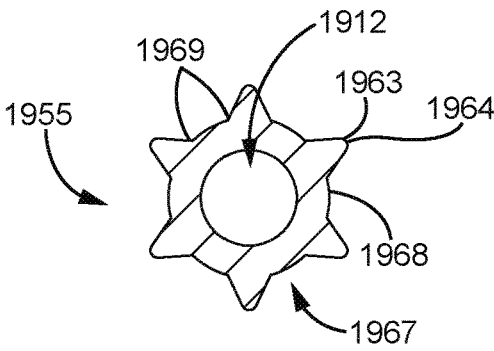

FIG. 19A is an isometric view of a male connector according to some examples. FIG. 19B is a side view of the male connector of FIG. 19A FIG. 19C is a cross-sectional view of the male connector of FIG. 19A along line C-C of FIG. 19B.

Figure 19D:
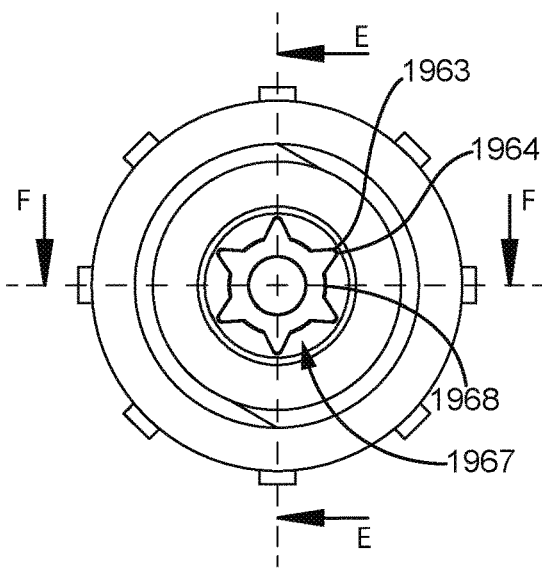

FIG. 19D is an end view of the male connector of FIG. 19A.

Figure 19E:
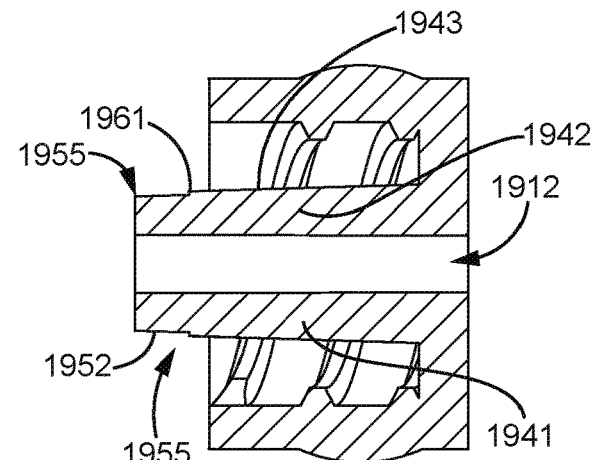

FIG. 19E is a cross-sectional view of the male connector of FIG. 19A along line E-E of FIG. 19D.

Figure 19F:
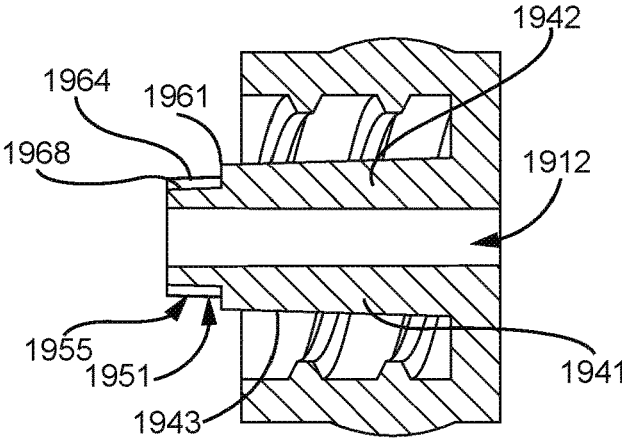

FIG. 19F is a cross-sectional view of the male connector of FIG. 19A along line F-F of FIG. 19D.

FIG. 20A is an isometric view of a male connector according to some examples. FIG. 20B is a side view of the male connector of FIG. 20A.

FIG. 20C is a cross-sectional view of the male connector of FIG. 20A along line C-C of FIG. 20B.

FIG. 20D is a cross-sectional view of the male connector of FIG. 20A along line D-D of FIG. 20B.

Figure 20E:
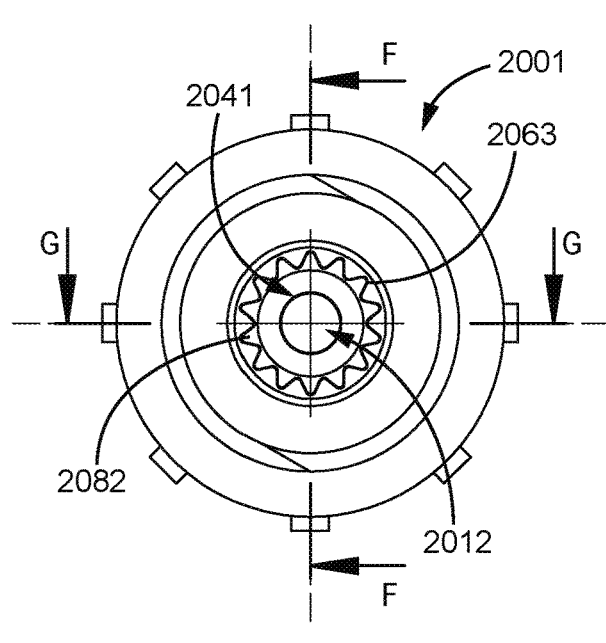

FIG. 20E is an end view of the male connector of FIG. 20A.

Figure 20F:
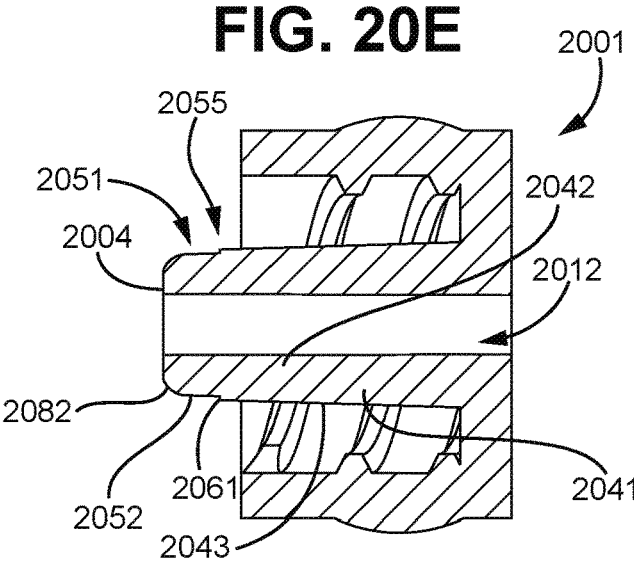

FIG. 20F is a cross-sectional view of the male connector of FIG. 20A along line F-F of FIG. 20E.

Figure 20G:
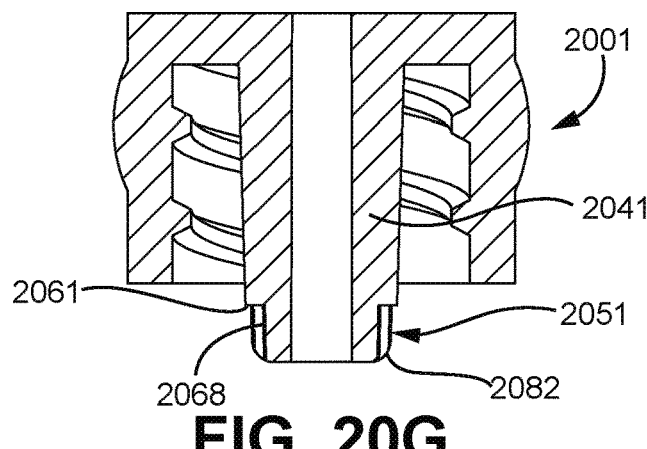

FIG. 20G is a cross-sectional view of the male connector of FIG. 20A along line G-G of FIG. 20E.

Figure 21A:
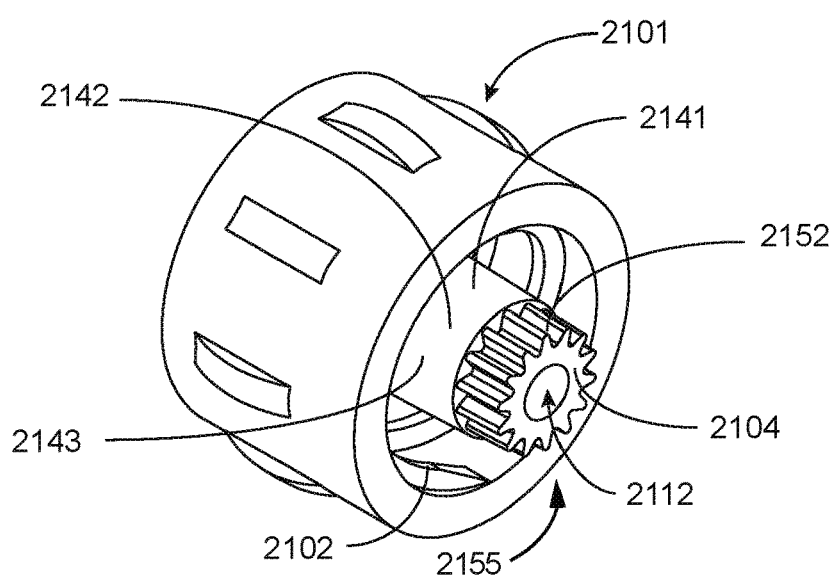
Figure 21B:
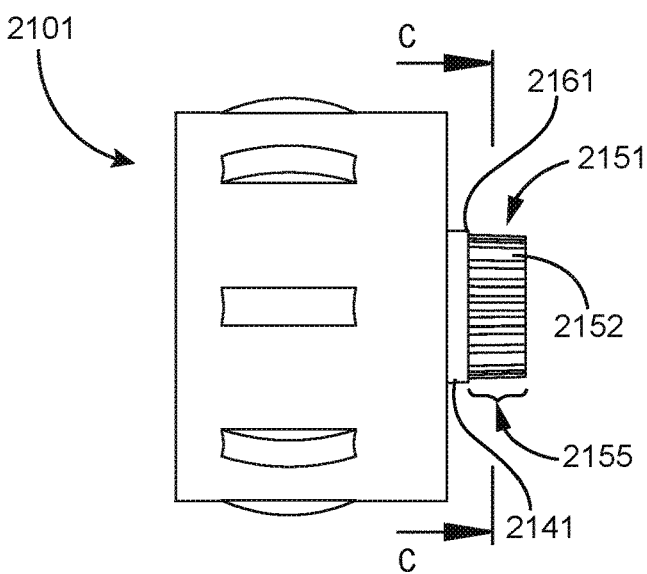

FIG. 21A is an isometric view of a male connector according to some examples. FIG. 21B is a side view of the male connector of FIG. 21A.

Figure 21C:
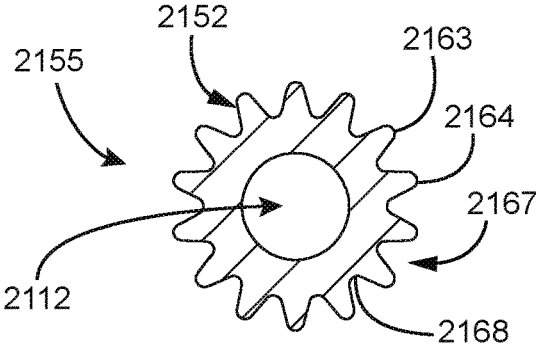

FIG. 21C is a cross-sectional view of the male connector of FIG. 21A along line C-C of FIG. 21B.

Figure 21D:
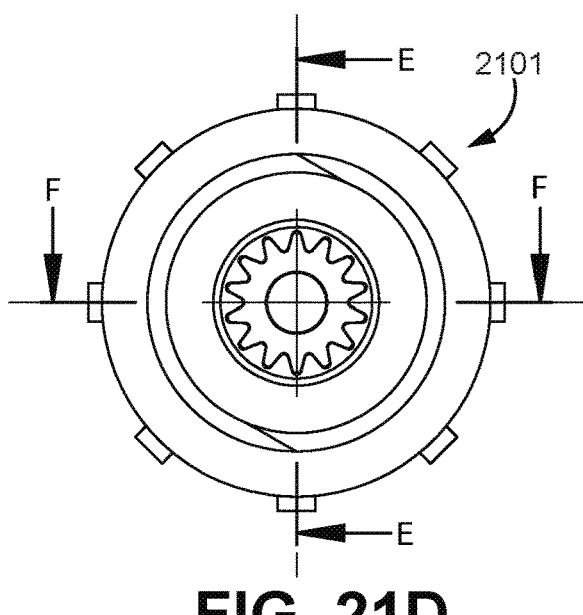

FIG. 21D is an end view of the male connector of FIG. 21A.

Figure 21E:
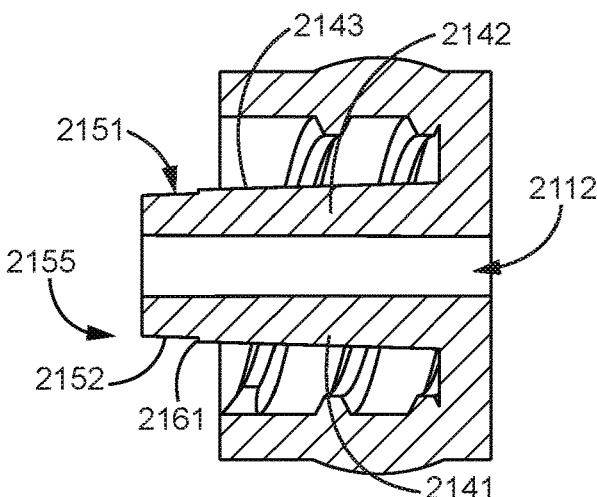

FIG. 21E is a cross-sectional view of the male connector of FIG. 21A along line E-E of FIG. 21D.

Figure 21F:
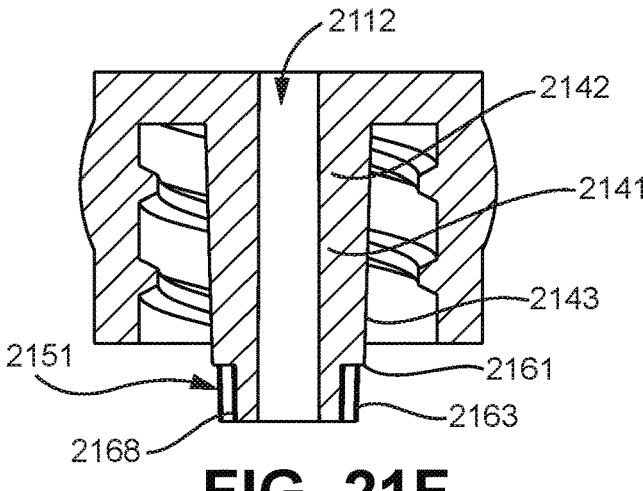

FIG. 21F is a cross-sectional view of the male connector of FIG. 21A along line F-F of FIG. 21D.

FIG. 22A is an isometric view of a male connector according to some examples. FIG. 22B is a side view of the male connector of FIG. 22A.

FIG. 22C is a cross-sectional view of the male connector of FIG. 22A along line C-C of FIG. 22B.

Figures 22D, 22E, 22F:
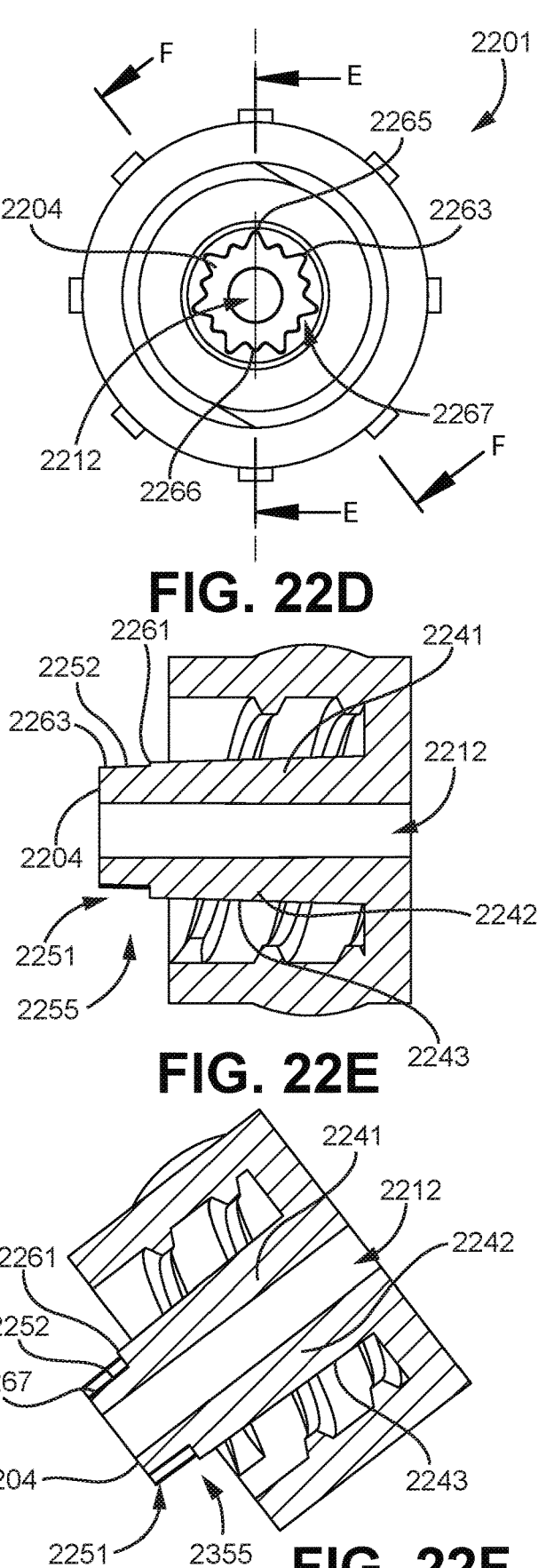

FIG. 22D is an end view of the male connector of FIG. 22A.

FIG. 22E is a cross-sectional view of the male connector of FIG. 22A along line E-E of FIG. 22D.

FIG. 22F is a cross-sectional view of the male connector of FIG. 22A along line F-F of FIG. 22D.

Figure 23A:
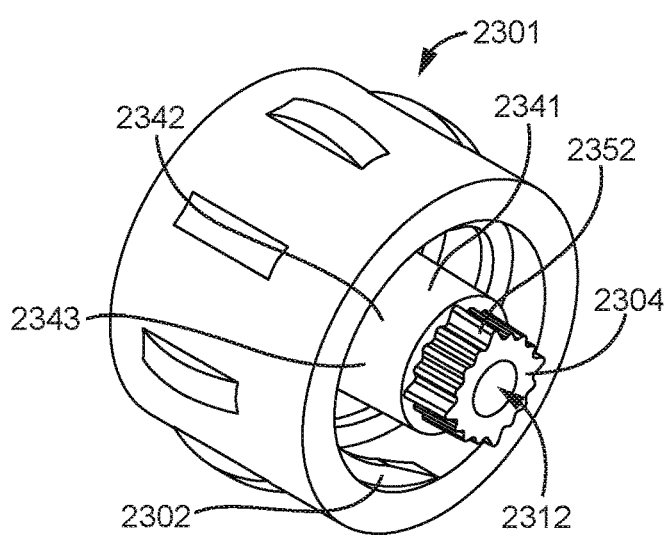
Figure 23B:
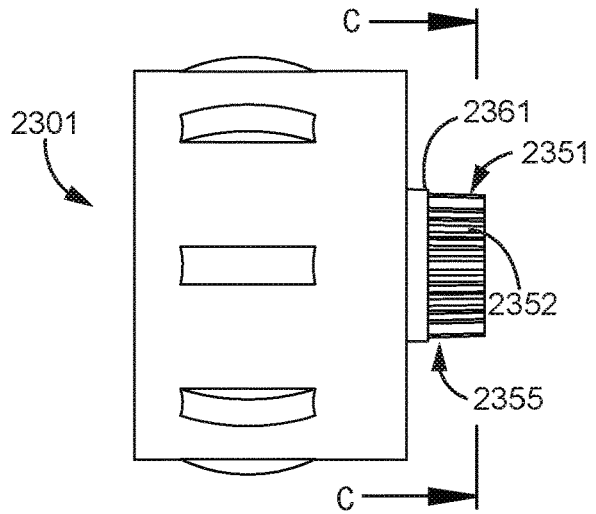

FIG. 23A is an isometric view of a male connector according to some examples. FIG. 23B is a side view of the male connector of FIG. 23A.

Figure 23C:
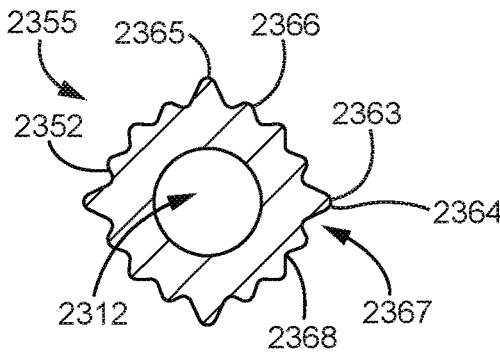

FIG. 23C is a cross-sectional view of the male connector of FIG. 23A along line C-C of FIG. 23B.

FIG. 23D is an end view of the male connector of FIG. 23A.

FIG. 23E is a cross-sectional view of the male connector of FIG. 23A along line E-E of FIG. 23D.

FIG. 23F is a cross-sectional view of the male connector of FIG. 23A along line F-F of FIG. 23D.

FIG. 23G is a cross-sectional view of the male connector of FIG. 23A along line G-G of FIG. 23D.

FIG. 24A is an isometric view of a male connector according to some examples. FIG. 24B is a side view of the male connector of FIG. 24A.

FIG. 24C is a cross-sectional view of the male connector of FIG. 24A along line C-C of FIG. 24B.

FIG. 24D is a cross-sectional view of the male connector of FIG. 24A along line D-D of FIG. 24B.

FIG. 24E is a cross-sectional view of the male connector of FIG. 24A along line E-E of FIG. 24B.

Figure 24F:
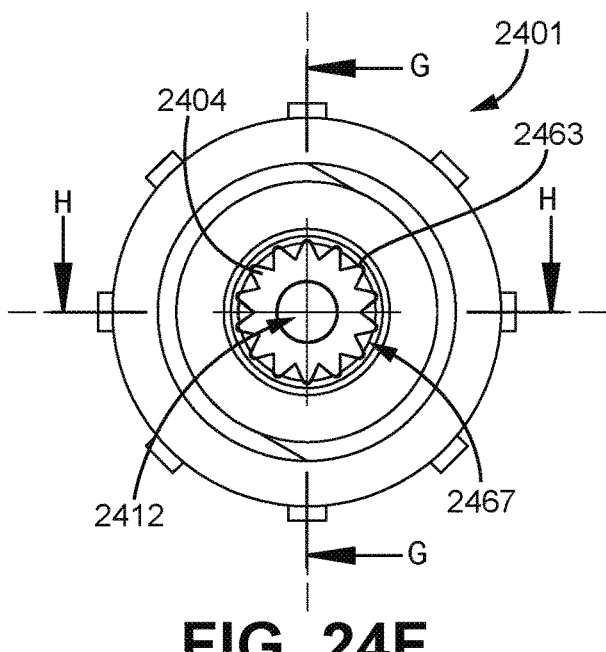

FIG. 24F is an end view of the male connector of FIG. 24A.

Figure 24G:
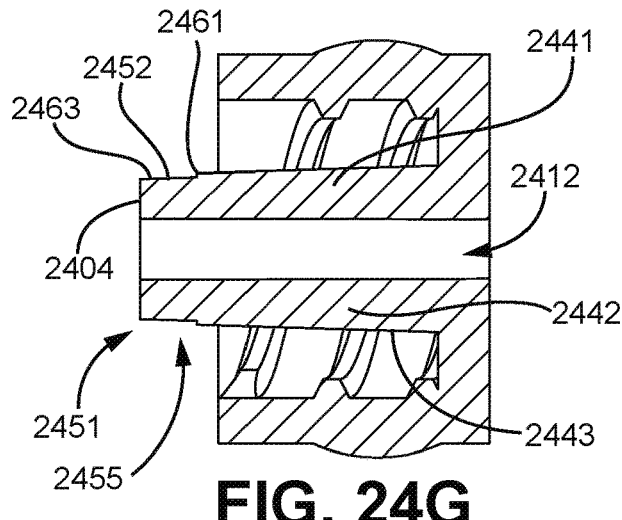

FIG. 24G is a cross-sectional view of the male connector of FIG. 24A along line G-G of FIG. 24F.

Figure 24H:
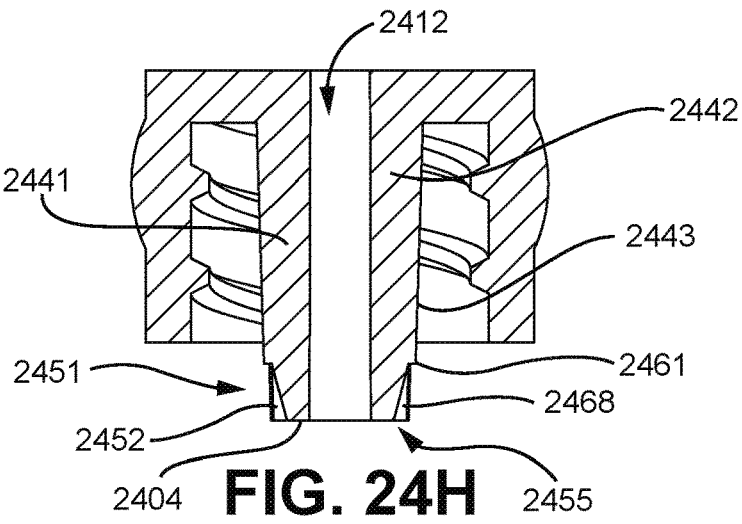

FIG. 24H is a cross-sectional view of the male connector of FIG. 24A along line H-H of FIG. 24F.

FIG. 25A is an isometric view of a male connector according to some examples. FIG. 25B is a side view of the male connector of FIG. 25A.

FIG. 25C is a cross-sectional view of the male connector of FIG. 25A along line C-C of FIG. 25B.

FIG. 25D is a cross-sectional view of the male connector of FIG. 25A along line D-D of FIG. 25B.

FIG. 25E is an end view of the male connector of FIG. 25A.

FIG. 25F is a cross-sectional view of the male connector of FIG. 25A along line F-F of FIG. 25E.

FIG. 25G is a cross-sectional view of the male connector of FIG. 25A along line G-G of FIG. 25E.

FIG. 26A is an isometric view of a male connector according to some examples. FIG. 26B is a side view of the male connector of FIG. 26A.

FIG. 26C is a cross-sectional view of the male connector of FIG. 26A along line C-C of FIG. 26B.

FIG. 26D is a cross-sectional view of the male connector of FIG. 26A along line D-D of FIG. 26B.

Figure 26E:
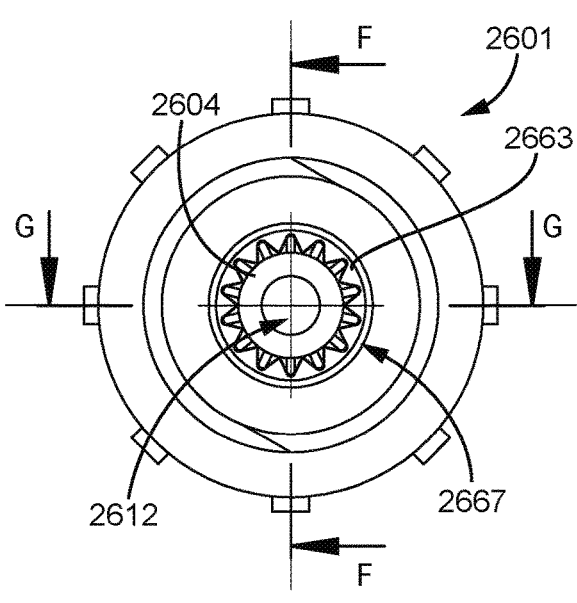

FIG. 26E is an end view of the male connector of FIG. 26A.

Figure 26F:
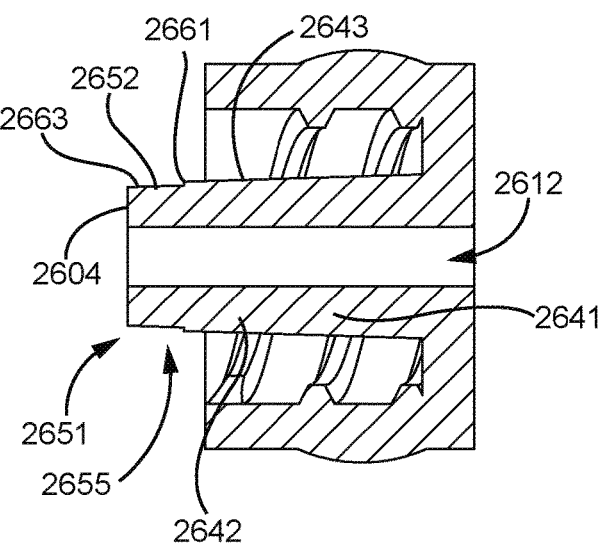

FIG. 26F is a cross-sectional view of the male connector of FIG. 26A along line F-F of FIG. 26E.

Figure 26G:
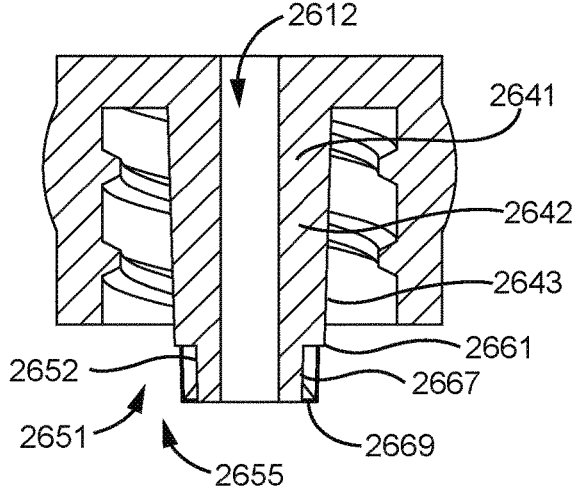

FIG. 26G is a cross-sectional view of the male connector of FIG. 26A along line G-G of FIG. 26E.

Figure 27A:
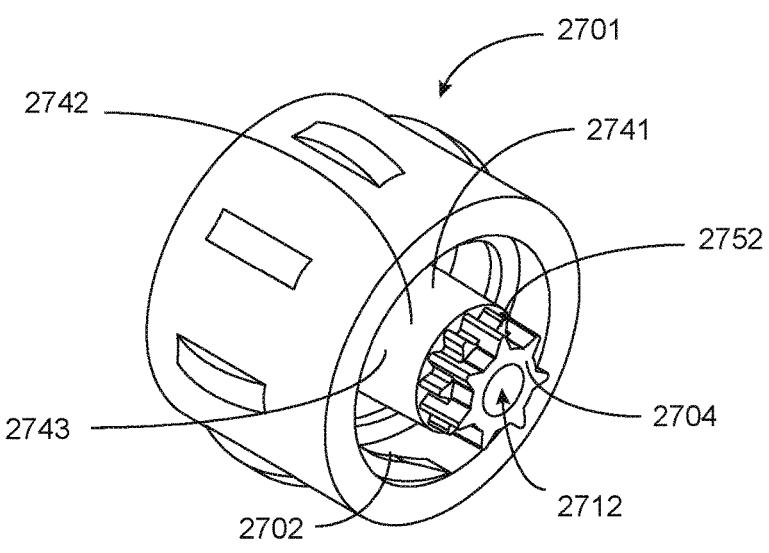
Figure 27B:
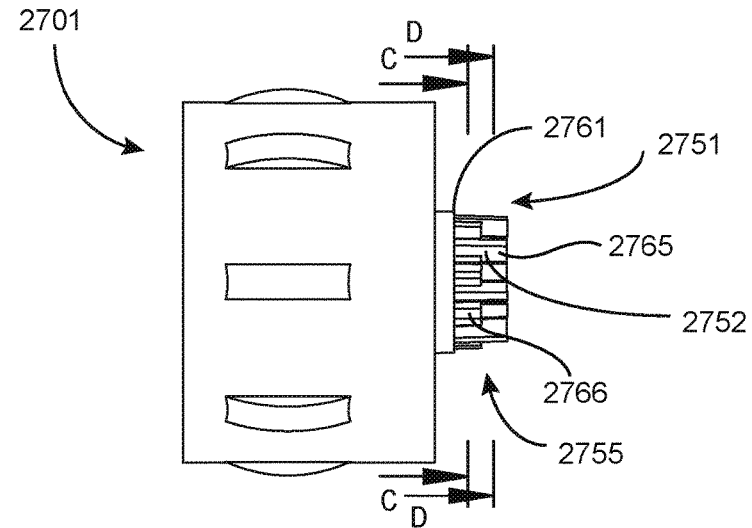

FIG. 27A is an isometric view of a male connector according to some examples. FIG. 27B is a side view of the male connector of FIG. 27A.

Figure 27C:
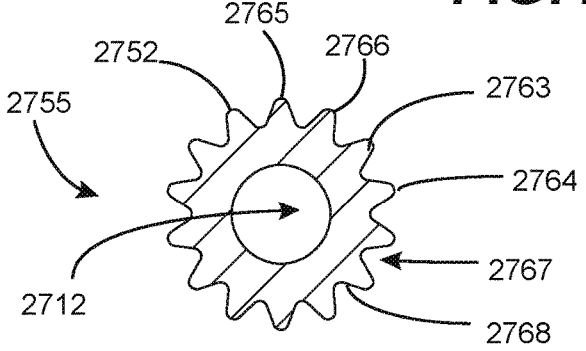

FIG. 27C is a cross-sectional view of the male connector of FIG. 27A along line C-C of FIG. 27B.

Figure 27D:
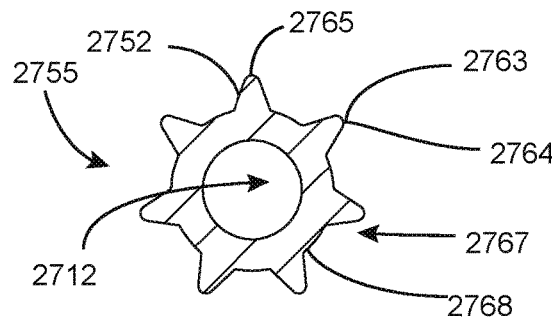

FIG. 27D is a cross-sectional view of the male connector of FIG. 27A along line D-D of FIG. 27B.

Figure 27E:
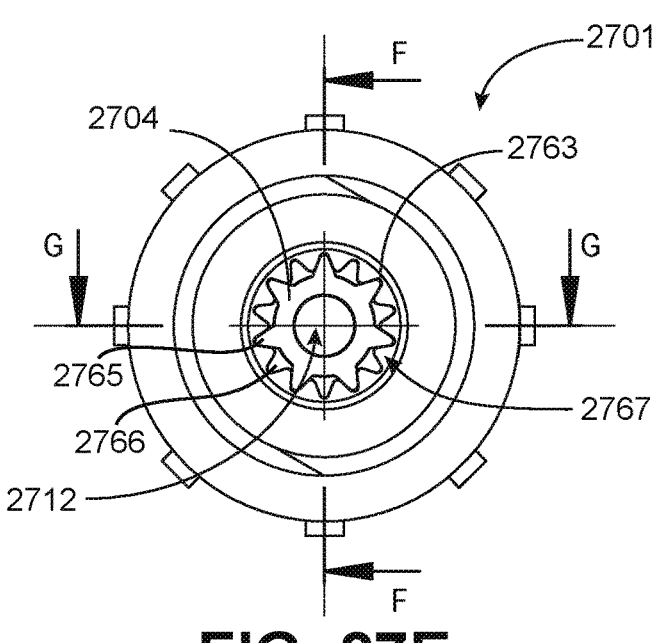

FIG. 27E is an end view of the male connector of FIG. 27A.

Figure 27F:
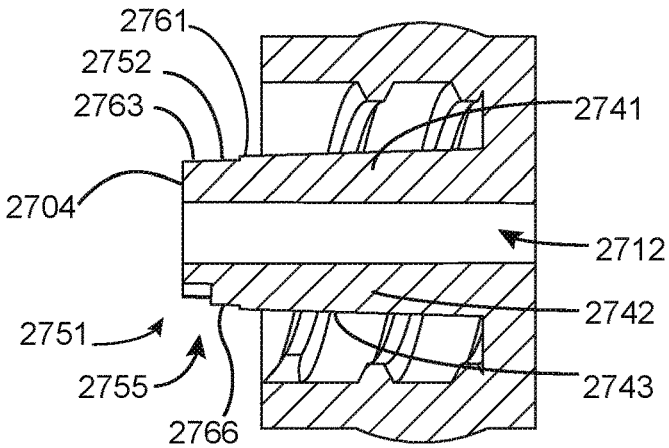

FIG. 27F is a cross-sectional view of the male connector of FIG. 27A along line F-F of FIG. 27E.

Figure 27G:
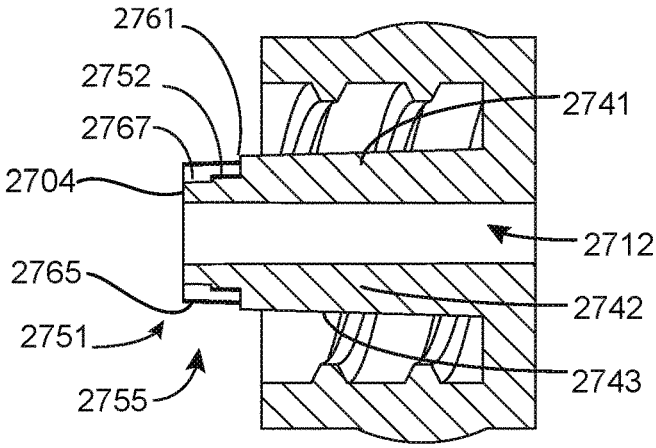

FIG. 27G is a cross-sectional view of the male connector of FIG. 27A along line G-G of FIG. 27E.

Figure 28A:
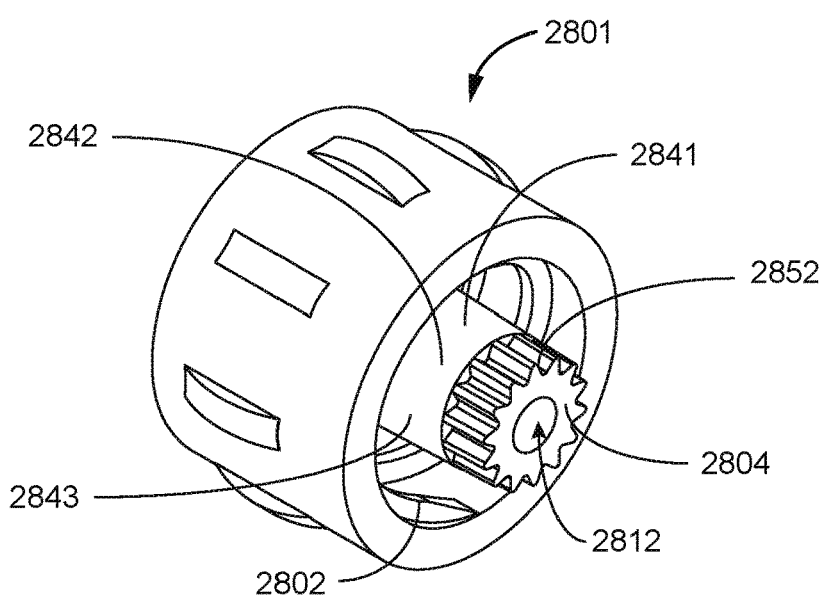
Figure 28B:
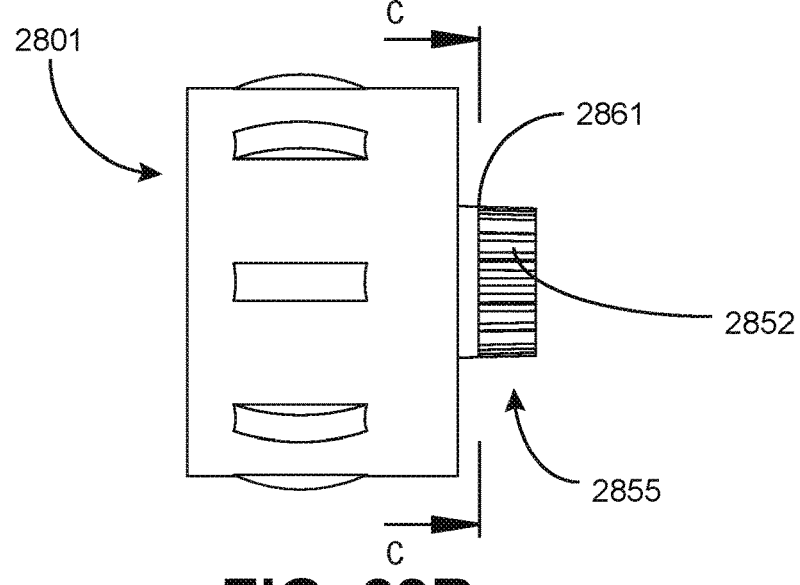

FIG. 28A is an isometric view of a male connector according to some examples. FIG. 28B is a side view of the male connector of FIG. 28A.

Figure 28C:
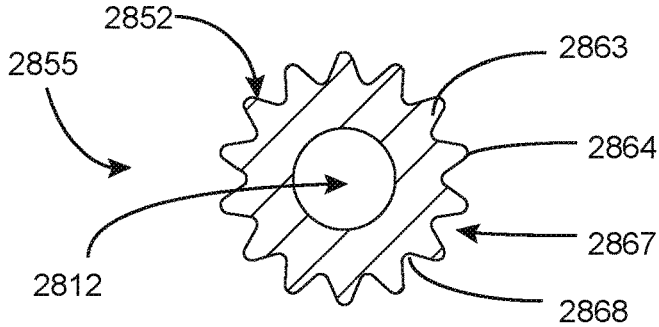

FIG. 28C is a cross-sectional view of the male connector of FIG. 28A along line C-C of FIG. 28B.

Figure 28D:
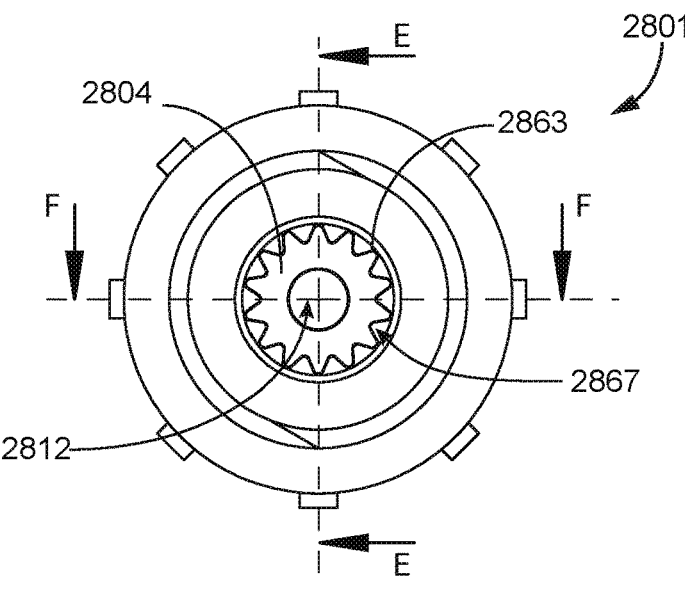

FIG. 28D is an end view of the male connector of FIG. 28A.

Figure 28E:
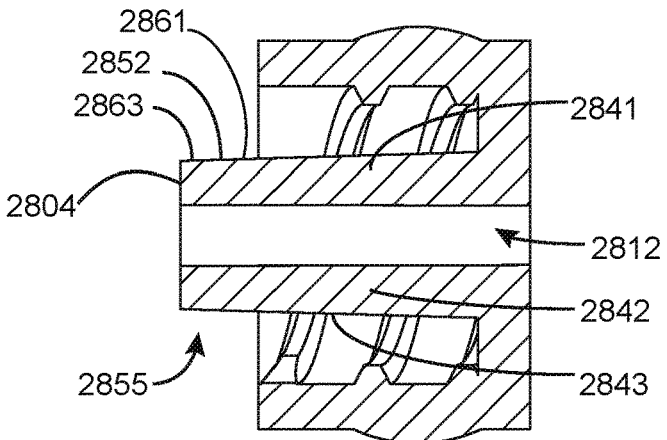

FIG. 28E is a cross-sectional view of the male connector of FIG. 28A along line E-E of FIG. 28D.

Figure 28F:
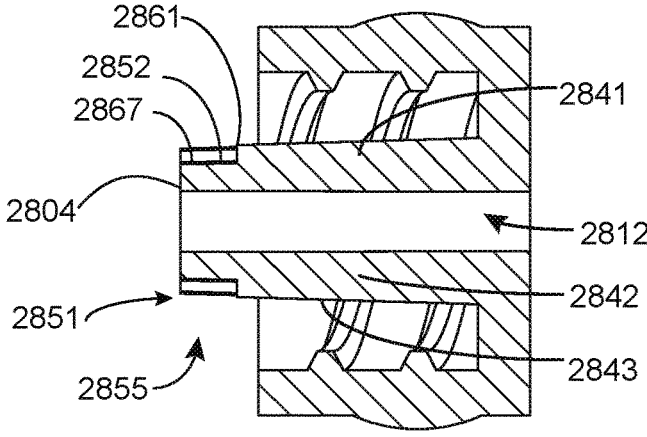

FIG. 28F is a cross-sectional view of the male connector of FIG. 28A along line F-F of FIG. 28D.

FIG. 29A is an isometric view of a male connector according to some examples. FIG. 29B is a side view of the male connector of FIG. 29A.

FIG. 29C is a cross-sectional view of the male connector of FIG. 29A along line C-C of FIG. 29B.

FIG. 29D is a cross-sectional view of the male connector of FIG. 29A along line D-D of FIG. 29B.

FIG. 29E is an end view of the male connector of FIG. 29A.

FIG. 29F is a cross-sectional view of the male connector of FIG. 29A along line F-F of FIG. 29E.

FIG. 29G is a cross-sectional view of the male connector of FIG. 29A along line G-G of FIG. 29E.

FIG. 30A is an isometric view of a male connector according to some examples. FIG. 30B is a side view of the male connector of FIG. 30A.

FIG. 30C is a cross-sectional view of the male connector of FIG. 30A along line C-C of FIG. 30B.

FIG. 30D is a cross-sectional view of the male connector of FIG. 30A along line D-D of FIG. 30B.

Figure 30E:
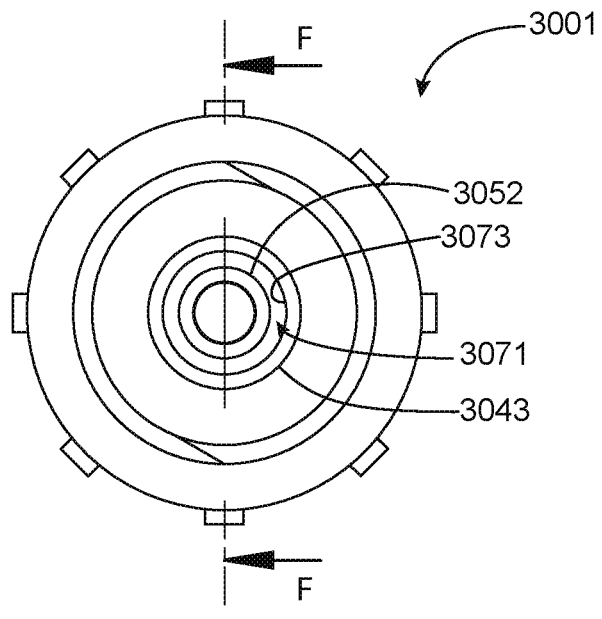

FIG. 30E is an end view of the male connector of FIG. 30A.

Figure 30F:
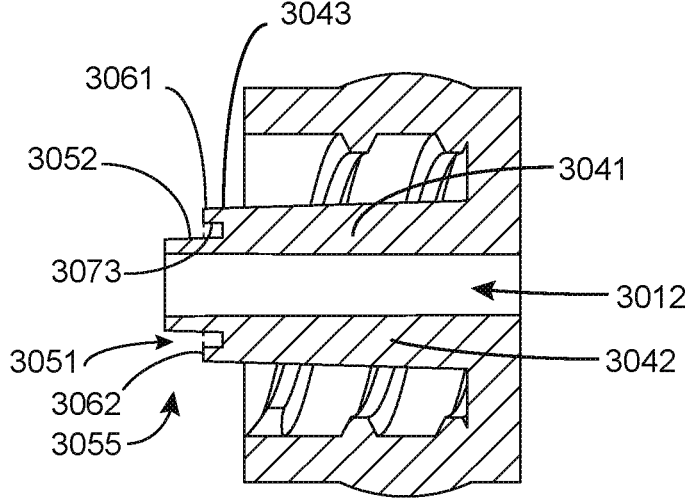

FIG. 30F is a cross-sectional view of the male connector of FIG. 30A along line F-F of FIG. 30E.

Figure 30G:
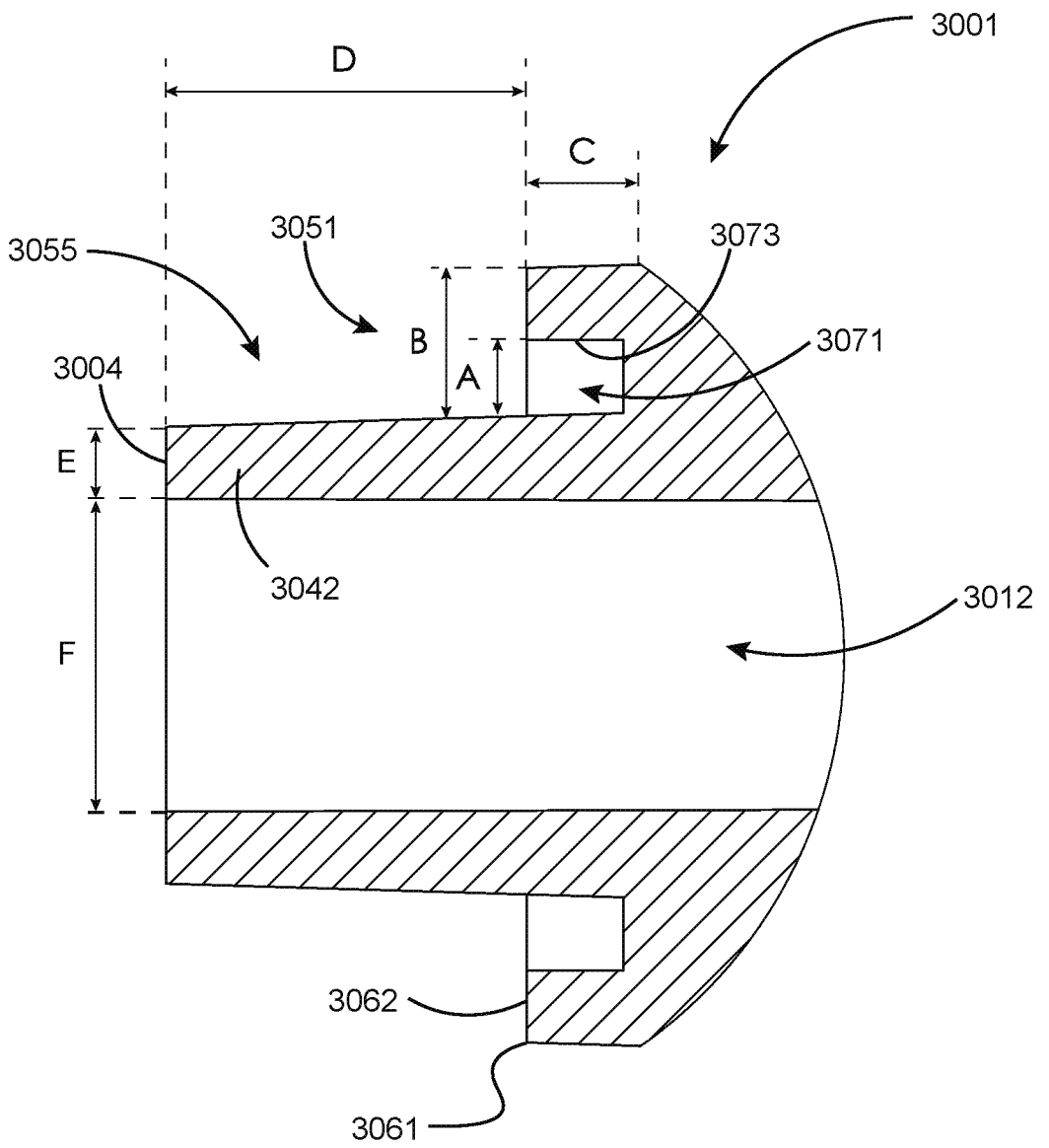

FIG. 30G is an enlarged cross-sectional view of the male connector of FIG. 30A along line F-F of FIG. 30E.

FIG. 31A is an isometric view of a male connector according to some examples. FIG. 31B is a side view of the male connector of FIG. 31A.

FIG. 31C is a cross-sectional view of the male connector of FIG. 31A along line C-C of FIG. 31B.

FIG. 31D is a cross-sectional view of the male connector of FIG. 31A along line D-D of FIG. 31B.

FIG. 31E is an end view of the male connector of FIG. 31A.

FIG. 31F is a cross-sectional view of the male connector of FIG. 31A along line F-F of FIG. 31E.

FIG. 31G is a cross-sectional view of the male connector of FIG. 31A along line G-G of FIG. 31E.

FIG. 32A is an isometric view of a male connector according to some examples. FIG. 32B is a side view of the male connector of FIG. 32A.

FIG. 32C is a cross-sectional view of the male connector of FIG. 32A along line C-C of FIG. 32B.

FIG. 32D is a cross-sectional view of the male connector of FIG. 32A along line D-D of FIG. 32B.

Figure 32E:
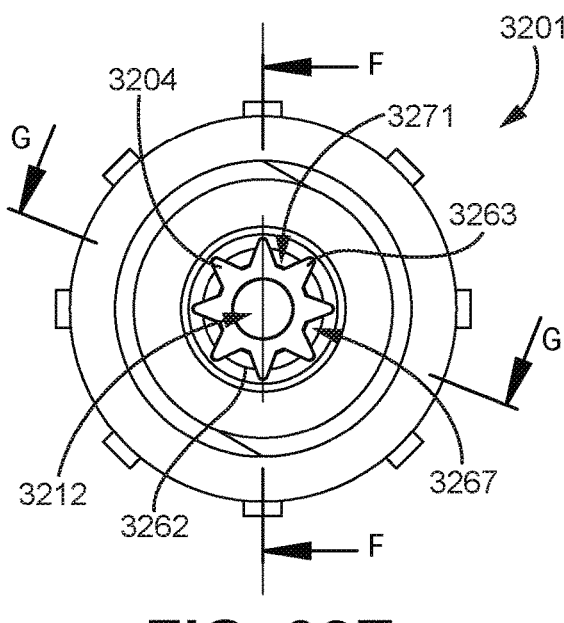

FIG. 32E is an end view of the male connector of FIG. 32A.

Figure 32F:
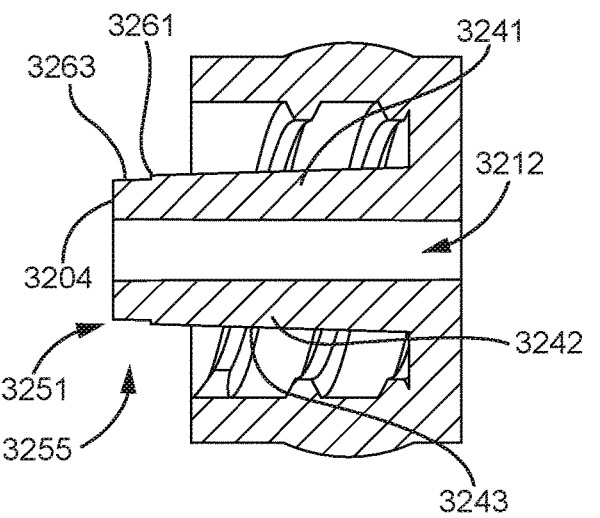

FIG. 32F is a cross-sectional view of the male connector of FIG. 32A along line F-F of FIG. 32E.

Figure 32G:
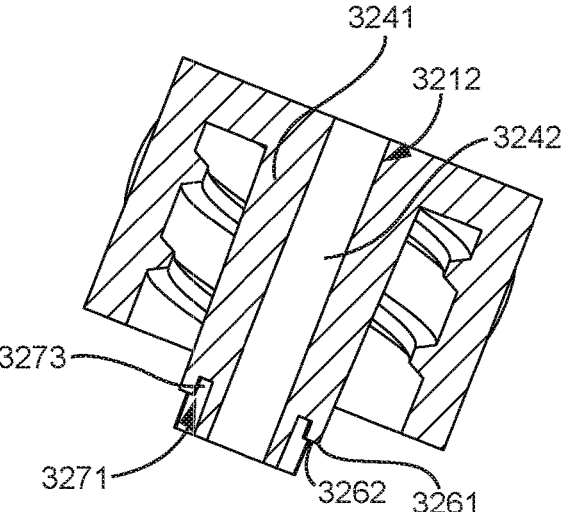

FIG. 32G is a cross-sectional view of the male connector of FIG. 32A along line G-G of FIG. 32E.

Figure 33A:
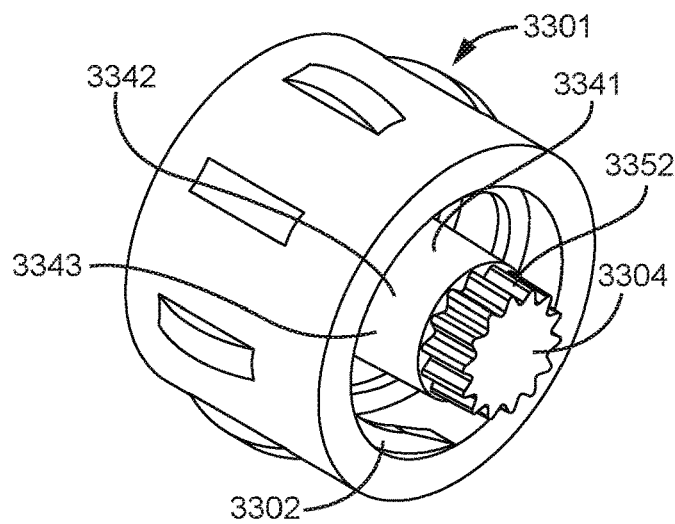
Figure 33B:
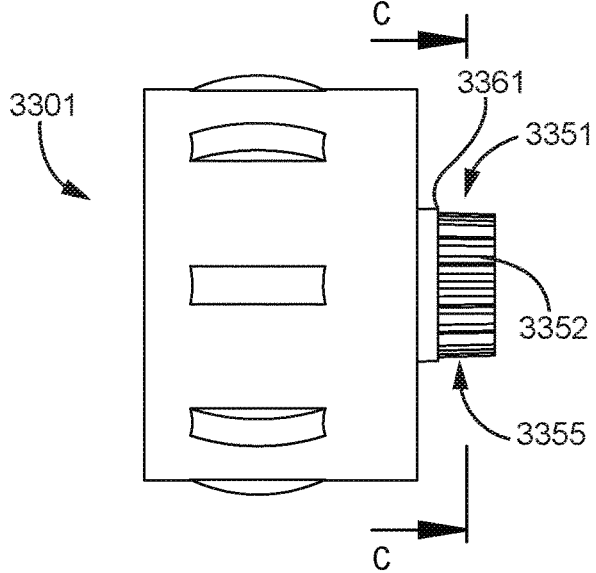

FIG. 33A is an isometric view of a male luer cap according to some examples. FIG. 33B is a side view of the male luer cap of FIG. 33A.

Figure 33C:
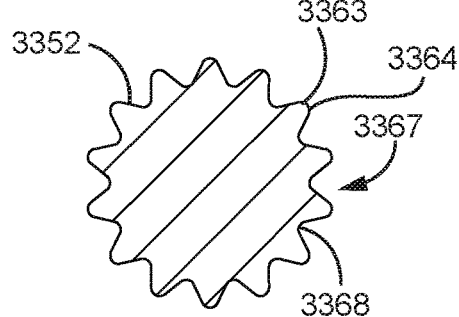

FIG. 33C is a cross-sectional view of the male luer cap of FIG. 33A along line C-C of FIG. 33B.

Figure 33D:
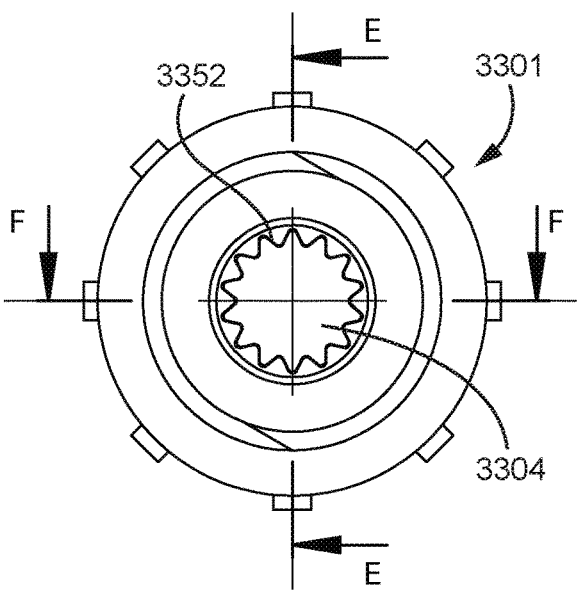

FIG. 33D is an end view of the male luer cap of FIG. 33A.

Figure 33E:
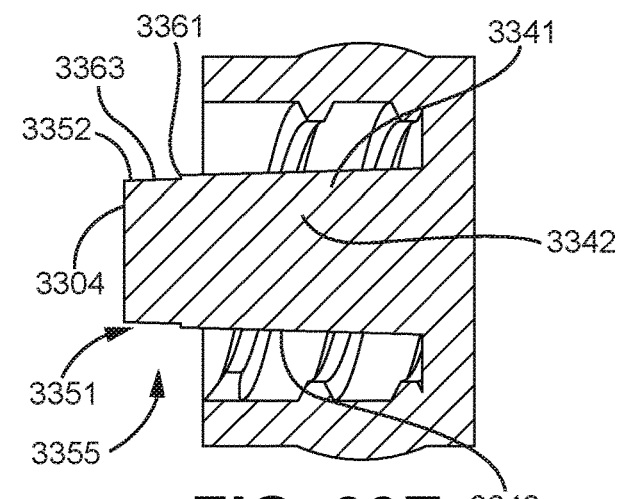

FIG. 33E is a cross-sectional view of the male luer cap of FIG. 33A along line E-E of FIG. 33D.

Figure 33F:
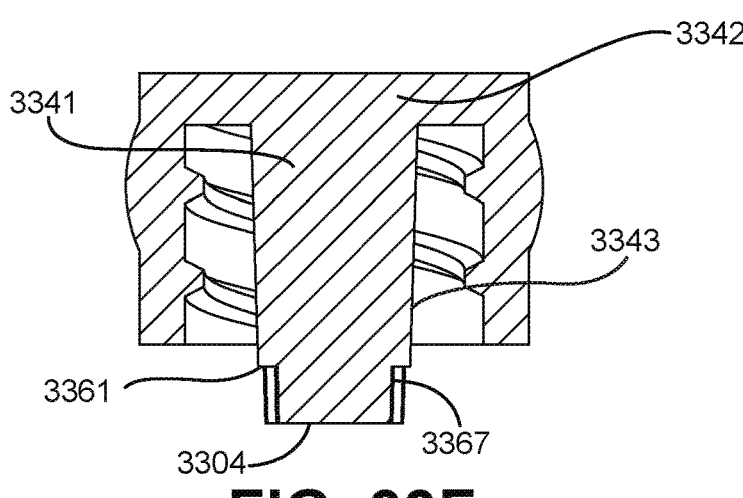

FIG. 33F is a cross-sectional view of the male luer cap of FIG. 33A along line F-F of FIG. 33D.

Figure 34A:
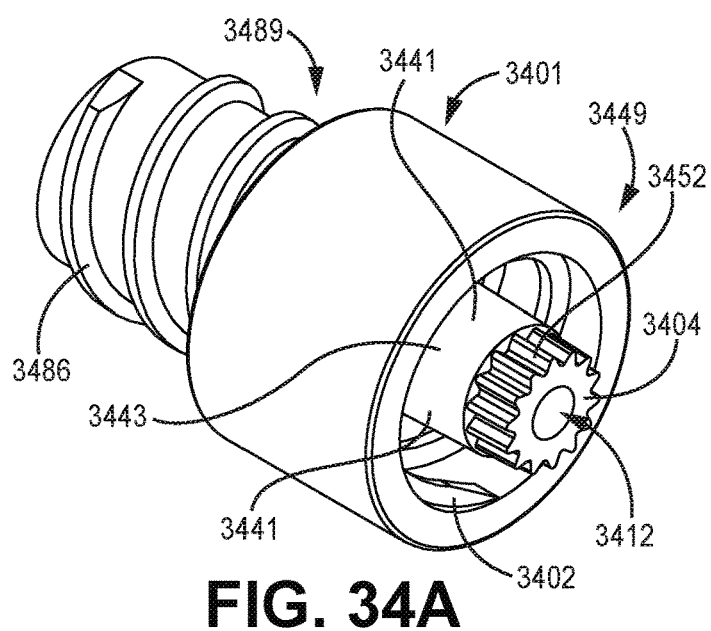

FIG. 34A is an isometric view of a luer coupler according to some examples.

Figure 34B:
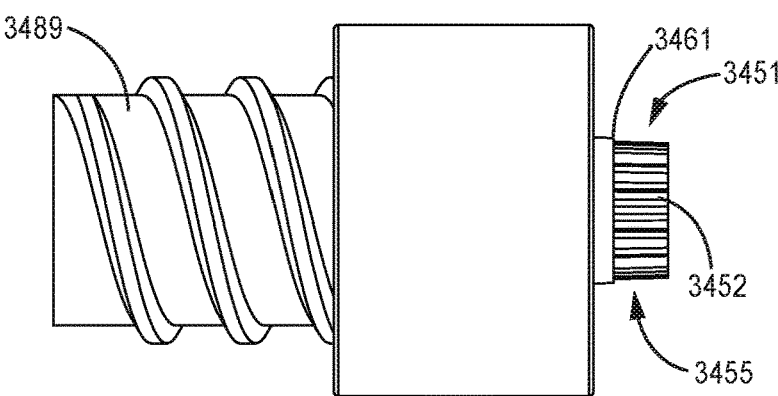

FIG. 34B is a side view of the luer coupler of FIG. 34A.

Figure 34C:
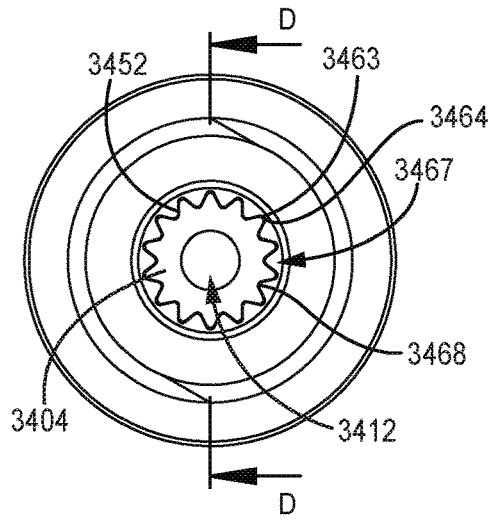

FIG. 34C is an end view of the luer coupler of FIG. 34A.

Figures 34D, 34E, 34F:
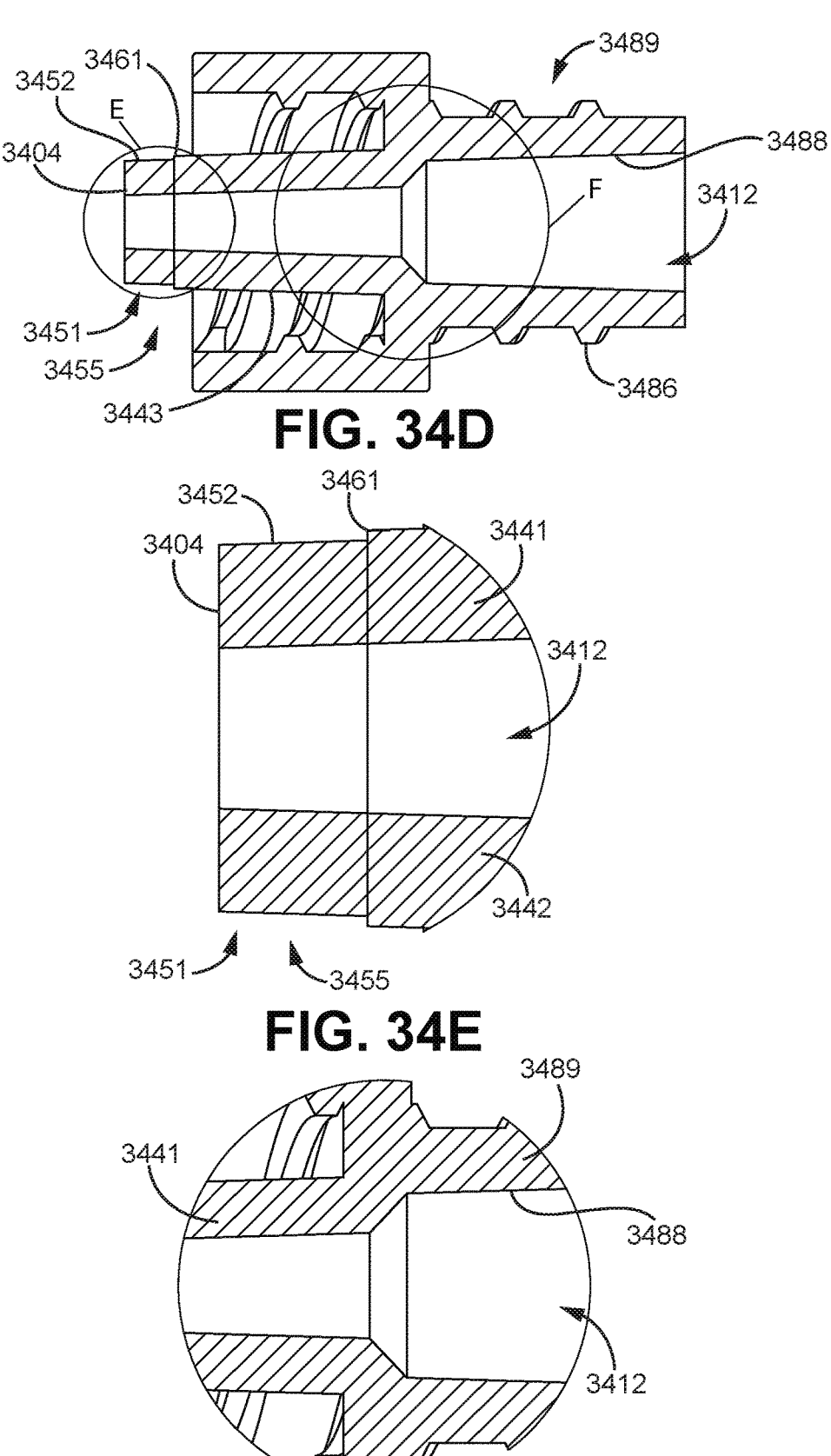

FIG. 34D is a cross-sectional view of the luer coupler of FIG. 34A along line D-D of FIG. 34C.

FIG. 34E is an enlarged view of FIG. 34D inside circle E.

FIG. 34F is an enlarged view of FIG. 34D inside circle F.

Figure 35A:
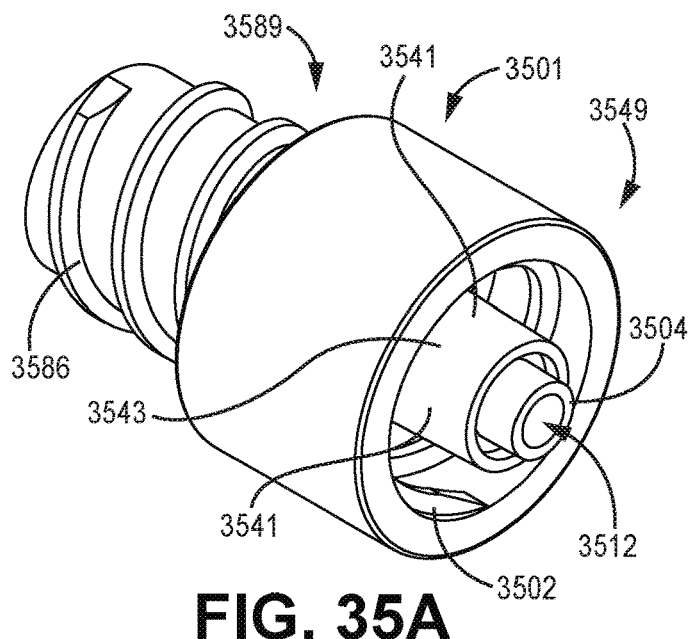

FIG. 35A is an isometric view of a luer coupler according to some examples.

Figure 35B:
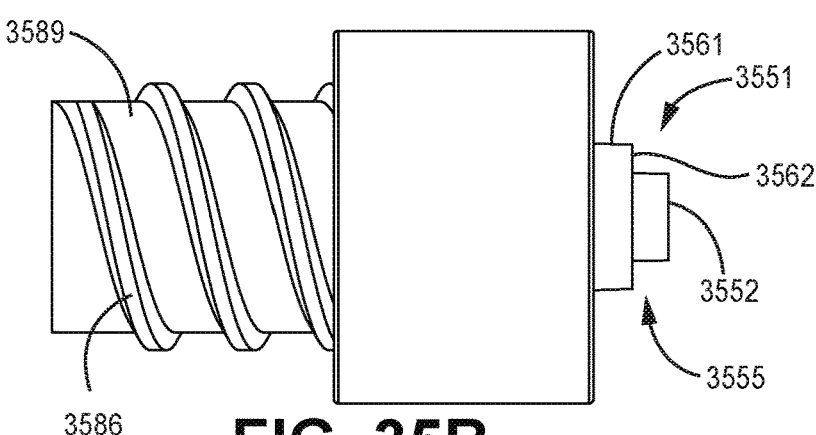

FIG. 35B is a side view of the luer coupler of FIG. 35A.

Figure 35C:
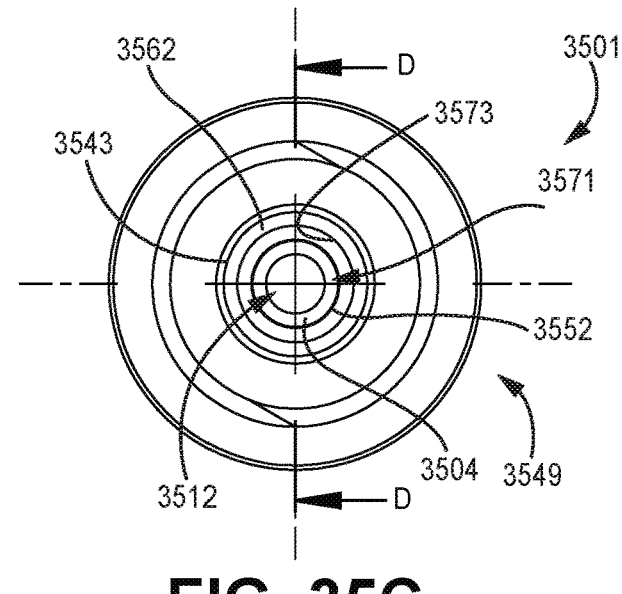

FIG. 35C is an end view of the luer coupler of FIG. 35A.

Figure 35D:
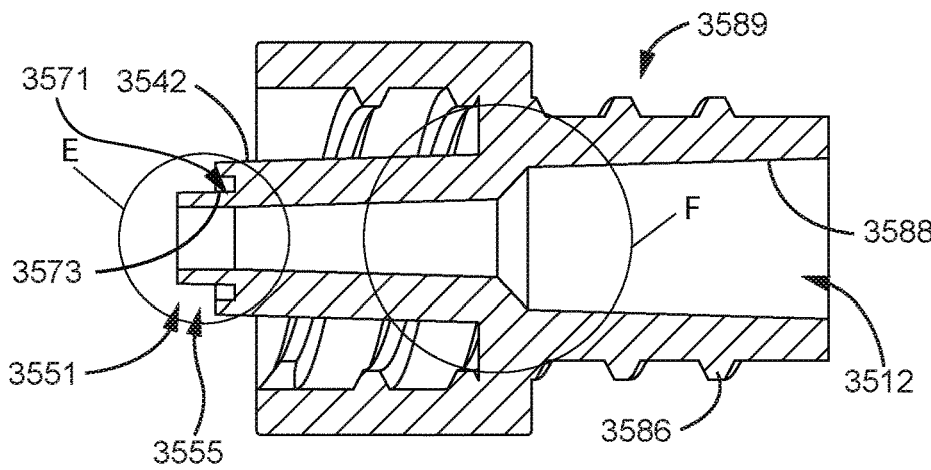

FIG. 35D is a cross-sectional view of the luer coupler of FIG. 35A along line D-D of FIG. 35C.

Figure 35E:
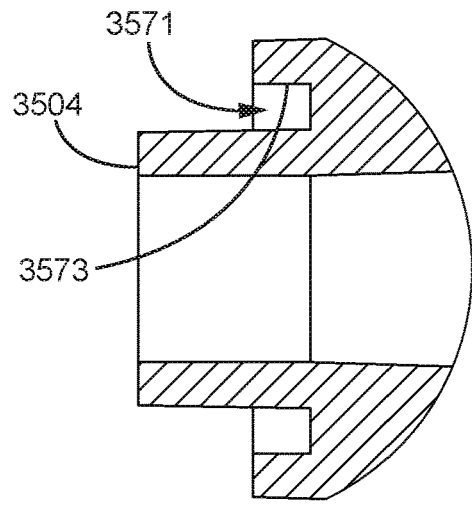

FIG. 35E is an enlarged view of FIG. 35D inside circle E.

Figure 35F:
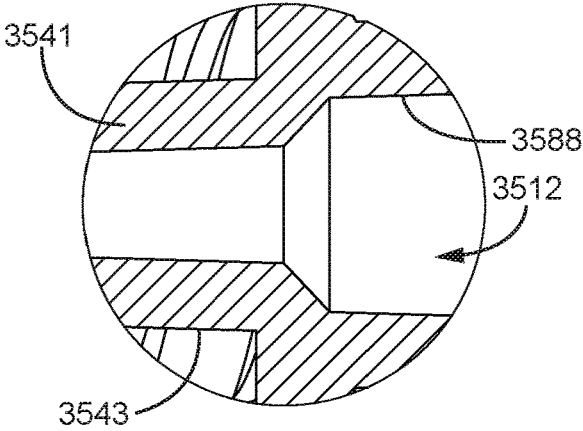

FIG. 35F is an enlarged view of FIG. 35D inside circle F.

Figure 36:
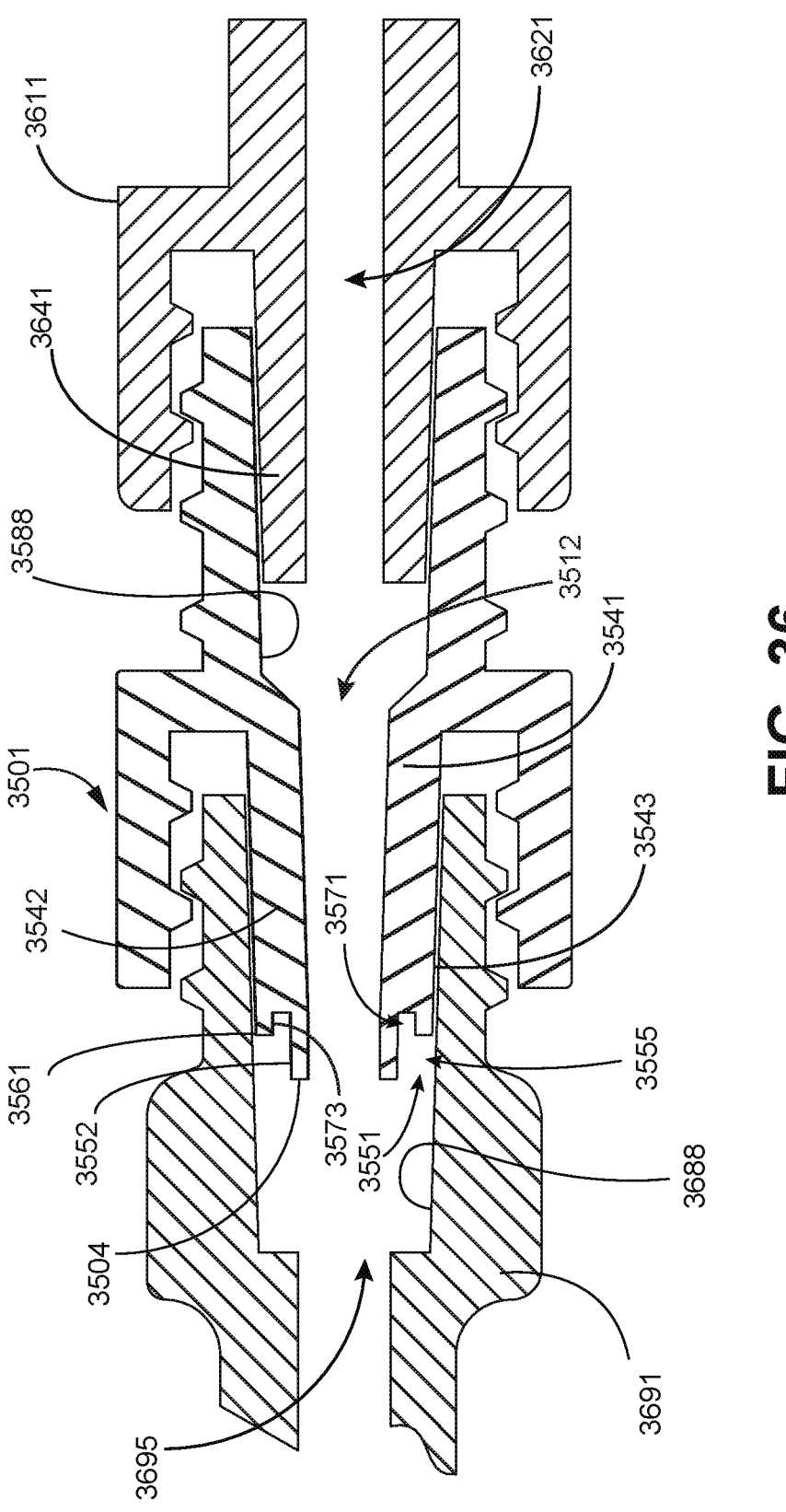

FIG. 36 is a cross-sectional view of the luer coupler of FIG. 34A installed between a female connector and a male connector according to some examples.

Figure 37:
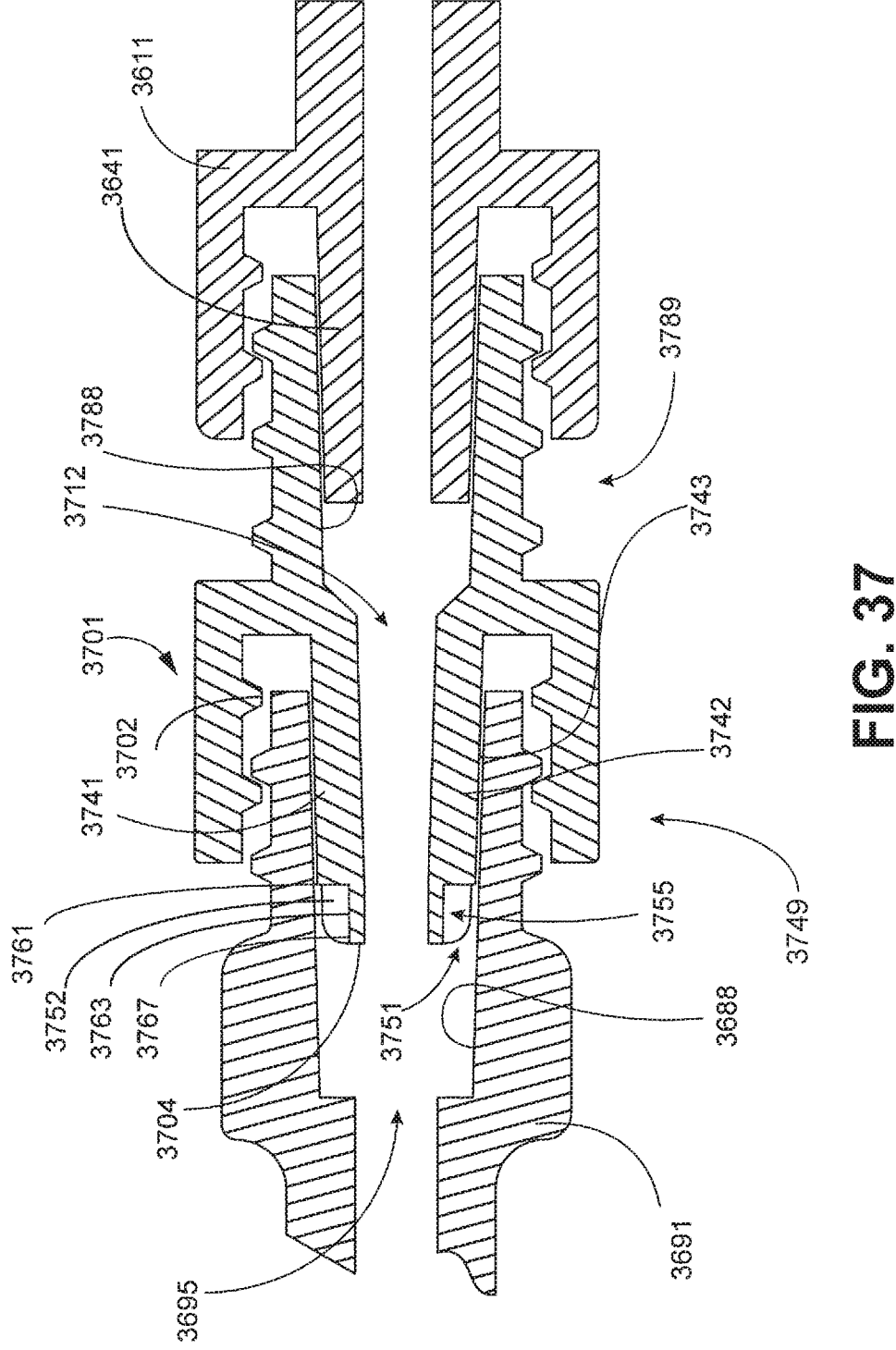

FIG. 37 is a cross-sectional view of the luer coupler of FIG. 35A installed between a female connector and a male connector according to some examples.

Figure 38:
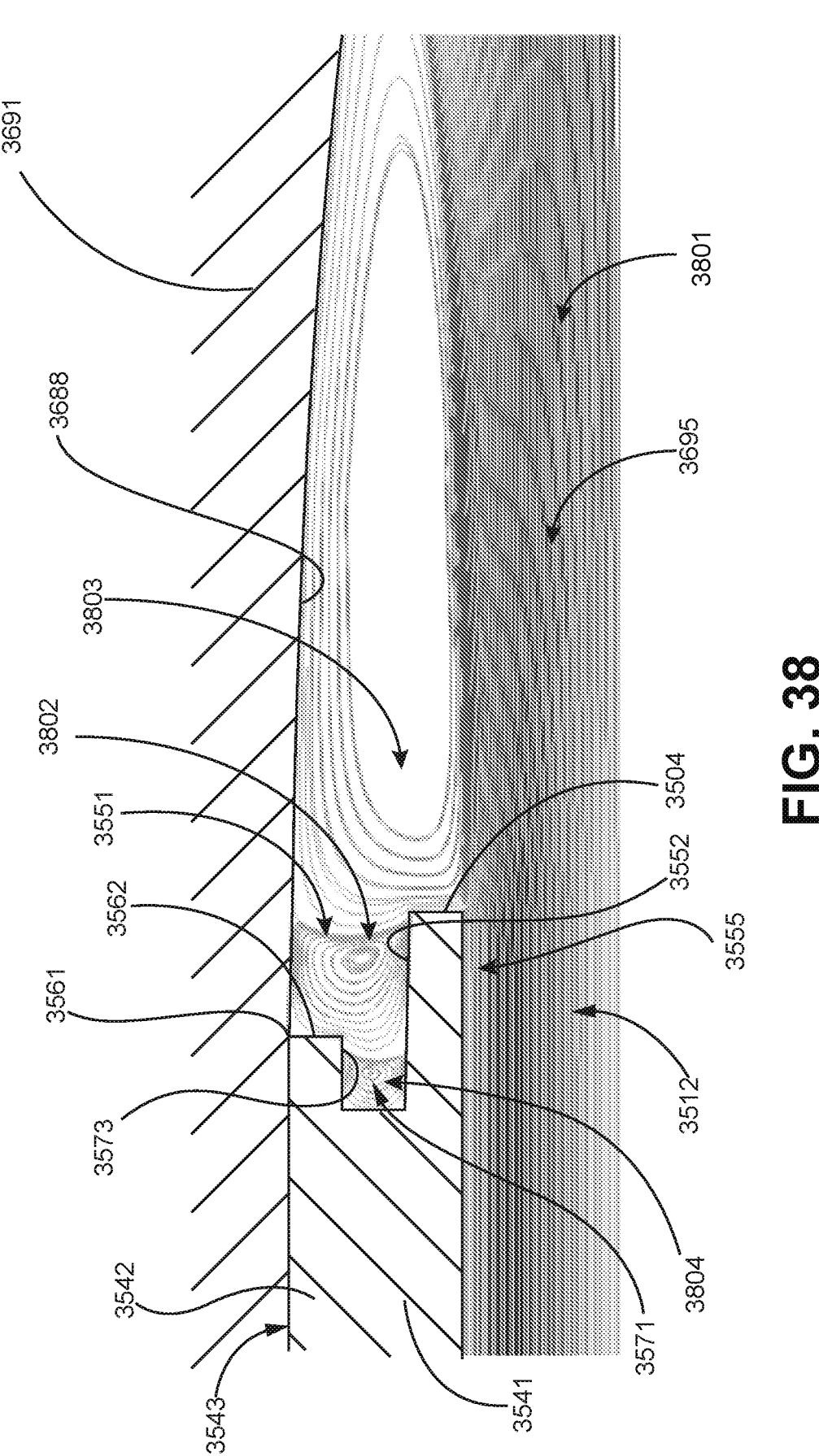

FIG. 38 is a fluid flow model showing recirculating flow within a male-female luer connection under syringe load conditions.

Figure 39:
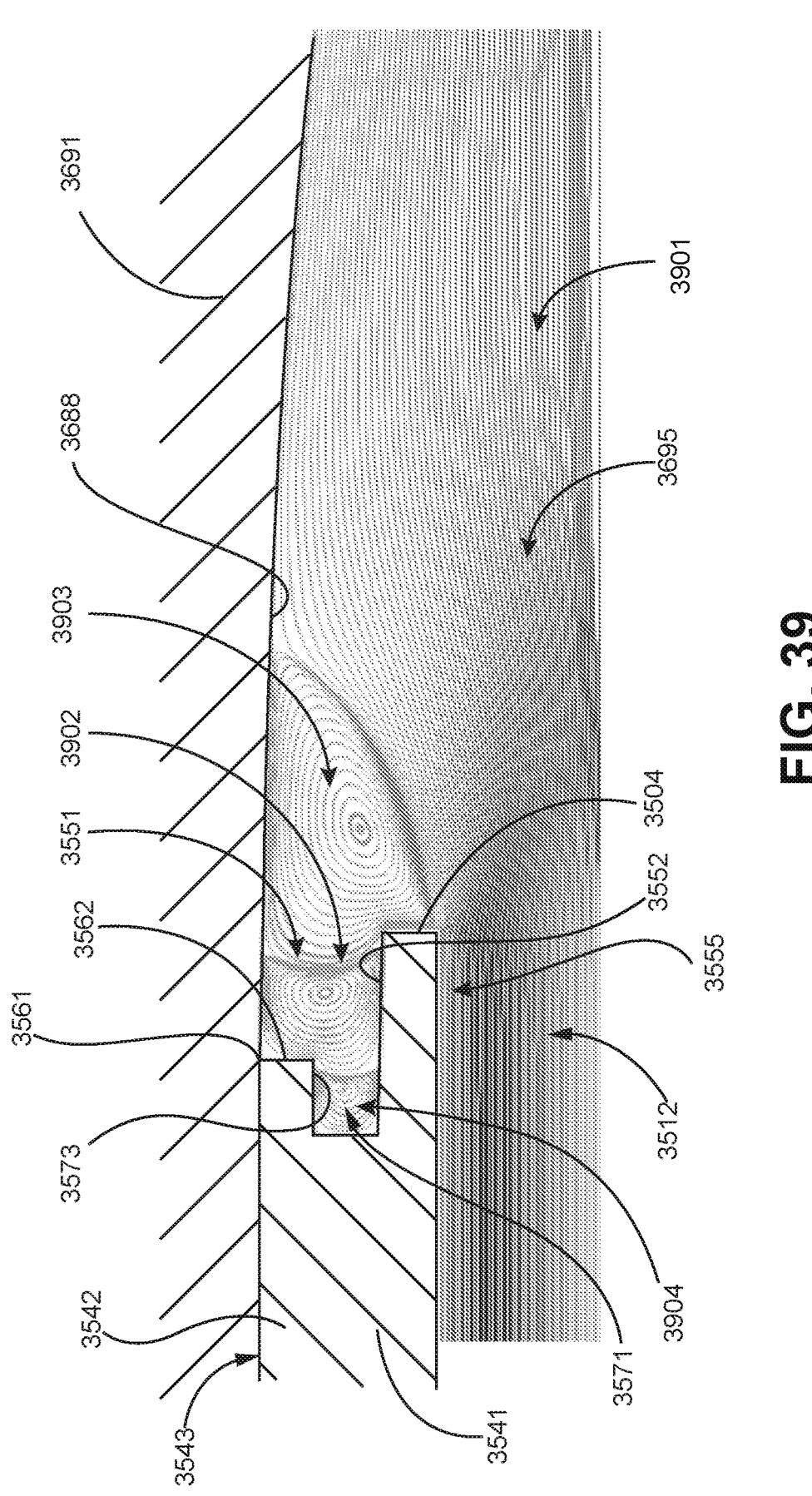

FIG. 39 is a fluid flow model showing recirculating flow within a male-female luer connection under IV drip conditions.

Figure 40A:
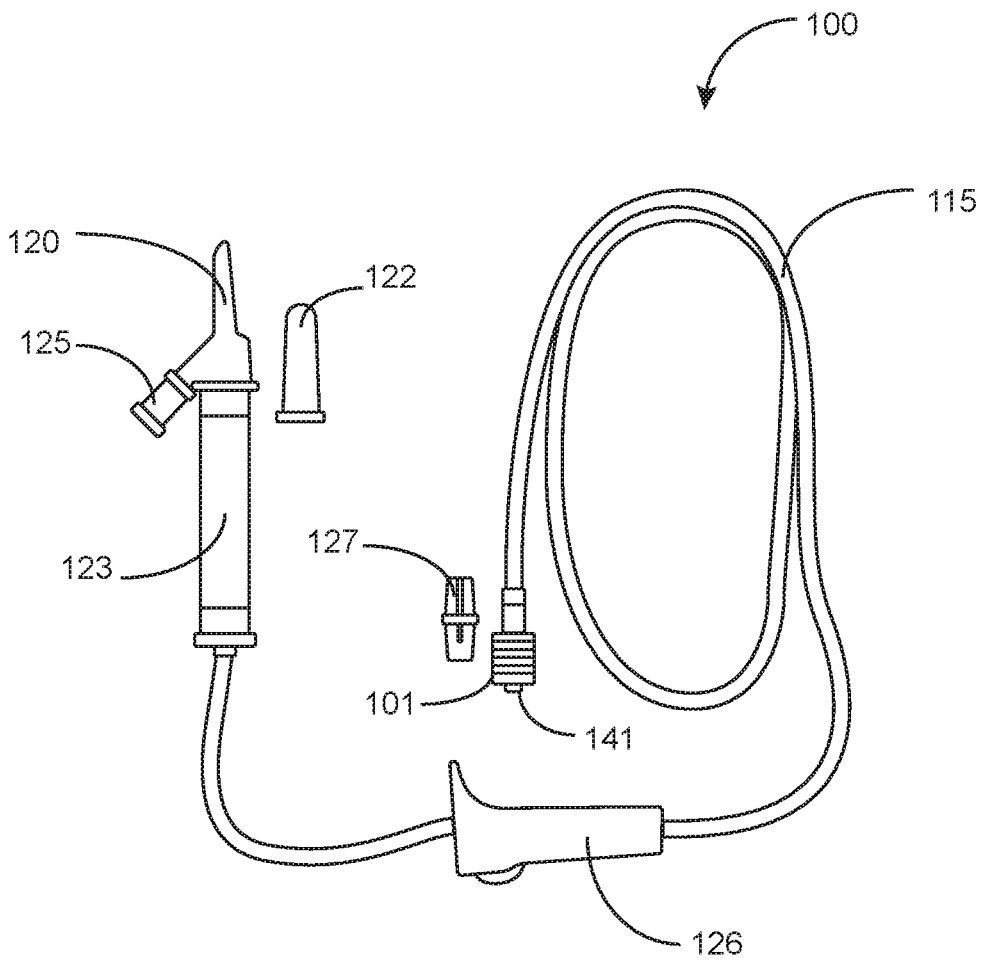

FIG. 40A is a perspective view of a medical tubing set.

FIG. 40B is a cross-sectional view of the medical tubing set of FIG. 40A

FIG. 40C is a perspective view of a medical tubing set of FIG. 40A

Figure 41A:
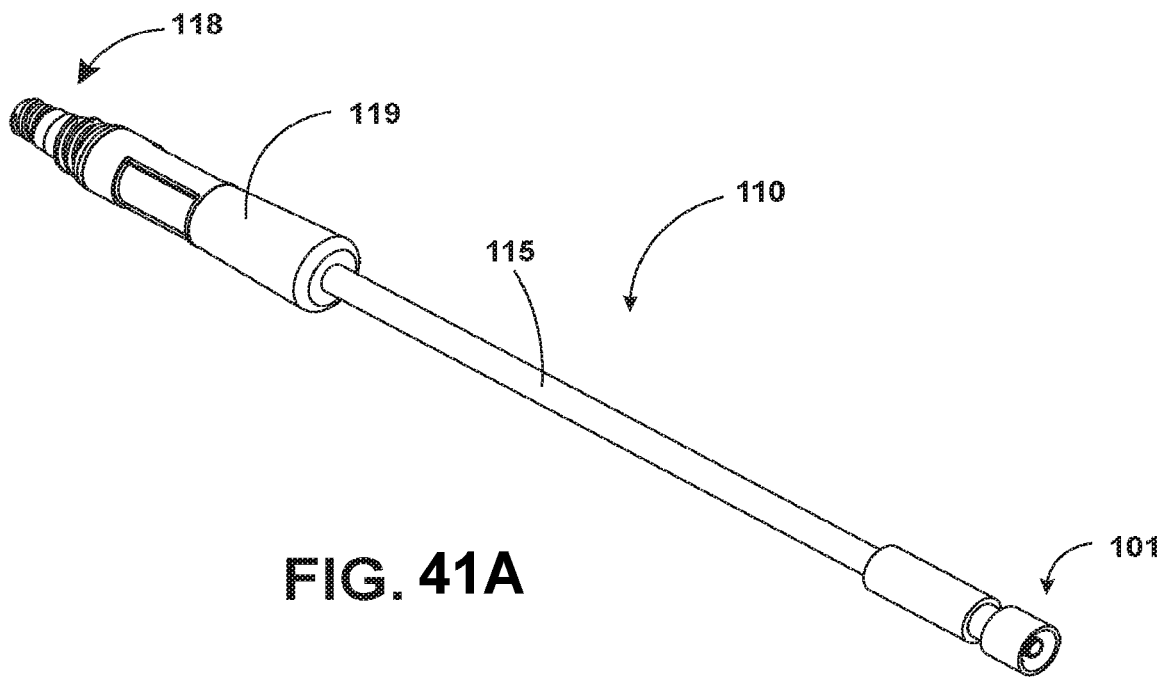

FIG. 41A is a perspective view of a peritoneal dialysis transfer set.

Figure 41B:
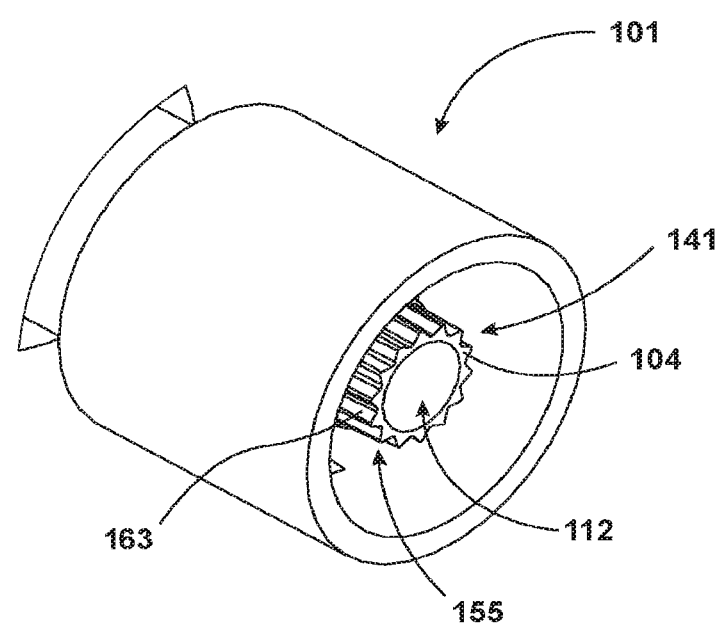
Figure 41C:
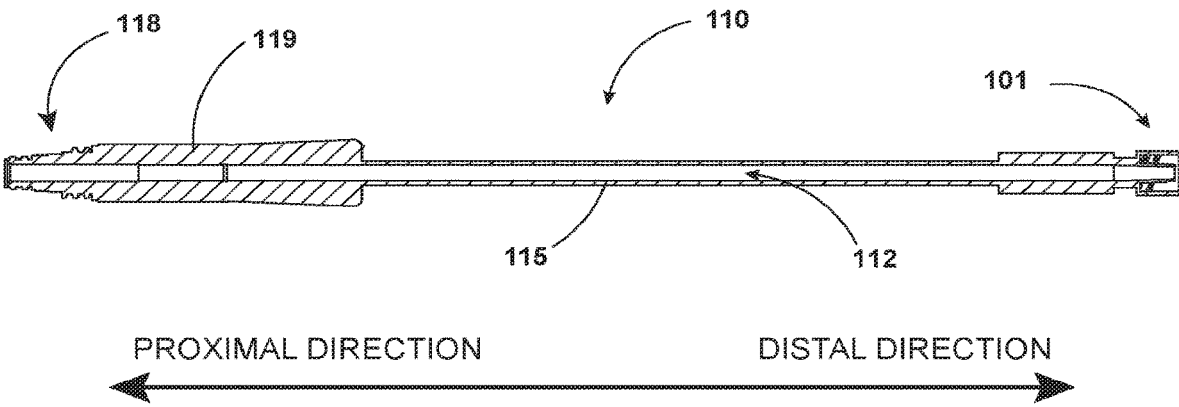
Figure 41D:
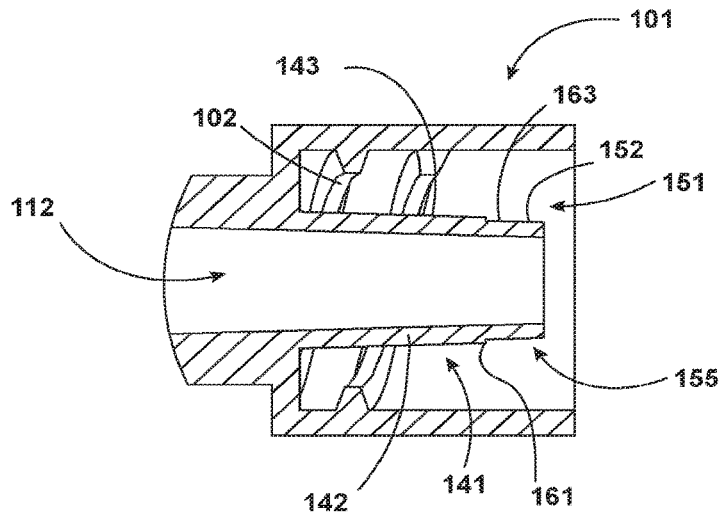

FIG. 41B is a cross-sectional view of a male connector of the peritoneal dialysis transfer set of FIG. 41A FIG. 41C is a cross-sectional view of a peritoneal dialysis transfer set of FIG. 41A FIG. 41D is a closeup cross-sectional view of the male connector of FIG. 41C.

FIG. 42A is an isometric view of a male luer connector according to some examples.

FIG. 42B is a cross-sectional view of the male luer connector of FIG. 42A.

FIG. 42C is an enlarged view inside circle C of FIG. 42B.

FIG. 43A is an isometric view of a male luer connector according to some examples.

FIG. 43B is a cross-sectional view of the male luer connector of FIG. 43A.

FIG. 43C is an enlarged view inside circle C of FIG. 43B.

Figure 44A:
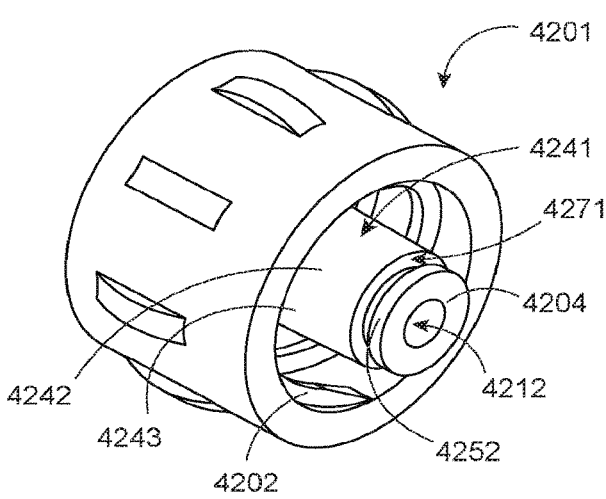

FIG. 44A is an isometric view of a male luer connector according to some examples.

Figure 44B:
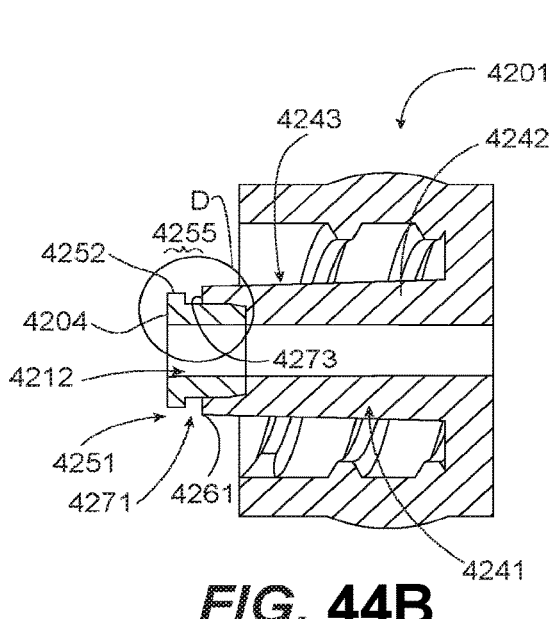

FIG. 44B is a side view of the male luer connector of FIG. 44A.

Figure 44C:
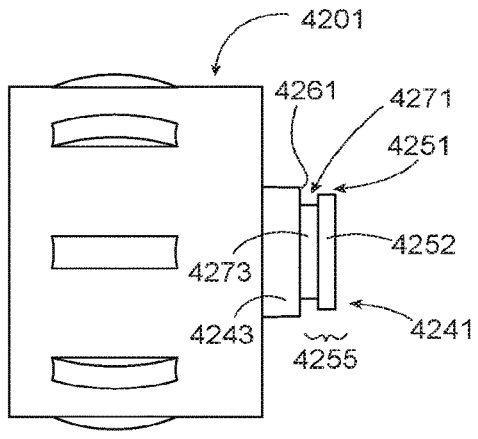

FIG. 44C is a cross-sectional view of the male luer connector of FIG. 44A.

Figure 44D:
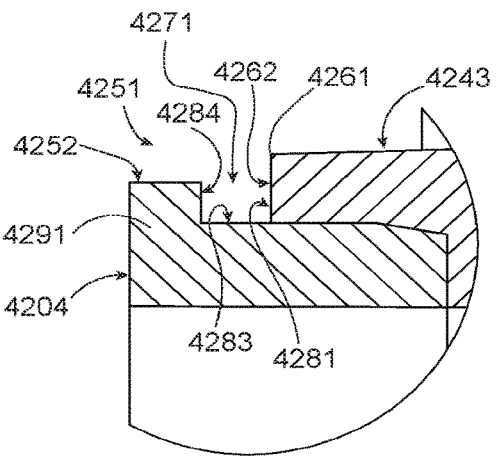

FIG. 44D is an enlarged view inside circle D of FIG. 44C.

FIG. 45A is an isometric view of a male luer connector according to some examples.

FIG. 45B is a side view of the male luer connector of FIG. 45A.

FIG. 45C is a first cross-sectional view that bisects the trough of a blade of the male luer connector of FIG. 45A.

FIG. 45D is an enlarged view inside circle D of FIG. 45C.

FIG. 45E is a second cross-sectional view that bisects the apex of a blade of the male luer connector of FIG. 45A.

FIG. 45F is an enlarged view inside circle F of FIG. 45E.

FIG. 46A is an isometric view of a male luer connector according to some examples.

FIG. 46B is a cross-sectional view of the male luer connector of FIG. 44A.

FIG. 46C is an enlarged view inside circle C of FIG. 46B.

Figure 47A:
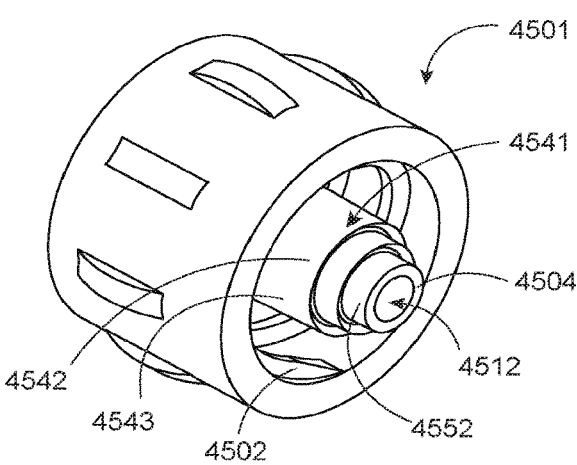

FIG. 47A is an isometric view of a male luer connector according to some examples.

Figure 47B:
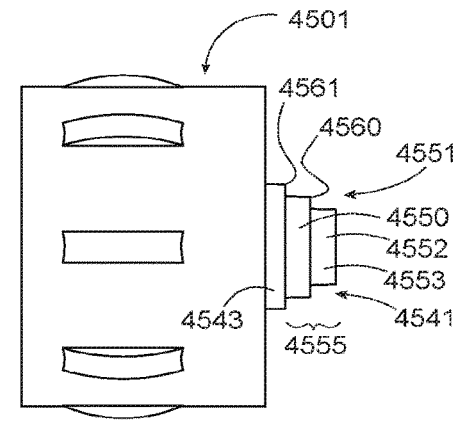

FIG. 47B is a side view of the male luer connector of FIG. 47A.

Figure 47D:
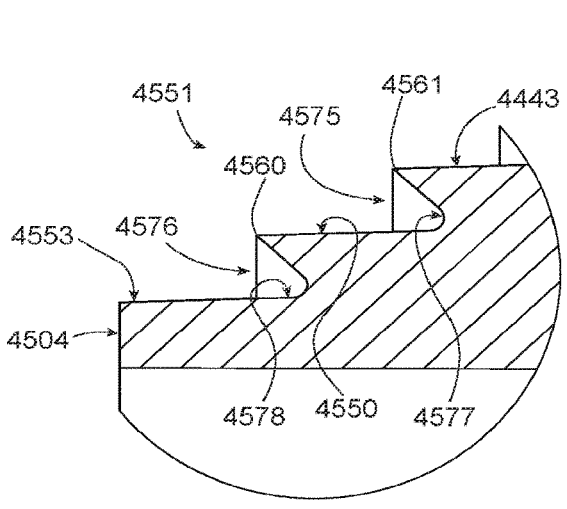
Figure 47C:
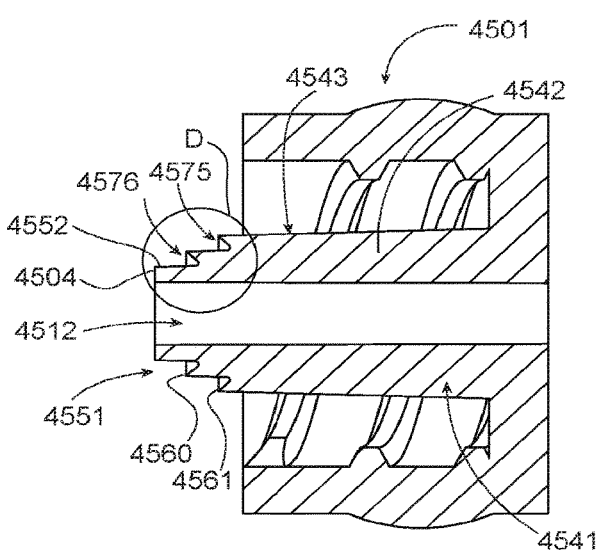

FIG. 47C is a cross-sectional view of the male luer connector of FIG. 47A.

FIG. 47D is a cross-sectional view of the male luer connector of FIG. 47A inside circle D of FIG. 47C.

FIG. 48A is a perspective view of a syringe with antimicrobial properties according to some examples.

FIG. 48B is an enlarged view of the syringe of FIG. 48A

Figure 48C:
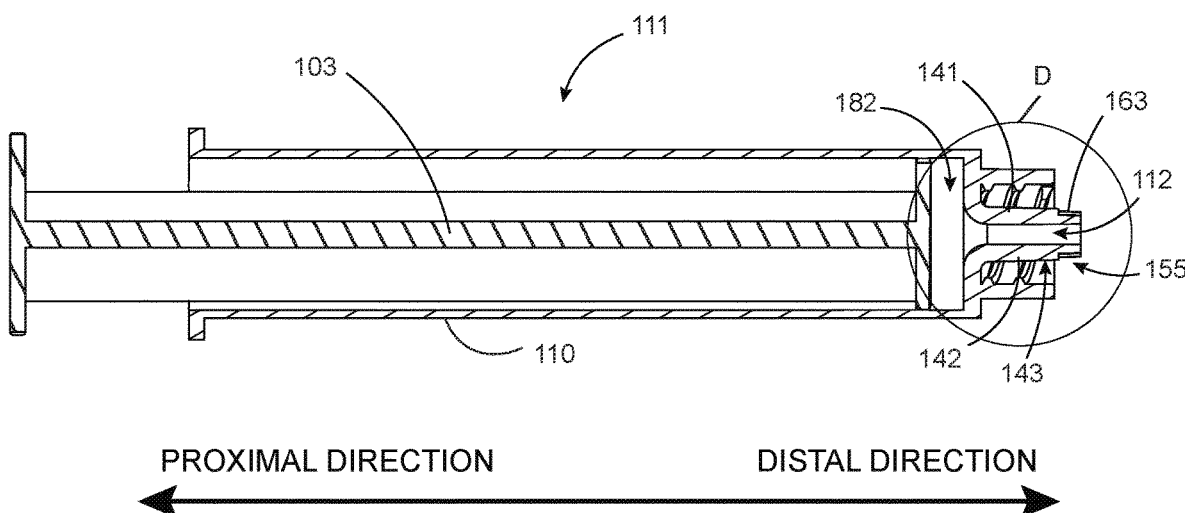

FIG. 48C is a cross-sectional view of the syringe of FIG. 48A

Figure 48D:
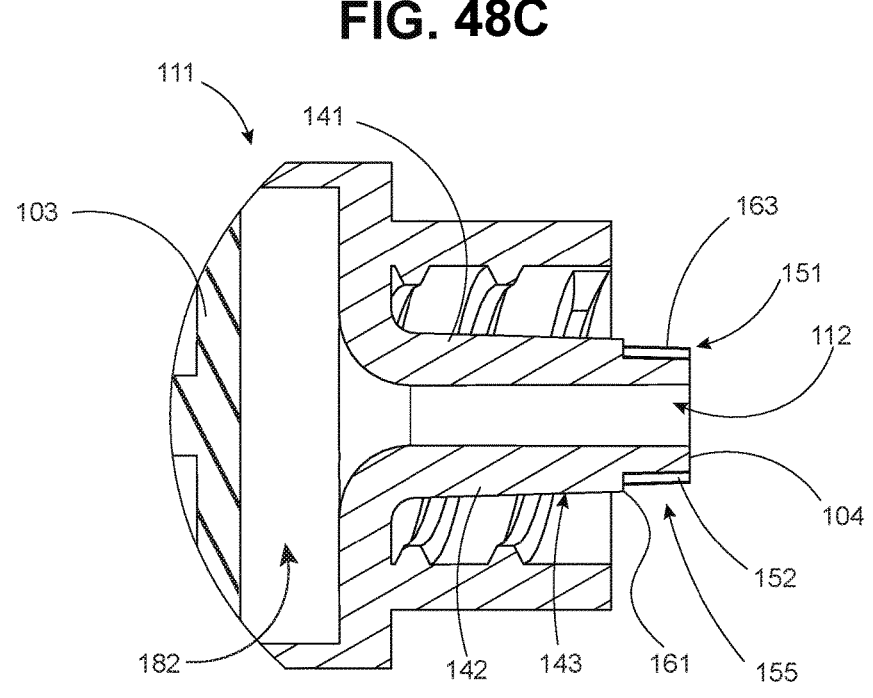

FIG. 48D is an enlarged view of the cross-section of FIG. 48C inside circle D.

Figures 48E, 48F:
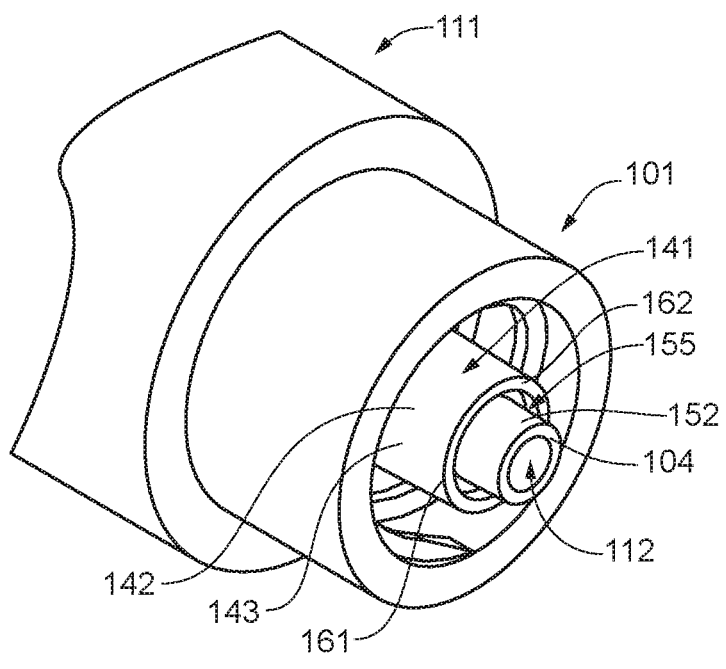

FIG. 48E is a perspective view of an alternative example of a syringe with antimicrobial properties according to some examples.

FIG. 48F is a cross-sectional view of the syringe of FIG. 48E.

Figure 48G:
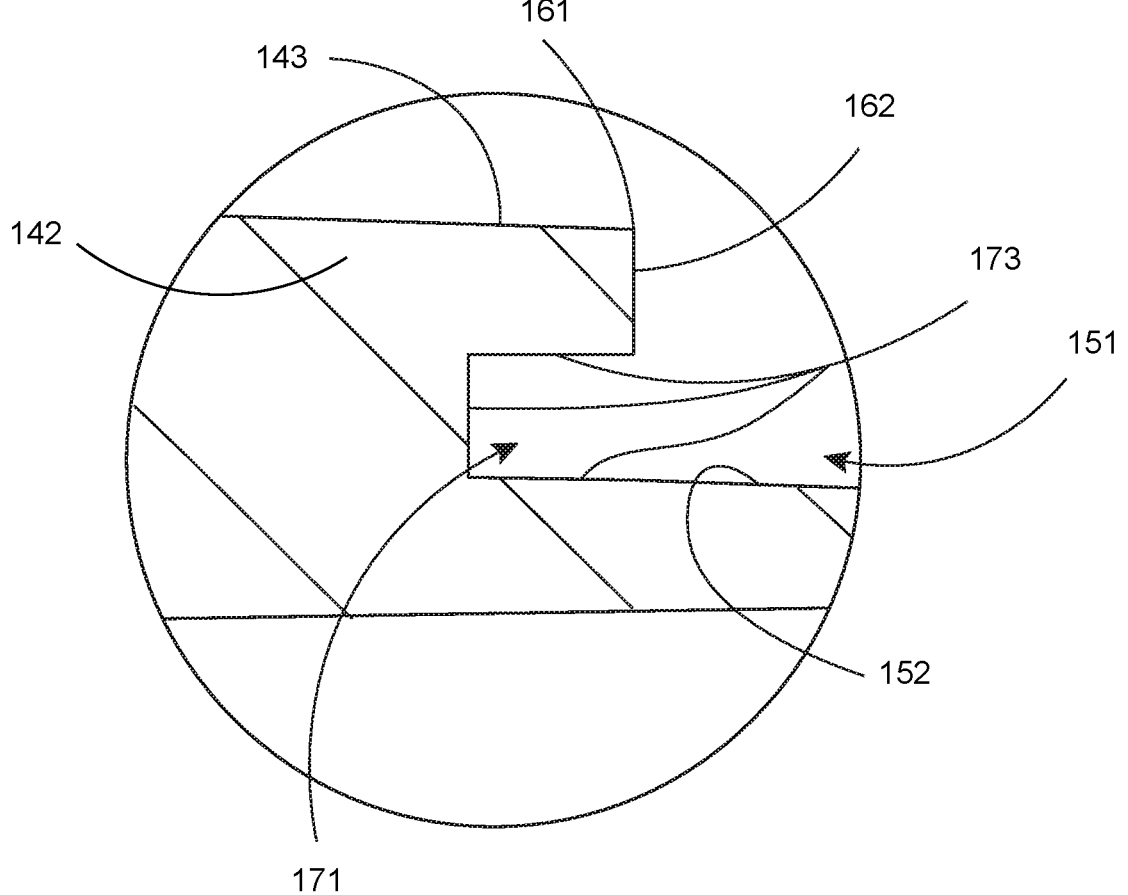

FIG. 48G is an enlarged view of FIG. 48F inside circle G.

It will be noted that in some cross-sectional figures the illustrations have been simplified, such as removal of the background threads on the sealing cover to make the various aspects of the invention more apparent. While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein. For example, the term "infusion device" of FIG. 9 was chosen to point out that the examples are not limited to a specific infusion device. The infusion device can be a needleless connector, a transfer set, an infusion set or other infusion devices having a male connector.

DETAILED DESCRIPTION

Numerous challenges are present for safely using medical devices incorporating male and female connectors. For example, medical devices such as catheters used in intravenous administration of fluids, hemodialysis, peritoneal dialysis, parenteral nutrition and chemotherapy are often worn for prolonged periods of time in the moist environment next to a patient's skin. This is an ideal environment for bacterial growth. Peripherally inserted central catheters and midline catheters will typically have dozens of connections made between a male and female luer over the course of use, and each time the device is connected it provides an opportunity for infection caused by ingress of organisms along the female luer.

And every infusion device that has a female luer hub is susceptible to the fact that the interior female luer surface is not readily accessible to sanitizing wipes. Conventional sterilization methods are not able to kill microorganisms once they ingress to the female luer surface. Thus, these organisms are free to continue to ingress until reaching the bloodstream and ultimately creating a bloodstream infection. In addition, drug resistant organisms are becoming more common in hospitals and outpatient healthcare settings, which makes treatment of bloodstream infections more difficult.

In contrast, the coupling between female connector of a peritoneal dialysis catheter and a male connector of a transfer set will typically have one disconnection and reconnection every one to six months. Although the timeframe between connections will vary by application, every infusion device that has a female luer hub is susceptible to microbial infusion into the female luer surface and is susceptible to the fact that the interior female luer surface is not readily accessible to sanitizing wipes. Conventional sterilization methods are not able to reliably kill microorganisms once they ingress to the female luer surface. Thus, these organisms are free to continue to ingress until reaching the interior of the body and ultimately creating peritonitis or a bloodstream infection. In addition, drug resistant organisms are becoming more common in hospitals and outpatient healthcare settings, which makes treatment of bloodstream infections more difficult.

Multiple ingress pathways can lead to contamination of the female luer surface. One source of female luer contamination occurs when the female luer is open, with no male luer inserted. During the time the female luer is open, it is susceptible to airborne organisms landing on the surface (such as from a person's breath or other source). Another source of female luer contamination is ingress along the threads and proximal end of the female hub, where organisms can then enter into the very small gap that exists between the proximal end of the male-female luer surfaces where the surfaces touch.

Those skilled in the art understand that organisms can ingress to the proximal end of the hub, but they are widely unaware that a gap exists between the male and female luers and that organisms can infiltrate this gap where standard cleaning procedures are ineffective. Thus, the common viewpoint is that cleaning the end of a female connector is sufficient to stop this route of organism ingress. The inventors have discovered that this is not sufficient; standard alcohol wiping/cleaning procedures are not effective at killing the organisms that enter the inside of the female luer. Once inside the female luer, organisms can be pushed by the end face of the male luer into the lumen of the female luer device.

For example, use of needleless connectors on infusion devices is common practice. The needleless connectors are typically replaced every 4-7 days, thus they are prone to contamination of the inside of the female luer, as described above, which can ultimately lead to bloodstream infection.

For example, use of a transfer set on a peritoneal dialysis catheter is common practice. The transfer set is typically replaced every 1-3 months, thus they are prone to contamination of the inside of the female luer, as described above, which can ultimately lead to peritonitis and, in too many cases, death.

The technology disclosed herein provides a distal recess at the distal tip of the male luer member. The distal tip surface contains a concentrated amount of an antimicrobial composition that remains confined within the cavity between the distal tip surface of the male luer and tapered sealing surface of the female luer. Organisms inside the female luer remain within the cavity, proximal to the lumen of the male luer. Various examples provided herein create an environment that confines the antimicrobial agent near the distal end of the male luer.

Disclosed herein are embodiments of a device for delivering an antimicrobial composition into a medical device. In some embodiments, the device for delivering an antimicrobial composition can have a male connector having a male tapered surface. The male connector can further include a distal tip having a distal end. The distal tip can have a recess surface proximal to the distal end, wherein the recess surface is radially inward of a line of taper extending along, and distal of, the male tapered surface at a first taper angle relative to a central longitudinal axis of the male connector. The device can also have a water-soluble antimicrobial composition positioned on the recess surface. In any embodiments disclosed herein, without limitation, the device for delivering an antimicrobial composition can be a cap, a connector, a needleless connector, a tubing set, a peritoneal dialysis transfer set, or a syringe.

Referring now to the drawings, in another aspect described in relation to FIGS. 1A, 1B, and 1C, one implementation of the disclosed technology provides a needleless connector 111 having a male luer 141 at a distal end of the needleless connector 111. The male luer 141 includes a distal tip 155 and a tapered sealing member 142 with a tapered sealing surface 143. The needleless connector 111 has a lumen 112 extending through the needleless connector 111 through which fluid can flow. At the proximal end of the needleless connector 111, first threads I 05 are provided for mating the needleless connector 111 with another medical device, such as a luer lock syringe. At the distal end of the needleless connector 111, second threads 102 are provided for coupling the male luer 141 with a medical device having a female luer, such as the proximal end of a catheter for infusion of fluids, medications, or the like. The distal tip 155 also includes a distal tip surface 152 and a distal end face 104. The tapered sealing member 142 has a tapered surface distal edge 161 situated at the proximal end of the distal tip 155 and at the distal end of the tapered sealing surface 143.

As will be discussed further below, the male luer 141 forms a distal recess 151 when inserted into a female connector. The distal tip surface 152 can include an antimicrobial agent. The distal tip 155 is recessed inside a line of taper of the tapered sealing member 142. As used herein, the line of taper is a representation of an imaginary frustoconical surface defining a conical taper extending beyond the tapered surface distal edge of the male luer. The line of taper is substantially coincident with the female luer surface after the tapered sealing member is inserted into the female luer. The distal recess 151 and a distal recess volume is defined by a space bounded by the female luer surface (which is similar to the line of taper), the tapered surface distal edge face 162, and a plane coincident with a distal end of the distal tip 155.

In the example of FIGS. 1A and 1B, the male luer 141 further includes a proximal trap 171 at the proximal end of the distal tip 155. The proximal trap 171 is defined as the space between a plane passing though tapered surface distal edge face 162 and the proximal trap walls 173. The proximal trap 171 is an annular cavity that is bounded on multiple sides. The proximal trap 171 opens on the distal recess 151. The proximal trap is adjacent to and proximal to the tapered surface distal edge face 162. As will be discussed below in relation to FIGS. 38 and 39, the proximal trap 171 can store an antimicrobial agent within the annular cavity defined by the proximal trap 171.

A number of examples of male luer configurations are described below. It should be understood that each example below could be used in place of the male luer 141 of the needleless connector 111 shown in FIGS. 1A-1C to create the needleless connector 111.

The needleless connector 111 may further comprise a compressible member 113 and a spire 114. In some examples, the compressible member 113 is made of a silicone material that forms a septum. In some examples, the spire can be formed from a hard material such as polycarbonate. There is an interference fit between the spire and silicone member.

Referring now to the drawings, FIG. 1 is a schematic diagram of a patient undergoing peritoneal dialysis, showing a peritoneal catheter 10 extending into a peritoneal cavity 12 (surrounded by peritoneum 13) of the patient into which a dialysis solution from source bag 15a flows into the patient. The dialysis solution is then later drained into drain bag 15b. The catheter 10 is in fluid communication with the bags 15a and 15b by means of a tubular transfer set 14 and an infusion set 16. Couplings 17 and 18 are positioned on either end of the transfer set 14. Coupling 17 joins the transfer set 14 to the catheter 10, while coupling 18 joins the transfer set 14 to the infusion set 16. Generally, the catheter 10 and transfer set 14 are kept joined at coupling 17 for long periods of time (weeks and months), while the transfer set 14 and infusion set 16 are only joined at coupling 18 for the dialysis solution (dialysate) exchange process. This dialysis solution exchange process can take, for example, 30 minutes up to four times a day for continuous ambulatory peritoneal dialysis (CAPD), or overnight once a day for automated peritoneal dialysis (APD).

In some examples, the transfer set 14 can be the peritoneal dialysis transfer set 110 as described above in relation to FIGS. 41A-41D. Coupling 17 is located at the distal end of the transfer set 14, which corresponds to the location of the male connector 101 in FIGS. 41A-41C. In clinical practice, the transfer set 14 is most often left attached to the catheter 10 (at coupling 17) and the fluid connections are broken at coupling 18. However, there are applications when the catheter 10 is capped.

During the CAPD exchange process the waste dialysis solution flows from the peritoneal cavity 12 through the catheter 10, on to the coupling 17 and transfer set 14, then through coupling 18 and finally through the lower portion of the infusion set 16 into the drain bag 15b. After the exchange process is complete, the infusion set 16 is separated at coupling 18 from transfer set 14 and the female connector of transfer set 14 is capped until the next dialysis solution exchange is initiated (not shown). Thus, in typical peritoneal dialysis the exchange process is initiated by removing a male cap from the female connector of transfer set 14 and then joining to the infusion set 16 to form coupling 18; and this process is reversed at the end of the exchange process by removing the infusion set 16 at coupling 18 and installing a new male cap.

It will be appreciated that FIG. 1 has been simplified for clarity. An automated machine or different tubing arrangement may be used to transfer dialysis solution from the source bag 15a to the peritoneal cavity 12 or from the peritoneal cavity 12 to the drain bag 15b. The movement of the dialysis solution can be advanced by gravity, pumps, or other mechanisms.

Referring now to FIG. 2A, a perspective view of the proximal end of a peritoneal catheter 24 with a male cap 30 installed on a female connector 40 is shown, while FIG. 2B is a perspective view of the proximal end of the peritoneal catheter 24 of FIG. 2A with the male cap removed, and FIG. 2C is a perspective view of the proximal end of the peritoneal catheter 24 of FIG. 2B connected to a transfer set 14. FIG. 2A specifically shows a perspective view of the proximal end of peritoneal catheter 24 having a tube 22 with a female connector 40 onto which a male cap 30 has been installed. Generally, the female connector 40 includes a female luer inside (not shown), while the male cap 30 includes a male luer (not shown). The proximal end of the peritoneal catheter 24 (that portion furthest from the patient) is shown along with female connector 40 and male cap 30. Also, the transfer set 14 of FIG. 2C is shown in a foreshortened construction for ease in illustration. Normally the transfer set 14 is from approximately 6 to 18 inches long but can be longer or shorter, and thus end 27 of tube 21 on transfer set 14 often includes an extended length before joining to a second connector (not shown) that is typically capped between dialysis treatments, but which is then uncapped and joined to an infusion set during dialysis.

FIG. 2B is a perspective view of the proximal end of the peritoneal catheter 24 of FIG. 2A with the male cap removed from the female connector 40, including a female luer 42. The female luer 42 is a volume within the interior area of the female connector 40 that receives and seals with a male luer from a male cap or male connector. FIG. 2C is a perspective view of the proximal end of the peritoneal catheter 24 of FIGS. 2A and 2B connected to a transfer set 14 by means of a male connector 50 comprising a male luer (the male luer is part of male connector 50 inside the end of the female connector 40 of peritoneal catheter 24, and not visible, but it will be understood that within the female connector 40 is a tapered male luer forming a seal with a female luer).

Now in reference to FIGS. 3A to 3F', various stages of traditional cap and connector installation and removal are shown, along with properties of microbial growth on the cap and connector. It should be noted that in some cross-sectional figures the illustrations have been simplified to make the various aspects of the embodiments more apparent. FIG. 3A is a cross-sectional view of a proximal end of a peritoneal catheter 24 with a male cap 30 installed. FIG. 3A' provides an enlarged cross-sectional view of the proximal end of the peritoneal catheter 24 with male cap 30 installed, corresponding for example to the construction of FIG. 2A, showing the female connector 40 with male cap 30. FIG. 3A shows directional arrows depicting the distal direction and the proximal direction (an intermediate location would be between the distal and proximal directions). FIG. 3A further shows a male cap 30, with the proximal and distal ends of the male cap 30 labeled. Thus "proximal" and "distal" are relative terms, showing the position relative to the patient and ends of a device.

As is shown in FIG. 3A, the male cap 30 includes a male luer 32 having a tapered outer surface 33, while the female connector 40 has a female luer 42 with a tapered inner sealing surface 43 designed to seal with the tapered outer surface 33 of the male luer 32. The end face 34 of the male luer 32 (which is at the distal end of the male cap 30) is exposed to the interior of a lumen 38 (open channel) through the female connector 40. In FIG. 3A the male cap 30 is shown having threads 19, which engage with corresponding threads 23 of the female connector 40. The female connector 40 includes a female luer 42 which is a volume within the female connector 40. The female luer 42 in this embodiment includes a tapered sealing surface 43. The female luer 42 of the female connector 40 and the male luer 32 of the male cap 30 form a fluid-tight connection at overlapping region 41. When the female connector 40 and male cap 30 are threaded together they still can provide an infiltration path into an interstitial space or gap 35 (and subsequently into the lumen 38) as shown in FIGS. 3A and 3A' where infiltration paths are shown, including past the threads 19, 23 to the interstitial space or gap 35 between the female connector 40 and male cap 30, more specifically (but not exclusively) between the tapered inner sealing surface 43 of the female luer 42 of the female connector 40 and the tapered outer surface 33 of male luer 32 of the male cap 30. This interstitial space or gap 35 within the overlapping region 41 between the tapered sealing surfaces 33, 43 of the male and female luers 32, 42 is present during installation and removal of the male cap 30 but our testing shows the gap 35 also often exists after the male cap 30 has been coupled to the female connector 40. When the male cap 30 is inserted into the female connector 40, the male and female luers 32, 42 generally form a fluid tight seal somewhere within the overlapping region 41 between them. However, the interstitial space or gap 35 commonly exists along at least a portion of the overlapping region 41, thus allowing microbes 28 to infiltrate into the gap 35 from the female connector end face 48 of the female connector 40.

FIGS. 3B and 3B' show the cross-sectional views of FIGS. 3A and 3A', but with microbes 28 having infiltrated past the threads 19 and 23 (the threads do not form a seal) and colonized portions of the interface between the female connector 40 and male cap 30 at gap 35. This infiltration and growth of microbes 28 is shown in schematic representation (the sizes of the microbes in reality is much smaller, and distribution can be irregular).

FIG. 3C is a cross-sectional view of the peritoneal catheter 24 of FIGS. 3A and 3B with the male cap 30 removed, exposing the female luer 42 into which the male luer 32 of a male cap or male connector can be inserted (not shown), and FIG. 3C' is a closeup cross-sectional view of a portion of the proximal end of the peritoneal catheter of FIG. 3C, including the female connector end face 48 of the female connector 40. In FIGS. 3C and 3C' the microbes 28 are present on the female connector end face 48 of the female connector 40, and even after removal of the male cap 30 many of the microbes 28 remain. Therefore, between dialysis treatments or other processes the female connector 40 often has high levels of microbes present, including on the exposed female connector end face 48 and threads 23 as well as on the tapered inner sealing surface 43 of the female luer 42 of the female connector 40. Thus, FIGS. 3C and 3C' are essentially a representation of the female connector 40 after removal of the male cap.

FIG. 3D is a cross-sectional view of the peritoneal catheter of FIG. 3C with the male cap removed, and FIG. 3D' is a closeup cross-sectional view of a portion of the proximal end of the peritoneal catheter of FIG. 3D. In FIGS. 3D and 3D' the female connector 40 has been cleaned, such as with an alcohol wipe, but microbes remain, in particular (in this embodiment) on the tapered inner sealing surface 43 in the female luer 42 of the female connector 40 because the cleaning wipes do not reach sufficiently inside the female luer 42 of the female connector 40 when using industry standard cleaning procedures.

FIG. 3E is a cross-sectional view of the peritoneal catheter 24 of FIG. 3D with a new male cap 30' installed, and FIG. 3E' is a closeup cross-sectional view of the peritoneal catheter of FIG. 3E. The new male cap 30' is typically a new, sterilized cap, and not the same male cap 30 shown in FIGS. 3A and 3B because caps are not generally reused. In FIGS. 3E and 3E' it is shown how microbes 28 are pushed into the lumen 38 when a new male cap 30' is installed. This occurs, in part, because a leading edge 36 of the end face 34 of the male luer 32 on the new male cap 30' can push microbes down into the lumen 38 during installation of the male cap 30'. These microbes, which in FIG. 3D were on the tapered sealing surface 43 of the female connector 40, are in FIG. 3E in a position distal to their position in FIG. 3D. The microbes are pushed in by the leading edge 36 of the male luer 32. Even if great care is taken to not scrape the walls of tapered inner sealing surface 43 of the female luer 42, some microbes 28 can be pressed into the lumen 38. Once the new male cap 30' is installed, the catheter or other infusion device is often left alone for hours, days or even weeks, during which time the microbes 28 can multiply and spread further into the lumen 38, as shown in FIGS. 3F and 3F'. FIGS. 3F and 3F' show a cross-sectional view of the peritoneal catheter 24 with the new male cap 30' installed of 3E and 3E', after a period of time during which microbes 28 have increased in population and begun colonizing down the walls of the lumen 38, where they can eventually reach into the patient either by continued growth and/or by becoming released from the walls of lumen 38 during fluid flow and thus flushed into a patient, thereby promoting infection in, and even death of, the patient.

FIG. 4A is a cross-sectional view of a peritoneal catheter containing a female connector 40, with a male cap 30 installed on the female connector 40; the male cap 30 containing an antimicrobial agent 29 on a male luer 32 of the male cap 30. More specifically, the antimicrobial agent 29 is on the tapered sealing surface 33 of the male luer 32. The antimicrobial agent 29 extends down into a gap 35 (similar to the gap 35 of FIGS. 3A to 3F, but now with the antimicrobial agent 29 present). FIG. 4A' is a closeup cross-sectional view of a portion of the proximal end of the peritoneal catheter of FIG. 4A.

FIG. 4B is a subsequent (in time) cross-sectional view of the peritoneal catheter of FIG. 4A with the male cap 30 installed, and FIG. 4B' is a closeup cross-sectional view of a portion of the proximal end of the peritoneal catheter of FIG. 4B. In FIGS. 4B and 4B' the microbes 28 that make contact with the antimicrobial agent 29 are represented as being dead microbes 28x. Thus, the number of surviving microbes 28 present is significantly smaller due to the antimicrobial agent 29. The microbes 28 and dead microbes 28x are shown as a schematic representation, rather than showing actual living or dead microbes drawn to scale. The dead microbes 28x thus represent either dead microbes themselves, as well as places where microbes have infiltrated and died (and possibly then fallen away or otherwise moved). Thus, FIGS. 4B and 4B' show how the presence of antimicrobial on the infiltration path can reduce microbes at the interface between the tapered sealing surfaces 33, 43 of the male and female luers 32, 42, thereby preventing movement and growth of microbes 28 down the infiltration path.

FIGS. 4C and 4C' show the end of the female connector 40 of FIGS. 4A and 4A' after removal of the male cap, showing dead microbes 28x on the tapered inner sealing surface 43 of the female luer 42 of the female connector 40. Even though there may be some microbes 28 on the female connector end face 48 of the female connector 40, the microbes on the tapered portions of the female luer 42 are shown dead (meaning they can be microbes that have been killed by the antimicrobial and/or can be places where microbes did not grow).

FIGS. 4D and 4D' show the female connector of FIGS. 4C and 4C' after cleaning the end of the female connector 40. In contrast to early FIGS. 3D and 3D', both the end and interior of the female connector 40 are free (or substantially free) of living microbes. Thereafter, upon insertion of a new male cap, with the new male cap containing an antimicrobial agent on a male luer of the male cap, as shown in FIGS. 4E and 4E', dead microbes 28x are pushed into the lumen 38, but these dead microbes 28x fail to grow, as shown in FIGS. 4F and 4F' (which represent a subsequent period in time, such as 48 to 72 hours, after the point shown in FIGS. 4E and 4E').

FIG. 5 is a cross-sectional view of a peritoneal catheter 24 with a distal end of a transfer set 14 connected. FIG. 5 corresponds generally to the dialysis stage of FIG. 2C, wherein the transfer set allows for fluid to flow between the dialysis solution and into and out of the patient's peritoneal cavity. In FIG. 5 a female connector 40 of the peritoneal catheter 24 is joined to a male connector 50 of the transfer set 14. The transfer set 14 further comprising a tube 57 (such as a tube for transferring dialysis fluid) that is attached to male connector 50. The male connector 50 comprises a male luer 52 with a tapered outer surface 53, and threads 23. Tube 57 includes an inner lumen 58. The male luer 52 of male connector 50 includes the tapered outer surface 53 that has a truncated conical surface, along with an end face 54. This design, similar to those shown in FIG. 3A to 3F, is also subject to infiltration and ingrowth of microbes, resulting in infections in a patient. The same principals of antimicrobial use in FIGS. 4A to 4F, in which the male luer 52 includes an antimicrobial, can be used to control microbial infiltration and growth and subsequent infections, specifically inclusion of a coating of antimicrobial agent on the outside of the male luer 52, such as at the distal end or intermediate portion of the male luer 52, or both (for example).

FIGS. 6A and 6B show an alternative infusion device, in this case a hemodialysis catheter 60 with female connectors 62, 64 and two tubes 61, 63 containing internal lumens (not shown) that run down the main section 65 of the catheter 60. FIG. 6A is a perspective view of the hemodialysis catheter, showing the hemodialysis catheter with two female connectors 62, 64 having caps 66, 68 installed. The hemodialysis catheter 60 is also shown with clamps 67, 69, the clamps shown in a closed orientation. The clamps 67, 69 are open during dialysis, but then closed between dialysis sessions and when the caps 66, 68 are being removed and inserted. FIG. 6B is a perspective view of the hemodialysis catheter 60, showing the hemodialysis catheter with two female connectors 62, 64 having caps removed. The female connectors 62, 64 are shown, as well as female luers 71, 73.

FIG. 7A is a cross-sectional view of an infusion set 16 connected to a female connector 40. The infusion set 16 has a male connector 50 and a tube 57. The male connector 50 has a male luer 52, the male luer 52 includes a distal recess 80 configured for delivery of an antimicrobial agent 29 (shown in FIG. 7A'). The distal recess 80 forms a cavity 81 once the male luer 52 is installed into a female luer 42 of the female connector 40. Female connector 40 includes a lumen 38 in fluid connection to lumen 58 in tube 57. The male luer 52 includes a tapered outer surface 53 that has a partial conical surface, along with an end face 54. Near the end face 54 is a distal recess 80 containing the antimicrobial agent 29 (shown in FIG. 7A'), such as chlorhexidine. The antimicrobial agent 29 is typically a dry-antimicrobial, and provides an antimicrobial effect to the interior surfaces of the female connector 40, especially at the region in the vicinity of the distal recess 80 of the male luer 52, and the area around where it meets the tapered inner sealing surface 43 of the female luer 42 of the female connector 40. As the male luer 52 is inserted into the female connector 40, the microbes 28 are pushed by tapered surface distal edge 55 of the male luer 52 rather than end face 54; thus, the microbes 28 are concentrated within the cavity 81 formed between the distal recess 80 and the female luer 42. The antimicrobial agent 29 may become wetted by fluid from lumens 58 and 38 when male connector 50 are connected with female connector 40. However, the fluid is (in certain embodiments) substantially retained within the cavity 81 even when fluid flows through the male connector 50 (which includes the male luer 52) because the cavity 81 only has a small opening (at the distal end of the distal recess 80, near the end face 54). This results in a high concentration of antimicrobial agent in the fluid in the cavity 81 without substantially depleting the antimicrobial agent 29 from the male luer 52. Thus, the antimicrobial agent within the fluid in the cavity 81 is at a lethal concentration for a sufficient time to kill the microbes 28 that were present on the female connector prior to connecting the male connector to the female connector.

FIG. 7B is a cross-sectional view of the male connector and female connector of 7A after a period of time. FIG. 7B' is a closeup cross-sectional view of a portion of the male and female luers of FIG. 7B. The microbes 28*x* are dead after being in contact with the antimicrobial agent 29 within the cavity 81 for the period of time. The dead microbes 28*x* will not multiply and will not cause an infection to a patient.

FIG. 8 is a cross-sectional view of an infusion set 16; the infusion set 16 including a male connector 50 and a tube 57, the male connector 50 comprising a male luer 52 including a distal recess 80, an end face 54 and an intermediate recess 82 configured for delivery of an antimicrobial agent. FIG. 8' is a close-up cross-sectional view of an intermediate recess 82 of the male luer 52. The male luer 52 includes a tapered outer surface 53 that has a truncated conical surface. The distal recess 80 contains an antimicrobial agent 29, and the intermediate recess 82 is proximal from the end face 54. The antimicrobial agent 29 is typically a dry-antimicrobial. FIG. 8' shows the intermediate recess 82, along with edges 83 and 84 of the recess. In some implementations the edges 83, 84 are smooth transitions with the tapered outer surface 53 of the male luer 52, while in other implementations the edges 83, 84 are more pronounced and defined, as shown in FIG. 8'. In one embodiment, edge 83 is removed and intermediate recess 82 continues distally until reaching the unmodified tapered sealing surface 53 of the male luer 52 (shown in FIG. 9"); this is for case of injection molding. The infusion set 16 may be used to connect to a female connector (not shown); thus providing similar infection prevention benefits described elsewhere herein.

FIG. 9 is a cross-sectional view of a portion of an infusion device 20 connected to a female connector 40. The infusion device 20 including a tube 57 joined to a male connector 50; the male connector 50 comprising a male luer 52 having a tapered outer surface 53. The male luer 52 of the male connector 50 includes an intermediate recess 82 in the tapered outer surface 53 containing an antimicrobial agent 29 and configured for delivery of the antimicrobial agent (intermediate recess referring to the recessed portion situated between the distal end and the proximal end of the tapered outer surface 53). The male luer 52 also includes a distal recess 80 at its distal end containing antimicrobial agent 29. The distal recess 80 forms a cavity 81 once the male luer 52 is installed into a female luer 42 of the female connector 40. FIG. 9' is a closeup cross-sectional view of the male luer 52 and female connector 40 of FIG. 9, showing an enlargement of the distal recess 80 which forms a cavity 81, the male luer 52, and female connector 40. Female connector 40 includes a lumen 38 in fluid connection to lumen 58 on tube 57 of the infusion set 16. The male luer 52 includes a tapered outer surface 53 that has a partial conical surface (a surface that corresponds substantially to the bottom of a cone), along with an end face 54. Near the end face 54 is the distal recess 80 containing antimicrobial agent 29.

FIG. 9" is a closeup cross-sectional view of the male luer 52 and the proximal end of the female connector 40 and the intermediate recess 82 of the male luer 52. In FIG. 9" the proximal edge 84 of intermediate recess 82 is shown. This proximal edge 84 can be, for example, a defined indent or a simple taper. The intermediate recess 82 extends both proximally and distally from a proximal-most end of the tapered inner sealing surface 43 of the female connector 40; thus providing a region for retaining a high concentration of the antimicrobial agent, which is retained by surface tension while the antimicrobial agent is in a dissolved state or partially dissolved state in a fluid. The antimicrobial reverts back to a dry-antimicrobial after the fluid had dried, with at least a portion of the antimicrobial agent being retained in the intermediate recess.

The antimicrobial agent is typically a dry-antimicrobial, and provides an antimicrobial effect to the interior of the female connector 40, especially at the region in the vicinity of the distal recess 80 of the male luer 52, the intermediate recess 82, and the overlapping region 41 (overlap of the tapered inner sealing surface 43 of the female luer 42, and the tapered outer surface 53). When the male luer 52 of the male connector 50 is inserted into the female luer 42 of the female connector 40, the microbes 28 are pushed by the tapered surface distal edge 55 of the male luer 52 rather than the end face 54; thus the microbes 28 are concentrated within the cavity 81. The antimicrobial agent 29 may become wetted by fluid in lumens 38 and 58 as the fluid flows into the recess while connecting male connector 50 to female connector 40. However, after connection, the fluid is substantially retained within the cavity 81 even when fluid flows through the male connector 50 because the cavity 81 only has one opening (at the distal end of the distal tip). This results in a high concentration of antimicrobial agent in the fluid in the cavity 81 without substantially depleting the antimicrobial agent 29 from the male connector 50. Thus, the antimicrobial agent within the fluid is at a lethal concentration for a sufficient time to kill the microbes 28.

The proximal edge 84 of intermediate recess 82 is located proximal to the proximal end of tapered inner sealing surface 43, but can optionally be located distal to the proximal end of the tapered inner sealing surface 43 of the female luer 42. Some benefits of intermediate recess 82 as shown in FIG. 9 are it provides a reservoir of antimicrobial agent 29 at the proximal end of the female connector 40 (killing the microbes where they enter) and, at the same time, it reduces the stress on the proximal end of the female connector 40, thus preventing stress cracking of the female connector.

In an example embodiment, the antimicrobial agent is located along the entire tapered outer surface 53 of the male connector 50, in the recesses 80, 82 and along male connector threaded surface 39 of a male connector 50 (the male connector threaded surface 39 including the proximal most surface that is adjacent to the proximal end of the tapered outer surface 53). The flow of a fluid in the lumen 38 is stopped by activating a first clamp, valve or other flow-stopping means (not shown) located distal to the female connector 40, and flow of a fluid in the lumen 58 is stopped by activating a second clamp, valve or other flow-stopping means (not shown) located proximal to the male connector 50. Prior to connecting the male connector 50 to the female connector 40, the first and second clamps are activated to prevent fluid flow within the lumens 38, 58. After activating the clamps, and as the male luer 52 is inserted into the female luer 42, the fluid inside the lumens 38, 58 is displaced creating an outward flow of the fluid between the tapered surfaces 43, 53 and into a channel 59 located outside the female connector 40 and inside the male connector threaded surface 39. As the fluid flow contacts the antimicrobial agent, a portion of the antimicrobial agent is dissolved and incorporated into the fluid; thus creating an antimicrobial fluid. The antimicrobial fluid then flows into the channel 59 where it contacts the female connector end face 48 and the female connector threaded surface 49, which subsequently kills microbes (not shown in FIG. 9, but similar to the microbes 28 shown in FIGS. 3B', 3C' and 4C') on the female connector end face 48 and threaded surface 49. This is beneficial for killing microbes that may remain after cleaning the female connector end face 48 and threaded surface 49 with a wipe as described in the narrative of FIGS. 3D' and 4D'. Over time, the antimicrobial fluid will dry, leaving a dry antimicrobial agent coating on the female connector 40 at the female connector end face 48 and threaded surface 49; thus creating an antimicrobial female connector in-situ. The antimicrobial is, for example, chlorhexidine acetate, which is dry and has a persistent antimicrobial effectiveness. In comparison, an alcohol antimicrobial, as found in many prior art devices, typically has no persistent antimicrobial effectiveness after the alcohol antimicrobial dries. As saline contacts chlorhexidine acetate, some of the chlorhexidine acetate is converted to chlorhexidine dihydrochloride, which adheres to the surfaces of the female connector; thus providing antimicrobial properties to the female connector in-situ.

In some embodiments it is desirable to apply a slowly dissolving ("time-release") coating on top of the antimicrobial agent to delay or slow the time for the antimicrobial agent to dissolve. A time-release coating, especially when applied to distal recess 80, is advantageous for ensuring a precise dose of antimicrobial agent is available within the cavity 81 once the connectors 40, 50 have been coupled together. In another embodiment it is desirable to use an antimicrobial mixture to slow the antimicrobial mixture's dissolution rate; the antimicrobial mixture comprising the antimicrobial agent and a material that dissolves slower, such as a hydrophilic water-soluble polymer. In yet another embodiment it is desirable to use chlorhexidine base with a chlorhexidine salt (such as chlorhexidine acetate) to achieve the intended dissolution rate; thus providing a means and method to control the amount of antimicrobial agent being removed from the recesses 80, 82 and tapered outer surface 53, transferring a portion of the antimicrobial agent to the female connector end face 48 and female connector threaded surface 49, where upon drying, a portion of the antimicrobial agent remains on the female connector end face 48 and female connector threaded surface 49. The benefit is this provides a persistent antimicrobial agent along the infiltration path (as shown in FIG. 3A) to prevent microbe ingress and subsequent infections.

FIG. 10 is a cross-sectional view of a female connector 40 having a male cap 30 installed; the male cap 30 comprising a male luer 32 including a distal recess 80 containing an antimicrobial agent; the male cap 30 configured for delivery of the antimicrobial agent. The distal recess 80 forms a cavity once the male luer 32 is installed into a female luer 42 of the female connector 40. Female connector 40 includes a lumen 38. The male luer 32 includes a tapered outer surface 33 that has a truncated conical surface, an end face 34, and near the end face 34 is a distal recess 80 containing the antimicrobial agent, such as chlorhexidine. In one embodiment, the distal recess 80 is a truncated conical surface that is recessed 0.001" to 0.015" below a projection of the tapered outer surface 33. The antimicrobial agent is typically a dry-antimicrobial that is water soluble, and provides an antimicrobial effect to an overlapping region 41 (overlap of a tapered outer surface 33 of a male luer 32 of the male cap 30 and the tapered inner sealing surface 43 of a female luer 42 of the female connector 40), especially at the region in the vicinity of the distal recess 80 of the male luer 32.

As the male luer 32 is inserted into the female luer 42 of the female connector 40, microbes are pushed by the tapered surface distal edge 55 of the male luer 32 rather than end face 34; thus the microbes are concentrated within the cavity. The antimicrobial agent in the cavity may become wetted by fluid in lumen 38 being displaced as male luer 32 is inserted into female luer 42. The fluid is substantially locked within the cavity in some embodiments because the cavity only has one opening (at the distal end of the recess) after the male luer 32 is fully inserted into the female connector 40. This results in a high concentration of antimicrobial agent in the fluid in the cavity without substantially depleting the antimicrobial agent. Thus, the antimicrobial agent within the fluid is at a lethal concentration for a sufficient time to kill the microbes and prevent ingrowth of microbes.

FIG. 11 is a cross-sectional view of a female connector 40 having an infusion set 16 connected, the male connector 50 having a male luer 52 including an intermediate recess 82 containing an antimicrobial agent 29 and configured for delivery of the antimicrobial agent. Near the end face 54 is the cavity containing an antimicrobial agent 29, and the intermediate recess 82 is set back proximal to the end face 54 and also contains an antimicrobial agent.

FIG. 12 is a cross-sectional view of a female connector 40 having an infusion set 16 connected. The tapered sealing surface 53 of the male luer 52 of the male connector 50 is bisected with an intermediate recess 82 containing an antimicrobial composition. The proximal and distal end of the bisected tapered sealing surface 53 reside on the same conical tapered geometry to form a fluid tight seal with the tapered sealing surface 43 of the female connector 40. The intermediate recess 82 of the male luer 52 contains an antimicrobial agent; the male luer 52 configured for delivery of the antimicrobial agent. The female connector 40 includes a lumen 38 in fluid connection with tube 57. The male luer 52 includes an end face 54. The intermediate recess 82 is set back proximal from the end face 54.

FIG. 13 is a cross-sectional view of an infusion set 16 connected to a female connector 40. The male luer 52 of a male connector 50 of the infusion set 16 including an intermediate recess 82 that bisects the tapered outer surface 53. The intermediate recess 82 contains an antimicrobial agent 29 and configured for delivery of the antimicrobial agent 29. The tapered outer surface 53 also contains the antimicrobial agent 29. FIG. 13' is a closeup cross-sectional view of the female connector 40 connected to the infusion set of FIG. 13, showing an enlargement of the female connector 40 and an intermediate recess 82 of the male luer 52. Female connector 40 includes a lumen 38 in fluid connection with a lumen 58 of tube 57. The male luer 52 includes a tapered outer surface 53 that has a truncated conical surface, along with an end face 54. The intermediate recess 82 is set back proximal from the end face 54 and includes an antimicrobial agent 29, as shown in FIG. 13'.

It will be appreciated that this is just an illustrated example, and that alternative peritoneal dialysis configurations are possible. Also, it will be appreciated that peritoneal dialysis is just one example of a use for the infusion connectors and systems disclosed herein, and that alternative uses and systems include hemodialysis catheters, peripherally inserted central catheters, midline catheters, drainage catheters, needleless connectors, intravenous (IV) administration sets, peritoneal dialysis lines, transfer set, syringes, valves and filters.

Examples of Antimicrobial Agents

The inventors have identified that it is desirable to use only a small amount of antimicrobial for safety because it reduces patient risk in the event antimicrobial escapes into the body. The amount considered a "low dose" is different from patient to patient. For example, a chlorhexidine acetate dose of 500 μg (micrograms) or higher may be considered safe for direct injection into a 60 kilogram person's bloodstream, but a dose significantly below this level is desirable for use in neonates.

The various embodiments herein have benefit over prior art from a safety standpoint because by delivering the antimicrobial agent between the luer surfaces, only a small amount of antimicrobial agent is required to kill microbes. In the various examples provided here, an annular cavity is formed between the male luer surface and the female luer surface when the male luer is installed into a female luer.

The concentration (e.g., in micrograms per milliliter) of antimicrobial agent in the cavity between the male luer surface and the female luer surface is high but the total dose (e.g., in micrograms) is low because the gap between the luer surfaces is very small (thus the volume of the cavity is very small) and there is little to no fluid flow away from this region, causing loss of the antimicrobial to be very low.

In some embodiments the antimicrobial agent can be chlorhexidine acetate. A concentration of greater than 200 μg/mL (micrograms per milliliter) of chlorhexidine acetate can quickly kill most microbes, including Gram positive bacteria, Gram negative bacteria, and fungi. In many cases, this concentration will kill microbes is well under 1 minute.

The concentration of antimicrobial agent is high but the total dose is low because the gap between the luer surfaces is very small and there is little to no fluid flow away from this region, causing loss of the antimicrobial to be very low.

In some embodiments the antimicrobial agent can be chlorhexidine acetate. A concentration of greater than 200 μg/mL (micrograms per milliliter) of chlorhexidine acetate can quickly kill most microbes, including Gram positive bacteria, Gram negative bacteria, and fungi.

In various embodiments the male luer has a recess surface (also referred to as distal tip surface) containing approximately 25 to 250 μg of chlorhexidine acetate. For example, in an embodiment, the radial depth of the recess is approximately 0.005 inches (0.127 millimeters) and the axial length is approximately 0.020 inches to 0.040 inches long (0.508 mm to 1.016 mm). The annular cavity formed between the male luer surface and the female luer surface can have a volume on the order of 1 μL (microliter) or 0.001 mL. If 10 μg of chlorhexidine acetate is in a 1 μL volume, the antimicrobial concentration is 10,000 μg/mL, which is 50 times higher than the minimum desired level of 200 μg/mL to kill microbes. This demonstrates how the invention can create very high microbe kill efficacy while at the same time providing excellent patient safety; 50 μg of chlorhexidine acetate distributed over the entire surface of the male luer is 10 times lower than the maximum total dose of 500 μg that is desired for patient safety.

In some embodiments the volume of the annular cavity is between about 1 and 10 microliters. In some embodiments, the volume of the annular cavity can fall within a range of 1 microliters to 25 microliters, or 5 microliters to 20 microliters, or 10 microliters to 15 microliters, or can be about 10 microliters. In some embodiments, the volume of the annular cavity can be greater than or equal to 1 microliters, 2 microliters, 3 microliters, 4 microliters, 5 microliters, 6 microliters, 6 microliters, 7 microliters, 8 microliters, 9 microliters, or 10 microliters. In some embodiments, the volume of the annular cavity can be less than or equal to 25 microliters, 24 microliters, 22 microliters, 20 microliters, 19 microliters, 18 microliters, 16 microliters, 14 microliters, 13 microliters, 12 microliters, or 10 microliters.

Additionally, a number of different examples of antimicrobial agents can be used with the various embodiments described herein. The antimicrobial compositions should kill and/or provide stasis of Gram-positive and Gram-negative bacteria and fungi. The agents may also have efficacy at killing organisms within an established biofilm and/or degrading the extracellular matrix of the film. However, this is not necessary for the invention to be beneficial because the invention is designed to kill organisms before they have an opportunity to form a biofilm. The antimicrobial composition can be chlorhexidine acetate, also known as chlorhexidine diacetate.

Other compounds containing chlorhexidine may be used, such as chlorhexidine free base, chlorhexidine gluconate and chlorhexidine with dyes. Chlorhexidine acetate has an advantage over chlorhexidine gluconate because the risks associated with para chloroaniline may be minimized.

Other suitable antimicrobial compositions may also be used. In general, the antimicrobials are soluble in water, they have a history of clinical use with a demonstrated safety profile, they are antibiotic-free, they can be applied onto a medical device, and they can be subsequently dissolved into a composition having an effective concentration to inhibit growth of bacterial and fungal organisms. Suitable materials include chlorhexidine, chlorhexidine salts (such as chlorhexidine acetate or chlorhexidine gluconate), tetrasodium ethylenediaminetetraacetic acid (tetrasodium EDTA), sodium citrate (yielding a concentration of 30% or higher), iodine, taurolidine, disodium EDTA, silver compounds (including silver nanoparticles and ions), silver sulfadiazine, and, triclosan. In some examples, a portion of the antimicrobial composition is dissolvable to form a chlorhexidine precipitate.

While one drug or antimicrobial composition may provide relief from a wide range of challenging organisms that could potentially lead to catheter-related bloodstream infection, two or more agents may be used to increase efficacy against a broad range of infectious organisms (bacteria and fungi).

In particular, catheter-related infections arise from three broad classes of organisms: fungi, Gram-negative bacteria, and Gram-positive bacteria. If an antimicrobial composition can be identified that would abate one or two of these types of organisms, while this would certainly be beneficial, it would leave the patient vulnerable to the remaining type(s). By pairing agents with different modes of action, infections by an increased spectrum of organisms can be prevented. This synergy would likely lead to further decreases in catheter-related morbidity and mortality, lessening the impact of the implanted catheter on the patient's quality of life. Example combinations of antimicrobial compositions are chlorhexidine acetate and EDTA, silver sulfadiazine and chlorhexidine acetate, and silver sulfadiazine and methylene blue.

In principle, antibiotics (rifampin, minocycline, etc.) can be incorporated into or onto the male luer or similar device and be as effective as non-antibiotic antimicrobials. However, continuous exposure to one antibiotic can lead to antibiotic resistant bacteria strains, for example, methicillin resistant S. aureus (MRSA). Therefore, an example embodiment uses an antimicrobial composition selected from the subset of those which are not antibiotics. If, for some reason, an antibiotic is used, the risk of developing antibiotic resistant strains of bacteria may be mitigated by preparing a second, complimentary, device containing a different antibiotic. By using the two devices in an alternating fashion with successive uses, infectious organisms that are resistant to one antibiotic may be killed by the other.

In certain implementations the antimicrobial agent comprises chlorhexidine, chlorhexidine base, chlorhexidine acetate and/or chlorhexidine gluconate. In certain implementations the antimicrobial agent is a dry coating.

In certain implementations the antimicrobial agent is water soluble at greater than 1 mg/mL. In certain implementations the agent is water soluble at greater than 10 mg/mL. In certain implementations a first antimicrobial agent is water soluble at less than 1 mg/mL and a second antimicrobial is soluble at greater than 10 mg/mL. In certain implementations the antimicrobial agent is impregnated into the luer surface. In certain implementations the antimicrobial agent is a broad-spectrum compound capable of killing Gram positive bacteria, Gram negative bacteria, and fungi. In certain implementations the antimicrobial agent is a non-antibiotic antimicrobial. In certain implementations the antimicrobial agent converts into chlorhexidine dihydrochloride in presence of saline.

In certain implementations the antimicrobial agent comprises silver or silver sulfadiazine. In certain implementations the antimicrobial agent contains more than one compound. In certain implementations the antimicrobial agent comprises chlorhexidine and silver sulfadiazine. In certain implementations the antimicrobial agent comprises the antibiotics minocycline and rifampin.

In certain implementations the antimicrobial agent is applied in a solvent-based coating process. In certain implementations the antimicrobial agent is applied in a spray process. In certain implementations the antimicrobial agent is applied in a dip process. In certain implementations the antimicrobial agent is dispersed in bulk material of an injection molding process. In certain implementations the antimicrobial agent is part of an antimicrobial solution that contains a solvent that swells the device material, which allows the antimicrobial agent to impregnate the device material, where it remains after solvent evaporates.

Needleless Connector (FIGS. 14A-C)

In another aspect described in relation to FIGS. 14A-14C, one implementation of the disclosed technology provides a needleless connector 1411 having a male connector 1401 at a distal end of the needleless connector 1411, the male connector 1401 includes a male luer 1441 and threads 1402. The male luer 1441 includes a tapered scaling member 1442 with a tapered sealing surface 1443. The needleless connector 1411 has a lumen 1412 extending through the needleless connector 1411 through which fluid can flow. At the needleless connector proximal end 1407 of the needleless connector 1411, threads 1405 are provided for connecting the needleless connector 1411 to another medical device, such as a syringe. At the distal end of the needleless connector 1411, threads 1402 are provided for coupling the male luer 1441 with a medical device having a female luer, such as the proximal end of a catheter for hemodialysis, peritoneal dialysis, parenteral nutrition, or chemotherapy. The distal tip 1455 also includes a distal tip surface 1452 and an end face 1404. The tapered scaling member 1442 has a tapered surface distal edge 1461 adjacent and proximal to the distal tip 1455. The tapered surface distal edge 1461 is situated at the distalmost end of the tapered scaling surface 1443.

As will be discussed further below, the male luer 1441 includes a distal recess 1451, and the distal tip 1455 has a distal tip surface 1452. The distal tip surface 1452 can include an antimicrobial agent as described above. When the male luer 1441 is installed into a female luer (not shown), a cavity is created between the tapered sealing surface of the female luer and the distal tip surface 1452 of the male luer 1441. The distal tip 1455 is recessed inside the line of taper of the tapered sealing surface 1443. As used herein, a line of taper is a representation of an imaginary conical surface defining a conical taper extending beyond the tapered surface distal edge 1461 of the male luer 1441.

In the example of FIGS. 14A-14C, the male luer 1441 further includes a plurality of blades 1463 at the distal tip 1455. Between the blades 1463 are a plurality of channels 1467. Blades 1463 and channels 1467 will be discussed further below.

A number of example implementations will now be described in relation to FIGS. 15A-32G. It should be understood that each example below could be combined with the needleless connector proximal end 1407 to create the needleless connector 1411. In addition, each of the male connectors described below are not limited to needleless connectors, and could be combined with other medical devices using luer couplings.

Male Connector with Distal Recess (FIGS. 15A-F & 16)

Turning now to FIGS. 15A-16, a male connector 1501 includes a male luer 1541. The male luer 1541 comprises a tapered sealing member 1542. The tapered scaling member 1542 has a frustoconical shape that tapers from a larger outer diameter at the proximal portion of the tapered sealing member 1542 to a smaller outer diameter at the distal portion of the tapered sealing member near the tapered surface distal edge 1561. The tapered sealing member 1542 has a tapered sealing surface 1543 that is configured to mate with a female luer to create a fluid tight fit. The male connector 1501 further includes threads 1502 that allow the male connector 1501 to couple with a female connector. A lumen 1512 runs through the male connector 1501.

The male luer 1541 includes a distal tip 1555 with an end face 1504. The distal tip 1555 of the male luer 1541 is recessed from the distal line of taper of the tapered scaling member 1542. FIG. 16 is a cross-section of the male connector 1501. FIG. 16 illustrates a distal line of taper 1614 extending in a straight line from the tapered sealing surface 1543. The distal line of taper 1614 of the tapered sealing member 1542 is a representation of an imaginary conical surface defining a conical taper extending beyond the tapered surface distal edge 1561 of the male luer 1541. The tapered sealing surface 1543 has a taper angle. In some examples, the taper angle of the tapered sealing member is between about 1.5 degrees and about 2 degrees relative to a central longitudinal axis 1610 of the male luer 1541. In some examples, the taper angle is about 1.72 degrees relative to the central longitudinal axis 1610 of the male luer 1541 of the male connector 1501. The conical taper defined by the distal line of taper 1614 surrounds the central longitudinal axis 1610 symmetrically.

The distal line of taper 1614 defines an outer diameter of the extension of the tapered sealing surface 1543. A distal recess 1551 is a radially recessed portion of the distal tip 1555, meaning that the distal tip surface 1552 of the distal tip 1555 defines an outer diameter that is smaller than the outer diameter of the extension of the tapered sealing surface 1543. The distal recess 1551 defines a space that is between the distal line of taper 1614 and distal tip surface 1552.

FIG. 16 further shows an antimicrobial composition 1621 coating the distal tip surface 1552 of the distal tip 1555. When the male luer 1541 is coupled with a female luer, the distal tip surface 1552 of the distal tip 1555 does not make contact with the inside surface of the female luer, and a cavity is formed between the distal tip surface 1552 and the female tapered surface, similar to that shown in FIG. 7A In this cavity, the antimicrobial composition 1621 is able to disperse within the volume created between the distal tip surface 1552 and the female tapered surface.

The male luer 1541 includes a tapered surface distal edge 1561 that defines a proximal end of the distal tip 1555. The tapered surface distal edge 1561 is situated at the distalmost end of the tapered sealing surface 1543 such that the proximal edge of the distal tip 1555 abuts the tapered surface distal edge 1561. The tapered surface distal edge 1561 has an outer diameter, the proximal edge of the distal tip 1555 has an outer diameter, and the outer diameter of the tapered surface distal edge 1561 is greater than the outer diameter of the proximal edge of the distal tip 1555. Since the tapered surface distal edge 1561 has a larger diameter than any outer diameter along the distal tip 1555, when the male luer 1541 is inserted into a female luer, the tapered surface distal edge 1561 of the tapered sealing member 1542 is capable of capturing microbes that may have infiltrated the inner surface of the female luer. As described above in relation to FIG. 7A, antimicrobial composition 1621 kills the microbes within the cavity between the tapered sealing surface of the female luer and the distal tip surface 1552 of the male luer 1541. In some examples, an antimicrobial composition 1621 is applied to the distal tip surface 1552 by coating, spraying, or dipping the distal tip 1555, although other methods of applying antimicrobial agent are contemplated and are within the scope of the technology. In some examples, antimicrobial composition 1621 is also applied to the tapered sealing surface 1543. The antimicrobial composition 1621 can also be applied to the end face 1504.

The distal recess 1551 (the space between the distal tip surface 1552 and the female luer surface, not shown) is designed to confine the antimicrobial agent between the inner surface of a female luer and the distal tip surface 1552 so that microbes are exposed to a high antimicrobial concentration. Confinement is a way to keep the antimicrobial agent within the distal recess region during use, while fluid is flowing through the lumen 1512. The structure of the distal recess 1551, which contains no through-channel for fluid flow, decreases fluid transfer between the lumen 1512 and the distal tip surface 1552.

Male Connector with Blades (FIGS. 17A-F)

Turning now to FIGS. 17A-F, a male connector 1701 includes a male luer 1741. The male luer 1741 comprises a tapered sealing member 1742. The tapered sealing member 1742 has a tapered sealing surface 1743 that is configured to mate with a female luer to create a fluid tight fit. The male connector 1701 further includes threads 1702 that allow the male connector 1701 to couple with a female connector. A lumen 1712 runs through the male connector 1701.

The male luer 1741 includes a distal tip 1755 with an end face 1704. The distal tip 1755 of the male luer 1741 is recessed from the distal line of taper 1714 of the tapered sealing member 1742. A distal recess 1751 is formed by a recessed portion of the distal tip 1755. When the male luer 1741 is sealed against a female luer and the tapered sealing surface 1743 forms a fluid tight fit with the inside surface of the female luer, the distal tip surface 1752 of the distal tip 1755 does not make contact with the inside surface of the female luer.

The male luer 1741 includes a tapered surface distal edge 1761 that defines a proximal end of the distal tip 1755. The tapered surface distal edge 1761 is situated at the distalmost end of the tapered sealing surface 1743. When the male luer 1741 is inserted into a female luer, the tapered surface distal edge 1761 of the tapered sealing member 1742 is capable of capturing microbes that may have infiltrated the inner surface of the female luer.

In some examples, an antimicrobial agent is applied to the distal tip surface 1752 by coating, spraying, or dipping the distal tip 1755 with an antimicrobial agent, although other methods of applying antimicrobial agent are contemplated and are within the scope of the technology. In some examples, antimicrobial agent is also applied to the tapered sealing surface 1743. As described above in relation to FIG. 7A, an antimicrobial agent on the distal tip surface 1752 of the distal tip 1755 kills microbes within the distal recess 1751 between the surface of the female luer and the distal tip surface 1752.

The male luer 1741 further includes multiple blades 1763 arrayed around the distal tip 1755 of the male luer 1741. In some examples, the blades 1763 are arranged substantially parallel to the central longitudinal axis of the male luer 1741. However, as will be described in further detail below, some embodiments can have blades that are not substantially parallel to the central longitudinal axis. Between the blades 1763 are a plurality of channels 1767. In the example of FIG. 17, the blades 1763 are elongated projections arranged around the axis of the tapered sealing member 1742, and the channels 1767 are elongated recesses disposed between the blades 1763 and running parallel to the lumen 1712. The blades 1763 and channels 1767 form alternating apexes 1764 and troughs 1768. The distal tip surface 1752 of the distal tip 1755 is defined by the blades 1763 and channels 1767, forming a plurality of blade surfaces. Furthermore, an antimicrobial agent on the distal tip surface 1752 can be stored within the volumes between the blades 1763. This can increase the amount of antimicrobial agent that can be stored on the distal tip 1755 of the male luer 1741. The blades 1763 on the distal tip 1755 may be manufactured using current manufacturing materials and methods, such as injection molding with bumpoff threads using polypropylene material.

In some examples, the distal tip 1755 has a length of about 0.060 inches (1.52 mm). The length of the distal tip 1755 is measured perpendicular to the diameter of the distal tip 1755. In some examples, the lumen 1712 has an inner diameter of about 0.065 inches (1.65 mm). In some examples, the distal tip 1755 has an outer diameter of about 0.095 inches (2.41 mm). In some examples, the wall of the distal tip 1755 has a thickness of about 0.015 inches (0.38 mm). In some examples, the tapered surface distal edge 1761 has an outer diameter of about 0.155 inches (3.94 mm).

At the apex 1764 of the blades 1763, the distal tip 1755 has an outer diameter of between about 0.148 inches and 0.152 inches. At the trough 1768 of the channels 1767, the distal tip 1755 has an outer diameter of between about 0.0118 inches and 0.0121 inches. Thus the difference in outer diameter from the trough 1768 to the apex 1764 is approximately 0.030 inches in this example. The distal tip 1755 has a tip length as shown in FIGS. 17A-F is 0.060 inches. In other examples the tip length is between about 0.025 and 0.125 inches; in another example the tip length is between 0.050 and 0.090 inches. The distal tip surface 1752 (which includes the surface of the blades) of the distal tip 1755 has a surface area of between about 0.0390 inches squared and 0.0370 inches squared. A male luer distal tip 1755 without blades 1763 and an outer diameter equal to the trough diameter has a surface area between about 0.0235 inches squared and 0.0215 inches squared. Thus, the blades 1763 and channels 1767 increase the surface area of the distal tip 1755 by about 68 percent. In some examples, increasing the distal tip surface 1752 can decrease the amount of antimicrobial that is removed from the distal tip surface 1752 when the connector is being inserted into an infusion device.

During insertion of the male luer 1741 into a female luer, portions of the distal tip 1755 may come in contact with the inside surface of the female luer. The apex 1764 of each blade 1763 may come in contact with the female luer surface, but the troughs 1768 of the channels 1767 will not come in contact with the female luer surface. Thus, in comparison to the tapered surface distal edge 1761, the blades 1763 have a relatively smaller contacting surface area near the end face 1704 of the distal tip 1755. This minimizes the amount of ingress of microbes that can be attributed to microbes being pushed into the body of the female luer by the blades 1763 compared to the tapered surface distal edge 1761 of the male luer 1741. Thus in some situations there is a greater probability of the microbes being located at the tapered surface distal edge 1761 compared to the end face 1704. This is desirable because the concentration of antimicrobial composition will be greater (it will be at a lethal concentration to kill microbes) at the tapered surface distal edge 1761 than the end face 1704.

The channels 1767 affect confinement of microbes within the distal recess 1751 because the channels 1767 provide a restricted space in which microbes can be trapped between the distal tip surface 1752 and an inside surface of a female luer. The apex 1764 of the blades 1763 provide a maximum outer diameter of the distal tip 1755, and the troughs 1768 of the channels 1767 provide a minimum outer diameter of the distal tip 1755. Although some fluid flow between adjacent channels 1767 is possible when the male luer 1741 is coupled with a female luer, the blades 1763 provide a partial physical barrier. As seen in FIGS. 17D-F, the distal tip 1755 has an outer diameter that is smaller than the outer diameter of the tapered scaling member 1742 at the tapered surface distal edge 1761, and the outer diameter of the distal tip 1755 is smaller than the outer diameter of the distal line of taper 1714 defined by the conical tapered sealing member 1742.

Male Connector with Elongated Blades (FIGS. 18A-F)

Turning now to FIGS. 18A-F, a male connector 1801 includes a male luer 1841. The male luer 1841 comprises a tapered sealing member 1842. The tapered scaling member 1842 has a frustoconical shape that tapers from a larger outer diameter at the proximal portion of the tapered sealing member 1842 to a smaller outer diameter at the distal portion of the tapered sealing member near the tapered surface distal edge 1861. The tapered sealing member 1842 has a tapered sealing surface 1843 that is configured to mate with a female luer to create a fluid tight fit. The male connector 1801 further includes threads 1802 that allow the male connector 1801 to couple with a female connector. A lumen 1812 runs through the male connector 1801.

The male luer 1841 includes a distal tip 1855 with an end face 1804. The distal tip 1855 of the male luer 1841 is recessed from the distal line of taper of the tapered scaling member 1842. A distal recess 1851 is formed by a recessed portion of the distal tip 1855. The distal tip surface 1852 of the distal tip 1855 defines an outer diameter that is smaller than the outer diameter of the extension of the tapered sealing surface 1843.

The male luer 1841 includes a tapered surface distal edge 1861 that defines a proximal end of the distal tip 1855. The tapered surface distal edge 1861 is situated at the distalmost end of the tapered sealing surface 1843. In some examples, an antimicrobial agent is applied to the distal tip surface 1852 by coating, spraying, or dipping the distal tip 1855 with an antimicrobial agent, although other methods of applying antimicrobial agent are contemplated and are within the scope of the technology. In some examples, antimicrobial agent is also applied to the tapered sealing surface 1843. An antimicrobial agent on the distal tip surface 1852 of the distal tip 1855 kills microbes within the distal recess 1851 between the surface of the female luer and the distal tip surface 1852. The distal recess 1851 is designed to confine the antimicrobial agent between the inner surface of a female luer and the distal tip surface 1852 so that microbes are exposed to a high antimicrobial concentration.

The male luer 1841 further includes multiple blades 1863 arrayed around the distal tip 1855 of the male luer 1841. Between the blades 1863 are a plurality of channels 1867. In the example of FIG. 18, the blades 1863 are elongated projections arranged around the axis of the tapered sealing member 1842, and the channels 1867 are elongated recesses disposed between the blades 1863 and running parallel to the lumen 1812. The blades 1863 and channels 1867 form alternating apexes 1864 and troughs 1868. The distal tip surface 1852 of the distal tip 1855 is defined by the blades 1863 and channels 1867. An antimicrobial agent on the distal tip surface 1852 can be stored within the volumes between the blades 1863.

During insertion of the male luer 1841 into a female luer, portions of the distal tip 1855 may come in contact with the inside surface of the female luer. The apex 1864 of each blade 1863 may come in contact with the female luer surface, but the troughs 1868 of the channels 1867 will not come in contact with the female luer surface. Thus, in comparison to the tapered surface distal edge 1861, the blades 1863 have a relatively smaller surface area near the end face 1804 of the distal tip 1855. This minimizes the amount of ingress of microbes that can be attributed to microbes being pushed into the body of the female luer by the male luer 1841.

The channels 1867 affect confinement of microbes within the distal recess because the channels 1867 provide a restricted space in which microbes can be trapped between the distal tip surface 1852 and an inside surface of a female luer. The apex 1864 of the blades 1863 provide a maximum outer diameter of the distal tip 1855, and the troughs 1868 of the channels 1867 provide a minimum outer diameter of the distal tip 1855. Although some fluid flow between adjacent channels 1867 is possible when the male luer 1841 is coupled with a female luer, the blades 1863 provide a partial physical barrier. As seen in FIGS. 18D and 18E, the distal tip 1855 has an outer diameter that is smaller than the outer diameter of the tapered sealing member 1842 at the tapered surface distal edge 1861, and the outer diameter of the distal tip 1855 is smaller than the outer diameter of a distal line of taper defined by the conical tapered sealing member 1842.

The distal tip 1855 has fourteen elongated blades 1863 that extend into the threaded cavity 1839 of the male connector 1801. The male luer 1841 of FIG. 18 has a shorter tapered scaling surface 1843 than the male luer 1741 of FIG. 17; however, the distal recess 1851 is longer and the distal tip surface 1852 of the distal tip 1855 has a greater surface area than the example of FIG. 17. In some examples, the length of the distal tip 1855 as measured perpendicular to the outer diameter of the distal tip 1855 is between about 0.025 and 0.125 inches (0.64-3.18 mm).

Male Connector with Six Blades (FIGS. 19A-F)

Turning now to FIGS. 19A-F, a male connector 1901 includes a male luer 1941. The male luer 1941 comprises a tapered sealing member 1942. The tapered sealing member 1942 has a frustoconical shape that tapers from a larger outer diameter at the proximal portion of the tapered sealing member 1942 to a smaller outer diameter at the distal portion of the tapered sealing member near the tapered surface distal edge 1961. The tapered sealing member 1942 has a tapered sealing surface 1943 that is configured to mate with a female luer to create a fluid tight fit. The male connector 1901 further includes threads 1902 that allow the male connector 1901 to couple with a female connector. A lumen 1912 runs through the male connector 1901.

The male luer 1941 includes a distal tip 1955 with an end face 1904. The distal tip 1955 of the male luer 1941 is recessed from the distal line of taper of the tapered sealing member 1942. A distal recess 1951 is formed by a recessed portion of the distal tip 1955. The distal tip surface 1952 of the distal tip 1955 defines an outer diameter that is smaller than the outer diameter of the extension of the tapered sealing surface 1943.

The male luer 1941 includes a tapered surface distal edge 1961 that defines a proximal end of the distal tip 1955. In some examples, an antimicrobial agent is applied to the distal tip surface 1952 by coating, spraying, or dipping the distal tip 1955 with an antimicrobial agent, although other methods of applying antimicrobial agent are contemplated and are within the scope of the technology. In some examples, antimicrobial agent is also applied to the tapered sealing surface 1943. An antimicrobial agent on the distal tip surface 1952 of the distal tip 1955 kills microbes within the distal recess 1951 between the surface of the female luer and the distal tip surface 1952. The distal recess 1951 is designed to confine the antimicrobial agent between the inner surface of a female luer and the distal tip surface 1952 so that microbes are exposed to a high antimicrobial concentration.

The male luer 1941 further includes multiple blades 1963 arrayed around the distal tip 1955 of the male luer 1941. Between the blades 1963 are a plurality of channels 1967. In the example of FIG. 19, the blades 1963 are elongated projections arranged around the axis of the tapered sealing member 1942, and the channels 1967 are elongated recesses disposed between the blades 1963 and running parallel to the lumen 1912. The blades 1963 and channels 1967 form alternating apexes 1964 and troughs 1968. The distal tip surface 1952 of the distal tip 1955 is defined by the blades 1963 and channels 1967. An antimicrobial agent on the distal tip surface 1952 can be stored within the volumes between the blades 1963.

During insertion of the male luer 1941 into a female luer, portions of the distal tip 1955 may come in contact with the inside surface of the female luer. The apex 1964 of each blade 1963 may come in contact with the female luer surface, but the troughs 1968 of the channels 1967 will not come in contact with the female luer surface. Thus, in comparison to the tapered surface distal edge 1961, the blades 1963 have a relatively smaller surface area near the end face 1904 of the distal tip 1955. This minimizes the amount of ingress of microbes that can be attributed to microbes being pushed into the body of the female luer by the male luer 1941.

The channels 1967 affect confinement of microbes within the distal recess because the channels 1967 provide a restricted space in which microbes can be trapped between the distal tip surface 1952 and an inside surface of a female luer. The apex 1964 of the blades 1963 provide a maximum outer diameter of the distal tip 1955, and the troughs 1968 of the channels 1967 provide a minimum outer diameter of the distal tip 1955. Although some fluid flow between adjacent channels 1967 is possible when the male luer 1941 is coupled with a female luer, the blades 1963 provide a partial physical barrier. As seen in FIGS. 19D and 19E, the distal tip 1955 has an outer diameter that is smaller than the outer diameter of the tapered sealing member 1942 at the tapered surface distal edge 1961, and the outer diameter of the distal tip 1955 is smaller than the outer diameter of a distal line of taper defined by the conical tapered sealing member 1942.

The distal tip 1955 of the male luer 1941 has six blades 1963 defining six channels 1967 with troughs 1968. In the example of FIG. 19C, the troughs 1968 are curved slightly outward, creating distinct creases 1969 at the base of the blades 1963.

Male Connector with Blades and Rounded Distal Tip (FIGS. 20A-G)

Turning now to FIGS. 20A-G, a male connector 2001 includes a male luer 2041. The male luer 2041 comprises a tapered sealing member 2042. The tapered sealing member 2042 has a frustoconical shape that tapers from a larger outer diameter at the proximal portion of the tapered sealing member 2042 to a smaller outer diameter at the distal portion of the tapered sealing member near the tapered surface distal edge 2061. The tapered sealing member 2042 has a tapered sealing surface 2043 that is configured to mate with a female luer to create a fluid tight fit. The male connector 2001 further includes threads 2002 that allow the male connector 2001 to couple with a female connector. A lumen 2012 runs through the male connector 2001.

The male luer 2041 includes a distal tip 2055 with an end face 2004. The distal tip 2055 of the male luer 2041 is recessed from the distal line of taper of the tapered sealing member 2042. A distal recess 2051 is formed by a recessed portion of the distal tip 2055. The distal tip surface 2052 of the distal tip 2055 defines an outer diameter that is smaller than the outer diameter of the extension of the tapered sealing surface 2043.

The male luer 2041 includes a tapered surface distal edge 2061 that defines a proximal end of the distal tip 2055. In some examples, an antimicrobial agent is applied to the distal tip surface 2052 by coating, spraying, or dipping the distal tip 2055 with an antimicrobial agent, although other methods of applying antimicrobial agent are contemplated and are within the scope of the technology. In some examples, antimicrobial agent is also applied to the tapered sealing surface 2043. An antimicrobial agent on the distal tip surface 2052 of the distal tip 2055 kills microbes within the distal recess 2051 between the surface of the female luer and the distal tip surface 2052. The distal recess 2051 is designed to confine the antimicrobial agent between the inner surface of a female luer and the distal tip surface 2052 so that microbes are exposed to a high antimicrobial concentration.

The male luer 2041 further includes multiple blades 2063 arrayed around the distal tip 2055 of the male luer 2041. Between the blades 2063 are a plurality of channels 2067. In the example of FIG. 20, the blades 2063 are elongated projections arranged around the axis of the tapered sealing member 2042, and the channels 2067 are elongated recesses disposed between the blades 2063 and running parallel to the lumen 2012. The blades 2063 and channels 2067 form alternating apexes 2064 and troughs 2068. The distal tip surface 2052 of the distal tip 2055 is defined by the blades 2063 and channels 2067. An antimicrobial agent on the distal tip surface 2052 can be stored within the volumes between the blades 2063.

During insertion of the male luer 2041 into a female luer, portions of the distal tip 2055 may come in contact with the inside surface of the female luer. The apex 2064 of each blade 2063 may come in contact with the female luer surface, but the troughs 2068 of the channels 2067 will not come in contact with the female luer surface. Thus, in comparison to the tapered surface distal edge 2061, the blades 2063 have a relatively smaller surface area near the end face 2004 of the distal tip 2055. This minimizes the amount of ingress of microbes that can be attributed to microbes being pushed into the body of the female luer by the male luer 2041.

The channels 2067 affect confinement of microbes within the distal recess because the channels 2067 provide a restricted space in which microbes can be trapped between the distal tip surface 2052 and an inside surface of a female luer. The apex 2064 of the blades 2063 provide a maximum outer diameter of the distal tip 2055, and the troughs 2068 of the channels 2067 provide a minimum outer diameter of the distal tip 2055. Although some fluid flow between adjacent channels 2067 is possible when the male luer 2041 is coupled with a female luer, the blades 2063 provide a partial physical barrier. As seen in FIGS. 20E and 20F, the distal tip 2055 has an outer diameter that is smaller than the outer diameter of the tapered scaling member 2042 at the tapered surface distal edge 2061, and the outer diameter of the distal tip 2055 is smaller than the outer diameter of a distal line of taper defined by the conical tapered scaling member 2042.

The distal tip 2055 has a plurality of blades 2063 separating a plurality of channels 2067. The blades 2063 have rounded blade tips 2082 that taper in width from the end face 1904 to the apex 2064 of the blades 2063. This structure makes the distal recess 2051 rounded at the boundary between the distal recess region and the bulk flow region when the male luer 2041 is coupled with a female luer.

Male Connector with Enhanced Crevices (FIGS. 21A-F)

Turning now to FIGS. 21A-F, a male connector 2101 includes a male luer 2141. The male luer 2141 comprises a tapered sealing member 2142. The tapered scaling member 2142 has a frustoconical shape that tapers from a larger outer diameter at the proximal portion of the tapered sealing member 2142 to a smaller outer diameter at the distal portion of the tapered sealing member near the tapered surface distal edge 2161. The tapered sealing member 2142 has a tapered sealing surface 2143 that is configured to mate with a female luer to create a fluid tight fit. The male connector 2101 further includes threads 2102 that allow the male connector 2101 to couple with a female connector. A lumen 2112 runs through the male connector 2101.

The male luer 2141 includes a distal tip 2155 with an end face 2104. The distal tip 2155 of the male luer 2141 is recessed from the distal line of taper of the tapered scaling member 2142. A distal recess 2151 is formed by a recessed portion of the distal tip 2155. The distal tip surface 2152 of the distal tip 2155 defines an outer diameter that is smaller than the outer diameter of the extension of the tapered sealing surface 2143.

The male luer 2141 includes a tapered surface distal edge 2161 that defines a proximal end of the distal tip 2155. In some examples, an antimicrobial agent is applied to the distal tip surface 2152 by coating, spraying, or dipping the distal tip 2155 with an antimicrobial agent, although other methods of applying antimicrobial agent are contemplated and are within the scope of the technology. In some examples, antimicrobial agent is also applied to the tapered sealing surface 2143. An antimicrobial agent on the distal tip surface 2152 of the distal tip 2155 kills microbes within the distal recess 2151 between the surface of the female luer and the distal tip surface 2152. The distal recess 2151 is designed to confine the antimicrobial agent between the inner surface of a female luer and the distal tip surface 2152 so that microbes are exposed to a high antimicrobial concentration.

The male luer 2141 further includes multiple blades 2163 arrayed around the distal tip 2155 of the male luer 2141. Between the blades 2163 are a plurality of channels 2167. In the example of FIG. 21, the blades 2163 are elongated projections arranged around the axis of the tapered sealing member 2142, and the channels 2167 are elongated recesses disposed between the blades 2163 and running parallel to the lumen 2112. The blades 2163 and channels 2167 form alternating apexes 2164 and troughs 2168. The distal tip surface 2152 of the distal tip 2155 is defined by the blades 2163 and channels 2167. An antimicrobial agent on the distal tip surface 2152 can be stored within the volumes between the blades 2163.

During insertion of the male luer 2141 into a female luer, portions of the distal tip 2155 may come in contact with the inside surface of the female luer. The apex 2164 of each blade 2163 may come in contact with the female luer surface, but the troughs 2168 of the channels 2167 will not come in contact with the female luer surface. Thus, in comparison to the tapered surface distal edge 2161, the blades 2163 have a relatively smaller surface area near the end face 2104 of the distal tip 2155. This minimizes the amount of ingress of microbes that can be attributed to microbes being pushed into the body of the female luer by the male luer 2141.

The channels 2167 affect confinement of microbes within the distal recess because the channels 2167 provide a restricted space in which microbes can be trapped between the distal tip surface 2152 and an inside surface of a female luer. The apex 2164 of the blades 2163 provide a maximum outer diameter of the distal tip 2155, and the troughs 2168 of the channels 2167 provide a minimum outer diameter of the distal tip 2155. Although some fluid flow between adjacent channels 2167 is possible when the male luer 2141 is coupled with a female luer, the blades 2163 provide a partial physical barrier. As seen in FIGS. 21D and 21E, the distal tip 2155 has an outer diameter that is smaller than the outer diameter of the tapered scaling member 2142 at the tapered surface distal edge 2161, and the outer diameter of the distal tip 2155 is smaller than the outer diameter of a distal line of taper defined by the conical tapered sealing member 2142.

The distal tip 2155 has a plurality of blades 2163 that separate a plurality of channels 2167. This example shows a large difference in height from the apex 2164 to the trough 2168. This in turn increases the surface area on which an antimicrobial agent can be stored. Furthermore, the depth of the channels 2167 allows an increased load of antimicrobial agent to be stored at the distal tip 2155.

Male Connector with Irregular Blade Heights (FIGS. 22A-F)

Turning now to FIGS. 22A-F, a male connector 2201 includes a male luer 2241. The male luer 2241 comprises a tapered sealing member 2242. The tapered sealing member 2242 has a frustoconical shape that tapers from a larger outer diameter at the proximal portion of the tapered sealing member 2242 to a smaller outer diameter at the distal portion of the tapered sealing member near the tapered surface distal edge 2261. The tapered sealing member 2242 has a tapered scaling surface 2243 that is configured to mate with a female luer to create a fluid tight fit. The male connector 2201 further includes threads 2202 that allow the male connector 2201 to couple with a female connector. A lumen 2212 runs through the male connector 2201.

The male luer 2241 includes a distal tip 2255 with an end face 2204. The distal tip 2255 of the male luer 2241 is recessed from the distal line of taper of the tapered sealing member 2242. A distal recess 2251 is formed by a recessed portion of the distal tip 2255. The distal tip surface 2252 of the distal tip 2255 defines an outer diameter that is smaller than the outer diameter of the extension of the tapered sealing surface 2243.

The male luer 2241 includes a tapered surface distal edge 2261 that defines a proximal end of the distal tip 2255. In some examples, an antimicrobial agent is applied to the distal tip surface 2252 by coating, spraying, or dipping the distal tip 2255 with an antimicrobial agent, although other methods of applying antimicrobial agent are contemplated and are within the scope of the technology. In some examples, antimicrobial agent is also applied to the tapered sealing surface 2243. An antimicrobial agent on the distal tip surface 2252 of the distal tip 2255 kills microbes within the distal recess 2251 between the surface of the female luer and the distal tip surface 2252. The distal recess 2251 is designed to confine the antimicrobial agent between the inner surface of a female luer and the distal tip surface 2252 so that microbes are exposed to a high antimicrobial concentration.

The male luer 2241 further includes multiple blades 2263 arrayed around the distal tip 2255 of the male luer 2241. Between the blades 2263 are a plurality of channels 2267. In the example of FIG. 22, the blades 2263 are elongated projections arranged around the axis of the tapered sealing member 2242, and the channels 2267 are elongated recesses disposed between the blades 2263 and running parallel to the lumen 2212. The blades 2263 and channels 2267 form alternating apexes 2264 and troughs 2268. The distal tip surface 2252 of the distal tip 2255 is defined by the blades 2263 and channels 2267. An antimicrobial agent on the distal tip surface 2252 can be stored within the volumes between the blades 2263.

During insertion of the male luer 2241 into a female luer, portions of the distal tip 2255 may come in contact with the inside surface of the female luer. The apex 2264 of each high blade 2265 may come in contact with the female luer surface, but the troughs 2268 of the channels 2267 and low blades 2266 will not come in contact with the female luer surface. Thus, in comparison to the tapered surface distal edge 2261, the high blades 2265 have a relatively smaller surface area near the end face 2204 of the distal tip 2255. This minimizes the amount of ingress of microbes that can be attributed to microbes being pushed into the body of the female luer by the male luer 2241.

The channels 2267 affect confinement of microbes within the distal recess because the channels 2267 provide a restricted space in which microbes can be trapped between the distal tip surface 2252 and an inside surface of a female luer. The apex 2264 of the blades 2263 provide a maximum outer diameter of the distal tip 2255, and the troughs 2268 of the channels 2267 provide a minimum outer diameter of the distal tip 2255. Although some fluid flow between adjacent channels 2267 is possible when the male luer 2241 is coupled with a female luer, the blades 2263 provide a partial physical barrier. As seen in FIGS. 22D and 22E, the distal tip 2255 has an outer diameter that is smaller than the outer diameter of the tapered sealing member 2242 at the tapered surface distal edge 2261, and the outer diameter of the distal tip 2255 is smaller than the outer diameter of a distal line of taper defined by the conical tapered sealing member 2242.

The distal tip 2255 has a plurality of blades 2263 that separate a plurality of channels 2267. In this example, the distal tip 2255 includes high blades 2265 and low blades 2266. The high blades 2265 have a greater outer diameter than the outer diameter of the low blades 2266. In this example, the troughs 2268 of the channels 2267 each have the same outer diameter. As can be seen in FIG. 22D, in this example, each high blade 2265 is 180° opposite a low blade 2266. As seen in FIG. 22E, the male luer 2241 has a tapered surface distal edge 2261, and the apex of a blade 2263 is inside the line of taper such that the outer diameter of the blade 2263 is less than the outer diameter of the tapered surface distal edge 2261.

Male Connector with Irregular Blade Heights (FIGS. 23A-G)

Turning now to FIGS. 23A-G, a male connector 2301 includes a male luer 2341. The male luer 2341 comprises a tapered scaling member 2342. The tapered scaling member 2342 has a frustoconical shape that tapers from a larger outer diameter at the proximal portion of the tapered sealing member 2342 to a smaller outer diameter at the distal portion of the tapered sealing member near the tapered surface distal edge 2361. The tapered scaling member 2342 has a tapered sealing surface 2343 that is configured to mate with a female luer to create a fluid tight fit. The male connector 2301 further includes threads 2302 that allow the male connector 2301 to couple with a female connector. A lumen 2312 runs through the male connector 2301.

The male luer 2341 includes a distal tip 2355 with an end face 2304. The distal tip 2355 of the male luer 2341 is recessed from the distal line of taper of the tapered sealing member 2342. A distal recess 2351 is formed by a recessed portion of the distal tip 2355. The distal tip surface 2352 of the distal tip 2355 defines an outer diameter that is smaller than the outer diameter of the extension of the tapered sealing surface 2343.

The male luer 2341 includes a tapered surface distal edge 2361 that defines a proximal end of the distal tip 2355. In some examples, an antimicrobial agent is applied to the distal tip surface 2352 by coating, spraying, or dipping the distal tip 2355 with an antimicrobial agent, although other methods of applying antimicrobial agent are contemplated and are within the scope of the technology. In some examples, antimicrobial agent is also applied to the tapered sealing surface 2343. An antimicrobial agent on the distal tip surface 2352 of the distal tip 2355 kills microbes within the distal recess 2351 between the surface of the female luer and the distal tip surface 2352. The distal recess 2351 is designed to confine the antimicrobial agent between the inner surface of a female luer and the distal tip surface 2352 so that microbes are exposed to a high antimicrobial concentration.

The male luer 2341 further includes multiple blades 2363 arrayed around the distal tip 2355 of the male luer 2341. Between the blades 2363 are a plurality of channels 2367. In the example of FIG. 23, the blades 2363 are elongated projections arranged around the axis of the tapered sealing member 2342, and the channels 2367 are elongated recesses disposed between the blades 2363 and running parallel to the lumen 2312. The blades 2363 and channels 2367 form alternating apexes 2364 and troughs 2368. The distal tip surface 2352 of the distal tip 2355 is defined by the blades 2363 and channels 2367. An antimicrobial agent on the distal tip surface 2352 can be stored within the volumes between the blades 2363.

The distal tip 2355 has a plurality of blades 2363 that separate a plurality of channels 2367. In this example, the distal tip 2355 includes high blades 2365 and low blades 2366. The high blades 2365 have a greater outer diameter than the outer diameter of the low blades 2366. As seen in FIG. 23E, the male luer 2341 has a tapered surface distal edge 2361, and the apex 2364 of blade 2363 is inside the line of taper such that the outer diameter of the blade 2363 is less than the outer diameter of the tapered surface distal edge 2361.

During insertion of the male luer 2341 into a female luer, portions of the distal tip 2355 may come in contact with the inside surface of the female luer. The apex 2364 of each high blade 2365 may come in contact with the female luer surface, but the troughs 2368 of the channels 2367 and low blades 2366 will not come in contact with the female luer surface. Thus, in comparison to the tapered surface distal edge 2361, the high blades 2365 have a relatively smaller surface area near the end face 2304 of the distal tip 2355. This minimizes the amount of ingress of microbes that can be attributed to microbes being pushed into the body of the female luer by the male luer 2341.

The channels 2367 affect confinement of microbes within the distal recess because the channels 2367 provide a restricted space in which microbes can be trapped between the distal tip surface 2352 and an inside surface of a female luer. The apex 2364 of the blades 2363 provide a maximum outer diameter of the distal tip 2355, and the troughs 2368 of the channels 2367 provide a minimum outer diameter of the distal tip 2355. Although some fluid flow between adjacent channels 2367 is possible when the male luer 2341 is coupled with a female luer, the blades 2363 provide a partial physical barrier. As seen in FIGS. 23D and 23E, the distal tip 2355 has an outer diameter that is smaller than the outer diameter of the tapered sealing member 2342 at the tapered surface distal edge 2361, and the outer diameter of the distal tip 2355 is smaller than the outer diameter of a distal line of taper defined by the conical tapered sealing member 2342.

Male Connector with Tapered Blades and Channels (FIGS. 24A-F)

Turning now to FIGS. 24A-F, a male connector 2401 includes a male luer 2441. The male luer 2441 comprises a tapered sealing member 2442. The tapered scaling member 2442 has a frustoconical shape that tapers from a larger outer diameter at the proximal portion of the tapered sealing member 2442 to a smaller outer diameter at the distal portion of the tapered sealing member near the tapered surface distal edge 2461. The tapered sealing member 2442 has a tapered sealing surface 2443 that is configured to mate with a female luer to create a fluid tight fit. The male connector 2401 further includes threads 2402 that allow the male connector 2401 to couple with a female connector. A lumen 2412 runs through the male connector 2401.

The male luer 2441 includes a distal tip 2455 with an end face 2404. The distal tip 2455 of the male luer 2441 is recessed from the distal line of taper of the tapered scaling member 2442. A distal recess 2451 is formed by a recessed portion of the distal tip 2455. The distal tip surface 2452 of the distal tip 2455 defines an outer diameter that is smaller than the outer diameter of the extension of the tapered sealing surface 2443.

The male luer 2441 includes a tapered surface distal edge 2461 that defines a proximal end of the distal tip 2455. In some examples, an antimicrobial agent is applied to the distal tip surface 2452 by coating, spraying, or dipping the distal tip 2455 with an antimicrobial agent, although other methods of applying antimicrobial agent are contemplated and are within the scope of the technology. In some examples, antimicrobial agent is also applied to the tapered sealing surface 2443. An antimicrobial agent on the distal tip surface 2452 of the distal tip 2455 kills microbes within the distal recess 2451 between the surface of the female luer and the distal tip surface 2452. The distal recess 2451 is designed to confine the antimicrobial agent between the inner surface of a female luer and the distal tip surface 2452 so that microbes are exposed to a high antimicrobial concentration.

The male luer 2441 further includes multiple blades 2463 arrayed around the distal tip 2455 of the male luer 2441. Between the blades 2463 are a plurality of channels 2467. In the example of FIG. 24, the blades 2463 are elongated projections arranged around the axis of the tapered sealing member 2442, and the channels 2467 are elongated recesses disposed between the blades 2463 and running parallel to the lumen 2412. The blades 2463 and channels 2467 form alternating apexes 2464 and troughs 2468. The distal tip surface 2452 of the distal tip 2455 is defined by the blades 2463 and channels 2467. An antimicrobial agent on the distal tip surface 2452 can be stored within the volumes between the blades 2463.

During insertion of the male luer 2441 into a female luer, portions of the distal tip 2455 may come in contact with the inside surface of the female luer. The apex 2464 of each blade 2463 may come in contact with the female luer surface, but the troughs 2468 of the channels 2467 will not come in contact with the female luer surface. Thus, in comparison to the tapered surface distal edge 2461, the blades 2463 have a relatively smaller surface area near the end face 2404 of the distal tip 2455. This minimizes the amount of ingress of microbes that can be attributed to microbes being pushed into the body of the female luer by the male luer 2441.

The channels 2467 affect confinement of microbes within the distal recess because the channels 2467 provide a restricted space in which microbes can be trapped between the distal tip surface 2452 and an inside surface of a female luer. The apex 2464 of the blades 2463 provide a maximum outer diameter of the distal tip 2455, and the troughs 2468 of the channels 2467 provide a minimum outer diameter of the distal tip 2455. Although some fluid flow between adjacent channels 2467 is possible when the male luer 2441 is coupled with a female luer, the blades 2463 provide a partial physical barrier. As seen in FIGS. 24F and 24G, the distal tip 2455 has an outer diameter that is smaller than the outer diameter of the tapered sealing member 2442 at the tapered surface distal edge 2461, and the outer diameter of the distal tip 2455 smaller than the outer diameter of a distal line of taper defined by the conical tapered sealing member 2442.

The distal tip 2455 has a plurality of blades 2463 separating a plurality of channels 2467. The blades 2463 have an apex 2464, and the channels 2467 have troughs 2468. In this example, the outer diameter of the apex 2464 is uniform, but the width of the blades 2463 increases toward the end face 2404 of the distal tip 2455. The outer diameter of the troughs 2468 decreases from the proximal portion to the distal portion of the distal tip 2455, causing the taper in the trough 2468 seen in FIG. 24H.

Male Connector with Blade Apex Taper (FIGS. 25A-G)

Turning now to FIGS. 25A-G, a male connector 2501 includes a male luer 2541. The male luer 2541 comprises a tapered sealing member 2542. The tapered sealing member 2542 has a frustoconical shape that tapers from a larger outer diameter at the proximal portion of the tapered sealing member 2542 to a smaller outer diameter at the distal portion of the tapered sealing member near the tapered surface distal edge 2561. The tapered sealing member 2542 has a tapered sealing surface 2543 that is configured to mate with a female luer to create a fluid tight fit. The male connector 2501 further includes threads 2502 that allow the male connector 2501 to couple with a female connector. A lumen 2512 runs through the male connector 2501.

The male luer 2541 includes a distal tip 2555 with an end face 2504. The distal tip 2555 of the male luer 2541 is recessed from the distal line of taper of the tapered scaling member 2542. A distal recess 2551 is formed by a recessed portion of the distal tip 2555. The distal tip surface 2552 of the distal tip 2555 defines an outer diameter that is smaller than the outer diameter of the extension of the tapered sealing surface 2543.

The male luer 2541 includes a tapered surface distal edge 2561 that defines a proximal end of the distal tip 2555. In some examples, an antimicrobial agent is applied to the distal tip surface 2552 by coating, spraying, or dipping the distal tip 2555 with an antimicrobial agent, although other methods of applying antimicrobial agent are contemplated and are within the scope of the technology. In some examples, antimicrobial agent is also applied to the tapered sealing surface 2543. An antimicrobial agent on the distal tip surface 2552 of the distal tip 2555 kills microbes within the distal recess 2551 between the surface of the female luer and the distal tip surface 2552. The distal recess 2551 is designed to confine the antimicrobial agent between the inner surface of a female luer and the distal tip surface 2552 so that microbes are exposed to a high antimicrobial concentration.

The male luer 2541 further includes multiple blades 2563 arrayed around the distal tip 2555 of the male luer 2541. Between the blades 2563 are a plurality of channels 2567. In the example of FIG. 25, the blades 2563 are elongated projections arranged around the axis of the tapered sealing member 2542, and the channels 2567 are elongated recesses disposed between the blades 2563 and running parallel to the lumen 2512. The blades 2563 and channels 2567 form alternating apexes 2564 and troughs 2568. The distal tip surface 2552 of the distal tip 2555 is defined by the blades 2563 and channels 2567. An antimicrobial agent on the distal tip surface 2552 can be stored within the volumes between the blades 2563.

During insertion of the male luer 2541 into a female luer, portions of the distal tip 2555 may come in contact with the inside surface of the female luer. The apex 2564 of each blade 2563 may come in contact with the female luer surface, but the troughs 2568 of the channels 2567 will not come in contact with the female luer surface. Thus, in comparison to the tapered surface distal edge 2561, the blades 2563 have a relatively smaller surface area near the end face 2504 of the distal tip 2555. This minimizes the amount of ingress of microbes that can be attributed to microbes being pushed into the body of the female luer by the male luer 2541.

The channels 2567 affect confinement of microbes within the distal recess because the channels 2567 provide a restricted space in which microbes can be trapped between the distal tip surface 2552 and an inside surface of a female luer. The apex 2564 of the blades 2563 provide a maximum outer diameter of the distal tip 2555, and the troughs 2568 of the channels 2567 provide a minimum outer diameter of the distal tip 2555. Although some fluid flow between adjacent channels 2567 is possible when the male luer 2541 is coupled with a female luer, the blades 2563 provide a partial physical barrier. As seen in FIGS. 25E and 25F, the distal tip 2555 has an outer diameter that is smaller than the outer diameter of the tapered sealing member 2542 at the tapered surface distal edge 2561, and the outer diameter of the distal tip 2555 is smaller than the outer diameter of a distal line of taper defined by the conical tapered sealing member 2542.

The distal tip 2555 has a plurality of blades 2563 separating a plurality of channels 2567. In this example, both the apex 2564 of the blades 2563 and the troughs 2568 of the channels 2567 are tapered such that the outer diameter decreases toward the end face 2504 of the distal tip 2555.

Male Connector with Distal Blade Taper (FIGS. 26A-G)

Turning now to FIGS. 26A-G, a male connector 2601 includes a male luer 2641. The male luer 2641 comprises a tapered sealing member 2642. The tapered scaling member 2642 has a frustoconical shape that tapers from a larger outer diameter at the proximal portion of the tapered sealing member 2642 to a smaller outer diameter at the distal portion of the tapered sealing member near the tapered surface distal edge 2661. The tapered scaling member 2642 has a tapered sealing surface 2643 that is configured to mate with a female luer to create a fluid tight fit. The male connector 2601 further includes threads 2602 that allow the male connector 2601 to couple with a female connector. A lumen 2612 runs through the male connector 2601.

The male luer 2641 includes a distal tip 2655 with an end face 2604. The distal tip 2655 of the male luer 2641 is recessed from the distal line of taper of the tapered sealing member 2642. A distal recess 2651 is formed by a recessed portion of the distal tip 2655. The distal tip surface 2652 of the distal tip 2655 defines an outer diameter that is smaller than the outer diameter of the extension of the tapered sealing surface 2643.

The male luer 2641 includes a tapered surface distal edge 2661 that defines a proximal end of the distal tip 2655. In some examples, an antimicrobial agent is applied to the distal tip surface 2652 by coating, spraying, or dipping the distal tip 2655 with an antimicrobial agent, although other methods of applying antimicrobial agent are contemplated and are within the scope of the technology. In some examples, antimicrobial agent is also applied to the tapered sealing surface 2643. An antimicrobial agent on the distal tip surface 2652 of the distal tip 2655 kills microbes within the distal recess 2651 between the surface of the female luer and the distal tip surface 2652. The distal recess 2651 is designed to confine the antimicrobial agent between the inner surface of a female luer and the distal tip surface 2652 so that microbes are exposed to a high antimicrobial concentration.

The male luer 2641 further includes multiple blades 2663 arrayed around the distal tip 2655 of the male luer 2641. Between the blades 2663 are a plurality of channels 2667. In the example of FIG. 26, the blades 2663 are elongated projections arranged around the axis of the tapered sealing member 2642, and the channels 2667 are elongated recesses disposed between the blades 2663 and running parallel to the lumen 2612. The blades 2663 and channels 2667 form alternating apexes 2664 and troughs 2668. The distal tip surface 2652 of the distal tip 2655 is defined by the blades 2663 and channels 2667. An antimicrobial agent on the distal tip surface 2652 can be stored within the volumes between the blades 2663.

During insertion of the male luer 2641 into a female luer, portions of the distal tip 2655 may come in contact with the inside surface of the female luer. The apex 2664 of each blade 2663 may come in contact with the female luer surface, but the troughs 2668 of the channels 2667 will not come in contact with the female luer surface. Thus, in comparison to the tapered surface distal edge 2661, the blades 2663 have a relatively smaller surface area near the end face 2604 of the distal tip 2655. This minimizes the amount of ingress of microbes that can be attributed to microbes being pushed into the body of the female luer by the male luer 2641.

The channels 2667 affect confinement of microbes within the distal recess because the channels 2667 provide a restricted space in which microbes can be trapped between the distal tip surface 2652 and an inside surface of a female luer. The apex 2664 of the blades 2663 provide a maximum outer diameter of the distal tip 2655, and the troughs 2668 of the channels 2667 provide a minimum outer diameter of the distal tip 2655. Although some fluid flow between adjacent channels 2667 is possible when the male luer 2641 is coupled with a female luer, the blades 2663 provide a partial physical barrier. As seen in FIGS. 26E and 26F, the distal tip 2655 has an outer diameter that is smaller than the outer diameter of the tapered sealing member 2642 at the tapered surface distal edge 2661, and the outer diameter of the distal tip 2655 is smaller than the outer diameter of a distal line of taper defined by the conical tapered sealing member 2642.

The distal tip 2655 has a plurality of blades 2663 separating a plurality of channels 2667. In this example, the base of the blades 2663 are wide at a proximal end of the distal tip 2655 and gradually taper such that the blades 2663 are narrow at a distal end of the distal tip 2655. Conversely, the channels 2667 are narrow at the proximal end and widen toward the distal end of the distal tip 2655. In some examples, the blades 2663 include a bevel 2669 at the distal end.

Male Connector with Irregular Blade Length (FIGS. 27A-G)

Turning now to FIGS. 27A-G, a male connector 2701 includes a male luer 2741. The male luer 2741 comprises a tapered sealing member 2742. The tapered sealing member 2742 has a frustoconical shape that tapers from a larger outer diameter at the proximal portion of the tapered sealing member 2742 to a smaller outer diameter at the distal portion of the tapered sealing member near the tapered surface distal edge 2761. The tapered sealing member 2742 has a tapered sealing surface 2743 that is configured to mate with a female luer to create a fluid tight fit. The male connector 2701 further includes threads 2702 that allow the male connector 2701 to couple with a female connector. A lumen 2712 runs through the male connector 2701.

The male luer 2741 includes a distal tip 2755 with an end face 2704. The distal tip 2755 of the male luer 2741 is recessed from the distal line of taper of the tapered sealing member 2742. A distal recess 2751 is formed by a recessed portion of the distal tip 2755. The distal tip surface 2752 of the distal tip 2755 defines an outer diameter that is smaller than the outer diameter of the extension of the tapered sealing surface 2743.

The male luer 2741 includes a tapered surface distal edge 2761 that defines a proximal end of the distal tip 2755. In some examples, an antimicrobial agent is applied to the distal tip surface 2752 by coating, spraying, or dipping the distal tip 2755 with an antimicrobial agent, although other methods of applying antimicrobial agent are contemplated and are within the scope of the technology. In some examples, antimicrobial agent is also applied to the tapered sealing surface 2743. An antimicrobial agent on the distal tip surface 2752 of the distal tip 2755 kills microbes within the distal recess 2751 between the surface of the female luer and the distal tip surface 2752. The distal recess 2751 is designed to confine the antimicrobial agent between the inner surface of a female luer and the distal tip surface 2752 so that microbes are exposed to a high antimicrobial concentration.

The male luer 2741 further includes multiple blades 2763 arrayed around the distal tip 2755 of the male luer 2741. Between the blades 2763 are a plurality of channels 2767. In the example of FIG. 27, the blades 2763 are elongated projections arranged around the axis of the tapered sealing member 2742, and the channels 2767 are elongated recesses disposed between the blades 2763 and running parallel to the lumen 2712. The blades 2763 and channels 2767 form alternating apexes 2764 and troughs 2768. The distal tip surface 2752 of the distal tip 2755 is defined by the blades 2763 and channels 2767. An antimicrobial agent on the distal tip surface 2752 can be stored within the volumes between the blades 2763.

During insertion of the male luer 2741 into a female luer, portions of the distal tip 2755 may come in contact with the inside surface of the female luer. The apex 2764 of each blade 2763 may come in contact with the female luer surface, but the troughs 2768 of the channels 2767 will not come in contact with the female luer surface. Thus, in comparison to the tapered surface distal edge 2761, the blades 2763 have a relatively smaller surface area near the end face 2704 of the distal tip 2755. This minimizes the amount of ingress of microbes that can be attributed to microbes being pushed into the body of the female luer by the male luer 2741.

The channels 2767 affect confinement of microbes within the distal recess because the channels 2767 provide a restricted space in which microbes can be trapped between the distal tip surface 2752 and an inside surface of a female luer. The apex 2764 of the blades 2763 provide a maximum outer diameter of the distal tip 2755, and the troughs 2768 of the channels 2767 provide a minimum outer diameter of the distal tip 2755. Although some fluid flow between adjacent channels 2767 is possible when the male luer 2741 is coupled with a female luer, the blades 2763 provide a partial physical barrier. As seen in FIGS. 27E and 27F, the distal tip 2755 has an outer diameter that is smaller than the outer diameter of the tapered sealing member 2742 at the tapered surface distal edge 2761, and the outer diameter of the distal tip 2755 is smaller than the outer diameter of a distal line of taper defined by the conical tapered scaling member 2742.

In this example, the distal tip 2755 includes a plurality of elongated blades 2765 and a plurality of truncated blades 2766.

Male Connector with Zero-Clearance Blades (FIGS. 28A-F)

Turning now to FIGS. 28A-F, a male connector 2801 includes a male luer 2841. The male luer 2841 comprises a tapered sealing member 2842. The tapered sealing member 2842 has a frustoconical shape that tapers from a larger outer diameter at the proximal portion of the tapered sealing member 2842 to a smaller outer diameter at the distal portion of the tapered sealing member near the tapered surface distal edge 2861. The tapered sealing member 2842 has a tapered sealing surface 2843 that is configured to mate with a female luer to create a fluid tight fit. The male connector 2801 further includes threads 2802 that allow the male connector 2801 to couple with a female connector. A lumen 2812 runs through the male connector 2801.

The male luer 2841 includes a distal tip 2855 with an end face 2804. As seen in FIG. 28F, a distal recess 2851 is formed by a recessed portion of the distal tip 2855.

The male luer 2841 includes a tapered surface distal edge 2861 that defines a proximal end of the distal tip 2855. In some examples, an antimicrobial agent is applied to the distal tip surface 2852 by coating, spraying, or dipping the distal tip 2855 with an antimicrobial agent, although other methods of applying antimicrobial agent are contemplated and are within the scope of the technology. In some examples, antimicrobial agent is also applied to the tapered sealing surface 2843. An antimicrobial agent on the distal tip surface 2852 of the distal tip 2855 kills microbes captured between the surface of the female luer and the distal tip surface 2852. The distal recess 2851 is designed to confine the antimicrobial agent between the inner surface of a female luer and the distal tip surface 2852 so that microbes are exposed to a high antimicrobial concentration.

The male luer 2841 further includes multiple blades 2863 arrayed around the distal tip 2855 of the male luer 2841. Between the blades 2863 are a plurality of channels 2867. In the example of FIG. 28, the blades 2863 are elongated projections arranged around the axis of the tapered sealing member 2842, and the channels 2867 are elongated recesses disposed between the blades 2863 and running parallel to the lumen 2812. The blades 2863 and channels 2867 form alternating apexes 2864 and troughs 2868. The distal tip surface 2852 of the distal tip 2855 is defined by the blades 2863 and channels 2867. An antimicrobial agent on the distal tip surface 2852 can be stored within the volumes between the blades 2863.

During insertion of the male luer 2841 into a female luer, portions of the distal tip 2855 may come in contact with the inside surface of the female luer. The apex 2864 of each blade 2863 may come in contact with the female luer surface, but the troughs 2868 of the channels 2867 will not come in contact with the female luer surface. Thus, in comparison to the tapered surface distal edge 2861, the blades 2863 have a relatively smaller surface area near the end face 2804 of the distal tip 2855. This minimizes the amount of ingress of microbes that can be attributed to microbes being pushed into the body of the female luer by the male luer 2841.

The channels 2867 affect confinement of microbes within the distal recess because the channels 2867 provide a restricted space in which microbes can be trapped between the distal tip surface 2852 and an inside surface of a female luer. The apex 2864 of the blades 2863 provide a maximum outer diameter of the distal tip 2855, and the troughs 2868 of the channels 2867 provide a minimum outer diameter of the distal tip 2855. The blades 2863 provide a physical barrier between adjacent channels 2867 when the male luer 2841 is mated with a female luer. As seen in FIGS. 28D and 28E, the outer diameter of the distal tip 2855 is the same as the outer diameter of the tapered sealing member 2842 at the apex 2864 of the blades 2863. As seen in FIG. 28F, the outer diameter of the distal tip 2855 is smaller than the outer diameter of the tapered sealing member 2842 at the trough 2868 of the channels 2867.

In this example, the apex 2864 of each blade 2863 has an outer diameter that follows the line of taper of the tapered sealing member 2842. When the male connector 2801 is coupled with a female connector such that the male and female luers form a fluid tight fit, the apex 2864 of each blade 2863 contacts the inner surface of the female luer.

The distal tip 2855 includes a distal recess 2851. In this example, the distal recess is present inside of the volume of the channels 2867 created between the blades 2863, where the outer diameter of the distal tip 2855 is inside the line of taper of the tapered sealing member 2842.

Male Connector with Threaded Blades (FIGS. 29A-G)

Turning now to FIGS. 29A-G, a male connector 2901 includes a male luer 2941. The male luer 2941 comprises a tapered sealing member 2942. The tapered sealing member 2942 has a frustoconical shape that tapers from a larger outer diameter at the proximal portion of the tapered sealing member 2942 to a smaller outer diameter at the distal portion of the tapered sealing member near the tapered surface distal edge 2961. The tapered sealing member 2942 has a tapered sealing surface 2943 that is configured to mate with a female luer to create a fluid tight fit. The male connector 2901 further includes threads 2902 that allow the male connector 2901 to couple with a female connector. A lumen 2912 runs through the male connector 2901.

The male luer 2941 includes a distal tip 2955 with an end face 2904. As seen in FIGS. 29F and 29G, a distal recess 2951 is formed by a recessed portion of the distal tip 2955.

The male luer 2941 includes a tapered surface distal edge 2961 that defines a proximal end of the distal tip 2955. In some examples, an antimicrobial agent is applied to the distal tip surface 2952 by coating, spraying, or dipping the distal tip 2955 with an antimicrobial agent, although other methods of applying antimicrobial agent are contemplated and are within the scope of the technology. In some examples, antimicrobial agent is also applied to the tapered sealing surface 2943. An antimicrobial agent on the distal tip surface 2952 of the distal tip 2955 kills microbes captured between the surface of the female luer and the distal tip surface 2952. The distal recess 2951 is designed to confine the antimicrobial agent between the inner surface of a female luer and the distal tip surface 2952 so that microbes are exposed to a high antimicrobial concentration.

An antimicrobial agent on the distal tip surface 2952 can be stored within the volumes between the blades 2963.

The distal tip 2955 includes a plurality of blades 2963 that separate a plurality of channels 2967. The blades 2963 spiral around the axis of the lumen 2912, and the troughs 2968 of the channels 2967 follow the spiral. In this example, the apex 2964 of each blade 2963 has an outer diameter that follows the line of taper of the tapered sealing member 2942. Thus, when the male connector 2901 is coupled with a female connector such that the male and female luers form a fluid tight fit, the apex 2964 of each blade 2963 contacts the inner surface of the female luer.

In some examples, the blades 2963 have a threaded pitch that is the same as the pitch of the threads 2902 inside of the male connector 2901. Rotating the male connector 2901 around the axis of the lumen 2912 when inserting the male luer 2941 into a female luer causes the blades 2963 to rotate along with the male luer 2941. From the perspective shown in FIG. 29E, the male connector 2901 would move in a counterclockwise direction. The blades 2963 have a leading edge 2981 that can contact the female luer inside surface. In this case, the apex 2964 serves as an extension of the tapered surface distal edge 2961. This rotation can allow the leading edge 2981 of the blades 2963 to act like a ramp, pushing any particles (such as microbes) on the surface of the female luer in a proximal direction.

The distal tip 2955 includes a distal recess 2951. In this example, the distal recess 2951 is present inside of the volume of the channels 2967 created between the blades 2963. As noted above, the leading edge 2981 can act as a ramp to push particles in a proximal direction, away from the end face 2904 of the distal tip 2955. An antimicrobial agent present on the distal tip surface 2952 of the distal tip 2955 can be dispersed inside the channels 2967 that form the distal recess 2951.

The channels 2967 affect confinement of microbes within the distal recess 2951 because the channels 2967 provide a restricted space in which microbes can be trapped between the distal tip surface 2952 and an inside surface of a female luer. The apex 2964 of the blades 2963 provide a maximum outer diameter of the distal tip 2955, and the troughs 2968 of the channels 2967 provide a minimum outer diameter of the distal tip 2955. The blades 2963 provide a physical barrier between adjacent channels 2967 when the male luer 2941 is mated with a female luer. The outer diameter of the distal tip 2955 is the same as the outer diameter of the tapered sealing member 2942 at the apex 2964 of the blades 2963. As seen in FIGS. 29F and 29G, the outer diameter of the distal tip 2955 is smaller than the outer diameter of the tapered sealing member 2942 at the trough 2968 of the channels 2967.

Male Connector with Proximal Trap (FIGS. 30A-F)

Turning now to FIGS. 30A-F, a male connector 3001 includes a male luer 3041. The male luer 3041 comprises a tapered sealing member 3042. The tapered sealing member 3042 has a frustoconical shape that tapers from a larger outer diameter at the proximal portion of the tapered sealing member 3042 to a smaller outer diameter at the distal portion of the tapered sealing member near the tapered surface distal edge 3061. The tapered sealing member 3042 has a tapered sealing surface 3043 that is configured to mate with a female luer to create a fluid tight fit. The male connector 3001 further includes threads 3002 that allow the male connector 3001 to couple with a female connector. A lumen 3012 runs through the male connector 3001.

The male luer 3041 includes a distal tip 3055 with an end face 3004. The distal tip 3055 of the male luer 3041 is recessed from the distal line of taper of the tapered sealing member 3042. A distal recess 3051 is formed by a recessed portion of the distal tip 3055. The distal tip surface 3052 of the distal tip 3055 defines an outer diameter that is smaller than the outer diameter of the extension of the tapered sealing surface 3043.

In some examples, an antimicrobial agent is applied to the distal tip surface 3052 by coating, spraying, or dipping the distal tip 3055 with an antimicrobial agent, although other methods of applying antimicrobial agent are contemplated and are within the scope of the technology. In some examples, antimicrobial agent is also applied to the tapered sealing surface 3043. An antimicrobial agent on the distal tip surface 3052 of the distal tip 3055 kills microbes within the distal recess 3051 between the surface of the female luer and the distal tip surface 3052. The distal recess 3051 is designed to confine the antimicrobial agent between the inner surface of a female luer and the distal tip surface 3052 so that microbes are exposed to a high antimicrobial concentration.

The distal recess 3051 affects confinement of microbes because the distal recess 3051 provides a restricted space in which microbes can be trapped between the distal tip surface 3052 and an inside surface of a female luer. As seen in FIGS. 30E and 30F, the distal tip 3055 has an outer diameter that is smaller than the outer diameter of the tapered sealing member 3042 at the tapered surface distal edge 3061, and the outer diameter of the distal tip 3055 is smaller than the outer diameter of a distal line of taper defined by the conical tapered sealing member 3042.

The distal tip 3055 has a distal tip surface 3052 and a distal recess 3051. In this example, the distal tip surface 3052 does not include blades. The male luer 3041 has a tapered surface distal edge 3061 at a distal end of the tapered sealing member 3042. The tapered surface distal edge 3061 has a tapered surface distal edge face 3062. A proximal trap 3071 is defined between the distal tip surface 3052 and the proximal trap walls 3073. The proximal trap 3071 is a cavity that is bounded on multiple sides by proximal trap walls 3073 formed in the male luer 3041. In the example shown in FIG. 30G, the proximal trap 3071 is an annular cavity in the male luer that is defined by a proximal wall 3081, an outer wall 3082, and an inner wall 3083. The proximal trap 3071 opens on the distal recess 3051 and is adjacent to the tapered surface distal edge face 3062. As will be discussed below in relation to FIGS. 38 and 39, an antimicrobial agent can be contained inside of the proximal trap 3071.

The proximal trap 3071 stores an antimicrobial agent within the annular cavity defined by the proximal trap 3071. In some examples, microbes reside near the interface between the tapered surface distal edge 3061 and a surface of a female luer. The antimicrobial agent stored in the proximal trap 3071 ensures that the concentration of the antimicrobial agent remains high (up to the level of saturation) in the vicinity of microbes.

The proximal trap 3071 and distal recess 3051 are both designed to confine microbes, fluid, and antimicrobial agent near the female luer surface of the female connector. There are differences between confinement of the fluid and the antimicrobial agent within the proximal trap 3071 and confinement within the distal recess 3051. Confinement of fluid and antimicrobial agent in the proximal trap 3071 occurs independently of the female luer surface.

The proximal trap walls 3073 create a cavity configured to prevent or minimize fluid flow out of the proximal trap 3071. The antimicrobial agent is not readily washed away from the proximal trap 3071 during or after insertion of the male connector 3001 into the female connector. The shape of the cavity of the proximal trap 3071 enables limited recirculation of the fluid and antimicrobial agent inside the proximal trap 3071 during fluid flow conditions, discussed in relation to FIGS. 38 and 39. Once the male luer 3041 is installed into a fluid filled female luer, or during fluid flow conditions, the antimicrobial agent on the surface of the proximal trap walls 3073 can diffuse out of the proximal trap 3071.

In contrast, confinement of the antimicrobial agent within the distal recess 3051 is dependent on the female luer surface; this confinement is optimized when the male connector 3001 is fully inserted into the female connector. When the male connector 3001 is coupled with the female connector, the cavity formed between the distal tip surface 3052 and the female luer surface limit fluid circulation and transfer of antimicrobial agent into the lumen of the female luer. Limited fluid circulation, in combination with confinement, keeps the antimicrobial agent at a high concentration within the distal recess 3051 cavity even while fluid flows through the lumen 3012.

Both the proximal trap 3071 and the distal recess 3051 are designed to minimize washout of the antimicrobial agent from the volume created between the female luer surface and the distal tip surface 3052. The proximal trap 3071 has no separate entrance and exit. The antimicrobial agent on the surface of the proximal trap wall 3073 will diffuse out of the proximal trap 3071 after the male luer 3041 has been installed inside a female luer. There are differences between confinement of microbes and washout of the antimicrobial agent from the distal recess 3051. Confinement keeps the antimicrobial agent within the distal recess 3051 while fluid flows through the lumen 3012. Washout refers to preventing the antimicrobial agent from being washed away from the distal recess 3051 into the lumen of the female luer while the male connector is coupled with the female connector. The proximal trap 3071 prevents or minimizes fluid flow within the volume of the proximal trap 3071 because there is no through path to the body of the female luer lumen. Therefore, the antimicrobial agent is not readily washed away from the proximal trap 3071.

FIG. 30G is an enlarged cross-sectional view of the distal end of the connector of FIG. 30F. The proximal trap 3071 has a depth A, and the distal recess 3051 has a depth B. The proximal trap 3071 has a width C, and the distal tip 3055 has a width D. As used in FIG. 30G, the term "width" indicates a distance measured parallel to the central longitudinal axis of the male luer, and the term "depth" indicates a distance measured perpendicular to the central longitudinal axis of the male luer.

In some embodiments, the proximal trap depth A can be greater than or equal to 0.10 mm, 0.15 mm, 0.20 mm, 0.25 mm, 0.30 mm, 0.35 mm, 0.40 mm, or 0.45 mm. In some embodiments, the proximal trap depth A can be less than or equal to 0.80 mm, 0.75 mm, 0.70 mm, 0.65 mm, 0.60 mm, 0.55 mm, 0.50 mm, or 0.45 mm. In some embodiments, the proximal trap depth A can fall within a range of 0.10 mm to 0.80 mm, or 0.15 mm to 0.75 mm, or 0.20 mm to 0.70 mm, or 0.25 mm to 0.65 mm, or 0.30 mm to 0.60 mm, or 0.35 mm to 0.55 mm, or 0.40 mm to 0.50 mm, or can be about 0.39 mm.

The distal recess depth B is greater than the proximal trap depth A In some embodiments, the distal recess depth B can be greater than or equal to 0.20 mm, 0.26 mm, 0.31 mm, 0.37 mm, 0.42 mm, 0.48 mm, 0.54 mm, 0.59 mm, or 0.65 mm. In some embodiments, the distal recess depth B can be less than or equal to 1.00 mm, 0.96 mm, 0.91 mm, 0.87 mm, 0.82 mm, 0.78 mm, 0.74 mm, 0.69 mm, or 0.65 mm. In some embodiments, the distal recess depth B can fall within a range of 0.20 mm to 1.00 mm, or 0.26 mm to 0.96 mm, or 0.31 mm to 0.91 mm, or 0.37 mm to 0.87 mm, or 0.42 mm to 0.82 mm, or 0.48 mm to 0.78 mm, or 0.54 mm to 0.74 mm, or 0.59 mm to 0.69 mm, or can be about 0.77 mm.

The distal recess depth B affects the depth of the cavity formed between the distal tip surface and the female tapered surface when the male luer is coupled with a female luer. In some embodiments, the distal tip can have an outer diameter that is less than 95 percent of an inner diameter of the female tapered surface at a point radially outward of the distal tip. In some embodiments, the distal tip can have an outer diameter that is between 50 percent and 95 percent of the inner diameter of the female tapered surface. In some embodiments, the outer diameter of the distal tip expressed as a percentage of the inner diameter of the female tapered surface can be greater than or equal to 50%, 55%, 60%, 65%, 70%, 75%, or 80% of the inner diameter of the female tapered surface. In some embodiments, the outer diameter of the distal tip expressed as a percentage of the inner diameter of the female tapered surface can be less than or equal to 95%, 90%, 85%, or 80% of the inner diameter of the female tapered surface. In some embodiments, the outer diameter of the distal tip expressed as a percentage of the inner diameter of the female tapered surface can fall within a range of 50% to 95%, or 55% to 90%, or 60% to 90%, or 65% to 85%, or 70% to 85%, or 70% to 80%, or 75% to 85%, or can be about 80% of the inner diameter of the female tapered surface. Various alternatives are possible based on particular applications of the technology.

Additionally, in examples where the distal tip includes blades (such as in the example of FIGS. 17A-F), the distal tip outer diameter is variable around the circumference of the distal tip, and the outer diameter of the distal tip expressed as a percentage of the inner diameter of the female tapered surface will likewise be variable.

In examples where the apex of the blade has an outer diameter equal to the inner diameter of the female tapered surface (such as in the example of FIGS. 28A-F), the distal tip can have an outer diameter that varies between 50 percent of the inner diameter of the female tapered surface and 100 percent of the inner diameter of the female tapered surface. Other examples are possible, and are within the scope of the disclosed technology.

In some embodiments, the proximal trap width C can be greater than or equal to 0.10 mm, 0.18 mm, 0.26 mm, 0.34 mm, 0.41 mm, 0.49 mm, 0.57 mm, 0.65 mm, 0.73 mm, 0.81 mm, 0.89 mm, 0.96 mm, 1.04 mm, 1.12 mm, or 1.20 mm. In some embodiments, the proximal trap width C can be less than or equal to 2.50 mm, 2.41 mm, 2.31 mm, 2.22 mm, 2.13 mm, 2.04 mm, 1.94 mm, 1.85 mm, 1.76 mm, 1.66 mm, 1.57 mm, 1.48 mm, 1.39 mm, 1.29 mm, or 1.20 mm. In some embodiments, the proximal trap width C can fall within a range of 0.10 mm to 2.50 mm, or 0.18 mm to 2.41 mm, or 0.26 mm to 2.31 mm, or 0.34 mm to 2.22 mm, or 0.41 mm to 2.13 mm, or 0.49 mm to 2.04 mm, or 0.57 mm to 1.94 mm, or 0.65 mm to 1.85 mm, or 0.73 mm to 1.76 mm, or 0.81 mm to 1.66 mm, or 0.89 mm to 1.57 mm, or 0.96 mm to 1.48 mm, or 1.04 mm to 1.39 mm, or 1.12 mm to 1.29 mm, or can be about 0.51 mm.

The distal tip width D may be larger than the proximal trap width C, but could alternatively be equal to or smaller than the proximal trap width C. In some embodiments, the distal tip width D can be greater than or equal to 0.10 mm, 0.30 mm, 0.50 mm, 0.70 mm, 0.90 mm, 1.10 mm, 1.30 mm, 1.50 mm, 1.70 mm, 1.90 mm, or 2.10 mm. In some embodiments, the distal tip width D can be less than or equal to 4.00 mm, 3.81 mm, 3.62 mm, 3.43 mm, 3.24 mm, 3.05 mm, 2.86 mm, 2.67 mm, 2.48 mm, 2.29 mm, or 2.10 mm. In some embodiments, the distal tip width D can fall within a range of 0.10 mm to 4.00 mm, or 0.30 mm to 3.81 mm, or 0.50 mm to 3.62 mm, or 0.70 mm to 3.43 mm, or 0.90 mm to 3.24 mm, or 1.10 mm to 3.05 mm, or 1.30 mm to 2.86 mm, or 1.50 mm to 2.67 mm, or 1.70 mm to 2.48 mm, or 1.90 mm to 2.29 mm, or can be about 2.41 mm. Conventional male luer connectors may have a radius or chamfer at an outside tip of the male taper. The international standard, ISO 80369-7: Connectors for Intravascular or Hypodermic Applications, specifies the maximum radius of the radius or chamfer be 0.5 mm.

The distal tip 3055 has a wall thickness E. In some embodiments, the wall thickness E can be greater than or equal to 0.10 mm, 0.15 mm, 0.20 mm, 0.25 mm, 0.30 mm, 0.35 mm, 0.40 mm, or 0.45 mm. In some embodiments, the wall thickness E can be less than or equal to 0.80 mm, 0.75 mm, 0.70 mm, 0.65 mm, 0.60 mm, 0.55 mm, 0.50 mm, or 0.45 mm. In some embodiments, the wall thickness E can fall within a range of 0.10 mm to 0.80 mm, or 0.15 mm to 0.75 mm, or 0.20 mm to 0.70 mm, or 0.25 mm to 0.65 mm, or 0.30 mm to 0.60 mm, or 0.35 mm to 0.55 mm, or 0.40 mm to 0.50 mm, or can be about 0.39 mm.

The lumen 3012 has an inner diameter F. In some embodiments, the lumen inner diameter F can be greater than or equal to 1.00 mm, 1.13 mm, 1.26 mm, 1.39 mm, 1.52 mm, or 1.65 mm. In some embodiments, the lumen inner diameter F can be less than or equal to 2.00 mm, 1.93 mm, 1.86 mm, 1.79 mm, 1.72 mm, or 1.65 mm. In some embodiments, the lumen inner diameter F can fall within a range of 1.00 mm to 2.00 mm, or 1.13 mm to 1.93 mm, or 1.26 mm to 1.86 mm, or 1.39 mm to 1.79 mm, or 1.52 mm to 1.72 mm, or can be about 1.65 mm.

Male Connector with Plurality of Proximal Cavities (FIGS. 31A-G)

Turning now to FIGS. 31A-G, a male connector 3101 includes a male luer 3141. The male luer 3141 comprises a tapered sealing member 3142. The tapered sealing member 3142 has a frustoconical shape that tapers from a larger outer diameter at the proximal portion of the tapered sealing member 3142 to a smaller outer diameter at the distal portion of the tapered sealing member near the tapered surface distal edge 3161. The tapered sealing member 3142 has a tapered sealing surface 3143 that is configured to mate with a female luer to create a fluid tight fit. The male connector 3101 further includes threads 3102 that allow the male connector 3101 to couple with a female connector. A lumen 3112 runs through the male connector 3101.

The male luer 3141 includes a distal tip 3155 with an end face 3104. The distal tip 3155 of the male luer 3141 is recessed from the distal line of taper of the tapered sealing member 3142. A distal recess 3151 is formed by a recessed portion of the distal tip 3155. The distal tip surface 3152 of the distal tip 3155 defines an outer diameter that is smaller than the outer diameter of the extension of the tapered sealing surface 3143.

In some examples, an antimicrobial agent is applied to the distal tip surface 3152 by coating, spraying, or dipping the distal tip 3155 with an antimicrobial agent, although other methods of applying antimicrobial agent are contemplated and are within the scope of the technology. In some examples, antimicrobial agent is also applied to the tapered sealing surface 3143. An antimicrobial agent on the distal tip surface 3152 of the distal tip 3155 kills microbes within the distal recess 3151 between the surface of the female luer and the distal tip surface 3152. The distal recess 3151 is designed to confine the antimicrobial agent between the inner surface of a female luer and the distal tip surface 3152 so that microbes are exposed to a high antimicrobial concentration.

The distal recess 3151 affects confinement of microbes because the distal recess 3151 provides a restricted space in which microbes can be trapped between the distal tip surface 3152 and an inside surface of a female luer. As seen in FIG. 31F, the distal tip 3155 has an outer diameter that is smaller than the outer diameter of the tapered sealing member 3142 at the tapered surface distal edge 3161, and the outer diameter of the distal tip 3155 is smaller than the outer diameter of a distal line of taper defined by the conical tapered sealing member 3142.

Like the example of FIG. 30, the tapered surface distal edge 3161 has a tapered surface distal edge face 3162. But the distal tip 3155 includes a plurality of proximal traps 3171 that are isolated from each other by proximal trap walls 3173. The proximal traps 3171 have no separate entrance and exit. Antimicrobial agent can be stored on the surface of the proximal trap walls 3173, and the antimicrobial agent will diffuse out of the proximal trap 3171 after the male luer 3141 has been installed inside a female luer.

Male Connector with Blade and Plurality of Proximal Cavities (FIGS. 32A-G)

Turning now to FIGS. 32A-G, a male connector 3201 includes a male luer 3241. The male luer 3241 comprises a tapered sealing member 3242. The tapered sealing member 3242 has a frustoconical shape that tapers from a larger outer diameter at the proximal portion of the tapered sealing member 3242 to a smaller outer diameter at the distal portion of the tapered sealing member near the tapered surface distal edge 3261. The tapered sealing member 3242 has a tapered sealing surface 3243 that is configured to mate with a female luer to create a fluid tight fit. The male connector 3201 further includes threads 3202 that allow the male connector 3201 to couple with a female connector. A lumen 3212 runs through the male connector 3201.

The male luer 3241 includes a distal tip 3255 with an end face 3204. The distal tip 3255 of the male luer 3241 is recessed from the distal line of taper of the tapered sealing member 3242. A distal recess 3251 is formed by a recessed portion of the distal tip 3255. The distal tip surface 3252 of the distal tip 3255 defines an outer diameter that is smaller than the outer diameter of the extension of the tapered sealing surface 3243.

The male luer 3241 includes a tapered surface distal edge 3261 that defines a proximal end of the distal tip 3255. In some examples, an antimicrobial agent is applied to the distal tip surface 3252 by coating, spraying, or dipping the distal tip 3255 with an antimicrobial agent, although other methods of applying antimicrobial agent are contemplated and are within the scope of the technology. In some examples, antimicrobial agent is also applied to the tapered sealing surface 3243. An antimicrobial agent on the distal tip surface 3252 of the distal tip 3255 kills microbes within the distal recess 3251 between the surface of the female luer and the distal tip surface 3252. The distal recess 3251 is designed to confine the antimicrobial agent between the inner surface of a female luer and the distal tip surface 3252 so that microbes are exposed to a high antimicrobial concentration.

The male luer 3241 further includes multiple blades 3263 arrayed around the distal tip 3255 of the male luer 3241. Between the blades 3263 are a plurality of channels 3267. In the example of FIG. 32, the blades 3263 are elongated projections arranged around the axis of the tapered sealing member 3242, and the channels 3267 are elongated recesses disposed between the blades 3263 and running parallel to the lumen 3212. The blades 3263 and channels 3267 form alternating apexes 3264 and troughs 3268. The distal tip surface 3252 of the distal tip 3255 is defined by the blades 3263 and channels 3267. An antimicrobial agent on the distal tip surface 3252 can be stored within the volumes between the blades 3263.

During insertion of the male luer 3241 into a female luer, portions of the distal tip 3255 may come in contact with the inside surface of the female luer. The apex 3264 of each blade 3263 may come in contact with the female luer surface, but the troughs 3268 of the channels 3267 will not come in contact with the female luer surface. Thus, in comparison to the tapered surface distal edge 3261, the blades 3263 have a relatively smaller surface area near the end face 3204 of the distal tip 3255. This minimizes the amount of ingress of microbes that can be attributed to microbes being pushed into the body of the female luer by the male luer 3241.

The channels 3267 affect confinement of microbes within the distal recess because the channels 3267 provide a restricted space in which microbes can be trapped between the distal tip surface 3252 and an inside surface of a female luer. The apex 3264 of the blades 3263 provide a maximum outer diameter of the distal tip 3255, and the troughs 3268 of the channels 3267 provide a minimum outer diameter of the distal tip 3255. Although some fluid flow between adjacent channels 3267 is possible when the male luer 3241 is coupled with a female luer, the blades 3263 provide a partial physical barrier. As seen in FIGS. 32E and 32F, the distal tip 3255 has an outer diameter that is smaller than the outer diameter of the tapered sealing member 3242 at the tapered surface distal edge 3261, and the outer diameter of the distal tip 3255 is smaller than the outer diameter of a distal line of taper defined by the conical tapered sealing member 3242.

The male luer 3241 includes a tapered surface distal edge 3261 having a tapered surface distal edge face 3262. Like this example of FIG. 31, a plurality of proximal traps 3271 are formed within a plurality of proximal trap walls 3273 that are proximal to the tapered surface distal edge face 3262. This can be seen most clearly and FIG. 32G. Each proximal trap 3271 is isolated from the other proximal traps.

Each proximal trap 3271 has only one entrance and exit, forming a cavity surrounded by the proximal trap walls 3273 on all sides. The proximal trap 3271 is defined between the distal tip surface 3252 and the proximal trap walls 3273. The proximal trap 3271 is a cavity that is bounded on multiple sides. The proximal trap 3271 opens on the distal recess 3251. The proximal trap is adjacent to the tapered surface distal edge face 3262. An antimicrobial agent can be contained inside of the proximal trap 3271.

Male Luer Cap with Blades (FIGS. 33A-F)

Turning now to FIGS. 33A-F, a male luer cap 3301 includes a male luer 3341. The male luer 3341 comprises a tapered sealing member 3342. The tapered scaling member 3342 has a frustoconical shape that tapers from a larger outer diameter at the proximal portion of the tapered sealing member 3342 to a smaller outer diameter at the distal portion of the tapered sealing member near the tapered surface distal edge 3361. The tapered scaling member 3342 has a tapered sealing surface 3343 that is configured to mate with a female luer to create a fluid tight fit. The male luer cap 3301 further includes threads 3302 that allow the male luer cap 3301 to couple with a female connector.

The male luer 3341 includes a distal tip 3355 with an end face 3304. The distal tip 3355 of the male luer 3341 is recessed from the distal line of taper of the tapered scaling member 3342. A distal recess 3351 is formed by a recessed portion of the distal tip 3355. The distal tip surface 3352 of the distal tip 3355 defines an outer diameter that is smaller than the outer diameter of the extension of the tapered sealing surface 3343.

The male luer 3341 includes a tapered surface distal edge 3361 that defines a proximal end of the distal tip 3355. In some examples, an antimicrobial agent is applied to the distal tip surface 3352 by coating, spraying, or dipping the distal tip 3355 with an antimicrobial agent, although other methods of applying antimicrobial agent are contemplated and are within the scope of the technology. In some examples, antimicrobial agent is also applied to the tapered sealing surface 3343. An antimicrobial agent on the distal tip surface 3352 of the distal tip 3355 kills microbes within the distal recess 3351 between the surface of the female luer and the distal tip surface 3352. The distal recess 3351 is designed to confine the antimicrobial agent between the inner surface of a female luer and the distal tip surface 3352 so that microbes are exposed to a high antimicrobial concentration.

The male luer 3341 further includes multiple blades 3363 arrayed around the distal tip 3355 of the male luer 3341. Between the blades 3363 are a plurality of channels 3367. In the example of FIG. 33, the blades 3363 are elongated projections arranged around the axis of the tapered sealing member 3342, and the channels 3367 are elongated recesses disposed between the blades 3363. The blades 3363 and channels 3367 form alternating apexes 3364 and troughs 3368. The distal tip surface 3352 of the distal tip 3355 is defined by the blades 3363 and channels 3367. An antimicrobial agent on the distal tip surface 3352 can be stored within the volumes between the blades 3363.

During insertion of the male luer 3341 into a female luer, portions of the distal tip 3355 may come in contact with the inside surface of the female luer. The apex 3364 of each blade 3363 may come in contact with the female luer surface, but the troughs 3368 of the channels 3367 will not come in contact with the female luer surface. Thus, in comparison to the tapered surface distal edge 3361, the blades 3363 have a relatively smaller surface area near the end face 3304 of the distal tip 3355. This minimizes the amount of ingress of microbes that can be attributed to microbes being pushed into the body of the female luer by the male luer 3341.

The channels 3367 affect confinement of microbes within the distal recess because the channels 3367 provide a restricted space in which microbes can be trapped between the distal tip surface 3352 and an inside surface of a female luer. The apex 3364 of the blades 3363 provide a maximum outer diameter of the distal tip 3355, and the troughs 3368 of the channels 3367 provide a minimum outer diameter of the distal tip 3355. Although some fluid flow between adjacent channels 3367 is possible when the male luer 3341 is coupled with a female luer, the blades 3363 provide a partial physical barrier. As seen in FIGS. 33D and 33E, the distal tip 3355 has an outer diameter that is smaller than the outer diameter of the tapered scaling member 3342 at the tapered surface distal edge 3361, and the outer diameter of the distal tip 3355 is smaller than the outer diameter of a distal line of taper defined by the conical tapered scaling member 3342.

The male luer cap 3301 does not include a lumen, as it is designed to prevent fluid flow out of a medical device having a female luer at the proximal end of the medical device. An antimicrobial agent can coat the distal tip surface 3352. In some examples, the antimicrobial agent can also coat the end face 3304. Although not shown in the drawings of FIG. 33, the male luer cap 3301 could further include one or more proximal traps similar to those described above.

Luer Coupler with Blades at Male Distal End (FIGS. 34A-F)

Turning now to FIGS. 34A-F, a luer coupler 3401 includes a male connector portion 3449 and a female connector portion 3489 integral with the male connector portion 3449. A lumen 3412 runs through both the female connector portion 3489 and the male connector portion 3449. The female connector portion 3489 of the luer coupler 3401 includes threads 3486 for coupling with a male connector. The female connector portion 3489 further includes a female luer tapered sealing surface 3488.

The male luer 3441 comprises a tapered sealing member 3442. The tapered scaling member 3442 has a frustoconical shape that tapers from a larger outer diameter at the proximal portion of the tapered sealing member 3442 to a smaller outer diameter at the distal portion of the tapered sealing member near the tapered surface distal edge 3461. The tapered scaling member 3442 has a tapered sealing surface 3443 that is configured to mate with a female luer to create a fluid tight fit. The luer coupler 3401 further includes threads 3402 that allow the luer coupler 3401 to couple with a female connector.

The male luer 3441 includes a distal tip 3455 with an end face 3404. The distal tip 3455 of the male luer 3441 is recessed from the distal line of taper of the tapered scaling member 3442. A distal recess 3451 is formed by a recessed portion of the distal tip 3455. The distal tip surface 3452 of the distal tip 3455 defines an outer diameter that is smaller than the outer diameter of the extension of the tapered sealing surface 3443.

The male luer 3441 includes a tapered surface distal edge 3461 that defines a proximal end of the distal tip 3455. In some examples, an antimicrobial agent is applied to the distal tip surface 3452 by coating, spraying, or dipping the distal tip 3455 with an antimicrobial agent, although other methods of applying antimicrobial agent are contemplated and are within the scope of the technology. In some examples, antimicrobial agent is also applied to the tapered sealing surface 3443. An antimicrobial agent on the distal tip surface 3452 of the distal tip 3455 kills microbes within the distal recess 3451 between the surface of the female luer and the distal tip surface 3452. The distal recess 3451 is designed to confine the antimicrobial agent between the inner surface of a female luer and the distal tip surface 3452 so that microbes are exposed to a high antimicrobial concentration.

The male luer 3441 further includes multiple blades 3463 arrayed around the distal tip 3455 of the male luer 3441. Between the blades 3463 are a plurality of channels 3467. In the example of FIG. 34, the blades 3463 are elongated projections arranged around the axis of the tapered sealing member 3442, and the channels 3467 are elongated recesses disposed between the blades 3463 and running parallel to the lumen 3412. The blades 3463 and channels 3467 form alternating apexes 3464 and troughs 3468. The distal tip surface 3452 of the distal tip 3455 is defined by the blades 3463 and channels 3467. An antimicrobial agent on the distal tip surface 3452 can be stored within the volumes between the blades 3463.

During insertion of the male luer 3441 into a female luer, portions of the distal tip 3455 may come in contact with the inside surface of the female luer. The apex 3464 of each blade 3463 may come in contact with the female luer surface, but the troughs 3468 of the channels 3467 will not come in contact with the female luer surface. Thus, in comparison to the tapered surface distal edge 3461, the blades 3463 have a relatively smaller surface area near the end face 3404 of the distal tip 3455. This minimizes the amount of ingress of microbes that can be attributed to microbes being pushed into the body of the female luer by the male luer 3441.

The channels 3467 affect confinement of microbes within the distal recess because the channels 3467 provide a restricted space in which microbes can be trapped between the distal tip surface 3452 and an inside surface of a female luer. The apex 3464 of the blades 3463 provide a maximum outer diameter of the distal tip 3455, and the troughs 3468 of the channels 3467 provide a minimum outer diameter of the distal tip 3455. Although some fluid flow between adjacent channels 3467 is possible when the male luer 3441 is coupled with a female luer, the blades 3463 provide a partial physical barrier. As seen in FIGS. 34C and 34D, the distal tip 3455 has an outer diameter that is smaller than the outer diameter of the tapered sealing member 3442 at the tapered surface distal edge 3461, and the outer diameter of the distal tip 3455 is smaller than the outer diameter of a distal line of taper defined by the conical tapered scaling member 3442.

Luer Coupler with Proximal Trap at Male Distal End (FIGS. 35A-F)

Turning now to FIGS. 35A-F, a luer coupler 3501 includes a male connector portion 3549 and a female connector portion 3589 integral with the male connector portion 3549. A lumen 3512 runs through both the female connector portion 3589 and the male connector portion 3549. The female connector portion 3589 of the luer coupler 3501 includes threads 3586 for coupling with a male connector. The female connector portion 3589 further includes a female luer tapered sealing surface 3588.

The male luer 3541 comprises a tapered sealing member 3542. The tapered sealing member 3542 has a frustoconical shape that tapers from a larger outer diameter at the proximal portion of the tapered sealing member 3542 to a smaller outer diameter at the distal portion of the tapered sealing member near the tapered surface distal edge 3561. The tapered scaling member 3542 has a tapered sealing surface 3543 that is configured to mate with a female luer to create a fluid tight fit. The luer coupler 3501 further includes threads 3502 that allow the luer coupler 3501 to couple with a female connector.

The male luer 3541 includes a distal tip 3555 with an end face 3504. The distal tip 3555 of the male luer 3541 is recessed from the distal line of taper of the tapered sealing member 3542. A distal recess 3551 is formed by a recessed portion of the distal tip 3555. The distal tip surface 3552 of the distal tip 3555 defines an outer diameter that is smaller than the outer diameter of the extension of the tapered sealing surface 3543.

The male luer 3541 includes a tapered surface distal edge 3561 that defines a proximal end of the distal tip 3555. In some examples, an antimicrobial agent is applied to the distal tip surface 3552 by coating, spraying, or dipping the distal tip 3555 with an antimicrobial agent, although other methods of applying antimicrobial agent are contemplated and are within the scope of the technology. In some examples, antimicrobial agent is also applied to the tapered sealing surface 3543. An antimicrobial agent on the distal tip surface 3552 of the distal tip 3555 kills microbes within the distal recess 3551 between the surface of the female luer and the distal tip surface 3552. The distal recess 3551 is designed to confine the antimicrobial agent between the inner surface of a female luer and the distal tip surface 3552 so that microbes are exposed to a high antimicrobial concentration.

The tapered surface distal edge 3561 has a tapered surface distal edge face 3562. A proximal trap 3571 is defined between the distal tip surface 3552 and the proximal trap walls 3573. The proximal trap 3571 is a cavity that is bounded on multiple sides. The proximal trap 3571 opens on the distal recess 3551. The proximal trap is adjacent to the tapered surface distal edge face 3562. As will be discussed below in relation to FIGS. 38 and 39, an antimicrobial agent can be contained inside of the proximal trap 3571.

The proximal trap 3571 stores an antimicrobial agent within the annular cavity defined by the proximal trap 3571. In some examples, microbes reside near the interface between the tapered surface distal edge 3561 and a surface of a female luer. The antimicrobial agent stored in the proximal trap 3571 ensures that the concentration of the antimicrobial agent remains high (up to the level of saturation) in the vicinity of microbes.

Both the proximal trap 3571 and the distal recess 3551 are designed to minimize washout of the antimicrobial agent from the volume created between the female luer surface and the distal tip surface 3552. The proximal trap 3571 has no separate entrance and exit. The antimicrobial agent on the surface of the proximal trap wall 3573 will diffuse out of the proximal trap 3571 after the male luer 3541 has been installed inside a female luer. The proximal trap 3571 prevents or minimizes fluid flow within the volume of the proximal trap 3571 because there is no through path to the body of the female luer lumen. Therefore, the antimicrobial agent is not readily washed away from the proximal trap 3571.

As seen in FIG. 35D, the distal tip 3555 has an outer diameter that is smaller than the outer diameter of the tapered sealing member 3542 at the tapered surface distal edge 3561, and the outer diameter of the distal tip 3555 is smaller than the outer diameter of a distal line of taper defined by the conical tapered sealing member 3542.

Luer Couplers Coupled with Male and Female Luers (FIGS. 36-37)

FIG. 36 shows the luer coupler 3501 coupled between a male connector 3611 and a female luer 3691. FIG. 37 shows a luer coupler 3701 coupled between the male connector 3611 and the female luer 3691. The male connector 3611 has a male luer 3641 and a lumen 3621. The male luer 3641 is mated with the female luer tapered sealing surface 3588 of the luer coupler 3501. The female luer 3691 has a female luer tapered sealing surface 3688 and a lumen 3695.

The luer coupler 3701 is similar to the luer coupler 3501, with similar features and functions. The male connector portion 3749 of the luer coupler 3501 is similar to the male connector 2001 described in connection with FIGS. 20A-G, described above.

The luer coupler 3701 includes a male connector portion 3749 and a female connector portion 3789 integral with the male connector portion 3749. A lumen 3712 runs through both the female connector portion 3789 and the male connector portion 3749. The female connector portion 3789 further includes a female luer tapered surface 3788.

The luer coupler 3701 includes a male luer 3741. The male luer 3741 comprises a tapered sealing member 3742 with a tapered surface distal edge 3761. The luer coupler 3701 further includes threads 3702 that allow the luer coupler 3701 to couple with a female connector. A lumen 3712 runs through the luer coupler 3701.

The male luer 3741 includes a distal tip 3755 with a distal recess 3751 and an end face 3704. The distal tip surface 3752 of the distal tip 3755 defines an outer diameter that is smaller than the outer diameter of the extension of the tapered sealing surface 3743. The distal recess 3751 forms a cavity once the male luer 3741 is installed into a female luer 3691.

The tapered surface distal edge 3761 defines a proximal end of the distal tip 3755. In some examples, an antimicrobial agent is applied to the distal tip surface 3752 by coating, spraying, or dipping the distal tip 3755 with an antimicrobial agent, although other methods of applying antimicrobial agent are contemplated and are within the scope of the technology. In some examples, antimicrobial agent is also applied to the tapered sealing surface 3743.

The male luer 3741 further includes multiple blades 3763 arrayed around the distal tip 3755 of the male luer 3741. Between the blades 3763 are a plurality of channels 3767.
Fluid Flow Analysis of Male Connector (FIGS. 38-39)

FIGS. 38-39 are visual representations of mathematical modeling of steady-state flow simulations of fluid flowing through a coupled male and female luer. Without wishing to be bound by theory, these models simulate a syringe delivering fluid to the female connector (FIG. 38) and an IV-drip delivery system (FIG. 39). The syringe load is characterized as a flow of 2 milliliters/second for up to five seconds. The IV drip load is characterized as a flow of 1 liter/hour for up to one hour. The simulation can be applied to systems such as the coupled male connector portion 3549 and female luer 3691 of FIG. 36.

FIG. 38 shows the operation of the system shown in FIG. 36. In FIG. 38, the male luer 3541 is inserted into the lumen 3695 of the female luer 3691. The tapered sealing surface 3543 of the male luer 3541 and the tapered sealing surface 3688 of the female luer 3691 form a male-female luer interface with a fluid tight seal. The distal tip 3555 of the male luer 3541 is set back from the female luer tapered sealing surface 3688.

The male luer 3541 has a distal recess 3551. The male luer 3541 includes a distal tip 3555 having a distal tip surface 3552. A cavity is formed between the distal tip surface 3552 and the tapered sealing surface 3688 of the female luer 3691. The cavity 3802 is also bounded by a tapered surface distal edge face 3562 adjacent to tapered surface distal edge 3561.

In the example of FIG. 38, the male luer 3541 further includes a proximal trap 3571 defined by proximal trap walls 3573.

A fluid passage is defined within the lumen 3512 of the male luer 3541 and the lumen 3695 of the female luer 3691. The fluid passage has multiple fluid flow regions. A bulk flow region 3801 is the space in which fluid travels through the connection of the male and female luers. A cavity 3802 is formed between the distal tip surface 3552 and the female luer tapered sealing surface 3688. A boundary region 3803 is situated between the bulk flow region 3801 and the cavity 3802. A proximal trap region 3804 is situated proximal to the tapered surface distal edge face 3562.

The distal tip surface 3552 contains a solid deposit of an antimicrobial agent, referred to as the load. An antimicrobial composition can be deposited in the proximal trap 3571 and on one or more of the walls, surfaces or faces of the female connector. The distal tip surface 3552 can be the predominant location at which surface-bound microbes are present within the luer connection.

The cavity 3802 confines recirculation of fluids while a fluid load passes through the luer connection. The antimicrobial composition disperses into the fluidic recirculation. The recirculating fluid within the cavity 3802 recirculates the antimicrobial composition, which increases the antimicrobial concentration within this region and distributes the antimicrobial agent onto the inner surface of the female connector. The presence of antimicrobial agent along the inner surface of the female connector within the cavity 3802 prevents microbes located at the male-female interface from propagating along the wall of the female luer tapered sealing surface 3688.

Fluid flow through the design generates a set of three fluidic recirculations, or vortexes. These vortexes create a fluidic boundary between passing fluid and a microbial load located at the male-female interface edge. The three vortices can be described by their location. A proximal trap vortex contained in the proximal trap 3571 contains a large antimicrobial load. The cavity vortex is located adjacent to the proximal trap vortex. A boundary vortex is sandwiched between the cavity vortex and the stream of fluid passing through the bulk flow region 3801.

In the example of FIG. 38, the luminal flow is modeled at 2 mL/s (milliliters per second) and vortexes are created in the boundary region 3803, the cavity 3802, and the proximal trap region 3804. Antimicrobial agent is contained and recirculated within each of these regions. In some examples, the proximal trap region 3804 contains a load of antimicrobial agent that is greater than can be dissolved into the cavity 3802 at saturation concentration; thus the proximal trap 3571 serves as an antimicrobial agent reservoir to maintain a high antimicrobial concentration. In some examples, including this example, the antimicrobial concentration in the cavity 3802 can be maintained at a minimum of 200 micrograms per milliliter (μg/ml) or greater of chlorhexidine for 1 minute or longer, even with luminal flow of greater than or equal to 2 mL/s, which is sufficient to produce a 4-log microbial reduction or greater (i.e., 99.99 percent reduction).

In some examples, the antimicrobial concentration can be around 200 micrograms per milliliter (μg/ml) of chlorhexidine. FIG. 39 shows the operation of the system shown in FIG. 36, as described above, under IV drip conditions. A bulk flow region 3901 is the space in which fluid travels through the connection of the male and female luers. A cavity 3902 is formed between the distal tip surface 3552 and the female luer tapered sealing surface 3688. A boundary region 3903 is situated between the bulk flow region 3901 and the recess region. A proximal trap region 3904 is situated proximal to the tapered surface distal edge face 3562.

In the example of FIG. 39, vortexes are created in the boundary region 3903, the cavity 3902, and the proximal trap region 3904. Antimicrobial agent is contained and recirculated within each of these regions. In this example, the antimicrobial concentration in the cavity 3902 is again maintained far in excess of the minimum 200 micrograms per milliliter (µg/ml) or more of chlorhexidine for 1 minute or longer needed to produce a 4-log microbial reduction.

Male Luer Connector with Wide Mouth Proximal Trap (FIGS. 42A-C)

Turning now to FIGS. 42A-C, a male connector 4001 includes a male luer 4041. The male luer 4041 comprises a tapered sealing member 4042. The tapered sealing member 4042 has a frustoconical shape that tapers from a larger outer diameter at the proximal portion of the tapered sealing member 4042 to a smaller outer diameter at the distal portion of the tapered sealing member near the tapered surface distal edge 4061. The tapered sealing member 4042 has a tapered sealing surface 4043 that is configured to mate with a female luer to create a fluid tight fit. The male connector 4001 further includes threads 4002 that allow the male connector 4001 to couple with a female connector. A lumen 4012 provides a fluid flow channel through the male connector 4001.

The male luer 4041 includes a distal tip 4055 with a distal end face 4004. The distal tip 4055 of the male luer 4041 is recessed from the distal line of taper (not shown, but similar to 1614 of FIG. 16) of the tapered sealing surface 4043. The distal tip 4055 has a distal tip surface 4052 and a distal recess 4051. The distal recess 4051 is formed by the distal tip 4055, which is the recessed portion of the male luer 4041. The distal tip surface 4052 of the distal tip 4055 defines an outer diameter that is smaller than the outer diameter of an extension of the tapered sealing surface 4043 along the distal line of taper.

In some examples, an antimicrobial agent is applied to the distal tip surface 4052 by coating, spraying, or dipping the distal tip 4055 with an antimicrobial agent, although other methods of applying antimicrobial agent are contemplated and are within the scope of the technology. In some examples, antimicrobial agent is also applied to the tapered sealing surface 4043. The male connector 4001 is configured to mate with a female connector. When the male luer 4041 is mated with a female luer, a cavity is formed between the distal tip surface 4052 and the female luer surface.

An antimicrobial agent on the distal tip surface 4052 of the distal tip 4055 is configured to dissolve in a fluid, forming an antimicrobial solution that kills microbes within a cavity formed between the surface of the female luer and the distal tip surface 4052. The distal recess 4051 is designed to confine the antimicrobial agent between the inner surface of a female luer and the distal tip surface 4052 so that microbes are exposed to a high antimicrobial concentration.

The distal recess 4051 affects confinement of microbes because the distal recess 4051 provides a restricted space in which microbes can be trapped between the distal tip surface 4052 and an inside surface of a female luer. Similar to the example shown in FIG. 30G, the distal tip 4055 has an outer diameter that is smaller than the outer diameter of the tapered sealing member 4042 at the tapered surface distal edge 4061, and the outer diameter of the distal tip 4055 is smaller than the outer diameter of a distal line of taper defined by the conical tapered sealing member 4042.

The male luer 4041 has a tapered surface distal edge 4061 at a distal end of the tapered sealing member 4042. A proximal trap 4071 is defined by proximal trap walls 4073. The proximal trap 4071 is a cavity bounded on multiple sides by proximal trap walls 4073 formed in the male luer 4041. In the example shown in FIGS. 42A-C, the proximal trap 4071 is an annular cavity in the male luer 4041 that is defined by proximal trap walls 4073, which includes a proximal wall 4081, an inner wall 4082, and an outer wall 4083. The proximal trap 4071 cavity opens on the distal recess 4051. The proximal trap is adjacent to the tapered surface distal edge face 4062. As seen more clearly in FIG. 42C, the depth of the proximal trap 4071 widens toward the tapered surface distal edge 4061. An antimicrobial agent can be contained inside of the proximal trap 4071.

The proximal trap 4071 stores an antimicrobial agent within the annular cavity defined by the proximal trap 4071. In some examples, microbes reside near the interface between the tapered surface distal edge 4061 and a surface of a female luer. The antimicrobial agent stored in the proximal trap 4071 ensures that the concentration of the antimicrobial agent remains high (up to the level of saturation) in the vicinity of microbes.

The tapered sealing surface 4043 is configured to contact the female luer surface when the male luer is coupled with the female luer. The tapered sealing surface 4043 is therefore susceptible to microbial contamination from the female luer surface, as described above in relation to FIG. 3B. The tapered surface distal edge 4061 may also contact and scrape the female luer surface during insertion, potentially enabling ingress of microbes, as described in relation to FIG. 3F. The confinement of the antimicrobial composition in the proximal trap 4071 provides a region of high antimicrobial concentration near the tapered surface distal edge 4061.

Furthermore, since the tapered surface distal edge 4061 has a larger diameter than the distal tip 4055, the distal tip 4055 is less able to scrape against the female luer surface while the male connector 4001 is being inserted into the female connector. The reduced amount of scraping by the distal tip minimizes microbial contamination from ingress of microbes in the vicinity of the distal tip 4055 when the male connector 4001 is coupled with a female connector, as described above in relation to FIG. 7A Thus, the proximal trap 4071 and the distal recess 4051 work in combination to concentrate both microbes and antimicrobial composition within the cavity formed between the distal tip surface 4052 and the female luer surface.

Both the proximal trap 4071 and the distal recess 4051 are designed to minimize washout of the antimicrobial agent from the cavity created between the female luer surface and the distal tip surface 4052.

The proximal trap 4071 and distal recess 4051 are both designed to confine microbes, fluid, and antimicrobial agent near the female luer surface of the female connector. There are differences between confinement of the fluid and the antimicrobial agent within the proximal trap 4071 and confinement within the distal recess 4051. Confinement of fluid and antimicrobial agent in the proximal trap 4071 occurs independently of the female luer surface.

The proximal trap walls 4073 create a cavity configured to prevent or minimize fluid flow out of the proximal trap 4071. The antimicrobial agent is not readily washed away from the proximal trap 4071 during or after insertion of the male connector 4001 into the female connector. The shape of the cavity of the proximal trap 4071 enables limited recirculation of the fluid and antimicrobial agent inside the proximal trap 4071 during fluid flow conditions, discussed in relation to FIGS. 38 and 39. Once the male luer 4041 is installed into a fluid filled female luer, or during fluid flow conditions, the antimicrobial agent on the surface of the proximal trap walls 4073 can diffuse out of the proximal trap 4071.

In contrast, confinement of the antimicrobial agent within the distal recess 4051 is dependent on the female luer surface; this confinement is optimized when the male connector 4001 is fully inserted into the female connector. When the male connector 4001 is coupled with the female connector, the cavity formed between the distal tip surface 4052 and the female luer surface limit fluid circulation and transfer of antimicrobial agent into the lumen of the female luer. Limited fluid circulation, in combination with confinement, keeps the antimicrobial agent at a high concentration within the distal recess 4051 cavity even while fluid flows through the lumen 4012.

As used here, the term "width" indicates a distance measured parallel to the central longitudinal axis of the male luer, and the term "depth" indicates a distance measured perpendicular to the central longitudinal axis of the male luer.

Like the example of FIG. 30G, the proximal trap 4071 has a depth and the distal recess 4051 has a depth. Although not explicitly notated in FIG. 42C, the depth of the proximal trap 4071 is analogous to the depth A of the proximal trap 3071 in FIG. 30G, and the depth of the distal recess 4051 is analogous to the depth B of the distal recess 3051 in FIG. 30G.

The proximal trap 4071 has a width, and the distal tip 4055 has a width. Although not explicitly notated in FIG. 42C, the width of the proximal trap 4071 is analogous to the width C of the proximal trap 3071 in FIG. 30G, and the width of the distal tip 4055 is analogous to the width D of the distal tip 3055 in FIG. 30G.

In some embodiments, the depth of proximal trap 4071 can be greater than or equal to 0.10 mm, 0.15 mm, 0.20 mm, 0.25 mm, 0.30 mm, 0.35 mm, 0.40 mm, or 0.45 mm. In some embodiments, the depth of proximal trap 4071 can be less than or equal to 0.80 mm, 0.75 mm, 0.70 mm, 0.65 mm, 0.60 mm, 0.55 mm, 0.50 mm, or 0.45 mm. In some embodiments, the depth of proximal trap 4071 can fall within a range of 0.10 mm to 0.80 mm, or 0.15 mm to 0.75 mm, or 0.20 mm to 0.70 mm, or 0.25 mm to 0.65 mm, or 0.40 mm to 0.60 mm, or 0.35 mm to 0.55 mm, or 0.40 mm to 0.50 mm, or can be about 0.39 mm.

The depth of distal recess 4051 is greater than the depth of proximal trap 4071. In some embodiments, the depth of distal recess 4051 can be greater than or equal to 0.20 mm, 0.26 mm, 0.31 mm, 0.37 mm, 0.42 mm, 0.48 mm, 0.54 mm, 0.59 mm, or 0.65 mm. In some embodiments, the depth of distal recess 4051 can be less than or equal to 1.12 mm, 1.08 mm, 1.04 mm, 1.00 mm, 0.96 mm, 0.91 mm, 0.87 mm, 0.82 mm, 0.78 mm, 0.74 mm, 0.69 mm, or 0.65 mm. In some embodiments, the depth of distal recess 4051 can fall within a range of 0.20 mm to 1.00 mm, or 0.26 mm to 0.96 mm, or 0.31 mm to 0.91 mm, or 0.37 mm to 0.87 mm, or 0.42 mm to 0.82 mm, or 0.48 mm to 0.78 mm, or 0.54 mm to 0.74 mm, or 0.59 mm to 0.69 mm, or can be about 0.77 mm.

The depth of distal recess 4051 affects the depth of the cavity formed formed between the distal tip surface 4052 and the female tapered surface when the male luer is coupled with a female luer. In some embodiments, the distal tip can have an outer diameter that is less than 95 percent of an inner diameter of the female tapered surface at a point radially outward of the distal tip. In some embodiments, the distal tip can have an outer diameter that is between 50 percent and 95 percent of the inner diameter of the female tapered surface. In some embodiments, the outer diameter of the distal tip expressed as a percentage of the inner diameter of the female tapered surface can be greater than or equal to 40%, 45%, 50%, 55%, 60%, 65%, 70%, 75%, or 80% of the inner diameter of the female tapered surface. In some embodiments, the outer diameter of the distal tip expressed as a percentage of the inner diameter of the female tapered surface can be less than or equal to 95%, 90%, 85%, or 80% of the inner diameter of the female tapered surface. In some embodiments, the outer diameter of the distal tip expressed as a percentage of the inner diameter of the female tapered surface can fall within a range of 50% to 95%, or 55% to 90%, or 60% to 90%, or 65% to 85%, or 70% to 85%, or 70% to 80%, or 75% to 85%, or can be about 80% of the inner diameter of the female tapered surface. Various alternatives are possible based on particular applications of the technology.

In some embodiments, the width of proximal trap 4071 can be greater than or equal to 0.10 mm, 0.18 mm, 0.26 mm, 0.34 mm, 0.41 mm, 0.49 mm, 0.57 mm, 0.65 mm, 0.73 mm, 0.81 mm, 0.89 mm, 0.96 mm, 1.04 mm, 1.12 mm, or 1.20 mm. In some embodiments, the width of proximal trap 4071 can be less than or equal to 2.50 mm, 2.41 mm, 2.31 mm, 2.22 mm, 2.13 mm, 2.04 mm, 1.94 mm, 1.85 mm, 1.76 mm, 1.66 mm, 1.57 mm, 1.48 mm, 1.39 mm, 1.29 mm, or 1.20 mm. In some embodiments, the width of proximal trap 4071 can fall within a range of 0.10 mm to 2.50 mm, or 0.18 mm to 2.41 mm, or 0.26 mm to 2.31 mm, or 0.34 mm to 2.22 mm, or 0.41 mm to 2.13 mm, or 0.49 mm to 2.04 mm, or 0.57 mm to 1.94 mm, or 0.65 mm to 1.85 mm, or 0.73 mm to 1.76 mm, or 0.81 mm to 1.66 mm, or 0.89 mm to 1.57 mm, or 0.96 mm to 1.48 mm, or 1.04 mm to 1.39 mm, or 1.12 mm to 1.29 mm, or can be about 0.51 mm.

The width of distal tip 4055 may be larger than the width of proximal trap 4071, but could alternatively be equal to or smaller than the width of proximal trap 4071. In some embodiments, the width of distal tip 4055 can be greater than or equal to 0.10 mm, 0.40 mm, 0.50 mm, 0.70 mm, 0.90 mm, 1.10 mm, 1.40 mm, 1.50 mm, 1.70 mm, 1.90 mm, or 2.10 mm. In some embodiments, the width of distal tip 4055 can be less than or equal to 4.00 mm, 3.81 mm, 3.62 mm, 3.43 mm, 3.24 mm, 3.05 mm, 2.86 mm, 2.67 mm, 2.48 mm, 2.29 mm, or 2.10 mm. In some embodiments, the width of distal tip 4055 can fall within a range of 0.10 mm to 4.00 mm, or 0.40 mm to 3.81 mm, or 0.50 mm to 3.62 mm, or 0.70 mm to 3.43 mm, or 0.90 mm to 3.24 mm, or 1.10 mm to 3.05 mm, or 1.40 mm to 2.86 mm, or 1.50 mm to 2.67 mm, or 1.70 mm to 2.48 mm, or 1.90 mm to 2.29 mm, or can be about 2.41 mm.

The distal tip 4055 has a wall thickness. Although not explicitly notated in FIG. 42C, the wall thickness of the distal tip 4055 can be similar to the wall thickness E of distal tip 3055 as shown in FIG. 30G. In some embodiments, the wall thickness of the distal tip 4055 can be greater than or equal to 0.10 mm, 0.15 mm, 0.20 mm, 0.25 mm, 0.40 mm, 0.35 mm, 0.40 mm, or 0.45 mm. In some embodiments, the wall thickness of the distal tip 4055 can be less than or equal to 0.80 mm, 0.75 mm, 0.70 mm, 0.65 mm, 0.60 mm, 0.55 mm, 0.50 mm, or 0.45 mm. In some embodiments, the wall thickness of the distal tip 4055 can fall within a range of 0.10 mm to 0.80 mm, or 0.15 mm to 0.75 mm, or 0.20 mm to 0.70 mm, or 0.25 mm to 0.65 mm, or 0.40 mm to 0.60 mm, or 0.35 mm to 0.55 mm, or 0.40 mm to 0.50 mm, or can be about 0.39 mm.

The lumen 4012 has an inner diameter, similar to inner diameter F shown in FIG. 30G. In some embodiments, the inner diameter of lumen 4012 can be greater than or equal to 1.00 mm, 1.13 mm, 1.26 mm, 1.39 mm, 1.52 mm, or 1.65 mm. In some embodiments, the inner diameter of lumen 4012 can be less than or equal to 2.00 mm, 1.93 mm, 1.86 mm, 1.79 mm, 1.72 mm, or 1.65 mm. In some embodiments, the inner diameter of lumen 4012 can fall within a range of 1.00 mm to 2.00 mm, or 1.13 mm to 1.93 mm, or 1.26 mm to 1.86 mm, or 1.39 mm to 1.79 mm, or 1.52 mm to 1.72 mm, or can be about 1.65 mm.

Male Luer Connector with Tapered Proximal Trap (FIGS. 43A-C)

Turning now to FIGS. 43A-C, a male connector 4101 includes a male luer 4141. The male luer 4141 comprises a tapered scaling member 4142. The tapered scaling member 4142 has a frustoconical shape that tapers from a larger outer diameter at the proximal portion of the tapered sealing member 4142 to a smaller outer diameter at the distal portion of the tapered sealing member near the tapered surface distal edge 4161. The tapered scaling member 4142 has a tapered sealing surface 4143 that is configured to mate with a female luer to create a fluid tight fit. The male connector 4101 further includes threads 4102 that allow the male connector 4101 to couple with a female connector. A lumen 4112 runs through the male connector 4101.

The male luer 4141 includes a distal tip 4155 with an end face 4104. The distal tip 4155 of the male luer 4141 is recessed from the distal line of taper of the tapered sealing member 4142. The distal tip 4155 has a distal tip surface 4152 and a distal recess 4151. The distal recess 4151 is formed by a recessed portion of the distal tip 4155. The distal tip surface 4152 of the distal tip 4155 defines an outer diameter that is smaller than the outer diameter of the extension of the tapered sealing surface 4143.

In some examples, an antimicrobial agent is applied to the distal tip surface 4152 by coating, spraying, or dipping the distal tip 4155 with an antimicrobial agent, although other methods of applying antimicrobial agent are contemplated and are within the scope of the technology. In some examples, antimicrobial agent is also applied to the tapered sealing surface 4143. An antimicrobial agent on the distal tip surface 4152 of the distal tip 4155 kills microbes within the distal recess 4151 between the surface of the female luer and the distal tip surface 4152. The distal recess 4151 is designed to confine the antimicrobial agent between the inner surface of a female luer and the distal tip surface 4152 so that microbes are exposed to a high antimicrobial concentration.

The distal recess 4151 affects confinement of microbes, because the distal recess 4151 provides a restricted space in which microbes can be trapped between the distal tip surface 4152 and an inside surface of a female luer. The distal tip 4155 has an outer diameter that is smaller than the outer diameter of the tapered sealing member 4142 at the tapered surface distal edge 4161, and the outer diameter of the distal tip 4155 is smaller than the outer diameter of a distal line of taper (not shown, but similar to the distal line of taper 1614 of FIG. 16) defined by the conical tapered sealing member 4142.

In this example, the distal tip surface 4152 does not include blades. The male luer 4141 has a tapered surface distal edge 4161 at a distal end of the tapered sealing member 4142. The tapered surface distal edge 4161 has a tapered surface distal edge face 4162. A proximal trap 4171 is defined by proximal trap walls 4173. The proximal trap 4171 is a cavity bounded on multiple sides by proximal trap walls 4173 formed in the male luer 4141. In the example shown in FIGS. 43A-C, the proximal trap 4171 is an annular cavity in the male luer that is defined by a proximal wall

4181 and an inner wall 4183. The proximal trap 4171 opens on the distal recess 4151. An antimicrobial agent can be contained inside of the proximal trap 4171.

The proximal trap 4171 stores an antimicrobial agent within the annular cavity defined by the proximal trap 4171. In some examples, microbes reside near the interface between the tapered surface distal edge 4161 and a surface of a female luer. The antimicrobial agent stored in the proximal trap 4171 ensures that the concentration of the antimicrobial agent remains high (up to the level of saturation) in the vicinity of microbes.

The proximal trap 4171 and distal recess 4151 are both designed to confine microbes, fluid, and antimicrobial agent near the female luer surface of the female connector. There are differences between confinement of the fluid and the antimicrobial agent within the proximal trap 4171 and confinement within the distal recess 4151. Confinement of fluid and antimicrobial agent in the proximal trap 4171 occurs independently of the female luer surface.

The proximal trap walls 4173 create a cavity configured to prevent or minimize fluid flow out of the proximal trap 4171. The antimicrobial agent is not readily washed away from the proximal trap 4171 during or after insertion of the male connector 4101 into the female connector. The shape of the cavity of the proximal trap 4171 enables limited recirculation of the fluid and antimicrobial agent inside the proximal trap 4171 during fluid flow conditions, discussed in relation to FIGS. 38 and 39. Once the male luer 4141 is installed into a fluid filled female luer, or during fluid flow conditions, the antimicrobial agent on the surface of the proximal trap walls 4173 can diffuse out of the proximal trap 4171.

In contrast, confinement of the antimicrobial agent within the distal recess 4151 is dependent on the female luer surface; this confinement is optimized when the male connector 4101 is fully inserted into the female connector. When the male connector 4101 is coupled with the female connector, the cavity formed between the distal tip surface 4152 and the female luer surface limit fluid circulation and transfer of antimicrobial agent into the lumen of the female luer. Limited fluid circulation, in combination with confinement, keeps the antimicrobial agent at a high concentration within the distal recess 4151 cavity even while fluid flows through the lumen 4112.

As used here, the term "width" indicates a distance measured parallel to the central longitudinal axis of the male luer, and the term "depth" indicates a distance measured perpendicular to the central longitudinal axis of the male luer.

Like the example of FIG. 42C, the proximal trap 4171 has a depth and the distal recess 4151 has a depth. Although not explicitly notated in FIG. 43C, the depth of the proximal trap 4171 is similar to the depth A of the proximal trap 3071 in FIG. 30G, and the depth of the distal recess 4151 is analogous to the depth B of the distal recess 3051 in FIG. 30G. In the example of FIG. 43C, the depth of the proximal trap is tapered. This tapered geometry ends at the tapered surface distal edge 4161; the tapered sealing member 4142 effectively does not have an end face, because the proximal wall 4181 of the proximal trap 4171 extends all the way to the tapered surface distal edge 4161. At the tapered surface distal edge 4161, the depth of the proximal trap 4171 is approximately equal to the depth of the distal recess 4151.

The proximal trap 4171 has a width, and the distal tip 4155 has a width. Although not explicitly notated in FIG. 43C, the width of the proximal trap 4171 is analogous to the width C of the proximal trap 3071 in FIG. 30G, and the width of the distal tip 4155 is analogous to the width D of the distal tip 3055 in FIG. 30G.

The measurements of the depth of the proximal trap 4171 and the depth of the distal recess 4151 are similar to the depths of the proximal trap 4071 and distal recess 4051, described above in relation to FIGS. 42A-C. The measurements of the width of the proximal trap 4171 and the width of the distal tip 4155 can be similar to the width of proximal trap 4071 and distal tip 4055 as shown and described above in relation to FIGS. 42A-C. The ratio of the outer diameter of the distal tip in relation to the inner diameter of a female tapered surface can be similar to that described above in relation to FIGS. 30G and 42C. The wall thickness of the distal tip 4155 and the inner diameter of the lumen 4112 can be similar to that described above in relation to distal tip 4055 and lumen 4012 of FIGS. 42A-C.

Male Luer Connector with Radially Recessed Proximal Trap (FIGS. 44A-D)

Turning now to FIGS. 44A-D, a male connector 4201 includes a male luer 4241. The male luer 4241 comprises a tapered sealing member 4242. The male luer 4241 has a tapered surface distal edge 4261 with a tapered surface distal edge face 4262 at a distal end of the tapered sealing member 4242. The tapered sealing member 4242 has a frustoconical shape that tapers from a larger outer diameter at the proximal portion of the tapered sealing member 4242 to a smaller outer diameter at the distal portion of the tapered sealing member near the tapered surface distal edge 4261. The tapered sealing member 4242 has a tapered scaling surface 4243 that is configured to mate with a female luer to create a fluid tight fit. The male connector 4201 further includes threads 4202 that allow the male connector 4201 to couple with a female connector. A lumen 4212 runs through the male connector 4201.

The male luer 4241 includes a distal tip 4255 with an end face 4204. The distal tip 4255 of the male luer 4241 is recessed from the distal line of taper of the tapered scaling member 4242. The distal tip 4255 has a distal tip surface 4252 and a distal recess 4251. The distal recess 4251 is formed by a recessed portion of the distal tip 4255. The distal tip surface 4252 of the distal tip 4255 defines an outer diameter that is smaller than the outer diameter of the extension of the tapered sealing surface 4243. In the example of FIGS. 44A-D, the male luer 4241 is made of two parts. An insert 4291 is seated inside the tapered scaling member 4242. The lumen 4212 runs through both the insert 4291 and the tapered sealing member 4242.

In some examples, an antimicrobial agent is applied to the distal tip surface 4252 by coating, spraying, or dipping the distal tip 4255 with an antimicrobial agent, although other methods of applying antimicrobial agent are contemplated and are within the scope of the technology. In some examples, antimicrobial agent is also applied to the tapered sealing surface 4243. An antimicrobial agent on the distal tip surface 4252 of the distal tip 4255 kills microbes within the distal recess 4251 between the surface of the female luer and the distal tip surface 4252. The distal recess 4251 is designed to confine the antimicrobial agent between the inner surface of a female luer and the distal tip surface 4252 so that microbes are exposed to a high antimicrobial concentration.

The distal recess 4251 affects confinement of microbes, because the distal recess 4251 provides a restricted space in which microbes can be trapped between the distal tip surface 4252 and an inside surface of a female luer. The distal tip 4255 has an outer diameter that is smaller than the outer diameter of the tapered sealing member 4242 at the tapered surface distal edge 4261, and the outer diameter of the distal tip 4255 is smaller than the outer diameter of a distal line of taper defined by the conical tapered sealing member 4242.

FIG. 44D shows an enlarged view of FIG. 44C inside circle D. A proximal trap 4271 is defined by proximal trap walls 4273. The proximal trap 4271 is a cavity bounded on multiple sides by proximal trap walls 4273 formed in the male luer 4241, between the tapered sealing member 4242 and the insert 4291.

The proximal trap 4271 is an annular cavity in the male luer 4241 that is defined by proximal trap walls 4273, which include a proximal wall 4281, which is the tapered surface distal edge face 4262, a distal wall 4284, and an inner wall 4283. In this example the distal wall 4284 and the inner wall 4283 are each surfaces of the insert 4291. In alternative examples, the male luer 4241 can be a single structure, in which case the proximal wall 4281, distal wall 4284, and inner wall 4283 of the proximal trap 4271 would be formed by surfaces of the distal tip 4255.

The proximal trap 4271 stores an antimicrobial agent within the cavity defined by the proximal trap 4271. The proximal trap 4271 opens on the distal recess 4251 and has no separate entrance and exit. The antimicrobial agent stored in the proximal trap 4271 ensures that the concentration of the antimicrobial agent remains high (up to the level of saturation) in the vicinity of microbes.

The proximal trap 4271 and distal recess 4251 are both designed to confine microbes, fluid, and antimicrobial agent near the female luer surface of the female connector. There are differences between confinement of the fluid and the antimicrobial agent within the proximal trap 4271 and confinement within the distal recess 4251. Confinement of fluid and antimicrobial agent in the proximal trap 4271 occurs independently of the female luer surface.

The proximal trap walls 4273 create a cavity configured to prevent or minimize fluid flow out of the proximal trap 4271. The antimicrobial agent is not readily washed away from the proximal trap 4271 during or after insertion of the male connector 4201 into the female connector. The shape of the cavity of the proximal trap 4271 enables limited recirculation of the fluid and antimicrobial agent inside the proximal trap 4271 during fluid flow conditions, discussed in relation to FIGS. 38 and 39. Once the male luer 4242 is installed into a fluid filled female luer, or during fluid flow conditions, the antimicrobial agent on the surface of the proximal trap walls 4273 can diffuse out of the proximal trap 4271.

In contrast, confinement of the antimicrobial agent within the distal recess 4251 is dependent on the female luer surface; this confinement is optimized when the male connector 4201 is fully inserted into the female connector. When the male connector 4201 is coupled with the female connector, the cavity formed between the distal tip surface 4252 and the female luer surface limit fluid circulation and transfer of antimicrobial agent into the lumen of the female luer. Limited fluid circulation, in combination with confinement, keeps the antimicrobial agent at a high concentration within the distal recess 4251 cavity even while fluid flows through the lumen 4212.

As used here, the term "width" indicates a distance measured parallel to the central longitudinal axis of the male luer, and the term "depth" indicates a distance measured perpendicular to the central longitudinal axis of the male luer.

The proximal trap 4271 has a depth and the distal recess 4251 has a depth. In this example, the depth of the proximal trap is larger than the depth of the distal recess 4251. Conceptually, this can be described as a radially recessed cavity in the distal tip 4255. It can also be described as a variation in the radial wall thickness of the distal tip 4255. The proximal trap 4271 provides an isolated fluid flow region within the volume defined by the proximal trap walls 4273.

The proximal trap 4271 has a width, and the distal tip 4255 has a width. The width of the distal tip 4255 is defined between the tapered surface distal edge face 4262 and the distal end face 4204 of the distal tip 4255. The width of the proximal trap 4271 is defined between the proximal wall 4281 and the distal wall 4284. In this example, the width of the proximal trap 4271 is smaller than the width of the distal tip 4255.

Male Luer Connector with Blades and Radially Recessed Proximal Trap (FIGS. 45A-F)

Turning now to FIGS. 45A-F, a male connector 4301 includes a male luer 4341. The male luer 4341 comprises a tapered sealing member 4342. The male luer 4341 has a tapered surface distal edge 4361 with a tapered surface distal edge face 4362 at a distal end of the tapered sealing member 4342. The tapered sealing member 4342 has a frustoconical shape that tapers from a larger outer diameter at the proximal portion of the tapered sealing member 4342 to a smaller outer diameter at the distal portion of the tapered sealing member near the tapered surface distal edge 4361. The tapered sealing member 4342 has a tapered sealing surface 4343 that is configured to mate with a female luer to create a fluid tight fit. The male connector 4301 further includes threads 4302 that allow the male connector 4301 to couple with a female connector. A lumen 4312 runs through the male connector 4301.

The male luer 4341 includes a distal tip 4355 with an end face 4304. The distal tip 4355 of the male luer 4341 is recessed from the distal line of taper of the tapered sealing member 4342. The distal tip 4355 has a distal tip surface 4352 and a distal recess 4351. The distal recess 4351 is formed by a recessed portion of the distal tip 4355. The distal tip surface 4352 of the distal tip 4355 defines an outer diameter that is smaller than the outer diameter of the extension of the tapered sealing surface 4343. In the example of FIGS. 45A-D, the male luer 4341 is made of two parts. An insert 4391 is seated inside the tapered sealing member 4342. The lumen 4312 runs through both the insert 4391 and the tapered sealing member 4342.

In some examples, an antimicrobial agent is applied to the distal tip surface 4352 by coating, spraying, or dipping the distal tip 4355 with an antimicrobial agent, although other methods of applying antimicrobial agent are contemplated and are within the scope of the technology. In some examples, antimicrobial agent is also applied to the tapered sealing surface 4343. An antimicrobial agent on the distal tip surface 4352 of the distal tip 4355 kills microbes within the distal recess 4351 between the surface of the female luer and the distal tip surface 4352. The distal recess 4351 is designed to confine the antimicrobial agent between the inner surface of a female luer and the distal tip surface 4352 so that microbes are exposed to a high antimicrobial concentration.

The distal recess 4351 affects confinement of microbes, because the distal recess 4351 provides a restricted space in which microbes can be trapped between the distal tip surface 4352 and an inside surface of a female luer. The distal tip 4355 has an outer diameter that is smaller than the outer diameter of the tapered sealing member 4342 at the tapered surface distal edge 4361, and the outer diameter of the distal tip 4355 is smaller than the outer diameter of a distal line of taper defined by the conical tapered sealing member 4342.

FIG. 45D shows an enlarged view circle D of FIG. 45C. FIG. 45F is an enlarged view inside circle F of FIG. 45E. Both FIG. 45C and FIG. 45E show a cross-sectional view of FIG. 45B, but FIG. 45C cross-section bisects a trough 4368 of a blade 4363 and FIG. 45E cross-section bisects an apex 4364 of a blade 4363. A proximal trap 4371 is defined by proximal trap walls 4373. The proximal trap 4371 is a cavity bounded on multiple sides by proximal trap walls 4373 formed in the male luer 4341, between the tapered sealing member 4342 and the insert 4391.

The proximal trap 4371 is an annular cavity in the male luer 4341 that is defined by proximal trap walls 4373, which include a proximal wall 4381, which is the tapered surface distal edge face 4362, a distal wall 4384, and an inner wall 4383. In this example the distal wall 4384 and the inner wall 4383 are each surfaces of the insert 4391. In alternative examples, the male luer 4341 can be a single structure, in which case the proximal wall 4381, distal wall 4384, and inner wall 4383 of the proximal trap 4371 would be formed by surfaces of the distal tip 4355.

The proximal trap 4371 stores an antimicrobial agent within the cavity defined by the proximal trap 4371. The proximal trap 4371 opens on the distal recess 4351 and has no separate entrance and exit. The antimicrobial agent stored in the proximal trap 4371 ensures that the concentration of the antimicrobial agent remains high (up to the level of saturation) in the vicinity of microbes.

The proximal trap 4371 and distal recess 4351 are both designed to confine microbes, fluid, and antimicrobial agent near the female luer surface of the female connector. There are differences between confinement of the fluid and the antimicrobial agent within the proximal trap 4371 and confinement within the distal recess 4351. Confinement of fluid and antimicrobial agent in the proximal trap 4371 occurs independently of the female luer surface.

The proximal trap walls 4373 create a cavity configured to prevent or minimize fluid flow out of the proximal trap 4371. The antimicrobial agent is not readily washed away from the proximal trap 4371 during or after insertion of the male connector 4301 into the female connector. The shape of the cavity of the proximal trap 4371 enables limited recirculation of the fluid and antimicrobial agent inside the proximal trap 4371 during fluid flow conditions, discussed in relation to FIGS. 38 and 39. Once the male luer 4343 is installed into a fluid filled female luer, or during fluid flow conditions, the antimicrobial agent on the surface of the proximal trap walls 4373 can diffuse out of the proximal trap 4371.

In contrast, confinement of the antimicrobial agent within the distal recess 4351 is dependent on the female luer surface; this confinement is optimized when the male connector 4301 is fully inserted into the female connector. When the male connector 4301 is coupled with the female connector, the cavity formed between the distal tip surface 4352 and the female luer surface limit fluid circulation and transfer of antimicrobial agent into the lumen of the female luer. Limited fluid circulation, in combination with confinement, keeps the antimicrobial agent at a high concentration within the distal recess 4351 cavity even while fluid flows through the lumen 4312.

As used here, the term "width" indicates a distance measured parallel to the central longitudinal axis of the male luer, and the term "depth" indicates a distance measured perpendicular to the central longitudinal axis of the male luer.

The proximal trap 4371 has a depth and the distal recess 4351 has a depth. Although not explicitly notated in FIG.

45C, the depth of the distal recess 4351 is analogous to the depth B of the distal recess 3051 in FIG. 30G. In the example of FIG. 45C, the depth of the proximal trap is larger than the depth of the distal recess 4351. Conceptually, this can be described as a radially recessed cavity in the distal tip 4355. It can also be described as a variation in the radial wall thickness of the distal tip 4355. The proximal trap 4371 provides an isolated fluid flow region within the volume defined by the proximal trap walls 4373.

The proximal trap 4171 has a width, and the distal tip 4155 has a width. The width of the distal tip 4155 is defined between the tapered surface distal edge face 4362 and the distal end face 4304 of the distal tip 4355. The width of the proximal trap 4171 is defined between the proximal wall 4381 and the distal wall 4384.

The measurements of the depth of the proximal trap 4171 and the depth of the distal recess 4151 are similar to the depths of the proximal trap 4071 and distal recess 4051, described above in relation to FIGS. 42A-C. The measurements of the width of the proximal trap 4171 and the width of the distal tip 4155 can be similar to the width of proximal trap 4071 and distal tip 4055 as shown and described above in relation to FIGS. 42A-C. The ratio of the outer diameter of the distal tip in relation to the inner diameter of a female tapered surface can be similar to that described above in relation to FIGS. 30G and 42C. The wall thickness of the distal tip 4155 and the inner diameter of the lumen 4112 can be similar to that described above in relation to distal tip 4055 and lumen 4012 of FIGS. 42A-C.

The distal tip 4355 includes a plurality of blades 4363 arrayed around the distal tip 4355 of the male luer 4341. Between the blades 4363 are a plurality of channels 4367. In the example of FIG. 45, the blades 4363 are elongated projections arranged around the axis of the tapered sealing member 4342, and the channels 4367 are elongated recesses disposed between the blades 4363 and running parallel to the lumen 4312. The blades 4363 and channels 4367 form alternating apexes 4364 and troughs 4368. The distal tip surface 4352 of the distal tip 4355 is defined by the blades 4363 and channels 4367, forming a plurality of blade surfaces. Furthermore, an antimicrobial agent on the distal tip surface 4352 can be stored within the volumes between the blades 4363. This can increase the amount of antimicrobial agent that can be stored on the distal tip 4355 of the male luer 4341.

During insertion of the male luer 4341 into a female luer, portions of the distal tip 4355 may come in contact with the inside surface of the female luer. The apex 4364 of each blade 4363 may come in contact with the female luer surface, but the troughs 4368 of the channels 4367 will not come in contact with the female luer surface. Thus, in comparison to the tapered surface distal edge 4361, the blades 4363 have a relatively smaller contacting surface area near the end face 4304 of the distal tip 4355. This minimizes the amount of ingress of microbes that can be attributed to microbes being pushed into the body of the female luer by the blades 4363 compared to the tapered surface distal edge 4361 of the male luer 4341. Thus in some situations there is a greater probability of the microbes being located at the tapered surface distal edge 4361 compared to the end face 4304. This is desirable because the concentration of antimicrobial composition will be greater (it will be at a lethal concentration to kill microbes) at the tapered surface distal edge 4361 than the end face 4304.

Male Luer Connector with Contoured Proximal Trap (FIGS. 46A-C)

Turning now to FIGS. 46A-C, a male connector 4401 includes a male luer 4441. The male luer 4441 comprises a tapered sealing member 4442. The male luer 4441 has a tapered surface distal edge 4461 with a tapered surface distal edge face 4462 at a distal end of the tapered sealing member 4442. The tapered sealing member 4442 has a frustoconical shape that tapers from a larger outer diameter at the proximal portion of the tapered sealing member 4442 to a smaller outer diameter at the distal portion of the tapered sealing member near the tapered surface distal edge 4461. The tapered sealing member 4442 has a tapered sealing surface 4443 that is configured to mate with a female luer to create a fluid tight fit. The male connector 4401 further includes threads 4402 that allow the male connector 4401 to couple with a female connector. A lumen 4412 runs through the male connector 4401.

The male luer 4441 includes a distal tip 4455 with an end face 4404. The distal tip 4455 of the male luer 4441 is recessed from the distal line of taper of the tapered sealing member 4442. The distal tip 4455 has a distal tip surface 4452 and a distal recess 4451. The distal recess 4451 is formed by a recessed portion of the distal tip 4455. The distal tip surface 4452 of the distal tip 4455 defines an outer diameter that is smaller than the outer diameter of the extension of the tapered sealing surface 4443.

In some examples, an antimicrobial agent is applied to the distal tip surface 4452 by coating, spraying, or dipping the distal tip 4455 with an antimicrobial agent, although other methods of applying antimicrobial agent are contemplated and are within the scope of the technology. In some examples, antimicrobial agent is also applied to the tapered sealing surface 4443. An antimicrobial agent on the distal tip surface 4452 of the distal tip 4455 kills microbes within the distal recess 4451 between the surface of the female luer and the distal tip surface 4452. The distal recess 4451 is designed to confine the antimicrobial agent between the inner surface of a female luer and the distal tip surface 4452 so that microbes are exposed to a high antimicrobial concentration.

The distal recess 4451 affects confinement of microbes, because the distal recess 4451 provides a restricted space in which microbes can be trapped between the distal tip surface 4452 and an inside surface of a female luer. The distal tip 4455 has an outer diameter that is smaller than the outer diameter of the tapered sealing member 4442 at the tapered surface distal edge 4461, and the outer diameter of the distal tip 4455 is smaller than the outer diameter of a distal line of taper defined by the conical tapered sealing member 4442.

FIG. 46C shows an enlarged view of FIG. 46B inside circle C. A proximal trap 4471 is defined by proximal trap walls 4473. The proximal trap 4471 is a cavity bounded on multiple sides by proximal trap walls 4473 formed in the male luer 4441.

In the example shown in FIGS. 46A-C, the proximal trap 4471 is an annular cavity in the male luer 4441 that is defined by proximal trap walls 4473, which include a proximal wall 4481, an outer wall 4483, and an inner wall 4482.

The proximal trap 4471 stores an antimicrobial agent within the cavity defined by the proximal trap 4471. The proximal trap 4471 opens on the distal recess 4451 and has no separate entrance and exit. The antimicrobial agent stored in the proximal trap 4471 ensures that the concentration of the antimicrobial agent remains high (up to the level of saturation) in the vicinity of microbes.

The proximal trap 4471 and distal recess 4451 are both designed to confine microbes, fluid, and antimicrobial agent near the female luer surface of the female connector. There are differences between confinement of the fluid and the antimicrobial agent within the proximal trap 4471 and confinement within the distal recess 4451. Confinement of fluid and antimicrobial agent in the proximal trap 4471 occurs independently of the female luer surface.

The proximal trap walls 4473 create a cavity configured to prevent or minimize fluid flow out of the proximal trap 4471. The antimicrobial agent is not readily washed away from the proximal trap 4471 during or after insertion of the male connector 4401 into the female connector. The shape of the cavity of the proximal trap 4471 enables limited recirculation of the fluid and antimicrobial agent inside the proximal trap 4471 during fluid flow conditions, discussed in relation to FIGS. 38 and 39. Once the male luer 4441 is installed into a fluid filled female luer, or during fluid flow conditions, the antimicrobial agent on the surface of the proximal trap walls 4473 can diffuse out of the proximal trap 4471.

In contrast, confinement of the antimicrobial agent within the distal recess 4451 is dependent on the female luer surface; this confinement is optimized when the male connector 4401 is fully inserted into the female connector. When the male connector 4401 is coupled with the female connector, the cavity formed between the distal tip surface 4452 and the female luer surface limit fluid circulation and transfer of antimicrobial agent into the lumen of the female luer. Limited fluid circulation, in combination with confinement, keeps the antimicrobial agent at a high concentration within the distal recess 4451 cavity even while fluid flows through the lumen 4412.

As used here, the term "width" indicates a distance measured parallel to the central longitudinal axis of the male luer, and the term "depth" indicates a distance measured perpendicular to the central longitudinal axis of the male luer.

Like the example of FIG. 30G, the proximal trap 4471 has a depth and the distal recess 4451 has a depth. Although not explicitly notated in FIG. 46C, the depth of the proximal trap 4471 is analogous to the depth A of the proximal trap 3071 in FIG. 30G, and the depth of the distal recess 4451 is analogous to the depth B of the distal recess 3051 in FIG. 30G.

The proximal trap 4471 has a width, and the distal tip 4455 has a width. Although not explicitly notated in FIG. 46C, the width of the proximal trap 4471 is analogous to the width C of the proximal trap 3071 in FIG. 30G, and the width of the distal tip 4455 is analogous to the width D of the distal tip 3055 in FIG. 30G.

The measurements of the depth of the proximal trap 4471 and the depth of the distal recess 4451 are similar to the depths of the proximal trap 4071 and distal recess 4051, described above in relation to FIGS. 42A-C. The measurements of the width of the proximal trap 4471 and the width of the distal tip 4455 can be similar to the width of proximal trap 4071 and distal tip 4055 as shown and described above in relation to FIGS. 42A-C. The ratio of the outer diameter of the distal tip in relation to the inner diameter of a female tapered surface can be similar to that described above in relation to FIGS. 30G and 42C. The wall thickness of the distal tip 4455 and the inner diameter of the lumen 4412 can be similar to that described above in relation to distal tip 4055 and lumen 4012 of FIGS. 42A-C.

Male Luer Connector with Multiple Proximal Traps (FIGS. 47A-D)

Turning now to FIGS. 47A-D, a male connector 4501 includes a male luer 4541. The male luer 4541 comprises a tapered sealing member 4542. The male luer 4541 has a tapered surface distal edge 4561 at a distal end of the tapered sealing member 4542. The tapered sealing member 4542 has a frustoconical shape that tapers from a larger outer diameter at the proximal portion of the tapered sealing member 4542 to a smaller outer diameter at the distal portion of the tapered sealing member near the tapered surface distal edge 4561. The tapered sealing member 4542 has a tapered sealing surface 4543 that is configured to mate with a female luer to create a fluid tight fit. The male connector 4501 further includes threads 4502 that allow the male connector 4501 to couple with a female connector. A lumen 4512 runs through the male connector 4501.

The male luer 4541 includes a distal tip 4555 with an end face 4504. The distal tip 4555 of the male luer 4541 is recessed from the distal line of taper of the tapered sealing member 4542. The distal tip 4555 has a distal tip surface 4552 and a distal recess 4551. The distal recess 4551 is formed by a recessed portion of the distal tip 4555. The distal tip surface 4552 of the distal tip 4555 defines an outer diameter that is smaller than the outer diameter of the extension of the tapered sealing surface 4543.

In the example of FIGS. 47A-D, the distal tip 4555 of the male luer 4541 has multiple tiered recess surfaces, including a first recess surface 4550 and a second recess surface 4553. The male luer 4541 also has multiple proximal traps, which include a first proximal trap 4575 and a second proximal trap 4576. FIG. 47D shows an enlarged view of FIG. 47C inside circle D. The first and second proximal traps 4575 and 4576 are cavities bounded on multiple sides by proximal trap walls formed in the male luer 4541. The first proximal trap 4575 is defined by first proximal trap walls 4577, and the second proximal trap 4576 is defined by second proximal trap walls 4578. The first and second proximal traps 4575 and 4576 can be similar to the proximal trap 4171 shown in FIGS. 43A-C.

In some examples, an antimicrobial agent is applied to the distal tip 4555 by coating, spraying, or dipping the distal tip 4555 with an antimicrobial agent, although other methods of applying antimicrobial agent are contemplated and are within the scope of the technology. In some examples, antimicrobial agent is also applied to the tapered sealing surface 4543. An antimicrobial agent on the first and second recess surfaces 4550, 4553 of the distal tip 4555 kills microbes within the distal recess 4551 between the surface of the female luer and the distal tip surfaces. The distal recess 4551 is designed to confine the antimicrobial agent between the inner surface of a female luer and the first and second recess surfaces 4550, 4553 so that microbes are exposed to a high antimicrobial concentration.

The distal recess 4551 affects confinement of microbes, because the distal recess 4551 provides a restricted space in which microbes can be trapped between the first and second recess surfaces 4550, 4553 and an inside surface of a female luer. The distal tip 4555 has an outer diameter at the first recess surface 4550 that is smaller than the outer diameter of the tapered sealing member 4542 at the tapered surface distal edge 4561, and the outer diameter of the second recess surface 4553 is smaller than the outer diameter of the first recess surface 4550. The first recess surface 4550 has a distal edge 4560 that defines an outer diameter of the proximal trap 4576.

The first and second proximal traps 4575 and 4576 each store an antimicrobial agent within the cavity defined by the proximal traps 4575 and 4576. The proximal traps 4575 and 4576 both open on the distal recess 4551 and have no separate entrance and exit. The antimicrobial agent stored in the proximal traps 4575 and 4576 ensures that the concentration of the antimicrobial agent remains high (up to the level of saturation) in the vicinity of microbes.

The first and second proximal traps 4575 and 4576 and the distal recess 4551 are both designed to confine microbes, fluid, and antimicrobial agent near the female luer surface of the female connector. There are differences between confinement of the fluid and the antimicrobial agent within the first and second proximal traps 4575 and 4576 and confinement within the distal recess 4551. Confinement of fluid and antimicrobial agent in the the first and second proximal traps 4575 and 4576 occurs independently of the female luer surface.

The first and second proximal trap walls 4577, 4578 create cavities configured to prevent or minimize fluid flow out of the first and second proximal traps 4575, 4576. The antimicrobial agent is not readily washed away from the first and second proximal traps 4575 and 4576 during or after insertion of the male connector 4501 into the female connector. The shape of the cavities of the proximal traps 4575, 4576 enables limited recirculation of the fluid and antimicrobial agent inside the proximal traps 4575, 4576 during fluid flow conditions, discussed in relation to FIGS. 38 and 39. Once the male luer 4541 is installed into a fluid filled female luer, or during fluid flow conditions, the antimicrobial agent on the surface of the first and second proximal trap walls 4577, 4578 can diffuse out of the first and second proximal traps 4575 and 4576.

In contrast, confinement of the antimicrobial agent within the distal recess 4551 is dependent on the female luer surface; this confinement is optimized when the male connector 4501 is fully inserted into the female connector. When the male connector 4501 is coupled with the female connector, the cavity formed between the distal tip surface 4552 and the female luer surface limit fluid circulation and transfer of antimicrobial agent into the lumen of the female luer. Limited fluid circulation, in combination with confinement, keeps the antimicrobial agent at a high concentration within the distal recess 4551 cavity even while fluid flows through the lumen 4512.

As used here, the term "width" indicates a distance measured parallel to the central longitudinal axis of the male luer, and the term "depth" indicates a distance measured perpendicular to the central longitudinal axis of the male luer.

The measurements of the depths of the proximal traps 4575 and 4576 and the depth of the distal recess 4551 are similar to the depths of the proximal trap 4071 and distal recess 4051 described above in relation to FIGS. 42A-C. The measurements of the width of the proximal traps 4575 and 4576 and the width of the distal tip 4555 can be similar to the width of proximal trap 4071 and distal tip 4055 as shown and described above in relation to FIGS. 42A-C.

Time-Release Materials

A recessed distal tip provides a means of confining the antimicrobial composition when the male connector is coupled with a female connector. However, the antimicrobial composition contained on the distal tip may be subjected to fluid flow during insertion of the male luer into a female luer prior to the male sealing surface engaging with the female sealing surface. In some implementations of the technology described herein, the antimicrobial composition may dissolve and release into non-targeted regions.

One way to reduce the amount of antimicrobial lost during installation of the male connector into a female connector is to place at least a portion of antimicrobial into a proximal trap, as described above. Since the trap only has one inlet, the fluid and antimicrobial within the trap are confined during installation.

Another way to reduce the amount of antimicrobial lost during installation is to use a time-release mechanism, such as a slower-dissolving material either on top of or incorporated within the antimicrobial composition. The material should be selected to slow the dissolution of the antimicrobial during installation of the male connector into the female connector while still allowing a fast release of the antimicrobial composition to kill microorganisms in a clinically relevant time once insertion is complete.

In one example, a fluid-soluble, time-release material initially covers the antimicrobial composition. The time-release material will dissolve when the male connector is first exposed to fluid. The fluid may flow over the surface of the male luer during installation, and the time-release material may be configured to dissolve over a given amount of time, such as a few seconds. After that time, the time-release material may be at least partially dissolved such that the underlying antimicrobial becomes exposed to the fluid and begins to rapidly dissolve into solution. The timing of the antimicrobial dissolution may thereby be tuned so it is optimized for the specific application.

For example, a syringe typically has a shorter time-of-use than a needleless connector. A syringe application may require a I-second time-delay material, while a needleless connector application may require a 1-minute, 5-minute, or 10-minute time-delay material for optimum antimicrobial utilization and microbial killing.

The time-release material may be chosen from a variety of biocompatible materials to obtain the desired delay time and release profile. The material may be an insoluble substance such as biocompatible cellulose, a soluble substance such as dextrose or sodium chloride, an encapsulating material such as microspheres, a swellable material such as polyvinyl alcohol or polyurethane hydrogel (e.g., Lubrizon Tecophilic TG-500), or other biocompatible materials.

It will be apparent to those having skill in the art that changes may be made to the details of the above-described embodiments without departing from the underlying principles of the invention. In addition, some elements may be used without other elements being present. As an example, the proximal trap may reside within the distal end face of the male luer without the use of a distal tip.

Needleless Connector:

In some embodiments, the device for delivering an antimicrobial composition into another medical device can be a needleless connector, having:

a male connector having a male tapered surface, the male connector further including a distal tip having a distal end, the distal tip having a recess surface proximal to the distal end, wherein the recess surface is radially inward of a line of taper extending along, and distal of, the male tapered surface at a first taper angle relative to a central longitudinal axis of the male connector, and a water-soluble antimicrobial composition positioned on the recess surface.

The needleless connector and methods of using same can be configured to prevent microbial ingress in medical device connections. Various examples herein provide a needleless connector including a male luer having a recessed distal tip surface containing a water-soluble antimicrobial composition. Further examples include a trap for retaining antimicrobial composition. As the needleless connector is inserted into a female connector, a tapered surface distal edge acts to push microorganisms, while the distal tip surface is configured to leave microorganisms undisturbed. After insertion of the needleless connector, microorganisms present on the female luer surface are biased to reside in the recess region. In any embodiments, the antimicrobial composition can include chlorhexidine acetate. The recess, trap, and antimicrobial composition are configured to facilitate a long-lasting supply of antimicrobial solution within the fluid-filled recess, at the same time confining the antimicrobial solution inside the recess. This produces a high concentration of antimicrobial solution for an extended time, killing microbes, stopping microbial ingress, and preventing infections in patients.

Tubing Sets:

Some embodiments of the disclosure are directed to a method for preventing infection and microbial ingress in medical device connections between tubing sets and medical devices. The tubing set can include a male connector with a distal tip and a recess at the distal tip configured to trap bacterial, and be configured to deliver and confine antimicrobial into solution within a cavity formed by the recess. The surface of the recess includes an antimicrobial composition. In certain implementations, a male luer comprises a tapered sealing member further comprising a recess containing chlorhexidine acetate.

Some embodiments disclosed herein relate to medical tubing sets and methods for killing microorganisms and providing in-situ antimicrobial properties to medical devices.

Tubing sets are commonly used in providing modern medical care to patients. For example, they are a commonly used means for infusing fluids into catheters such as central venous catheters, peripherally inserted central catheters, midline catheters, hemodialysis catheters, peritoneal dialysis catheters and drainage catheters. Tubing sets are also used with other infusion devices, such as needleless connectors, valves and filters.

These tubing sets are useful for treating various medical conditions. For example, medical tubing can be used to connect an IV drip bag to an access port into the patient's body. In other uses, tubing sets allow patients with renal disease to have waste and fluid removed from their bodies, and patients in need of total parental nutrition (TPN) use tubing sets to deliver nutrients from an IV bag to a TPN catheter. Thus, tubing sets make critical medical care possible and are often essential to providing improved health care outcomes.

However, use of tubing sets has a serious drawback in that a significant percentage of patients develop infections, resulting in elevated mortality rates and significantly increased healthcare costs associated with treatment. Furthermore, infections are a leading cause of death in the United States, and many of those infections are attributable to microorganisms entering infusion devices through the tubing set connection. The mortality rate associated with such infections is considerable. Therefore, a need exists for a manner to reduce infections relating from the use of tubing sets.

Tubing sets are used to make fluid connections between medical devices, typically for infusing fluids and drugs into the body. For instance, they are commonly used to transfer fluid from saline bag to an IV catheter and ultimately the bloodstream.

Some embodiments of the present disclosure are directed, in part, to tubing sets used to form a coupling with medical device, the coupling typically comprising both a male connector and a female connector. In certain embodiments, the male connector will form a fluid tight seal with a female connector that complies with International Standard ISO 80369-7 Connectors for intravascular or hypodermic applications.

It should be appreciated that the various embodiments disclosed here may also be applied to other types of infusion devices. Examples disclosed herein include needleless connectors and caps. These examples are used to illustrate the broader application of the invention, but it should be further appreciated that the unique aspects of these embodiments may also be applied to tubing sets.

Some examples herein provide a method for delivering an antimicrobial composition from a medical tubing set to a medical device, the method comprising: inserting a male connector of a medical tubing set into a female connector of an infusion device; the male connector having a male tapered surface and the female connector having a female tapered surface, such that the male tapered surface engages the female tapered surface to form a substantially fluid-tight seal, the male connector having: a distal tip having a distal end face; the distal tip having a recess surface proximal to the distal end face, wherein the recess surface is radially inward of a line of taper extending along, and distal of, the male tapered surface at a first taper angle relative to a central longitudinal axis of the male connector; and a water-soluble antimicrobial composition positioned on the recess surface; wherein, upon insertion of the male connector into the female connector, the recess surface and the female tapered surface form a cavity and a fluid at least partially fills the cavity, and wherein at least a portion of the antimicrobial composition is dispersed within the fluid in the cavity.

In some examples, the male connector further comprising a tapered surface distal edge proximal to the distal end face of the male connector. In some examples, the tapered surface distal edge being at a distalmost end of the male tapered surface. In some examples, the tapered surface distal edge is proximal to at least part of the cavity formed between the female tapered surface and the recess surface. In some examples, the tapered surface distal edge has an inner diameter, the distal tip has an outer diameter, and the inner diameter of the tapered surface distal edge is greater than the outer diameter of the distal tip. In some examples, the male connector further comprises a fluid flow channel through the male connector. In some examples, the antimicrobial composition comprises chlorhexidine. In some examples, a portion of the antimicrobial composition dissolves into the fluid and forms a chlorhexidine precipitate on a portion of the female tapered surface. In some examples, after a portion of the antimicrobial composition is dispersed within the fluid in the cavity, the dispersed antimicrobial composition retains a concentration in the cavity of at least 200 micrograms per milliliter for a time period of at least I hour. In some examples, the cavity defines a volume within a range of I microliters to 25 microliters. In some examples, a plurality of blades extend radially outward from the recess surface into the cavity to at least partially divide the cavity. In some examples, the first taper angle is equal to a second taper angle of the recess surface relative to the central longitudinal axis. In some examples, the male connector further comprises a proximal trap comprising an annular cavity at least partially opening into the cavity formed between the female tapered surface and the recess surface.

Some further examples provide a method for delivering an antimicrobial composition from a medical tubing set to a medical device, the method comprising: inserting a male connector of a medical tubing set having a male tapered surface into a female connector of an infusion device, the female connector having a female tapered surface, such that the male tapered surface engages the female tapered surface to form a fluid-tight seal, the male connector having: a conical taper defined in part by the male tapered surface; a distal tip having a distal end face, and a recess surface proximal to the distal end face and inside the conical taper; a tapered surface distal edge of the male tapered surface and proximal to the distal tip; a fluid flow channel through the male connector; a water-soluble antimicrobial composition positioned on the recess surface; wherein, upon insertion of the male connector into the female connector, an annular cavity is formed between, and at least partly defined by, the recess surface and the female tapered surface of the female connector, the annular cavity having a proximal end coincident with the tapered surface distal edge and a distal end coincident with the distal tip end face, a volume between the proximal end and the distal end, a depth measured radially, and a length measured axially; wherein the distal end of the annular cavity is in fluid communication with a fluid lumen of the infusion device, and the length of the annular cavity is at least twice the depth of the annular cavity; and wherein a fluid at least partially fills the annular cavity, and at least a portion of the antimicrobial composition is dispersed within the fluid in the annular cavity.

Some further examples provide a medical tubing set configured to deliver an antimicrobial composition to a medical device, the medical tubing set comprising: a medical tube; a male connector secured to the medical tube, the male connector having a male tapered surface, the male connector further including: a distal tip having a distal end face; a radially-outward-facing recess surface proximal to the distal end face, wherein the recess surface is radially inward of a line of taper extending along, and distal of, the male tapered surface at a first taper angle relative to a central longitudinal axis of the male connector; and a water-soluble antimicrobial composition positioned on the recess surface.

In some examples, the male connector further comprising a tapered surface distal edge proximal to the distal end face of the male connector, the tapered surface distal edge being at the distalmost end of the male tapered surface. In some examples, the tapered surface distal edge is proximal to at least part of the recess surface. In some examples, a plurality of blades extend radially outward from the recess surface and divide the recess surface. In some examples, the plurality of blades comprise a plurality of blade surfaces and at least a portion of the antimicrobial composition is located on the plurality of blade surfaces. In some examples, the male tapered surface further comprises a proximal trap comprising an annular cavity proximal to a distal end of the male tapered surface.

Referring now to the drawings, FIG. 40A is a perspective view of a medical tubing set. The medical tubing set 100 includes a tubing 115. At the distal end of the tubing 115 is a male connector 101 with a male luer 141. The medical tubing set 100 further includes a spike 120 that is couplable with a spike cap 122. The spike 120 is located at a proximal end of the medical tubing set 100. In the example of FIG. 40A, the medical tubing set 100 further includes a drip chamber 123 for regulating fluid flow from an IV bag for intravenous administration of fluids.

The medical tubing set 100 can include a vent 125 and a flow control clamp 126. An end cap 127 can be provided that is couplable with the male connector 101.

FIG. 40B is a cross-sectional view of the medical tubing set 100 of FIG. 40A As seen in FIG. 40B, the male connector 101 has a male luer 141 with a male tapered sealing member 142 having a tapered sealing surface 143. The male connector 101 can include threads 102 that are compatible with threads of a female connector. A lumen 112 runs through the male luer 141, allowing infusion of fluid through the male connector 101. The male luer 141 further includes a distal tip 155 having a distal tip surface 152 and a distal tip end face 104. As will be discussed further below, the distal tip surface 152 can contain a water-soluble antimicrobial composition.

The male connector 101 can assume any of a number of different configurations. For example, the male connector 101 can have features similar to those disclosed in relation to one or more of the embodiments provided herein below.

FIG. 40C is a perspective view of the medical tubing set 100 of FIG. 40A The distal tip 155 can have features similar to those disclosed in relation to one or more of the embodiments provide herein below. The blade design, as shown at the distal tip 155, facilitates low-cost manufacturing and large lumen size for high flow applications.

Disclosed herein are embodiments of a method for delivering an antimicrobial composition from a medical tubing set to a medical device. In some embodiments, the method can include inserting a male connector of a medical tubing set into a female connector of an infusion device, the male connector having a male tapered surface and the female connector having a female tapered surface, such that the male tapered surface engages the female tapered surface to form a substantially fluid-tight seal, the male connector having: a distal tip having a distal end face, the distal tip having a recess surface proximal to the distal end face, wherein the recess surface is radially inward of a line of taper extending along, and distal of, the male tapered surface at a first taper angle relative to a central longitudinal axis of the male connector, and a water-soluble antimicrobial composition positioned on the recess surface. In some embodiments, upon insertion of the male connector into the female connector, the recess surface and the female tapered surface form a cavity and a fluid at least partially fills the cavity, and wherein at least a portion of the antimicrobial composition is dispersed within the fluid in the cavity. In some embodiments, the male connector can further include a tapered surface distal edge proximal to the distal end face of the male connector. In some embodiments, the tapered surface distal edge can be at a distalmost end of the male tapered surface.

In some embodiments, the tapered surface distal edge is proximal to at least part of the cavity formed between the female tapered surface and the recess surface. In some embodiments, the tapered surface distal edge has an inner diameter, the distal tip has an outer diameter, and the inner diameter of the tapered surface distal edge is greater than the outer diameter of the distal tip. In some embodiments, the method can further include comprising a fluid flow channel through the male connector. The antimicrobial composition can include chlorhexidine.

In some embodiments, the tubing set can be configured so that a portion of the antimicrobial composition dissolves into the fluid and forms a chlorhexidine precipitate on a portion of the female tapered surface. Further, after a portion of the antimicrobial composition is dispersed within the fluid in the cavity, the dispersed antimicrobial composition retains a concentration in the cavity of at least 200 micrograms per milliliter for a time period of at least 1 hour. The cavity can define a volume within a range of 1 microliters to 25 microliters. In some embodiments, a plurality of blades can extend radially outward from the recess surface into the cavity to at least partially divide the cavity. In some embodiments, the first taper angle can be equal to a second taper angle of the recess surface relative to the central longitudinal axis. The tubing set can further include a proximal trap comprising an annular cavity at least partially opening into the cavity formed between the female tapered surface and the recess surface.

Also disclosed herein are embodiments of a method for delivering an antimicrobial composition from a medical tubing set to a medical device, the method comprising inserting a male connector of a medical tubing set having a male tapered surface into a female connector of an infusion device, the female connector having a female tapered surface, such that the male tapered surface engages the female tapered surface to form a fluid-tight seal, the male connector having a conical taper defined in part by the male tapered surface, a distal tip having a distal end face, and a recess surface proximal to the distal end face and inside the conical taper, a tapered surface distal edge of the male tapered surface and proximal to the distal tip, a fluid flow channel through the male connector, a water-soluble antimicrobial composition positioned on the recess surface, wherein, upon insertion of the male connector into the female connector, an annular cavity is formed between, and at least partly defined by, the recess surface and the female tapered surface of the female connector, the annular cavity having a proximal end coincident with the tapered surface distal edge and a distal end coincident with the distal tip end face, a volume between the proximal end and the distal end, a depth measured radially, and a length measured axially. The distal end of the annular cavity can be in fluid communication with a fluid lumen of the infusion device, and the length of the annular cavity is at least twice the depth of the annular cavity, a fluid can at least partially fill the annular cavity, and at least a portion of the antimicrobial composition can be dispersed within the fluid in the annular cavity.

In some embodiments, a medical tubing set can be configured to deliver an antimicrobial composition to a medical device, the medical tubing set comprising: a medical tube, a male connector secured to the medical tube, the male connector having a male tapered surface, the male connector further including: a distal tip having a distal end face, a radially-outward-facing recess surface proximal to the distal end face, wherein the recess surface is radially inward of a line of taper extending along, and distal of, the male tapered surface at a first taper angle relative to a central longitudinal axis of the male connector, and a water-soluble antimicrobial composition positioned on the recess surface.

Peritoneal Dialysis Transfer Sets:

Also disclosed herein are peritoneal dialysis transfer sets. Peritoneal dialysis transfer sets are used to make fluid connections between a peritoneal dialysis catheter and a patient line, for instilling and removing dialysate from the peritoneal cavity.

Disclosed herein are embodiments of a method for preventing infection and microbial ingress in medical device connections between peritoneal dialysis transfer sets and peritoneal dialysis catheters. A peritoneal dialysis transfer set includes a male connector with a distal tip and a recess at the distal tip configured to deliver and confine an antimicrobial composition into solution within a cavity formed by the recess. The surface of the recess includes an antimicrobial composition. In certain implementations the antimicrobial composition contains chlorhexidine acetate.

Disclosed herein are embodiments of a method for delivering an antimicrobial composition from a peritoneal dialysis transfer set to a medical device, the method comprising inserting a male connector of a peritoneal dialysis transfer set into a female connector of a peritoneal dialysis catheter, the male connector having a male tapered surface and the female connector having a female tapered surface, such that the male tapered surface engages the female tapered surface to form a substantially fluid-tight seal, the male connector having a distal tip having a distal end face, ii) the distal tip having a recess surface proximal to the distal end face, wherein the recess surface is radially inward of a line of taper extending along, and distal of, the male tapered surface at a first taper angle relative to a central longitudinal axis of the male connector, a water-soluble antimicrobial composition positioned on the recess surface, and a fluid flow channel through the male connector. Upon insertion of the male connector into the female connector, the recess surface and the female tapered surface form a cavity and a fluid at least partially fills the cavity, and wherein at least a portion of the antimicrobial composition is dispersed within the fluid in the cavity.

Also disclosed herein are embodiments of a peritoneal dialysis transfer set configured to deliver an antimicrobial composition to a medical device, the peritoneal dialysis transfer set comprising a medical tube, and a male connector secured to the medical tube, the male connector having a male tapered surface, the male connector further including a distal tip having a distal end face, a radially-outward-facing recess surface proximal to the distal end face, wherein the recess surface is radially inward of a line of taper extending along, and distal of, the male tapered surface, a water-soluble antimicrobial composition positioned on the recess surface, and a fluid flow channel through the male connector.

The male connector further can further include a tapered surface distal edge proximal to the distal end face of the male connector, the tapered surface distal edge being at the distalmost end of the male tapered surface. The tapered surface distal edge can be proximal to at least part of the recess surface. A plurality of blades can extend radially outward from the recess surface and divide the recess surface. The plurality of blades can include a plurality of blade surfaces and at least a portion of the antimicrobial composition is located on the plurality of blade surfaces. The peritoneal dialysis transfer set can further include a proximal trap comprising an annular cavity proximal to a distal end of the male tapered surface. The peritoneal dialysis transfer set can further include a fluid-soluble, time-release material covering the antimicrobial composition. The time-release material can be configured to dissolve in fluid to expose the antimicrobial composition to the fluid in a time interval of between 1 second and 60 seconds. The time-release material can be configured to dissolve in fluid to expose the antimicrobial composition to the fluid in a time interval of between 1 minute and 10 minutes. The recess surface can have a width greater than 0.5 mm.

It should be appreciated that the various embodiments disclosed here may also be applied to other types of infusion devices. Examples disclosed herein include needleless connectors, couplers and caps, including caps for the proximal end of the peritoneal dialysis transfer set. These examples are used to illustrate the broader application of the invention, but it should be further appreciated that the unique aspects of these embodiments may also be applied to the male connector located at the distal end of the peritoneal dialysis transfer set.

Some examples of the disclosed technology provide a method for delivering an antimicrobial composition from a peritoneal dialysis transfer set to a medical device. The method comprises the steps of inserting a male connector of a peritoneal dialysis transfer set into a female connector of a peritoneal dialysis catheter; the male connector having a male tapered surface and the female connector having a female tapered surface, such that the male tapered surface engages the female tapered surface to form a substantially fluid-tight seal. There is a fluid flow channel through the male connector. The male connector has a distal tip with a distal end face. The distal tip has a recess surface proximal to the distal end face, and the recess surface is radially inward of a line of taper extending along, and distal of, the male tapered surface at a first taper angle relative to a central longitudinal axis of the male connector. A water-soluble antimicrobial composition is positioned on the recess surface, and upon insertion of the male connector into the female connector, the recess surface and the female tapered surface form a cavity. A fluid at least partially fills the cavity, and at least a portion of the antimicrobial composition is dispersed within the fluid in the cavity.

In some examples, the recess surface has a width greater than 0.5 mm. In some examples, the male connector further includes a tapered surface distal edge proximal to the distal tip of the male connector. In some examples, the tapered surface distal edge is positioned at a distalmost end of the male tapered surface. In some examples, the tapered surface distal edge is proximal to at least part of the cavity formed between the female tapered surface and the recess surface. In some examples, the tapered surface distal edge has an inner diameter, the distal tip has an outer diameter, and the inner diameter of the tapered surface distal edge is greater than the outer diameter of the distal tip.

In some examples, the male connector is a distal end portion of the peritoneal dialysis transfer set. In some examples, the antimicrobial composition comprises chlorhexidine. In some examples, a portion of the antimicrobial composition dissolves into the fluid and forms a chlorhexidine precipitate on a portion of the female tapered surface. In some examples, after a portion of the antimicrobial composition is dispersed within the fluid in the cavity, the dispersed antimicrobial composition retains a concentration in the cavity of at least 200 micrograms per milliliter for a time period of at least I minute. In some examples, the cavity defines a volume within a range of I microliter to 25 microliters.

In some examples, a plurality of blades extend radially outward from the recess surface into the cavity to at least partially divide the cavity. In some examples, the first taper angle is equal to a second taper angle of the recess surface relative to the central longitudinal axis. Some examples further include a proximal trap comprising an annular cavity at least partially opening into the cavity formed between the female tapered surface and the recess surface.

Further examples of the disclosed technology provide a method for delivering an antimicrobial composition from a peritoneal dialysis transfer set to a medical device. The method includes inserting a male connector of a peritoneal dialysis transfer set having a male tapered surface into a female connector of a peritoneal dialysis catheter, the female connector having a female tapered surface, such that the male tapered surface engages the female tapered surface to form a fluid-tight seal. The male connector has a conical taper defined in part by the male tapered surface; a distal tip having a distal end face, and a recess surface proximal to the distal end face and inside the conical taper; a tapered surface distal edge of the male tapered surface and proximal to the distal tip; a fluid flow channel through the male connector; and a water-soluble antimicrobial composition positioned on the recess surface. Upon insertion of the male connector into the female connector, an annular cavity is formed between the recess surface and the female tapered surface of the female connector. The annular cavity having a proximal end coincident with the tapered surface distal edge and a distal end coincident with the distal end face, a volume between the proximal end and the distal end, a depth measured radially, and a length measured axially. The distal end of the annular cavity is in fluid communication with a fluid lumen of the peritoneal dialysis catheter, and the length of the annular cavity is at least twice the depth of the annular cavity. A fluid at least partially fills the annular cavity, and at least a portion of the antimicrobial composition is dispersed within the fluid in the annular cavity.

Further examples of the disclosed technology provide a peritoneal dialysis transfer set configured to deliver an antimicrobial composition to a medical device. The peritoneal dialysis transfer set includes a medical tube and a male connector secured to the medical tube. The male connector has a male tapered surface and further includes a distal tip having a distal end face; a radially-outward-facing recess surface proximal to the distal end face, wherein the recess surface is radially inward of a line of taper extending along, and distal of, the male tapered surface; a water-soluble antimicrobial composition positioned on the recess surface; and a fluid flow channel through the male connector.

In some examples, the male connector further includes a tapered surface distal edge proximal to the distal end face of the male connector, the tapered surface distal edge being at the distalmost end of the male tapered surface. In some examples, the tapered surface distal edge is proximal to at least part of the recess surface.

In some examples, a plurality of blades extend radially outward from the recess surface and divide the recess surface. In some examples, the plurality of blades comprise a plurality of blade surfaces and at least a portion of the antimicrobial composition is located on the plurality of blade surfaces. Some examples further include a proximal trap comprising an annular cavity proximal to a distal end of the male tapered surface.

Some examples further include a fluid-soluble, time-release material covering the antimicrobial composition. In some examples, the time-release material is configured to dissolve in fluid to expose the antimicrobial composition to the fluid in a time interval of between 1 second and 60 seconds. In some examples, the time-release material is configured to dissolve in fluid to expose the antimicrobial composition to the fluid in a time interval of between 1 minute and 10 minutes.

Referring now to the drawings, FIG. 41A is a perspective view of a peritoneal dialysis transfer set 110, and FIG. 41B is an enlarged view of the distal end of the peritoneal dialysis transfer set 110. FIG. 41C is a cross-sectional view of the peritoneal transfer set 110, and FIG. 41D is a closeup cross-sectional view of the distal end of the male connector. The peritoneal dialysis transfer set 110 includes a tubing 115. At the distal end of the tubing 115 is a male connector 101 with a male luer 141. The male connector 101 is a distal end portion of the peritoneal dialysis transfer set 110. Opposite the male connector 101 is a female connector 118 that is configured to couple with a patient line. In some examples, the female connector 118 is configured to couple with a patient line. The male connector 101 and the female connector 118 are in fluid communication via a fluid lumen 112 through the tubing 115. Clamp 119 may be used to stop fluid flow through the fluid lumen 112.

The male luer 141 has a male tapered sealing member 142 with a tapered sealing surface 143 for mating with a tapered sealing surface of a female connector (not shown). The male connector 101 can include threads 102 that are compatible with threads of a female connector. A lumen 112 runs through the male luer 141, allowing infusion of fluid through the male connector 101. The male luer 141 further includes a distal tip 155 having a distal tip surface 152 and a distal tip end face 104. As will be discussed further below, the distal tip surface 152 can contain a water-soluble antimicrobial composition.

The male luer 141 includes a distal tip 155 with an end face 104. The distal tip 155 of the male luer 141 is recessed from the distal line of taper of the tapered scaling member 142. The distal line of taper will be discussed further in relation to FIGS. 16 and 17E. When the male luer 141 is sealed against a female luer and the tapered sealing surface 143 forms a fluid tight fit with the inside tapered sealing surface of the female luer, the distal tip surface 152 of the distal tip 155 does not make contact with the inside surface of the female luer, thus forming a cavity.

The male luer 141 includes a tapered surface distal edge 161 that defines a proximal end of the distal tip 155. The tapered surface distal edge 161 is situated at the distalmost end of the tapered sealing surface 143. When the male luer 141 is inserted into a female luer, the tapered surface distal edge 161 of the tapered sealing member 142 is capable of capturing microbes that may have infiltrated the inner surface of the female luer. The distal tip 155 of the male luer 141 further includes multiple blades 163 arrayed around the distal tip 155 of the male luer 141.

In some examples, an antimicrobial agent is applied to the distal tip surface 152 by coating, spraying, or dipping the distal tip 155 with an antimicrobial agent, although other methods of applying antimicrobial agent, such as impregnation into the distal tip 155, are contemplated and are within the scope of the technology. In some examples, antimicrobial agent is also applied to the tapered sealing surface 143. As described herein, an antimicrobial agent on the distal tip surface 152 of the distal tip 155 kills microbes within the distal recess 151, which forms a cavity between the surface of the female luer and the distal tip surface 152.

The male connector 101 can assume any of a number of different configurations. For example, the male connector 101 can have features similar to those disclosed in relation to one or more of the embodiments provided herein below. The distal tip 155 can have features similar to those disclosed in relation to one or more of the embodiments provide herein below. The blade design, as shown at the distal tip 155, facilitates low-cost manufacturing and large lumen size for high flow applications.

Syringes:

Syringes are commonly used in providing modern medical care to patients. Syringes are typically used for infusing drugs and other fluids into the body. For example, they are a commonly used means for infusing medications into, or aspirating fluids from, catheters such as central venous catheters, peripherally inserted central catheters, midline catheters, hemodialysis catheters and peritoneal dialysis catheters. Syringes are also used with other infusion devices, such as needleless connectors, valves and filters.

However, use of syringes has a serious drawback in that a significant percentage of patients develop infections, resulting in elevated mortality rates and significantly increased healthcare costs associated with treatment. Furthermore, infections are a leading cause of death in the United States, and many of those infections are attributable to syringes pushing microorganisms into infusion devices. The mortality rate associated with such infections is considerable. Therefore, a need exists for a manner to reduce infections relating from the use of syringes.

If a syringe is then inserted into the female luer, some of the organisms on the wall of the female luer can be pushed past the sealing surface and into the fluid path (during insertion of the male luer of the syringe into the female luer). Once organisms are in the fluid path they can multiply, spread, and cause an infection.

The present disclosure is directed, in part, to a syringe used to form a coupling with a medical device, the coupling typically comprising both a male connector and a female connector. In certain embodiments, the male connector of the syringe will form a fluid tight seal with a female connector that complies with International Standard ISO 80369-7. Connectors for Intravascular or Hypodermic Applications.

In other applications, the male connector will form a fluid tight seal with a female connector that does not comply with ISO 80369-7, such as the female end of a needleless connector; in this application, the syringe makes a fluid tight seal with the silicone septum of the needleless connector. Organisms are often present on the septum and adjacent surfaces, and this seal occasionally leaks. Thus, it is beneficial to have an antimicrobial composition along the syringe luer tip to create an antimicrobial solution to kill the organisms and create a persistent barrier against organisms within the female connector.

It should be appreciated that the various embodiments disclosed here may also be applied to male connector of other types of medical devices. Examples disclosed herein include needleless connectors and caps. These examples are used to illustrate the broader application of the invention, but it should be further appreciated that the unique aspects of these embodiments may also be applied to syringes.

Examples herein provide a syringe comprising: a fluid reservoir; and a male connector comprising a fluid flow channel in fluid communication with the fluid reservoir, the male connector including a male luer having: a tapered sealing surface configured to mate with a female tapered surface of a female connector to form a substantially fluid-tight seal; a distal tip having a recess defined by a recess surface that is distal to the tapered sealing surface; and a water-soluble antimicrobial composition disposed on the recess surface; wherein the male luer is configured such that, when the male connector is mated with a female connector to form a substantially fluid-tight seal, a cavity is formed between the female tapered surface and the recess surface.

In some examples, the male luer further includes a tapered surface distal edge disposed between the tapered sealing surface and the recess surface. In some examples, the male luer is configured such that the tapered surface distal edge is proximal to at least part of the cavity formed between the female tapered surface and the recess surface. In some examples, the male luer is configured such that the cavity has a volume within a range of I microliter to 25 microliters.

In some examples, the distal tip further comprises a plurality of blades divided by a plurality of channels, wherein the blades comprise elongated projections and the plurality of channels comprise elongated recesses disposed between the blades. In some examples, the antimicrobial composition is stored between the blades.

In some examples, the antimicrobial composition comprises chlorhexidine. In some examples, the antimicrobial composition is configured to dissolve into a fluid and form a chlorhexidine precipitate on a portion of the female tapered surface. In some examples, the male connector is configured such that the antimicrobial composition can disperse in the cavity at a concentration of at least 200 micrograms per milliliter for a time period of at least I minute.

Some examples further include a fluid-soluble, time-release material covering the antimicrobial composition. In some examples, the time-release material is configured to dissolve in fluid to expose the antimicrobial composition to the fluid in a time interval of between I second and 60 seconds.

Some examples further includes an annular cavity in the male luer. In some examples, the annular cavity is proximal to a distalmost end of the tapered sealing surface.

Additional examples herein provide a syringe comprising: a male connector having a male tapered surface configured to engage a female tapered surface of a female connector to form a fluid-tight seal, the male connector having: i) a conical taper defined by the male tapered surface; ii) a distal tip having a distal end face and a recess surface proximal to the distal end face, the recess surface being inside the conical taper; iii) the male tapered surface having a tapered surface distal edge proximal to the distal tip; iv) a fluid flow channel through the male connector; and v) a water-soluble antimicrobial composition positioned on the recess surface; wherein, upon insertion of the male connector into the female connector, an annular cavity is formed between, and at least partly defined by, the recess surface and the female tapered surface of the female connector.

Additional examples herein provide a syringe comprising: a barrel enclosing a fluid reservoir; a male connector secured to the barrel, the male connector having a male tapered surface, the male connector further including: i) a distal tip having a distal end face; ii) a radially-outward-facing recess surface proximal to the distal end face, wherein the recess surface is radially inward of a line of taper extending along, and distal of, the male tapered surface at a first taper angle relative to a central longitudinal axis of the male connector; and iii) a water-soluble antimicrobial composition positioned on the recess surface; and iv) a fluid flow channel in fluid communication with the fluid reservoir.

In some examples, the male connector further comprises a tapered surface distal edge proximal to the distal end face of the male connector, the tapered surface distal edge being at the distalmost end of the male tapered surface. In some examples, the tapered surface distal edge is proximal to at least part of the recess surface.

In some examples, the distal tip further comprises a plurality of blades divided by a plurality of channels, wherein the blades comprise elongated projections and the plurality of channels comprise elongated recesses disposed between the blades. In some examples, the plurality of blades comprise a plurality of blade surfaces and at least a portion of the antimicrobial composition is located on the plurality of blade surfaces.

In some examples, the syringe further includes a proximal trap comprising one or more cavities proximal to a distal end of the male tapered surface, wherein the proximal trap contains an antimicrobial composition. In some examples, the syringe further includes a proximal trap comprising at least one radially recessed cavity in the distal tip, wherein the proximal trap contains an antimicrobial composition.

For example, use of syringes on infusion devices is common practice. The syringes are typically in contact with an infusion device for a relatively short period of time, but because the female luer must be open when coupling the female connector on the infusion device with a male connector on the syringe, contamination of the inside of the open female luer can happen, as described above, which can ultimately lead to infection.

In another example, the syringe connects to a female connector at the proximal end of a needleless connector. The female connector comprises a septum designed to make a fluid tight seal with the male connector. In this example, bacteria may be present on a septum of the needleless connector and on surfaces adjacent to the septum. The seal between the male luer of the male connector and the septum often leaks, allowing fluid to be transferred between an intended fluid flow path and an extraluminal region (an unintended fluid flow path); thus allowing transfer of organisms between these regions via fluid or mechanical transfer.

Referring now to the drawings, FIG. 48A is a perspective view of a syringe with antimicrobial properties, and FIG. 48B is an enlarged view of the syringe of FIG. 48A. FIG. 48C is a cross-sectional view of the syringe of FIG. 48A, and FIG. 48D is an enlarged view of the cross-section of FIG. 48C inside circle D. Referring to FIGS. 48A-48D, the syringe 111 includes a barrel 110 and a plunger 103. The barrel 110 encloses a fluid reservoir 182. At the distal end of the barrel 110 is a male connector 101 with a male luer 141. The male connector 101 is couplable with a female connector (not shown).

The male luer 141 includes a male tapered sealing member 142 having a tapered sealing surface 143 for mating with a tapered sealing surface of a female connector (not shown). The male connector 101 can include threads 102 that are compatible with threads of a female connector. A fluid flow path 112 in fluid communication with the fluid reservoir 182 runs through the male luer 141, allowing a fluid to be dispensed through the male connector 101. The male luer 141 further includes a distal tip 155 having a distal tip surface 152 and a distal tip end face 104. As will be discussed further below, the distal tip surface 152 can contain a water-soluble antimicrobial composition.

The distal tip 155 of the male luer 141 is recessed from the distal line of taper of the tapered sealing member 142. The distal line of taper will be discussed further in relation to FIGS. 16 and 17E. When the male luer 141 is sealed against a female luer and the tapered sealing surface 143 forms a fluid tight fit with the inside tapered sealing surface of the female luer, the distal tip surface 152 of the distal tip 155 does not make contact with the inside surface of the female luer, thus forming a cavity between the inside surface of the female luer and the distal tip surface 152, from a tapered surface distal edge 161 to the end face 104.

The male luer 141 includes a tapered surface distal edge 161 that defines a proximal end of the distal tip 155. The tapered surface distal edge 161 is situated at the distalmost end of the tapered sealing surface 143. The distal tip 155 of the male luer 141 further includes multiple blades 163 arrayed around the distal tip 155 of the male luer 141. The plurality of blades extend radially outward from the recess surface and divide the cavity. The structure and function of the blades 163 will be discussed further below in relation to various embodiments, e.g., in FIGS. 14A and 17A through 29A, etc.

In some examples, an antimicrobial agent is applied to the distal tip surface 152 by coating, spraying, or dipping the distal tip 155 with an antimicrobial agent, although other methods of applying antimicrobial agent, such as impregnation into the distal tip 155, are contemplated and are within the scope of the technology. In some examples, antimicrobial agent is also applied to the tapered sealing surface 143. As described below in relation to FIG. 7A, an antimicrobial agent on the distal tip surface 152 of the distal tip 155 kills microbes within the distal recess 151, which forms a cavity between the surface of the female luer and the distal tip surface 152.

FIG. 48E is a perspective view of an alternative example of a syringe with antimicrobial properties according to some examples. FIG. 48F is a cross-sectional view of the syringe of FIG. 48E, and FIG. 48G is an enlarged view of FIG. 48F inside circle G. In the example of FIGS. 48E-48G, the syringe 111 has a male connector 101, but the male connector 101 does not have blades. Instead, the male luer 141 has a proximal trap 171 at the proximal end of the distal tip 155. The proximal trap 171 is an annular cavity that is bounded on multiple sides by proximal trap walls 173. The proximal trap 171 is defined as the space between a plane passing though tapered surface distal edge face 162 and the proximal trap walls 173. The proximal trap 171 opens on the distal recess 151. The proximal trap is adjacent to and proximal to the tapered surface distal edge face 162. As will be discussed below in relation to FIGS. 38 and 39, the proximal trap 171 can store an antimicrobial agent within the annular cavity defined by the proximal trap 171.

Alternatively, the male connector 101 can assume any of a number of different configurations. For example, the male connector 101 and the distal tip 155 of the male connector 101 can have features similar to those disclosed in relation to one or more of the embodiments provided herein below. Additionally, the male connector 101 is not limited to having a design that only has blades or only has a proximal trap; as described below in relation to FIGS. 32A-32G, it is possible for the male connector to include both blades and a proximal trap.

The embodiment of the male connector 1701 described in relation to FIGS. 17A-F can be used in combination with the syringe shown in FIGS. 48A-G. In the context of syringe 111, the blades 1763 are desirable because they provide for rapid diffusion of the antimicrobial composition into fluid within the distal recess 1751, especially when the distal recess depth (defined later in relation to FIG. 30G) is less than 0.50 mm, or in another example is less than 0.25 mm. The rapid diffusion of the antimicrobial composition results in rapid kill of microorganisms, which is beneficial for syringe applications because the syringe is often connected to the female connector for a relatively short period (e.g., less than one minute). In comparison, other infusion devices may be left connected for days.

In addition, the antimicrobial composition at the troughs 1768 of the channels 1767 may be made thicker or denser than the antimicrobial composition at the apex 1764 of the blades 1763. The thicker coating at or near the troughs 1768 of the channels 1767 provide an antimicrobial reservoir for a longer-lasting, high-concentration antimicrobial solution within the distal recess 1751. In one example, the antimicrobial composition is greater than two times thicker (or denser) at the trough 1768 of the channel 1767 than at the apex 1764 of the blade 1763. Having the antimicrobial reservoir extend along the length of the distal tip surface 1752, including up to the end face 1704, is beneficial for killing microorganisms at a septum of a needleless connector because fluid often leaks between syringe tips and septums. When the syringe 111 is coupled with a needless connector, the end face 1704 contacts the septum of the needleless connector; if some fluid leaks, fluid will be drawn along the distal tip surface 1752 by a capillary action that is produced by the geometry of the blade distal tip surface 1752 (drawn along the troughs of the channels), creating an antimicrobial solution that can kill microorganisms.

Disclosed herein are embodiments of a syringe, comprising a fluid reservoir; and a male connector comprising a fluid flow channel in fluid communication with the fluid reservoir, the male connector including a male luer having a tapered sealing surface configured to mate with a female tapered surface of a female connector to form a substantially fluid-tight seal; a distal tip having a recess defined by a recess surface that is distal to the tapered sealing surface; and a water-soluble antimicrobial composition disposed on the recess surface; wherein the male luer is configured such that, when the male connector is mated with a female connector to form a substantially fluid-tight seal, a cavity is formed between the female tapered surface and the recess surface. The male luer further can further include a tapered surface distal edge disposed between the tapered sealing surface and the recess surface. The male luer can be configured such that the tapered surface distal edge is proximal to at least part of the cavity formed between the female tapered surface and the recess surface. The male luer can be configured such that the cavity has a volume within a range of 1 microliter to 25 microliters. In some embodiments, the distal tip further comprises a plurality of blades divided by a plurality of channels, wherein the blades comprise elongated projections and the plurality of channels comprise elongated recesses disposed between the blades. In some embodiments, at least a portion of the antimicrobial composition is stored between the blades. The antimicrobial composition can comprise chlorhexidine. In some embodiments, the antimicrobial composition can be configured to dissolve into a fluid and form a chlorhexidine precipitate on a portion of the female tapered surface. The male connector can be configured such that the antimicrobial composition can disperse in the cavity at a concentration of at least 200 micrograms per milliliter for a time period of at least 1 minute. The syringe can further include a fluid-soluble, time-release material covering the antimicrobial composition. The time-release material can be configured to dissolve in fluid to expose the antimicrobial composition to the fluid in a time interval of between 1 second and 60 seconds.

What is claimed is:

1. A male connector device for coupling with a female connector, the male connector device comprising:

a male luer comprising a male tapered surface extending axially away from a wall of the male connector device;

a shroud extending axially away from the wall of the male connector device, the shroud configured to surround at least a portion of a length of the male luer;

an inner thread of the shroud configured to engage with corresponding threads of the female connector;

a fluid flow channel through the male connector device;

a plurality of recesses formed in a distal portion of the male luer, each recess of the plurality of recesses extends proximally from a distal end of the male luer, wherein the plurality of recesses are configured to create a space between a surface of each of the plurality of recesses and a female tapered surface of the female connector that can receive a liquid when the male connector device is coupled with the female connector; and a water-soluble antimicrobial composition positioned on the surface of each of the plurality of recesses.

2. The connector device of claim 1, wherein the plurality of recesses extend along a length of the male luer in the distal portion of the male luer.

3. The connector device of claim 1, wherein the plurality of recesses are circumferentially arranged about the male tapered surface in the distal portion of the male luer.

4. The connector device of claim 1, wherein the plurality of recesses are formed only in a portion of the male luer that extends past a distal surface of the shroud.

5. The connector device of claim 1, wherein the male connector device comprises a tapered surface distal edge proximal to a distal tip of the male connector device, the tapered surface distal edge being at a distalmost end of the male tapered surface.

6. The connector device of claim 5, wherein the tapered surface distal edge is coincident with a proximal edge of the plurality of recesses.

7. The connector device of claim 1, wherein an axial length of the plurality of recesses is approximately 0.020 inches to 0.040 inches.

8. The connector device of claim 1, wherein the water-soluble antimicrobial composition comprises chlorhexidine.

9. The connector device of claim 1, wherein the plurality of recesses are separated by a plurality of blades that extend radially outward.

10. The connector device of claim 9, wherein the plurality of blades are arranged substantially parallel to a central longitudinal axis.

11. The connector device of claim 1, wherein the male connector device further comprises a proximal trap comprising a cavity.

12. The connector device of claim 11, wherein at least a portion of the water-soluble antimicrobial composition is contained within the proximal trap.

13. The connector device of claim 1, wherein upon insertion of the male connector device into the female connector, an annular cavity is formed between the surface of each of the plurality of recesses and the female tapered surface of the female connector.

14. The connector device of claim 1, wherein the male luer, including the distal portion thereof, is monolithically formed.

15. The connector device of claim 1, wherein a distal edge is proximal to the distal end of the male luer, wherein the distal edge is at a distalmost end of the male tapered surface, wherein each recess of the plurality of recesses is entirely distal to the distal edge.

16. A connector device for delivering an antimicrobial composition into a medical device, the connector device comprising:

a male connector comprising a male tapered surface configured to engage a female connector of the medical device, the female connector having a female tapered surface, such that the male tapered surface engages the female tapered surface to form a fluid-tight seal, the male connector further comprising:

a conical taper defined in part by the male tapered surface;

a distal tip having a distal end;

a plurality of recesses each comprising a recess surface, each recess of the plurality of recesses extends proximally from the distal end of the male connector, the recess surface of each of the plurality of recesses are configured to extend radially inward of the male tapered surface;

a fluid flow channel through the male connector; and a water-soluble antimicrobial composition positioned on the recess surface of the plurality of recesses;

wherein:

the connector device is configured such that, upon insertion of the male connector into the female connector, at least one cavity is formed between the recess surface of the plurality of recesses and the female tapered surface of the female connector.

17. The connector device of claim 16, wherein the connector device is configured such that the at least one cavity defines a volume between the male connector and the female connector that is configured to receive a fluid therein, and wherein a portion of the antimicrobial composition is dissolvable into a fluid to form a chlorhexidine precipitate on a portion of the female tapered surface.

18. The connector device of claim 16, wherein the recess surface of the plurality of recesses are recessed 0.001" to 0.015" radially inwardly from a line of taper extending along the male tapered surface.

19. The connector device of claim 16, wherein the plurality of recesses are formed in the male connector.

20. The connector device of claim 16, wherein when the distal end of the male connector is inserted into the medical device, a fluid inside the medical device at least partially fills the at least one cavity and at least a portion of the antimicrobial composition is dispersed within the fluid in the at least one cavity.

* * * * *